(12) United States Patent
Segev

(10) Patent No.: US 9,156,865 B2
(45) Date of Patent: *Oct. 13, 2015

(54) SYSTEM FOR DELIVERING THERAPEUTIC AGENTS INTO LIVING CELLS AND CELLS NUCLEI

(71) Applicant: DELIVERSIR LTD., Tel Aviv (IL)

(72) Inventor: David Segev, Mazkeret Batia (IL)

(73) Assignee: DELIVERSIR LTD, Tel Aviv (IL)

( * ) Notice: Subject to any disclaimer, the term of this patent is extended or adjusted under 35 U.S.C. 154(b) by 177 days.

This patent is subject to a terminal disclaimer.

(21) Appl. No.: 13/656,803

(22) Filed: Oct. 22, 2012

(65) Prior Publication Data

US 2013/0137755 A1 May 30, 2013

Related U.S. Application Data

(63) Continuation-in-part of application No. 12/604,017, filed on Oct. 22, 2009, now Pat. No. 8,293,209, which is a continuation-in-part of application No. PCT/IL2008/000548, filed on Apr. 27, 2008.

(60) Provisional application No. 60/924,490, filed on May 17, 2007, provisional application No. 60/907,929, filed on Apr. 23, 2007.

(51) Int. Cl.
| A61K 51/00 | (2006.01) |
| C07F 9/09 | (2006.01) |
| A61K 49/00 | (2006.01) |
| C07J 51/00 | (2006.01) |
| C07K 1/113 | (2006.01) |
| C12N 15/87 | (2006.01) |
| C07H 21/04 | (2006.01) |
| C07F 9/6561 | (2006.01) |
| A61K 47/48 | (2006.01) |
| A61K 31/66 | (2006.01) |
| A61K 31/661 | (2006.01) |
| A61K 48/00 | (2006.01) |

(52) U.S. Cl.
CPC ........... *C07F 9/093* (2013.01); *A61K 47/48046* (2013.01); *A61K 47/48223* (2013.01); *A61K 48/0008* (2013.01); *A61K 49/0043* (2013.01); *A61K 49/0054* (2013.01); *C07F 9/6561* (2013.01); *C07H 21/04* (2013.01); *C07J 51/00* (2013.01); *C07K 1/1133* (2013.01); *C12N 15/87* (2013.01); *A61K 31/66* (2013.01); *A61K 31/661* (2013.01); *A61K 47/48* (2013.01); *A61K 47/48061* (2013.01); *A61K 47/48023* (2013.01); *A61K 47/48061* (2013.01); *A61K 48/00* (2013.01)

(58) Field of Classification Search
None
See application file for complete search history.

(56) References Cited

U.S. PATENT DOCUMENTS

| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,873,316 A | 10/1989 | Meade et al. |
| 4,879,219 A | 11/1989 | Wands et al. |
| 5,011,771 A | 4/1991 | Bellet et al. |
| 5,013,830 A | 5/1991 | Ohtsuka et al. |
| 5,149,797 A | 9/1992 | Pederson et al. |
| 5,192,659 A | 3/1993 | Simons |
| 5,220,007 A | 6/1993 | Pederson et al. |
| 5,256,775 A | 10/1993 | Froehler |
| 5,272,057 A | 12/1993 | Smulson et al. |
| 5,281,521 A | 1/1994 | Trojanowski et al. |
| 5,366,878 A | 11/1994 | Pederson et al. |
| 5,403,711 A | 4/1995 | Walder et al. |
| 5,491,133 A | 2/1996 | Walder et al. |
| 5,565,350 A | 10/1996 | Kmiec |

(Continued)

FOREIGN PATENT DOCUMENTS

| EP | 264166 | 4/1988 |
| WO | WO 99/32619 | 7/1999 |
| WO | WO 2005/025513 A2 | 3/2005 |
| WO | WO 2006/010084 | 1/2006 |
| WO | WO 2008/129548 A2 | 10/2008 |

OTHER PUBLICATIONS

Banerji et al., "A Lymphocyte-Specific Cellular Enhancer Is Located Downstream of the Joining Region in Immunoglobulin Heavy Chain Genes", 1983, Cell, vol. 33, pp. 729-740.

Beaucage et al.; "Deoxynucleoside Phosphoramidites-A New Class of Key Intermediates for Deoxypolynucleotide Synthesis", Tetrahedron Letters, Vol.22, No. 20, pp. 1859-1862, 1981.

(Continued)

Primary Examiner — James Rogers
(74) Attorney, Agent, or Firm — Pearl Cohen Zedek Latzer Baratz LLP; Mark S. Cohen

(57) ABSTRACT

The present invention relates to a novel delivery system for delivering therapeutic agents into living cells, and more particularly, to novel chemical moieties that are designed capable of targeting and/or penetrating cells or other targets of interest and further capable of binding therapeutic agents to be delivered to these cells, and to delivery systems containing same.

14 Claims, 18 Drawing Sheets

(56) References Cited

U.S. PATENT DOCUMENTS

| | | | |
|---|---|---|---|
| 5,623,065 | A | 4/1997 | Cook et al. |
| 5,652,355 | A | 7/1997 | Metelev et al. |
| 5,652,356 | A | 7/1997 | Agrawal |
| 5,700,922 | A | 12/1997 | Cook |
| 7,169,814 | B2 | 1/2007 | Rothbard et al. |
| 2006/0160763 | A1 | 7/2006 | Segev |

OTHER PUBLICATIONS

Byrne et al., "Multiplex gene ergulation: A two-tiered approach to transgene regulation in transgenic mice", 1989, Proc. Natl. Acad. Sci. USA, vol. 86, pp. 5473-5477.

Calame et al., "Transcriptional Controlling Elements in the Immunoglobulin and T Cell Receptor Loci", 1988, Adv. Immunol., vol. 43 pp. 235-275.

Chang et al., "Gene therapy: Applications to the treatment of gastrointestinal and liver diseases", Gastroenterology 106, 1076-1084 (1994).

Clarenc et al. "Delivery of antisense oligonucleotides by poly(L-lysine) conjugation and liposome encapsulation", Anticancer Drug Design, 1993, 8(1):81-94.

Cogoni et al.; "Gene silencing in Neurospora crassa requires a protein homologous to RNA-dependent RNA polymerase", Nature, 1999, vol. 399:pp. 166-169.

Draper et al.; "Attachment of reporter groups to specific, selected cytidine residues in RNA using a bisulfite-catalyzed transamination reaction", Nucleic Acids Res., 1984 12(2):989-1002.

Edlund et al.; "Cell-Specific Expression of the Rat Insulin Gene: Evidence for Role of Two Distinct 5' Flanking Elements", 1985, Science vol. 230:912-916.

Elbashir et al.; "Duplexes of 21-nucleotide RNAs mediate RNA interference in cultured mammalian cells", Nature, 2001, 411:494-529.

Farber et al.; "Optimal Conditions for Uptake of Exogenous DNA by Chinese Hamster Lung Cells Deficient in Hypoxanthineguanine Phosphoribosyltransferase", Biochim. Biophys. Acta, 1975, 390, pp. 298-311.

Fraley et al.; "Entrapment of a bacterial plasmid in phospholipid vesicles: Potential for gene transfer", Proc. Natl. Acad. Sci. USA, 1979, vol. 76, No. 7, pp. 3348-3352.

Felgner et al.; "Lipofection: A highly efficient, lipid-mediated DNA-transfection procedure", Proc. Natl. Acad. Sci. USA, 1987, vol. 84, pp. 7413-7417.

Fire et al.; "Potent and specific genetic interference by double-stranded RNA in Caenorhabditis elegans", Nature, 1998, vol. 391, pp. 806-811.

Freier et al.; "The ups and downs of nucleic acid duplex stability: structure-stability studies on chemically-modified DNA:RNA duplexes", Nucleic Acids Res., 1997, 25(22): 4429-4443.

Gait, M.J., ed.; "Oligonucleotide Synthesis", 1984, pp. 217, IRL Press. Oxford.

Green et al.; "The Role of Antisense RNA in Gene Regulation", Annu. Rev. Biochem., 1986, 55:569-597.

Hamilton et al.; "A Species of Small Antisense RNA in Post-transcriptional Gene Silencing in Plants", Science, 1999, 286:950-952.

Hutvagner et al.; "RNAi: nature abhors a double-strand", 2002, Curr. Opin. Genetics and Development 12:225-232.

Kennerdell et al.; "Use of dsRNA-Mediated Genetic Interference to Demonstrate that frizzled and frizzled 2 Act in the Wingless Pathway", Cell, 1998, vol. 95, pp. 1017-1026.

Ledoux et al.; "Uptake of DNA by Living Cells", Prog. Nucl. Acid Res., 1965, 4, 231-267.

Ngo et al.; "Double-stranded RNA induces mRNA degradation in Trypanosoma brucei", Proc. Natl. Acad. Sci USA, vol. 95, pp. 14687-14692,1998.

Peer et al.; "Nanocarriers as an emerging platform for cancer therapy", nature nanotechnology, vol. 2, Dec. 2007.

Peer et al.; "Systemic Leukocyte-Directed siRNA Delivery Revealing Cyclin D1 as an Anti-Inflammatory Target", Science vol. 319, Feb. 1, 2008.

Peer et al.; "Tumor-Targeted Hyaluronan Nanoliposomes Increase the Antitumor Activity of Liposomal Doxorubicin in Syngeneic and Human Xenograft Mouse Tumor Models", Neoplasia, vol. 6, No. 4, Jul./Aug. 2004, pp. 343-353.

Pinkert et al.; "An albumin enhancer located 10 kb upstream functions along with its promoter to direct efficient, liver-specific expression in transgenic mice", 1987, Genes Dev. 1:268-276.

Sambrook et al.; Molecular Cloning: A laboratory Manual., 1989, section 7.37.

Search Report and Written Opinion of corresponding International Application No. PCT/IL08/00548 dated Nov. 21, 2008.

Smith; "Viral Vectors in Gene Therapy", Annual. Rev. Microbiol., 1995, 49:807-838.

Timmons et al.;, "Specific interference by ingested dsRNA", Nature, 1998, 395:854.

Wagner et al.; "Transferrin-polycation conjugates as carriers for DNA uptake into cells" Proc. Natl. Acad. Sci. USA, 1990, 87, 3410.

Waterhouse et al.; "Virus resistance and gene silencing in plants can be induced by simultaneous expression of sense and antisense RNA", Proc. Natl. Acad. Sci. USA, 1998, vol. 95, pp. 13959-13964.

Winoto et al., "A novel, inducible and T cell-specific enhancer located at the 3' end of the T cell receptor α locus", 1989, The EMBO J., vol. 8, No. 3, pp. 729-733.

Now, Compound 14 and Fluorescein amidite (FAM-HPA) can be condensed sequentially to CPG support by the well known DNA synthesis protocol, followed by deprotection and guanidization protocol to obtain Compound 23.

Wherein G is a guanidine group.    Compound 23

SYSTEM FOR DELIVERING THERAPEUTIC AGENTS INTO LIVING CELLS AND CELLS NUCLEI

CROSS REFERENCE TO RELATED APPLICATIONS

This application is a Continuation-in-Part of U.S. application Ser. No. 12/604,017, filed Oct. 22, 2009, which is a Continuation-in-Part of International Application Number PCT/IL2008/000548 filed 27 Apr. 2008, which claims priority of U.S. Ser. No. 60/907,929, filed 23 Apr., 2007 and U.S. Ser. No. 60/924,490, filed 17 May 2007, each of which is hereby incorporated by reference in it's entirety.

FIELD OF THE INVENTION

The present invention relates to a novel delivery system for delivering therapeutic agents into living cells, and more particularly, to novel chemical moieties that are designed capable of targeting and/or penetrating cells or other targets of interest and further capable of binding therapeutic agents to be delivered to these cells, and to delivery systems containing same.

BACKGROUND OF THE INVENTION

One of the most challenging targets is to deliver genetic materials to cells safely. The identification of defective genes responsible for disease states, either through defective control of gene expression, which leads to overproduction or underproduction of key proteins, or the production of defective proteins, offers new possibilities for the treatment of disease. By controlling the defect at the genetic level, a range of diseases could potentially be treated effectively rather than by merely treating the symptoms of these diseases.

The use of genetic material to deliver genes for therapeutic purposes has been practiced for many years.

Generation of therapeutic gene products (such as polypeptides, proteins, mRNA and RNAi) by expression of therapeutic gene product-encoding DNA in transformed cells has attracted wide attention as a method to treat various mammalian diseases and enhance production of specific proteins or other cellular products. This promising technology, often referred to as gene therapy (Crystal et al., Science 1995, 270, 404), is generally accomplished by introducing exogenous genetic material into a mammalian patient's cells. Transformed cells can be accomplished by either direct transformation of target cells within the mammalian subject (in vivo gene therapy) or transformation of cells in vitro and subsequent implantation of the transformed cells into the mammalian subject (ex vivo gene therapy) (for reviews, see Chang et al. 1994 *Gastroenterol.* 106:1076-84). The introduced genetic material can be designed to replace an abnormal (defective) gene of the mammalian patient ("gene replacement therapy"), or can be designed for expression of the encoded protein or other therapeutic product without replacement of any defective gene ("gene augmentation"). Because many congenital and acquired medical disorders result from inadequate production of various gene products, gene therapy provides means to treat these diseases through either transient or stable expression of exogenous nucleic acid encoding the therapeutic product. Although the initial motivation for gene therapy was the treatment of genetic disorders, it is becoming increasingly apparent that gene therapy will be useful for the treatment of a broader range of acquired diseases such as cancer, infectious disorders (such as AIDS), heart disease, arthritis, and neurodegenerative disorders such as Parkinson's and Alzheimer's diseases.

DNA is inherently an unstable material in an active biological environment where many specific enzymes capable of degrading and metabolizing DNA are found (Ledoux et al., *Prog. NucL Acid. Res.,* 1965, 4, 231). In addition, natural protection against alien DNA exists in the body. Thus, the gene therapy, antisense oligonucleotide therapy and gene vaccination approaches described above require that the DNA and DNA analogues would survive in such a hostile biological environment and in addition, that the DNA and DNA analogs would penetrate biological barriers, be taken up into cells and be delivered to the correct subcellular compartment to exert their therapeutic effects. While some DNA is taken up naturally into cells, the amount taken up is typically small and inconsistent, and expression of added DNA is therefore poor and unpredictable.

A number of strategies have been proposed to achieve delivery of DNA into living cells. These include the use of liposomes (Fraley et al., *Proc. Natl. Acad. Sci. USA,* 1979, 76, 3348), cationic lipids (Feigner et al., *Proc. Natl. Acad. Sci USA,* 1987, 84, 7413), and the use of cationic polymers, or polycations, such as polylysine and polyornithine as DNA delivery agents (Farber et al., *Biochim. Biophys. Acta,* 1975, 390, 298 and Wagner et al., *Proc. Natl. Acad. Sci. USA,* 1990, 87, 3410).

Therapeutic approaches that involve intervention at the gene level are widely recognized as promising technologies, these methods are limited by the absence of an efficient and reliable method of delivering DNA and RNA.

There is thus a widely recognized need for, and it would be highly advantageous to have, a novel delivery system for delivering therapeutic agents such as DNA and RNA molecules into living cells, which would overcome the present limitations associated with gene therapy.

SUMMARY OF THE INVENTION

The present invention is directed to a phosphate based oligomeric compound, comprising a repeating unit represented by the structure of formula (A):

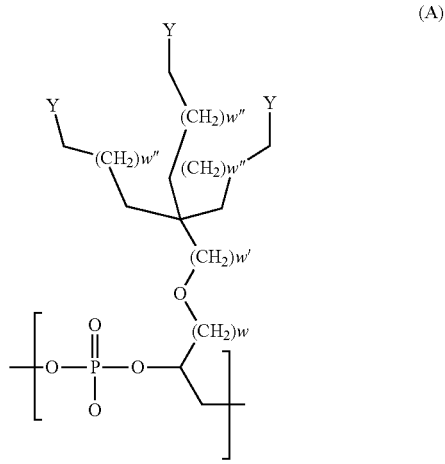

wherein

Y is a delivery group; wherein said delivery group is amine, histidine, guanidine, polyguanidine, imidazole, polyimidzole or any combination thereof; and w, w' and w" are each independently an integer between 0 and 10.

In another embodiment, the phosphate based oligomeric compound further comprises linker units, which link between phosphate moieties, wherein said linker comprises a substituted or unsubstituted linear alkyl chain of 2-50 carbon atoms, substituted or unsubstituted branched alkylphosphate chain of 2-50 carbon atoms, substituted or unsubstituted linear alkylether chain of 2-50 carbon atoms or any combination thereof. In another embodiment the alkyl chain is hexyl. In another embodiment, the alkyl ether chain of said linker is polyethyleneglycol (PEG). In another embodiment, the alkylphosphate chain is represented by the structure of formula (B):

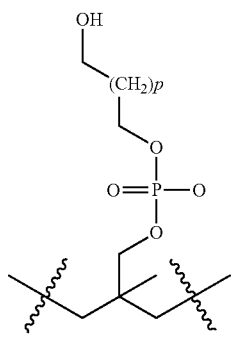

wherein p is an integer between 0 and 10.

In another embodiment, the phosphate based oligomeric compound is represented by the structure of formula III(c):

wherein each of $Z_1$ and $Z_2$ is independently a reactive group capable of binding a biologically active moiety; or a hydrogen atom, provided that at least one of $Z_1$ and $Z_2$ is a reactive group wherein said reactive group is hydroxy, amine, halide, a phosphorous-containing group, phosphoramidite, —N=C=S, —NH—CO—NH$_2$, —NH—CS—NH$_2$ C-amide, N-amide, thiol or COOH;

E is a third linking group or absent; wherein said third linking group is a linear alkyl of 2-50 carbon atoms;

Y is a delivery group; wherein said delivery group is amine, histidine, guanidine, polyguanidine, imidazole, polyimidzole or any combination thereof;

L is a substituted or unsubstituted linear or branched alkyl phosphate; and each of r and r' is independently an integer number of between 0 and 50; and q is an integer between 0 and 50.

In another embodiment, the oligomer compound is represented by the structure of formula III:

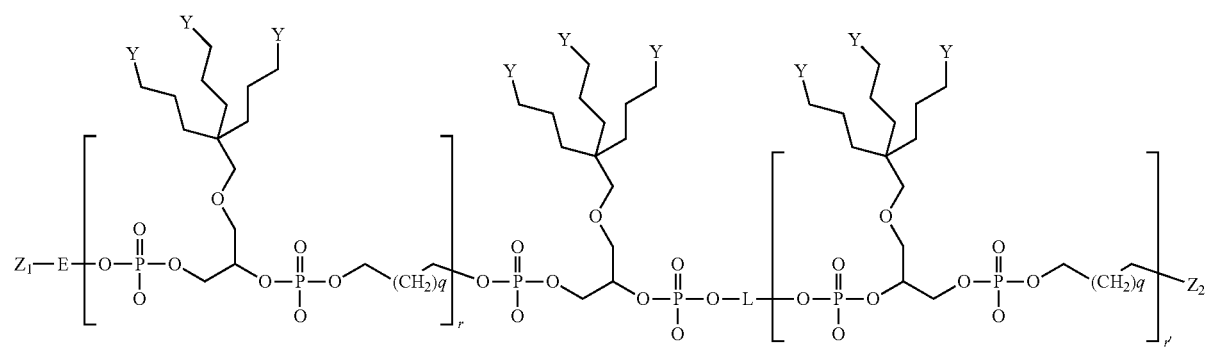

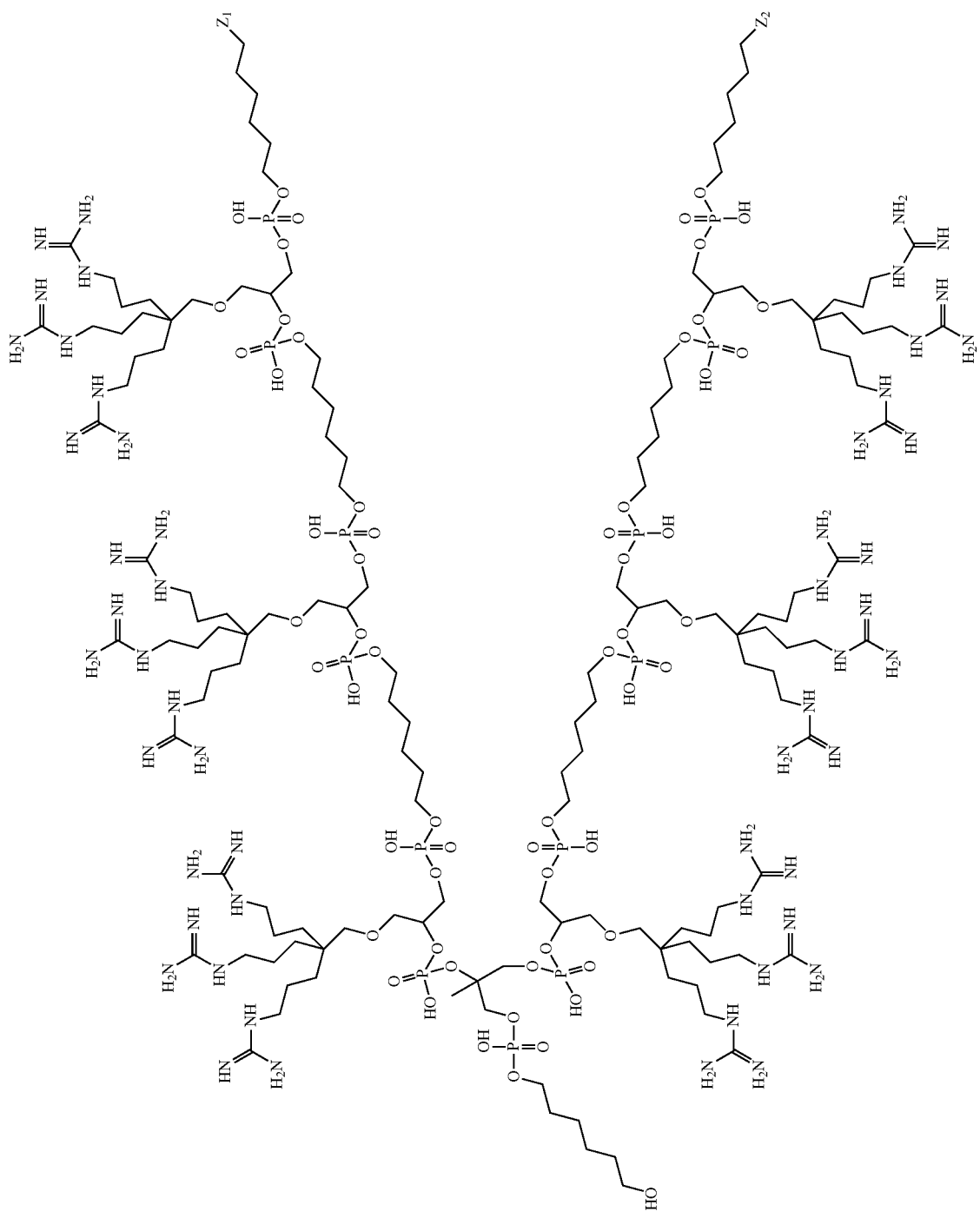

In one embodiment, this invention is directed to a conjugate of the phosphate based oligomeric compound as described hereinabove and at least one biologically active substance.

In another embodiment, the conjugate is represented by the structure of formula IV(c):

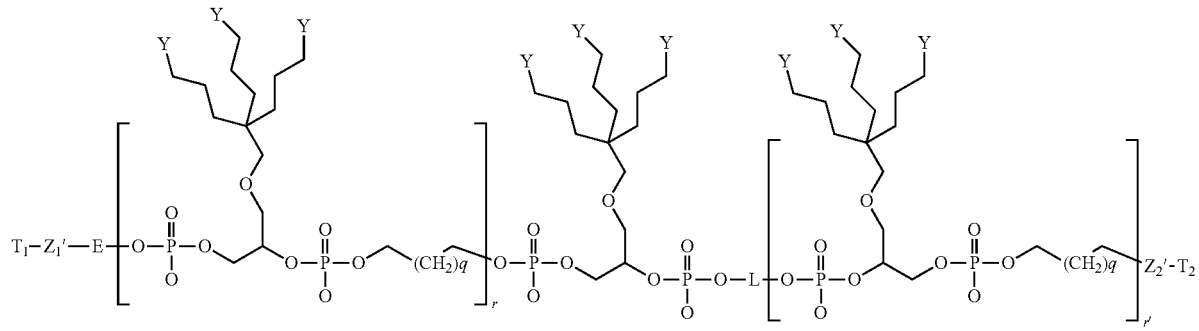

IV(c)

wherein
each of $T_1$ and $T_2$ is independently a biologically active moiety or absent, wherein at least one of $T_1$ and $T_2$ is present; and wherein said biologically active substance is a therapeutically active agent, a labeling moiety, or combination thereof;

each of $Z_1'$, $Z_2'$, is independently a derivative of $Z_1$ and $Z_2$, respectively, as a result of binding the biologically active group, wherein said $Z_1$ and $Z_2$ reactive group is hydroxyl, amine, halide, a phosphorous-containing group, a phosphate, phosphoramidite, C-amide, N-amide, thiol or COOH;

wherein if $T_1$ or $T_2$ is absent then $Z_1'$ or $Z_2'$ connected to it is replaced with $Z_1$ or $Z_2$ respectively.

In another embodiment, the conjugate is represented by the structure of formula V:

V
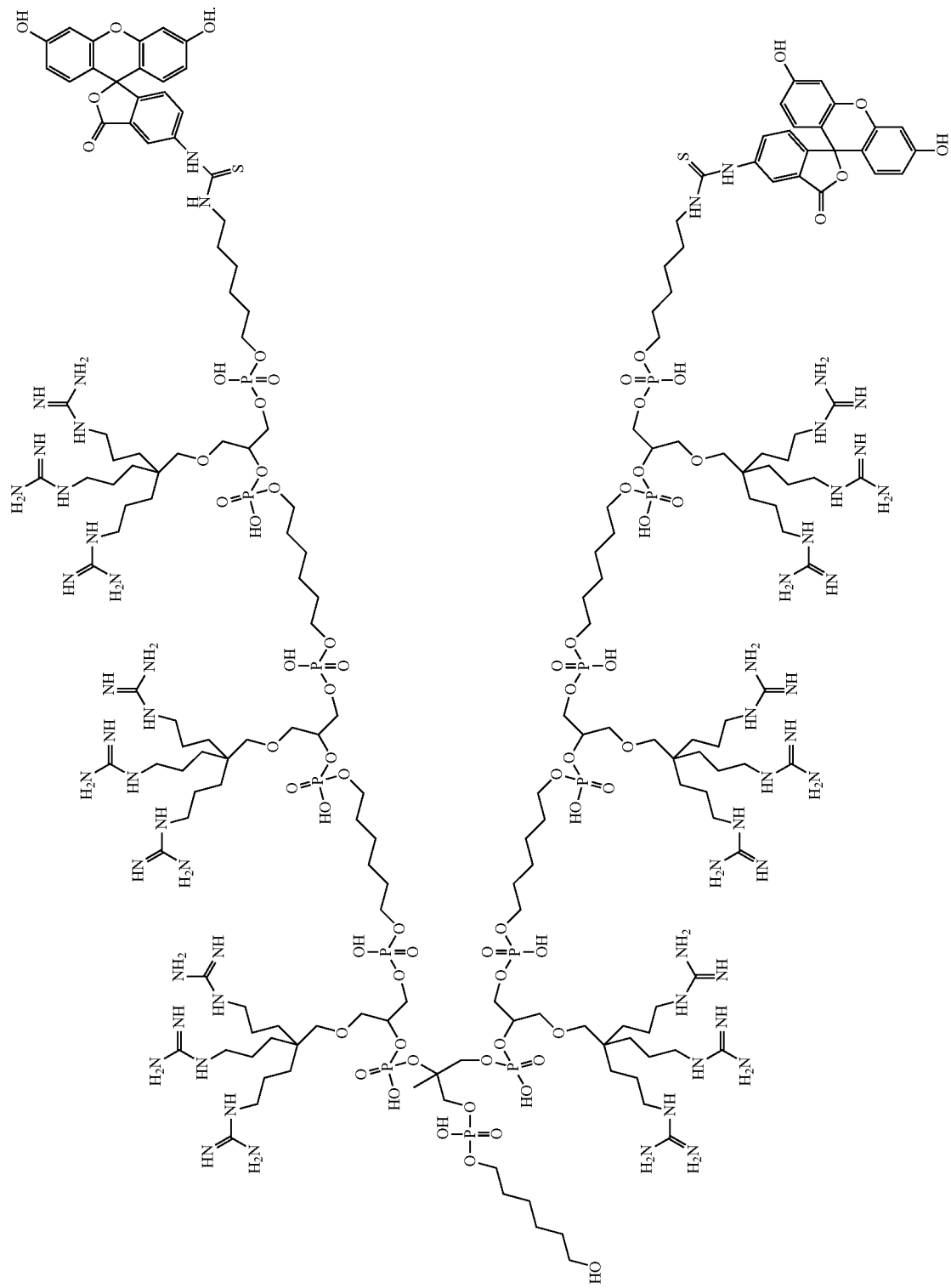

In one embodiment, this invention is directed to a complex of a conjugate as described hereinabove, and an oligonucleotide, wherein said oligonucleotide, is electrostatically bound to said conjugate. In another embodiment, the oligonucleotide is DNA, RNA or combination thereof.

In one embodiment, this invention is directed to an oligomeric compound represented by the structure of formula I(a):

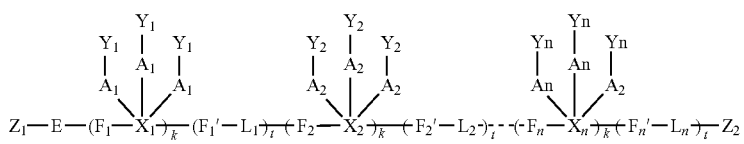

I(a)

wherein:
n is an integer of between 3 to 50;
each k is independently an integer between 1 to 50;
each t is independently an integer between 0 to 50;
each of $X_1$-$X_n$ is independently a cyclic or an acyclic group; wherein said $X_1$-$X_n$ is substituted or unsubstituted alkyl of 2-50 carbon atoms, substituted or unsubstituted alkylether of 2-50 carbon atoms, or substituted or unsubstituted alkylphosphate of 2-50 carbon atoms;
each of $L_1$-$L_n$ is independently a first linking group; wherein said $L_1$-$L_n$ is a substituted or unsubstituted linear alkyl of 2-50 carbon atoms, substituted or unsubstituted linear alkylether of 2-50 carbon atoms, or substituted or unsubstituted branched alkylphosphate of 2-50 carbon atoms;
each of $A_1$-$A_n$ is independently a second linking group; wherein said $A_1$-$A_n$ is a substituted or unsubstituted linear or branched alkyl of 2-8 carbon atoms, or substituted or unsubstituted linear or branched alkylether of 2-8 carbon atoms;
E is a third linking group or absent; wherein said E is a substituted or unsubstituted linear alkyl of 2-50 carbon atoms, substituted or unsubstituted linear alkylether of 2-50 carbon atoms, or substituted or unsubstituted linear alkylphosphate of 2-50 carbon atoms;
each of $Y_1$-$Y_n$ is independently a delivering group or absent, provided that at least one of $Y_1$-$Y_n$ is the delivering group, wherein each of said delivering group is independently an amine, histidine, guanidine, polyguanidine, imidazole or polyimidazole; and
each of $F_1$-$F_n$ and $F_1'$-$F_n'$ is independently a phosphate or absent.

In another embodiment, the oligomeric compound is represented by the structure of formula I(b):

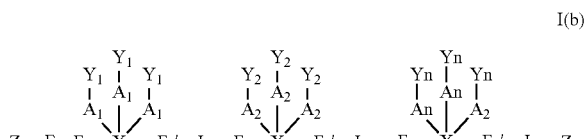

I(b)

In another embodiment, this invention is directed to a complex of the conjugate of this invention and an oligonucleotide. In another embodiment, the oligonucleotide is DNA, RNA or combination thereof. In another embodiment, the oligonucleotide is electrostatically bound to the conjugate.

In one embodiment, this invention is directed to a method of delivering a DNA, RNA or combination thereof to a cell, said method comprises contacting the complex of this invention with said cell, thereby delivering said DNA, RNA or combination thereof to said cell. In another embodiment, the cell is cancerous.

In another embodiment, this invention is directed to a method of treating cancer, comprising contacting a complex of this invention with a cancer cell, thereby treating cancer.

In another embodiment, this invention is directed to a pharmaceutical composition comprising the conjugate of this invention and a pharmaceutically acceptable carrier.

In another embodiment, this invention is directed to a pharmaceutical composition comprising a complex of this invention and a pharmaceutically acceptable carrier.

According to an additional aspect of the present invention this invention is directed to a method of delivering a biologically active moiety into the cell using a conjugate or a complex of this invention.

In one embodiment, this invention provides a method of treating cancer, comprising administering a complex of this invention, thereby treating cancer.

In one embodiment, this invention provides a method of delivering a biologically active moiety into a cell, said method comprises contacting a conjugate of this invention with said cell, thereby delivering said biologically active moiety to said cell.

In one embodiment, this invention provides a method of delivering a biologically active moiety into a cell, said method comprises contacting a complex of this invention with said cell, thereby delivering said biologically active moiety to said cell.

In one embodiment, this invention provides a method of treating cancer, comprising administering a conjugate of this invention to a subject, thereby treating cancer.

In one embodiment, this invention provides a method of diagnosing a condition, comprising contacting a conjugate of this invention with a cell, thereby delivering the labeling moiety of said conjugate to said cell and diagnosing said condition.

According to still an additional aspect of the present invention there is provided use of the conjugate described herein for the preparation of a medicament for treating cancer.

The present invention successfully addresses the shortcomings of the presently known configurations by providing novel chemical moieties, which are characterized by capability to penetrate cells and/or nuclei membranes, and/or as targeting moieties, and conjugates of such chemical moieties and biologically active agents, which can be beneficially used for efficient delivery of such agents into bodily targets such as living cells and/or cells nuclei.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1A:
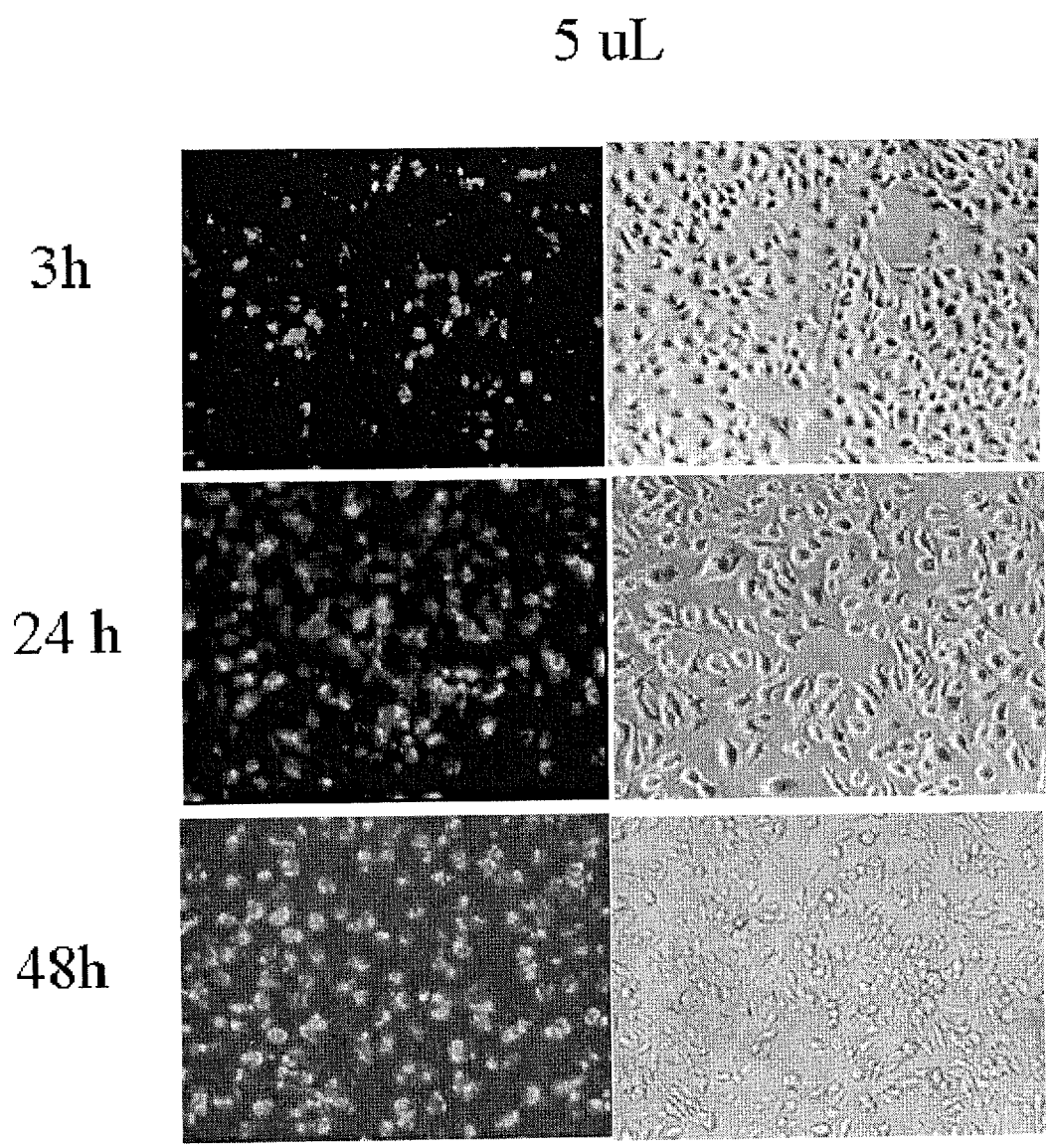
FIG. 1 depicts in vitro testing of delivery of Compound 38 into human glioblastoma cells and testing the cytotoxicity by exponentially growing cells; 5 uL of Compound 38 (FIG. 1A), 10 uL of Compound 38 (FIG. 1B) and 15 uL of Compound 38 (FIG. 1C).
FIG. 1D depicts untreated cells.
Figure 1B:
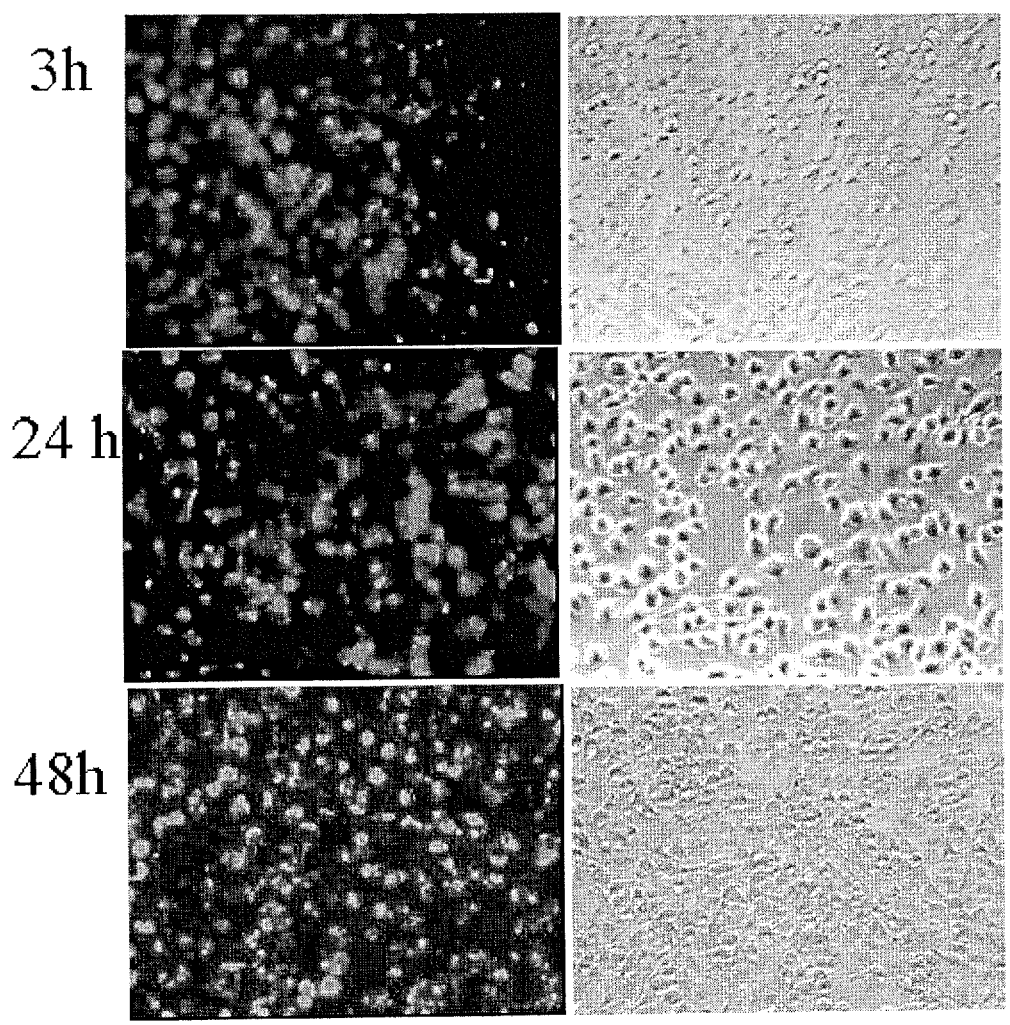
Figure 1C:
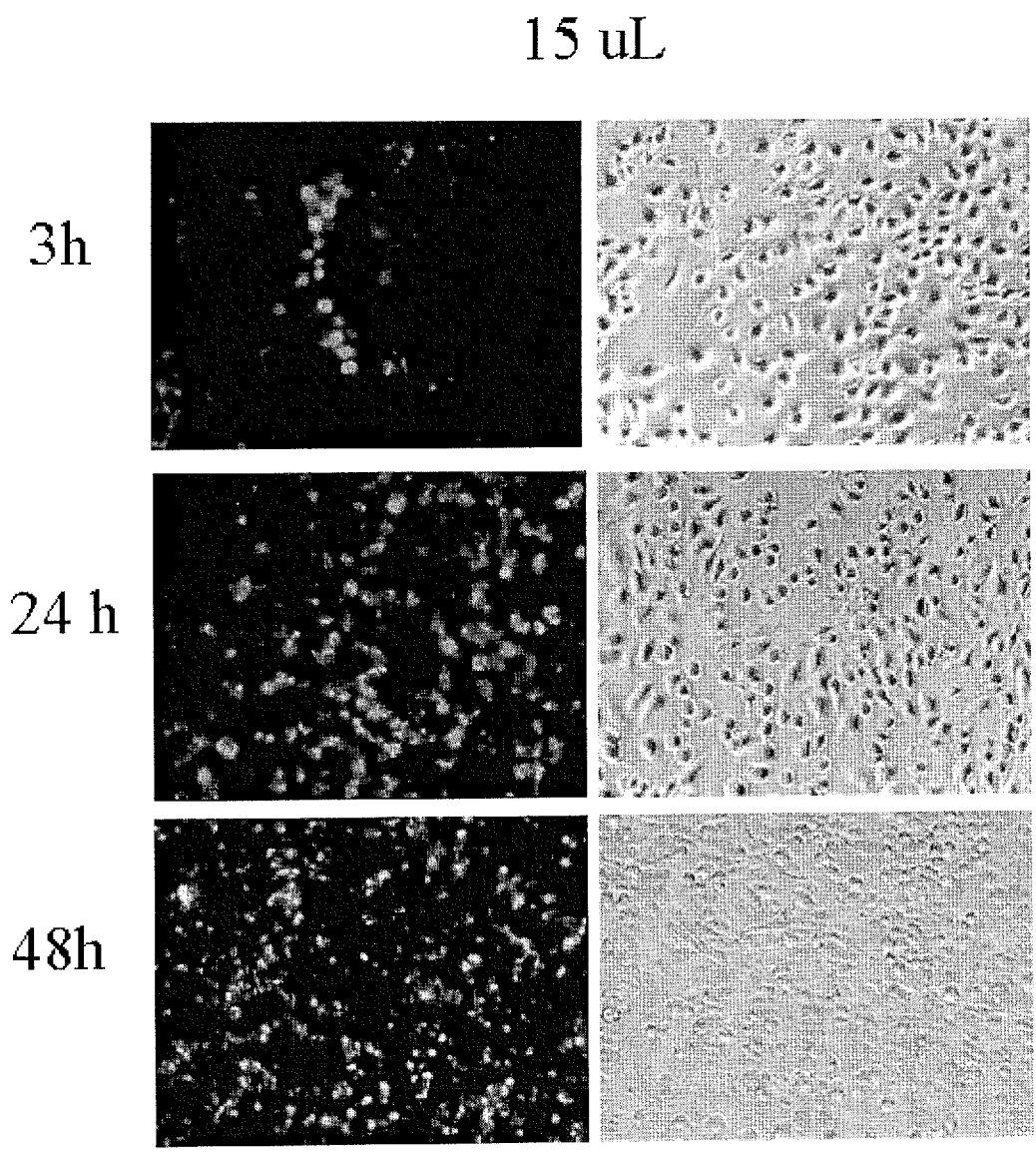
Figure 1D:
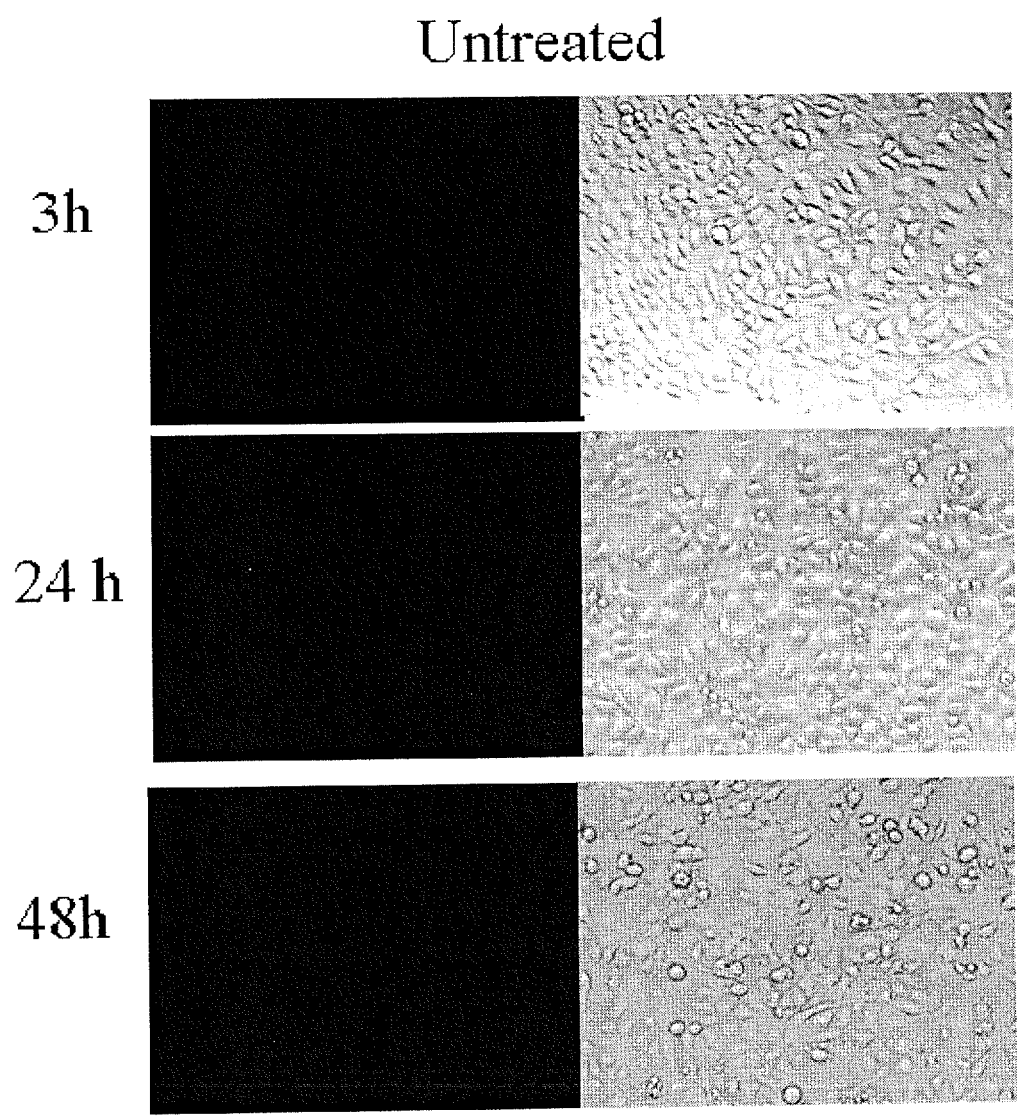

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present invention is of a novel class of oligomeric compounds designed for forming conjugates and complexes with biologically active substances and delivering these substances to the desired target. The present invention is thus further of conjugates/complexers of biological moieties and such oligomeric compounds, of pharmaceutical compositions containing the conjugates/complexes, and of uses of these conjugates/complexes for delivering the biologically active substances to a desired target, and thus for treating a myriad of medical conditions. The present invention further provides processes of preparing the conjugates/complexes and the oligomeric compounds and of novel intermediates designed for and used in these processes.

In one embodiment, the delivery system of this invention comprises a biocompatible oligomeric compounds, which are designed so as to incorporate delivering groups such as cell-penetrative groups, recognition groups and/or other groups which may direct the conjugated moiety to the desired target, be it an organ, a tissue, a cell, a cellular compartment and the like, as is detailed herein. The oligomeric compound is further designed to include reactive groups, optionally and preferably protected reactive group, which are selected suitable to attach a desired biologically active moiety, and thus form the delivery system. The delivery system provided herein may therefore be efficiently used for therapy and/or diagnosis applications and particularly for cell therapy.

In one embodiment, this invention is directed to phosphate based oligomeric compounds designed for forming conjugates with biologically active substances and complexes thereof with oligonucleotide such as RNA and/or DNA in order to deliver these substances, and/or the oligonucleotide to the desired target. In another embodiment, the oligomeric compounds comprise phosphate repeating units. In another embodiment, the oligomeric compounds further comprise delivering groups. In another embodiment, the delivering groups comprise amine, histidine, guanidine, polyguanidine, imidazole, polyimidzole or any combination thereof. In another embodiment, the oligomeric compounds further comprise a repeating unit represented by the structure of formula (A):

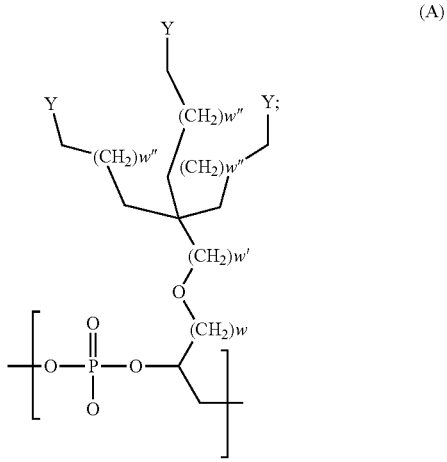

(A)

wherein Y is a delivery group; and w, w' and w" are each independently an integer between 0 and 10. In another embodiment, w, w' and w" are each independently an integer between 0 and 3. In another embodiment, w, w' and w" are each independently 0 or 1. In another embodiment each of w, w' and w" is 1.

In another embodiment, the oligomeric compounds further comprise linker units, which link between phosphate moieties of the oligomeric compound. In another embodiment, the linker is a substituted or unsubstituted alkyl chain of 2-50 carbon atoms. In another embodiment, the linker is a substituted or unsubstituted alkyl chain of 2-8 carbon atoms. In another embodiment, the alkyl chain is linear. In another embodiment, the linker is a hexyl chain. In another embodiment, the linker is a substituted or unsubstituted alkylether chain of 2-50 carbon atoms. In another embodiment, the linker is a substituted or unsubstituted alkylether chain of 2-8 carbon atoms. In another embodiment, the alkylether chain is linear. In another embodiment, the linker is a polyethyleneglycol (PEG). In another embodiment, the alkyl chain is branched. In another embodiment, the alkyl chain is interrupted by one or more heteroatoms. In another embodiment, the alkyl chain is interrupted by an oxygen atom. In another embodiment, the alkyl chain is interrupted by a phosphate unit. In another embodiment, the linker is a substituted or unsubstituted linear or branched alkylphosphate chain of 2-50 carbon atoms. In another embodiment, the linker is a substituted or unsubstituted linear or branched alkylphosphate chain of 2-8 carbon atoms. In another embodiment, the linker is a hexyl phosphate. In another embodiment, the linker is represented by the structure of formula (B):

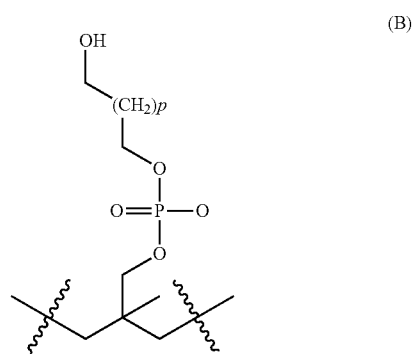

(B)

wherein p is an integer between 0 and 10. In another embodiment, p is 1. In another embodiment, p is 2. In another embodiment, p is 3. In another embodiment, p is 4.

In one embodiment, this invention is directed to phosphate based oligomeric compounds, which further comprise delivering groups, linker units which link between phosphate moieties of the oligomeric compound, and reactive groups capable of binding a biologically active moiety, wherein the delivering group is amine, histidine, guanidine, polyguanidine, imidazole, polyimidzole or any combination thereof; the linker units are substituted or unsubstituted linear or branched alkyl chains of 2-50 carbon atoms, substituted or unsubstituted linear or branched alkyl phosphate chains of 2-50 carbon atoms substituted or unsubstituted linear or branched alkylether chains of 2-50 carbon atoms, or any combination thereof; and the reactive groups are hydroxy, amine, halide, a phosphorous-containing group, phosphoramidite, —N=C=S, —NH—CO—NH$_2$, —NH—CS—NH$_2$ C-amide, N-amide, thiol or COOH. In another embodiment, the alkyl, alkylether and/or alkyl phosphate chain has 2-8 carbon atoms.

In another embodiment, this invention is directed to phosphate based oligomeric compounds, which comprise a repeating unit represented by the structure of formula (A):

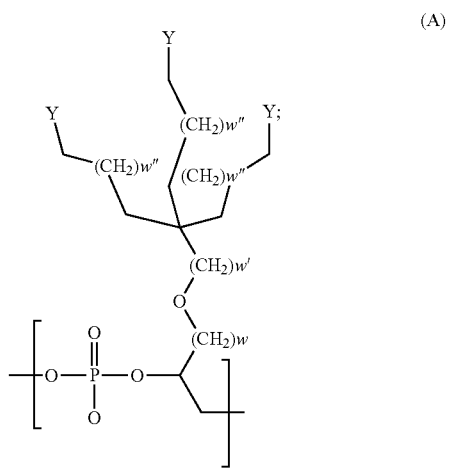

(A)

linker units which link between phosphate moieties of the oligomeric compound, and reactive groups capable of binding a biologically active moiety,
wherein
Y is a delivery group; wherein said delivery group is amine, histidine, guanidine, polyguanidine, imidazole, polyimidzole or any combination thereof; and w, w' and w" are each independently an integer between 0 and 10; and wherein the linker units are substituted or unsubstituted linear or branched alkyl chains of 2-50 carbon atoms, alkyl phosphate chains of 2-50 carbon atoms, alkylether chains of 2-50 carbon atoms or any combination thereof; and wherein the reactive groups are hydroxy, amine, halide, a phosphorous-containing group, phosphoramidite, —N═C═S, —NH—CO—NH$_2$, —NH—CS—NH$_2$ C-amide, N-amide, thiol or COOH.

In another embodiment, w, w' and w" are each independently an integer between 0 and 3.

In another embodiment, w, w' and w" are each independently 0 or 1. In another embodiment each of w, w' and w" is 1. In another embodiment, the alkyl, alkylether and/or alkyl phosphate chain has 2-8 carbon atoms.

In another embodiment, this invention is directed to phosphate based oligomeric compounds, comprising:

(a) between 2 and 50 repeating units represented by the structure of formula (A):

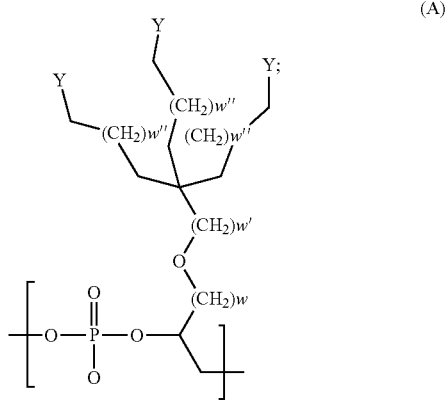

(A)

(b) between 2 and 50 linker units, which link between phosphate moieties, selected from substituted or unsubstituted linear alkyl chains of 2-50 carbon atoms, substituted or unsubstituted linear or branched alkyl phosphate chains of 2-50 carbon atoms, substituted or unsubstituted linear or branched alkylether chains of 2-50 carbon atoms, or any combination thereof; and (c) 1 or 2 reactive groups capable of binding a biologically active moiety, selected from hydroxy, amine, halide, a phosphorous-containing group, phosphoramidite, —N═C═S, —NH—CO—NH$_2$, —NH—CS—NH$_2$ C-amide, N-amide, thiol or COOH;

wherein Y is a delivery group; wherein said delivery group is amine, histidine, guanidine, polyguanidine, imidazole, polyimidzole or any combination thereof; and w, w' and w" are each independently an integer between 0 and 10. In another embodiment, w, w' and w" are each independently an integer between 0 and 3. In another embodiment, w, w' and w" are each independently 0 or 1. In another embodiment each of w, w' and w" is 1. In another embodiment, the alkyl, alkylether and/or alkyl phosphate chain has 2-8 carbon atoms.

In another embodiment, the oligomeric compounds further comprise a substituted alkyl phosphate linker unit represented by the structure of formula (B):

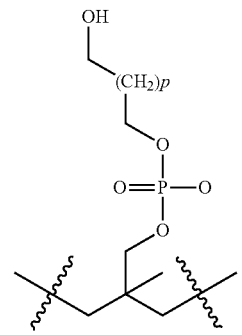

(B)

wherein p is an integer between 0 and 10. In another embodiment, p is 1. In another embodiment, p is 2. In another embodiment, p is 3. In another embodiment, p is 4.

In one embodiment, this invention is directed to phosphate based oligomeric compound conjugated to a biologically active substance(s) ("conjugate"). In another embodiment, the conjugate of this invention is delivered to a desired target. In another embodiment, the conjugate is complexed to an oligonucleotide, such as RNA and/or DNA. In another embodiment, the complex is delivered to a desired target. In another embodiment, the conjugate comprises phosphate repeating units. In another embodiment, the conjugate further comprises delivering groups. In another embodiment, the delivering groups comprise amine, histidine, guanidine, polyguanidine, imidazole, polyimidazole or any combination thereof. In another embodiment, the delivering groups comprise guanidine moieties. In another embodiment, the conjugate further comprises a repeating unit represented by the structure of formula (A):

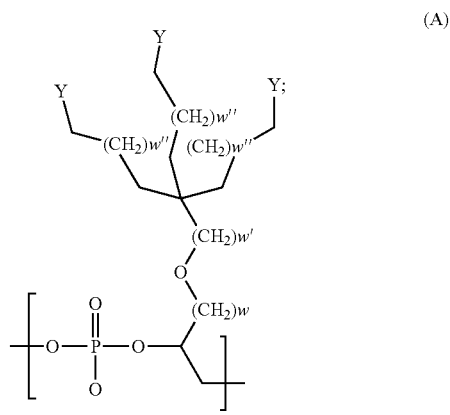

(A)

wherein Y is an amine, histidine, guanidine, polyguanidine, imidazole, polyimidazole or any combination thereof; and w, w' and w" are each independently an integer between 0 and 10. In another embodiment, w, w' and w" are each independently an integer between 0 and 3. In another embodiment, w, w' and w" are each independently 0 or 1. In another embodiment each of w, w' and w" is 1. In another embodiment, Y is a guanidine group.

In another embodiment, the conjugate of this invention further comprises linker units, which link between phosphate moieties of the conjugate. In another embodiment, the linker is a substituted or unsubstituted alkyl chain of 2-50 carbon atoms. In another embodiment, the linker is a substituted or unsubstituted alkyl chain of 2-8 carbon atoms. In another embodiment, the alkyl chain is linear. In another embodiment, the linker is a hexyl chain. In another embodiment, the linker is a substituted or unsubstituted alkylether chain of 2-50 carbon atoms. In another embodiment, the linker is a substituted or unsubstituted alkylether chain of 2-8 carbon atoms. In another embodiment, the alkylether chain is linear. In another embodiment, the linker is a polyethyleneglycol (PEG). In another embodiment, the alkyl chain is branched. In another embodiment, the alkyl chain is interrupted by one or more heteroatoms. In another embodiment, the alkyl chain is interrupted by an oxygen atom. In another embodiment, the alkyl chain is interrupted by a phosphate unit. In another embodiment, the linker is a substituted or unsubstituted linear or branched alkylphosphate chain of 2-50 carbon atoms. In another embodiment, the linker is a substituted or unsubstituted linear or branched alkylphosphate chain of 2-8 carbon atoms. In another embodiment, the linker is a hexyl phosphate. In another embodiment, the linker is represented by the structure of formula (B):

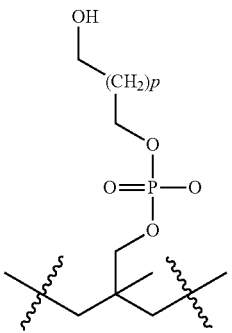

(B)

wherein p is an integer between 0 and 10. In another embodiment, p is 1. In another embodiment, p is 2. In another embodiment, p is 3. In another embodiment, p is 4.

In another embodiment, the conjugate is represented by the structure of Compound 33:

21 22
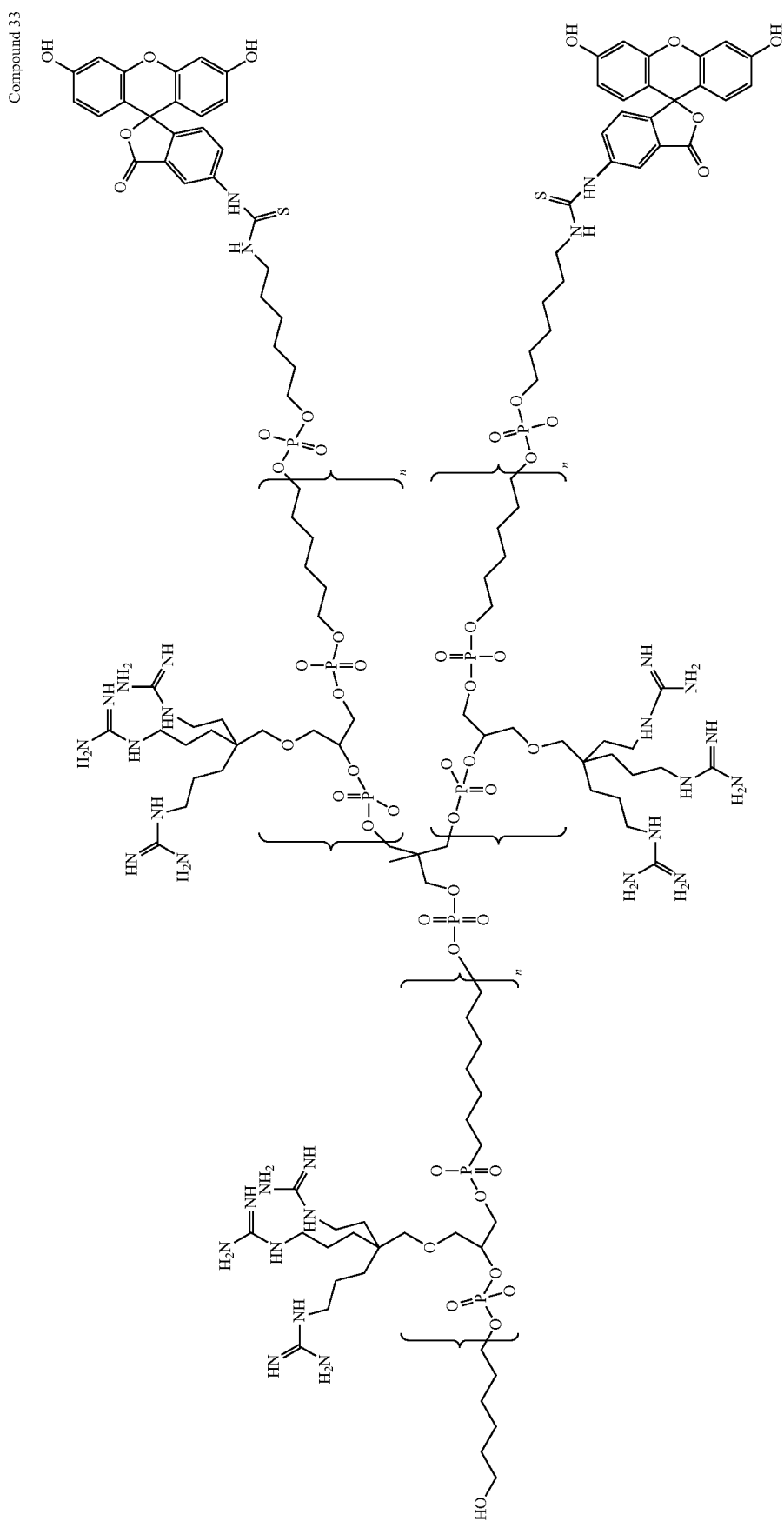
Compound 33 wherein each n is independently an integer between 1 and 50.

In one embodiment, this invention is directed to phosphate based oligomeric compound conjugated to a biologically active substance(s) ("conjugate"). In another embodiment, the conjugate of this invention is delivered to a desired target. In another embodiment, the conjugate of this invention comprises delivering groups, linkers and between 1 and 2 biologically active moieties, wherein the delivering groups comprise amine, histidine, guanidine, polyguanidine, imidazole, polyimidazole or any combination thereof; the linkers are substituted or unsubstituted linear or branched alkyl chains of 2-50 carbon atoms, alkyl phosphate chains of 2-50 carbon atoms, substituted or unsubstituted linear or branched alkylether chains of 2-50 carbon atoms, or any combination thereof, and the biologically active moiety is a therapeutically active agent, a labeling moiety, or combination thereof. In another embodiment, the biologically active moiety is a dye. In another embodiment, the biologically active moiety is a fluorescent moiety. In another embodiment, the biologically active moiety is Fluorescein. In another embodiment, the conjugate is complexed to an oligonucleotide such as RNA and/or DNA. In another embodiment, the complex of this invention is delivered to a desired target. In another embodiment, the alkyl, alkylether and/or alkyl phosphate chain has 2-8 carbon atoms.

In another embodiment, this invention is directed to phosphate based oligomeric compound conjugated to a biologically active moiety(ies) ("conjugate") which comprise a repeating unit represented by the structure of formula (A):

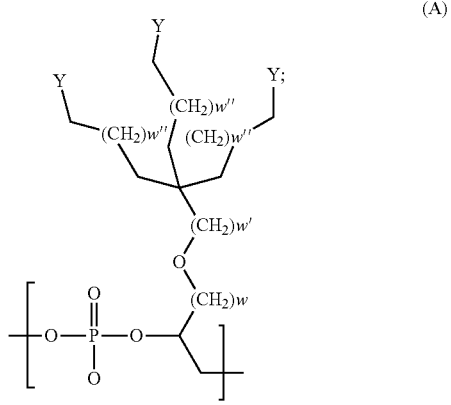

(A)

linkers, which link between phosphate moieties of said conjugate; and between 1 and 2 biologically active moieties, wherein Y is a delivery group. In another embodiment, Y is an amine, histidine, guanidine, polyguanidine, imidazole, polyimidzole or any combination thereof; and w, w' and w" are each independently an integer between 0 and 10; and wherein the linkers are substituted or unsubstituted linear or branched alkyl chains of 2-50 carbon atoms, substituted or unsubstituted linear or branched alkyl phosphate chains of 2-50 carbon atoms, substituted or unsubstituted linear or branched alkylether chains of 2-50 carbon atoms, or any combination thereof; and wherein the biologically active moiety is a therapeutically active agent, a labeling moiety, or combination thereof. In another embodiment, the conjugate is complexed to an oligonucleotide such as RNA and/or DNA. In another embodiment, the complex of this invention is delivered to a desired target. In another embodiment, the delivering groups comprise guanidine moieties. In another embodiment, the biologically active moiety is a dye. In another embodiment,
the biologically active moiety is a fluorescent moiety. In another embodiment, the biologically active moiety is Fluorescein. In another embodiment, w, w' and w" are each independently an integer between 0 and 3. In another embodiment, w, w' and w" are each independently 0 or 1. In another embodiment each of w, w' and w" is 1. In another embodiment, the alkyl, alkylether and/or alkyl phosphate chain has 2-8 carbon atoms.

In another embodiment, this invention is directed to phosphate based oligomeric compound conjugated to a biologically active moiety(ies) ("conjugate") comprising:

(a) between 2 and 50 repeating units represented by the structure of formula (A):

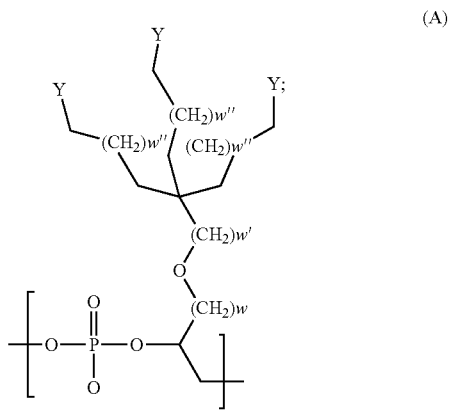

(A)

(b) between 2 and 50 linker units selected from substituted or unsubstituted linear alkyl chains of 2-50 carbon atoms, substituted or unsubstituted alkyl phosphate chains of 2-50 carbon atoms, substituted or unsubstituted linear or branched alkylether chains of 2-50 carbon atoms, or any combination thereof; and (c) 1 or 2 biologically active moieties selected from: a therapeutically active agent, a labeling moiety, or combination thereof.

wherein Y is a delivery group selected from an amine, histidine, guanidine, polyguanidine, imidazole, polyimidazole and any combination thereof; and w, w' and w" are each independently an integer between 0 and 10. In another embodiment, w, w' and w" are each independently an integer between 0 and 3. In another embodiment, w, w' and w" are each independently 0 or 1. In another embodiment each of w, w' and w" is 1. In another embodiment, the alkyl, alkylether and/or alkyl phosphate chain has 2-8 carbon atoms.

In another embodiment, the conjugate is complexed to an oligonucleotide such as RNA and/or DNA moiety, which is delivered to a desired target.

In another embodiment, the biologically active moiety is a dye. In another embodiment, the biologically active moiety is a fluorescent moiety. In another embodiment, the biologically active moiety is Fluorescein.

In another embodiment, the conjugate further comprises a substituted branched alkyl phosphate linker unit represented by the structure of formula (B):

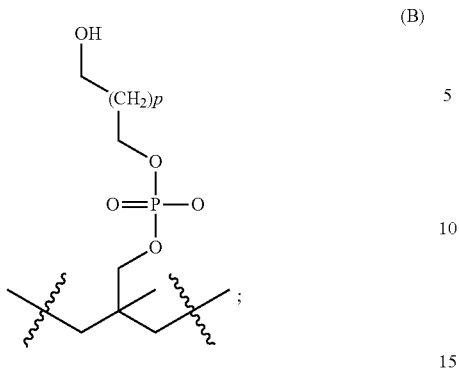
wherein p is an integer between 0 and 10. In another embodiment, p is 1. In another embodiment, p is 2. In another embodiment, p is 3. In another embodiment, p is 4.
In one embodiment, this invention is directed to phosphate based oligomeric compound conjugated to a biologically active moiety(ies) ("conjugate"), represented by the structure of Compound 33:

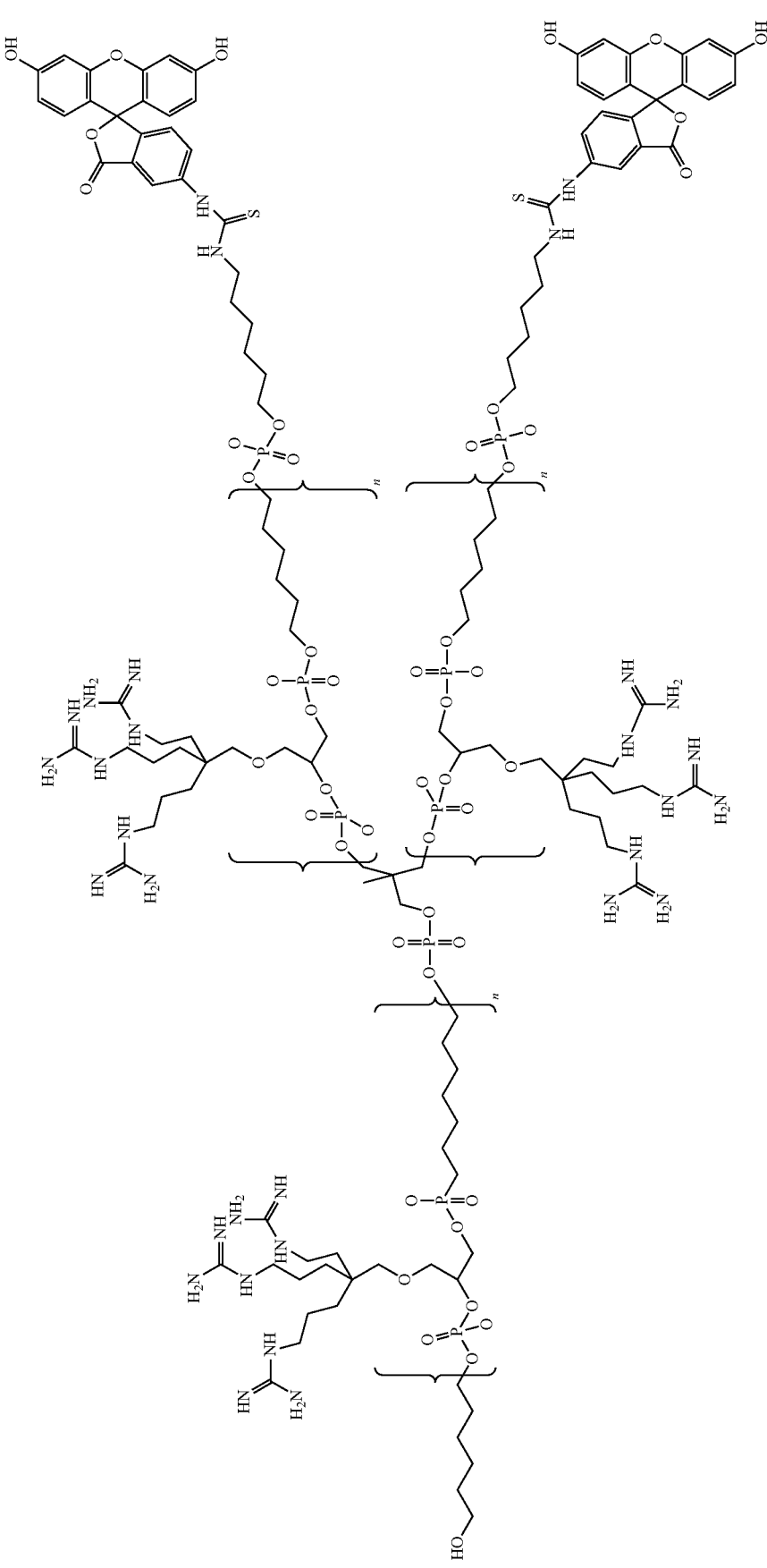
Compound 33 wherein each n is independently an integer between 1 and 50.

According to one aspect of the present invention, there is provided an oligomeric compound represented by the structure of Formula I:

Formula I

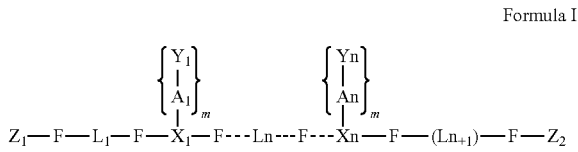

wherein:

n is an integer of between 0 to 100; in another embodiment between 2 to 20; in another embodiment, between 2 to 10; in another embodiment between 2-50; in another embodiment between 2-100;

m is an integer of between 1 to 6;

each of $X_1$-$X_n$ is independently a cyclic or an acyclic group;

each of $L_1$-$L_n$ is independently a first linking group;

each of $A_1$-An is independently a second linking group;

each of $Y_1$-Yn is independently a delivering group or absent, provided that at least one of $Y_1$-Yn is the delivering group;

each of F is independently nothing, N, O, S phosphate, amide, amine, or a —C(O)O— group; and each of $Z_1$ and $Z_2$ is independently a reactive group capable of binding a biologically active moiety; or a hydrogen atom, provided that at least one of $Z_1$ and $Z_2$ is a reactive group wherein said reactive group is hydroxy, amine, halide, a phosphorous-containing group, phosphoramidite, —N=C=S, —NH—CO—NH$_2$, —NH—CS—NH$_2$ C-amide, N-amide, thiol or COOH.

According to another aspect of the present invention, there is provided an oligomeric compound represented by the structure of Formula I(a):

Formula I(a)

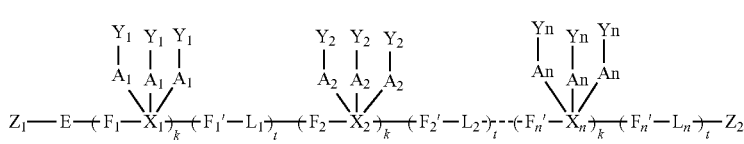

wherein:

n is an integer of between 0 to 100; in another embodiment n is an integer of between 2 to 20, in another embodiment n is an integer of between 2 to 50, in another embodiment n is an integer of between 2 to 10;

each k is independently an integer between 1 to 100; in another embodiment k is an integer between 1 to 50; in another embodiment k is an integer between 1 to 10; in another embodiment k is 1;

each t is independently an integer between 0 to 100; in another embodiment t is an integer between 0 to 10; in another embodiment t is an integer between 0 to 50; in another embodiment t is 1;

each of $X_1$-$X_n$ is independently a cyclic or an acyclic group;

each of $L_1$-$L_n$ is independently a first linking group;

each of $A_1$-$A_n$ is independently a second linking group; E is a third linking group or absent;

each of $Y_1$-Yn is independently a delivering group or absent, provided that at least one of $Y_1$-Yn is the delivering group;

each of $F_1$-$F_n$ and $F_1'$-$F_n'$ is independently nothing, N, O, S phosphate, amide, amine, or a —C(O)O— group; in another embodiment, each of $F_1$-$F_n$ and $F_1'$-$F_n'$ is independently phosphate or nothing; and each of $Z_1$ and $Z_2$ is independently a reactive group capable of binding a biologically active moiety; or is a hydrogen atom, provided that at least one of $Z_1$ and $Z_2$ is a reactive group wherein said reactive group is hydroxy, amine, halide, a phosphorous-containing group, phosphoramidite, —N=C=S, —NH—CO—NH$_2$, —NH—CS—NH$_2$, C-amide, N-amide, thiol or COOH.

According to another aspect of the present invention, there is provided an oligomeric compound represented by the structure of Formula I(b):

Formula I(b)

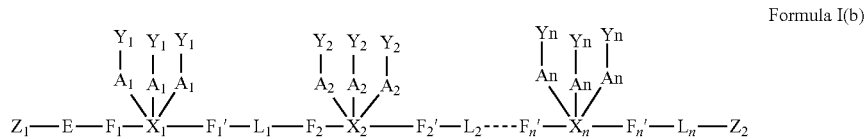

wherein:

n is an integer of between 0 to 100; in another embodiment, n is an integer of between 0.2 to 50; in another embodiment, n is an integer of between 2 to 20; in another embodiment, n is an integer of between 2 to 10;

each of $X_1$-$X_n$ is independently a cyclic or an acyclic group;

each of $L_1$-$L_n$ is independently a first linking group;

each of $A_1$-$A_n$ is independently a second linking group;

E is a third linking group or absent;

each of $Y_1$-Yn is independently a delivering group or absent, provided that at least one of $Y_1$-Yn is the delivering group;

each of $F_1$-$F_n$ and $F_1'$-$F_n'$ is independently nothing, N, O, S phosphate, amide, amine, or a —C(O)O— group; and each of $Z_1$ and $Z_2$ is independently a reactive group capable of binding a biologically active moiety; or is a hydrogen atom, provided that at least one of $Z_1$ and $Z_2$ is a reactive group wherein said reactive group is hydroxy, amine, halide, a phosphorous-containing group, phosphoramidite, —N=C=S, —NH—CO—NH$_2$, —NH—CS—NH$_2$, C-amide, N-amide, thiol or COOH.

According to one aspect of the present invention there is provided a conjugate comprising at least one delivery moiety (Y1-Yn) and at least one biologically active moiety (T1-T4) being linked thereto, represented by the structure of Formula II:

wherein F, L, X, A, Y, m and n are as described above; and COM$_1$ and COM$_2$ are optional;

each of $Z_1'$, $Z_2'$, is independently a derivative of $Z_1$ and $Z_2$, respectively, as a result of binding the biologically active group, wherein said $Z_1$ and $Z_2$ reactive group is hydroxyl, amine, halide, a phosphorous-containing group, phosphoramidite, C-amide, N-amide, thiol or COOH.

Formula II

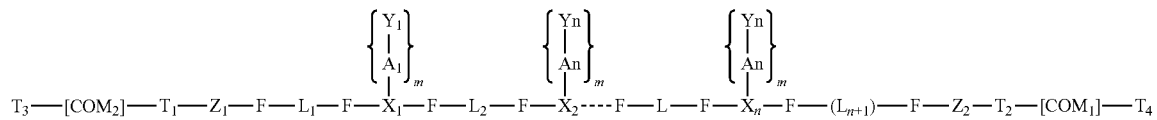

wherein:

n is an integer of between 0 to 100; in another embodiment, n is an integer of between 2 to 50; in another embodiment, n is an integer of between 2 to 20; in another embodiment, n is an integer of between 2 to 10;

In another embodiment, this invention provides a conjugate comprising at least three delivery groups and at least one biologically active moiety being linked thereto, represented by the structure of Formula II(a):

Formula II(a)

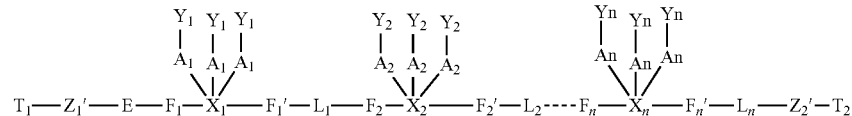

m is an integer of between 1 to 3;

each of $X_1$-Xn is independently a cyclic or an acyclic group;

each of $L_1$-Ln is independently a first linking group;

each of $A_1$-An is independently a second linking group;

each of $Y_1$-Yn is independently a delivering group or absent, provided that at least one of $Y_1$-Yn is the delivering group; wherein said delivering group is amine, histidine, guanidine, polyguanidine, imidazole and polyimidazole.

each of F is independently nothing, N, O, S phosphate, amide, amine, or a —C(O)O— group;

each of $T_1$, $T_2$, $T_3$ and $T_4$ is independently a biologically active moiety, wherein at least one of $T_1$ and $T_2$ being a biologically active moiety and $T_3$ and $T_4$ are optionally; wherein said biologically active moiety is a therapeutically active agent, a labeling moiety, or any combination thereof;

wherein said therapeutically active agent is an oligonucleotide, a nucleic acid construct, an antisense, a plasmid, a polynucleotide, an amino acid, a peptide, a polypeptide, a hormone, a steroid, an antigen, a radioisotope, a chemotherapeutic agent, a toxin, an anti-inflammatory agent, a growth factor and any combination thereof; and wherein said labeling moiety is a fluorescent moiety, a radiolabeled moiety, a phosphorescent moiety, a heavy metal cluster moiety or any combination thereof;

[COM$_A$] and [COM$_2$] are an oligomer represented by the following:

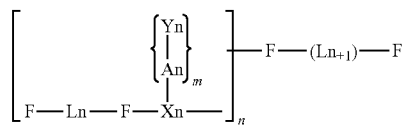

wherein:

n is an integer of between 0 to 100; in another embodiment, n is an integer of between 2 to 50; in another embodiment, n is an integer of between 2 to 20; in another embodiment, n is an integer of between 2 to 10;

each of $X_1$-Xn is independently a cyclic or an acyclic group;

each of $L_1$-Ln is independently a first linking group;

each of $A_1$-An is independently a second linking group;

E is a third linking group or absent;

each of $Y_1$-Yn is independently a delivering group or absent, provided that there are at least three of $Y_1$-Yn delivering group;

each of $F_1$-$F_n$ and $F_1'$-$F_n'$ is independently nothing, N, O, S phosphate, amide, amine, or a —C(O)O— group;

each of $T_1$ and $T_2$ is independently a biologically active moiety or absent, wherein at least one of $T_1$ and $T_2$ is present; and each of $Z_1'$, $Z_2'$, is independently a derivative of $Z_1$ and $Z_2$, respectively, as a result of binding the biologically active group, wherein said $Z_1$ and $Z_2$ reactive group is hydroxyl, amine, halide, a phosphorous-containing group, a phosphate, phosphoramidite, C-amide, N-amide, thiol, —N=C=S, —NH—CO—NH$_2$, —NH—CS—NH$_2$ or COOH.

It is understood that in the case $T_1$ or $T_2$ is absent, $Z_1'$ or $Z_2'$ respectively is replaced with $Z_1$ or $Z_2$ respectively.

In one embodiment, this invention provides a conjugate comprising at least one delivery moiety and at least one biologically active moiety being linked thereto, represented by the structure of Formula II(b):

Formula II(b)

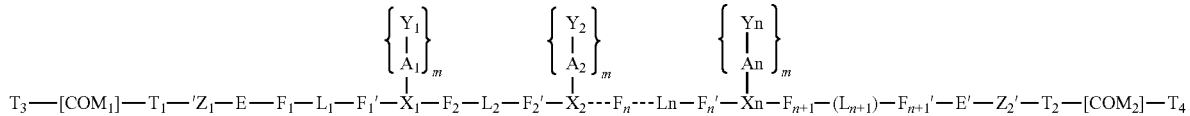

wherein $X_1$-$X_n$, $A_1$-$A_n$, $Y_1$-$Y_n$, $F_1$-$F_n$, $F_1'$-$F_n'$ and $L_1$-$L_n$, and n are as described hereinabove for Formulas I, I(a), I(b), II and II(a);

each of $T_1$, $T_2$, $T_3$ and $T_4$ is independently a biologically active moiety or absent, wherein at least one of $T_1$ and $T_2$ is present and $T_3$ and $T_4$ are optional;

[COM$_1$] and [COM$_2$] are absent or an oligomer represented by the following—

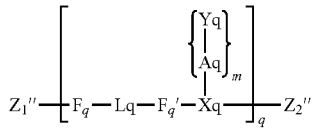

wherein m is between 1 to 3;

each of Fq and Fq' is independently nothing, N, O, S phosphate, amide, amine, or a —C(O)O— group;

each of Lq is independently a first linking group;

each of Xq is independently a cyclic or an acyclic group;

each of Aq is independently a second linking group;

each of Yq is independently a delivering group or absent;
q is an integer of between 2 to 10;

each of $Z_1'$, $Z_2'$, $Z_1''$ and $Z_2''$ is independently absent or a derivative of $Z_1$ and $Z_2$, respectively, as a result of binding the biologically active group, wherein said $Z_1$ and $Z_2$ reactive group is hydroxyl, amine, halide, a phosphorous-containing group, phosphoramidite, C-amide, N-amide, thiol, —N=C=S, —NH—CO—NH$_2$, —NH—CS—NH$_2$ or COOH.

In another embodiment, this invention provides a conjugate comprising at least three delivery moieties and at least one biologically active moiety being linked thereto, represented by the structure of Formula II(c):

wherein:

n is an integer of between 0 to 100; in another embodiment, n is an integer of between 2 to 50; in another embodiment, n is an integer of between 2 to 20; in another embodiment, n is an integer of between 2 to 10;

each k is independently an integer between 1 to 100; in another embodiment k is an integer between 1 to 50; in another embodiment k is an integer between 1 to 10; in another embodiment k is 1;

each t is independently an integer between 0 to 100; in another embodiment t is an integer between 0 to 50; in another embodiment t is an integer between 0 to 10; in another embodiment t is 1;

each of $X_1$-$X_n$ is independently a cyclic or an acyclic group;

each of $L_1$-$L_n$ is independently a first linking group;

each of $A_1$-$A_n$ is independently a second linking group;

E is a third linking group or absent;

each of $Y_1$-$Y_n$ is independently a delivering group or absent, provided that there are at least three of $Y_1$-$Y_n$ delivering group;

each of $F_1$-$F_n$ and $F_1'$-$F_n'$ is independently nothing, N, O, S phosphate, amide, amine, or a —C(O)O— group; in another embodiment, each of $F_1$-$F_n$ and $F_1'$-$F_n'$ is independently phosphate or nothing;

each of $T_1$ and $T_2$ is independently a biologically active moiety or absent, wherein at least one of $T_1$ and $T_2$ is present; and each of $Z_1'$, $Z_2'$, is independently a derivative of $Z_1$ and $Z_1$ respectively, as a result of binding the biologically active group, wherein said $Z_1$ and $Z_2$ reactive group is hydroxyl, amine, halide, a phosphorous-containing group, phosphoramidite, —N=C=S, —NH—CO—NH$_2$, —NH—CS—NH$_2$, C-amide, N-amide, thiol or COOH.

It is understood that in the case $T_1$ or $T_2$ is absent, $Z_1'$ or $Z_2'$ respectively is replaced with $Z_1$ or $Z_2$ respectively.

In another embodiment, this invention provides an oligomer represented by the structure of Formula III:

Formula II(c)

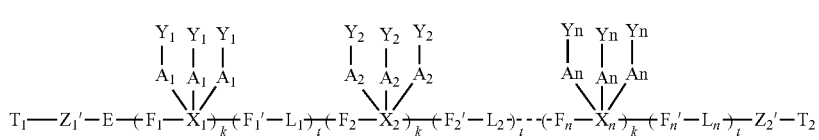

(III)
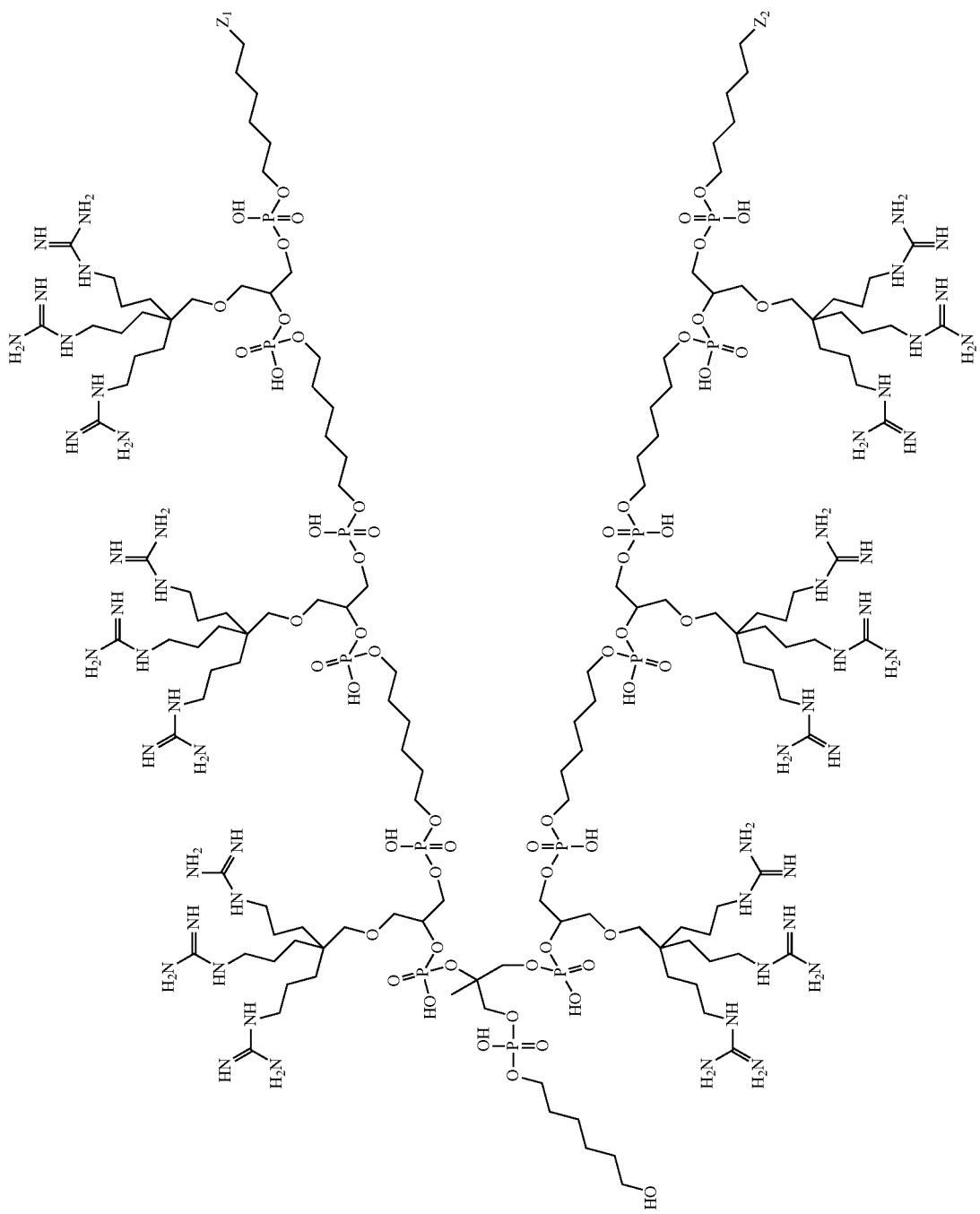

wherein each of $Z_1$ and $Z_2$ is independently a reactive group capable of binding a biologically active moiety; or a hydrogen atom, provided that at least one of $Z_1$ and $Z_2$ is a reactive group wherein said reactive group is hydroxy, amine, halide, a phosphorous-containing group, phosphoramidite, —N=C=S, —NH—CO—NH$_2$, —NH—CS—NH$_2$ C-amide, N-amide, thiol or COOH.

In another embodiment, this invention provides an oligomer represented by the structure of Formula III(a):

III(a)
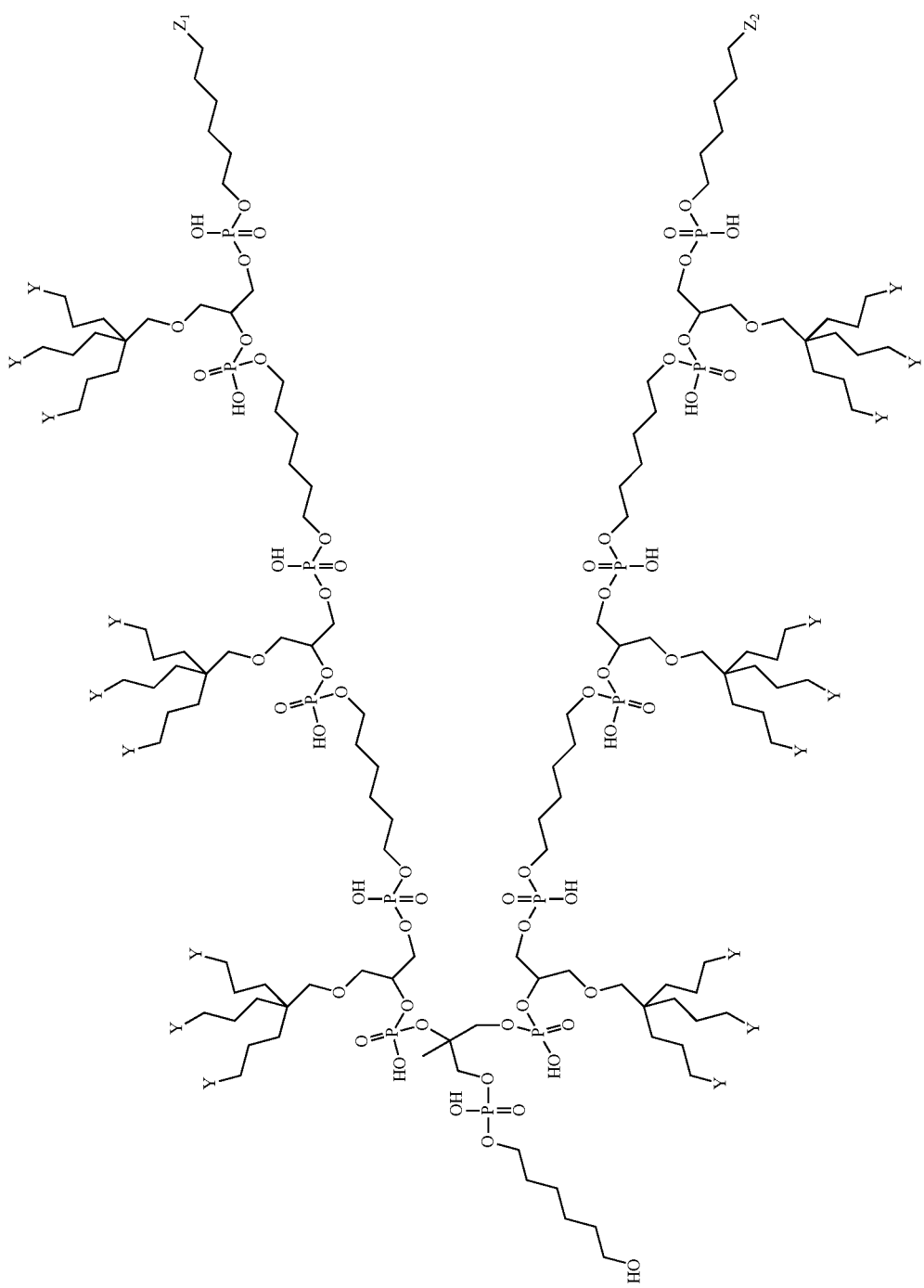

wherein,

Y is an amine, histidine, guanidine, polyguanidine, imidazole, polyimidazole or any combination thereof, each of $Z_1$ and $Z_2$ is independently a reactive group capable of binding a biologically active moiety; or a hydrogen atom, provided that at least one of $Z_1$ and $Z_2$ is a reactive group wherein said reactive group is hydroxy, amine, halide, a phosphorous-containing group, phosphoramidite, —N=C=S, —NH—CO—NH$_2$, —NH—CS—NH$_2$ C-amide, N-amide, thiol or COOH.

In another embodiment, this invention provides an oligomer represented by the structure of Formula III(b):

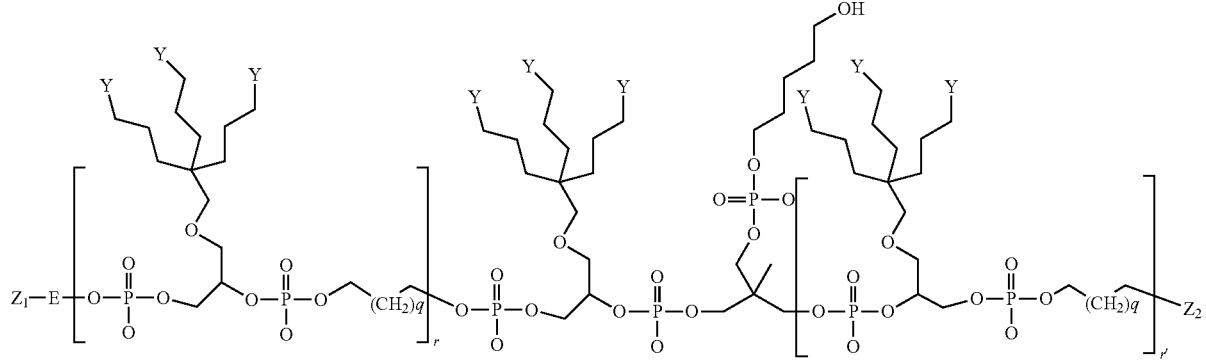

III(b)

wherein

Y is an amine, histidine, guanidine, polyguanidine, imidazole, polyimidazole or any combination thereof;

each of $Z_1$ and $Z_2$ is independently a reactive group capable of binding a biologically active moiety; or a hydrogen atom, provided that at least one of $Z_1$ and $Z_2$ is a reactive group wherein said reactive group is hydroxy, amine, halide, a phosphorous-containing group, phosphoramidite, —N=C=S, —NH—CO—NH$_2$, —NH—CS—NH$_2$ C-amide, N-amide, thiol or COOH;

E is a third linking group or absent;

r and r' are each independently an integer number of between 0 and 50; in another embodiment, between 1 and 10; in another embodiment, 2 and 3 respectively; and q is an integer number of between 0 and 20; In another embodiment, q is between 0 and 10. In another embodiment, q is 1. In another embodiment, q is 2. In another embodiment, q is 3. In another embodiment, q is 4. In another embodiment, q is 5.

In another embodiment, this invention provides an oligomer represented by the structure of Formula III(c):

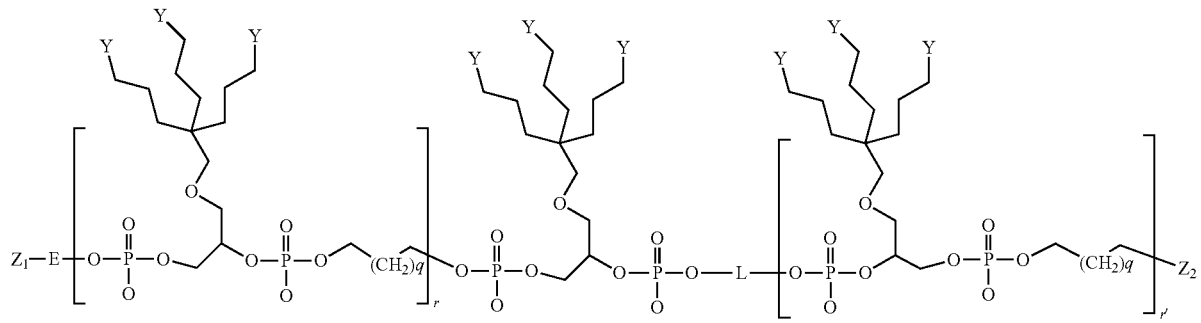

III(c)

wherein

Y is a delivering group, wherein Y is an amine, histidine, guanidine, polyguanidine, imidazole, polyimidazole or any combination thereof;

each of $Z_1$ and $Z_2$ is independently a reactive group capable of binding a biologically active moiety; or a hydrogen atom, provided that at least one of $Z_1$ and $Z_2$ is a reactive group wherein said reactive group is hydroxy, amine, halide, a phosphorous-containing group, phosphoramidite, —N=C=S, —NH—CO—NH$_2$, —NH—CS—NH$_2$ C-amide, N-amide, thiol or COOH;

E is a third linking group or absent;

r and r' are each independently an integer number of between 0 and 50; in another embodiment, between 1 and 10; in another embodiment, 2 and 3 respectively; and q is an integer number of between 0 and 20; In another embodiment, q is between 0 and 10. In another embodiment, q is 1. In another embodiment, q is 2. In another embodiment, q is 3. In another embodiment, q is 4. In another embodiment, q is 5;

and

L is a substituted or unsubstituted linear or branched alkyl of 2-50 carbon atoms or substituted or unsubstituted linear or branched alkyl phosphate of 2-50 carbon atoms. In another embodiment, the alkyl or alkylphosphate is of 2-8 carbon atoms. In another embodiment, L is alkylphosphate chain, represented by the structure of formula (B):

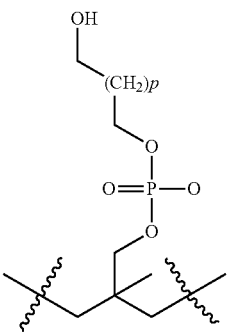

(B)

wherein p is an integer between 0 and 10. In another embodiment, p is 1. In another embodiment, p is 2. In another embodiment, p is 3. In another embodiment, p is 4. In another embodiment, L is a linear alkyl of 2-50 carbon atoms. In another embodiment, L is a linear alkyl of 2-8 carbon atoms. In another embodiment, L is a branched alkyl of 2-50 carbon atoms. In another embodiment, L is a branched alkyl of 2-8 carbon atoms. In another embodiment, L is a —(CH$_2$)$_s$—, wherein s is an integer of between 1 and 10. In another embodiment, s is 4. In another embodiment, s is 5. In another embodiment, s is 6. In another embodiment, s is 7. In another embodiment, L is hexyl.

In another embodiment, this invention provides an oligomer represented by the structure of Formula III(d):

III(d)
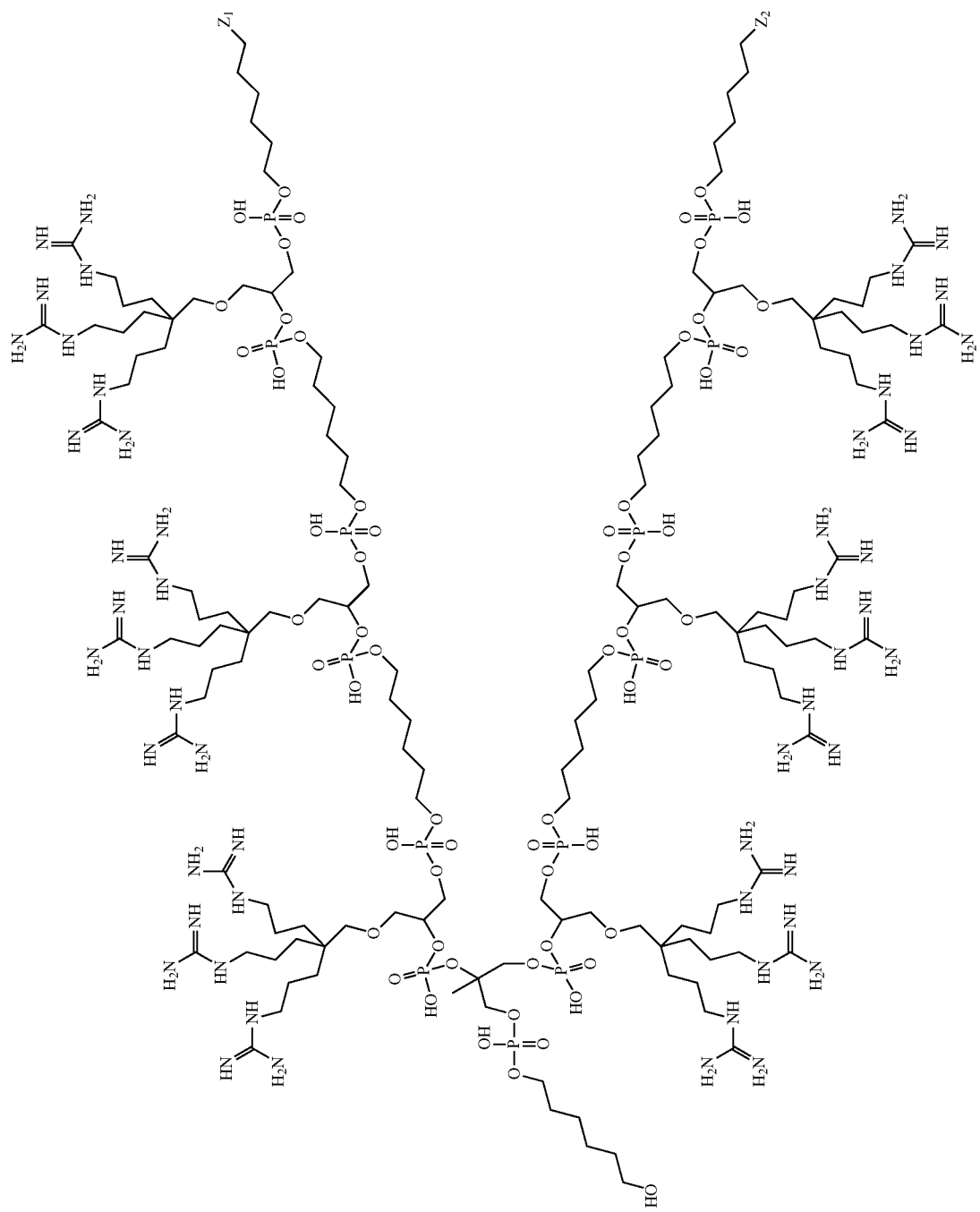

wherein each of $Z_1$ and $Z_2$ is independently a reactive group capable of binding a biologically active moiety; or a hydrogen atom, provided that at least one of $Z_1$ and $Z_2$ is a reactive group wherein said reactive group is hydroxy, amine, halide, a phosphorous-containing group, phosphoramidite, —N=C=S, —NH—CO—NH$_2$, —NH—CS—NH$_2$ C-amide, N-amide, thiol or COOH.

In another embodiment, this invention provides an oligomer represented by the structure of Formula III(e):

III(e)
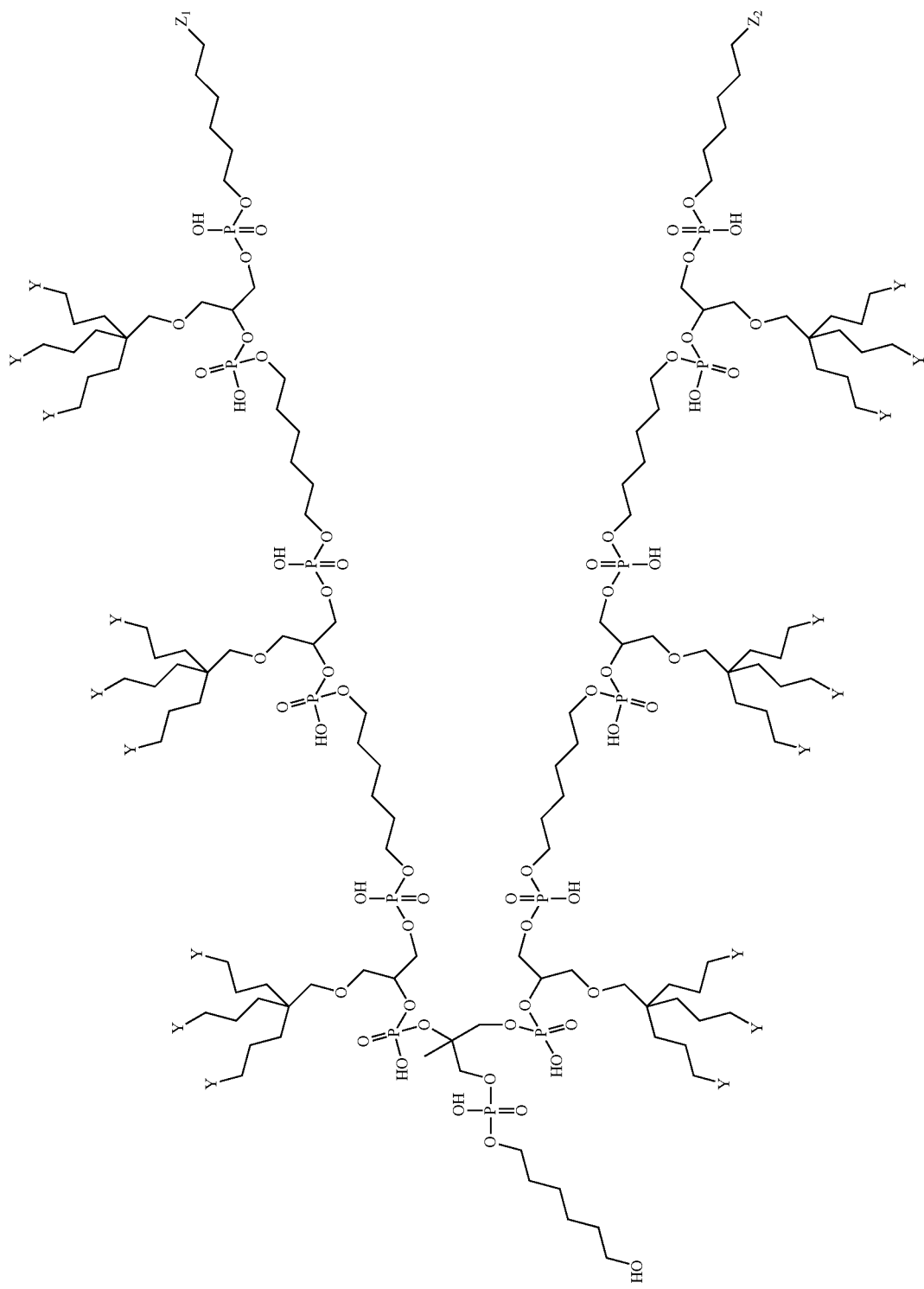

wherein,

Y is an amine, histidine, guanidine, polyguanidine, imidazole, polyimidazole or any combination thereof, each of $Z_1$ and $Z_2$ is independently a reactive group capable of binding a biologically active moiety; or a hydrogen atom, provided that at least one of $Z_1$ and $Z_2$ is a reactive group wherein said reactive group is hydroxy, amine, halide, a phosphorous-containing group, phosphoramidite, —N=C=S, —NH—CO—NH$_2$, —NH—CS—NH$_2$ C-amide, N-amide, thiol or COOH.

In another embodiment, this invention provides an oligomer represented by the structure of Formula III(f)

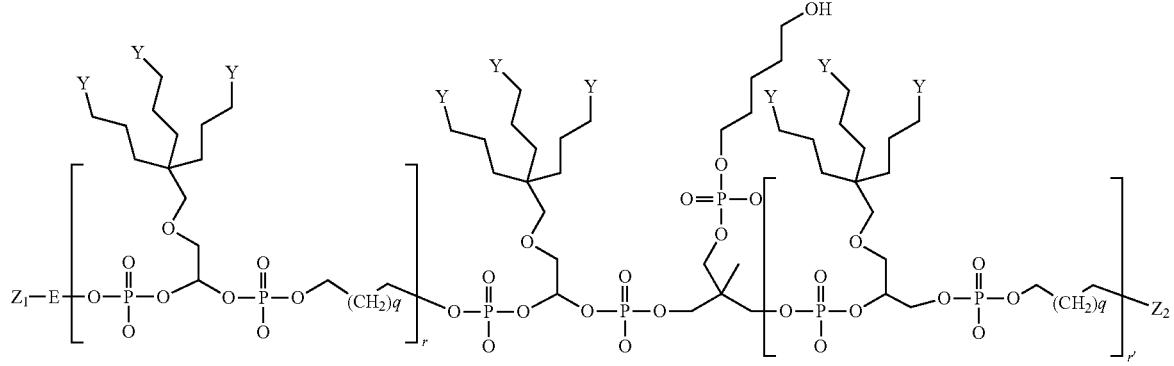

III(f)

wherein

Y is an amine, histidine, guanidine, polyguanidine, imidazole, polyimidazole or any combination thereof;

each of $Z_1$ and $Z_2$ is independently a reactive group capable of binding a biologically active moiety; or a hydrogen atom, provided that at least one of $Z_1$ and $Z_2$ is a reactive group wherein said reactive group is hydroxy, amine, halide, a phosphorous-containing group, phosphoramidite, —N=C=S, —NH—CO—NH$_2$, —NH—CS—NH$_2$ C-amide, N-amide, thiol or COOH;

E is a third linking group or absent;

r and r' are each independently an integer number of between 0 and 50; in another embodiment, between 1 and 10; in another embodiment, 2 and 3 respectively; and q is an integer number of between 0 and 20; In another embodiment, q is between 0 and 10. In another embodiment, q is 1. In another embodiment, q is 2. In another embodiment, q is 3. In another embodiment, q is 4. In another embodiment, q is 5.

In another embodiment, this invention provides an oligomer represented by the structure of Formula III(g):

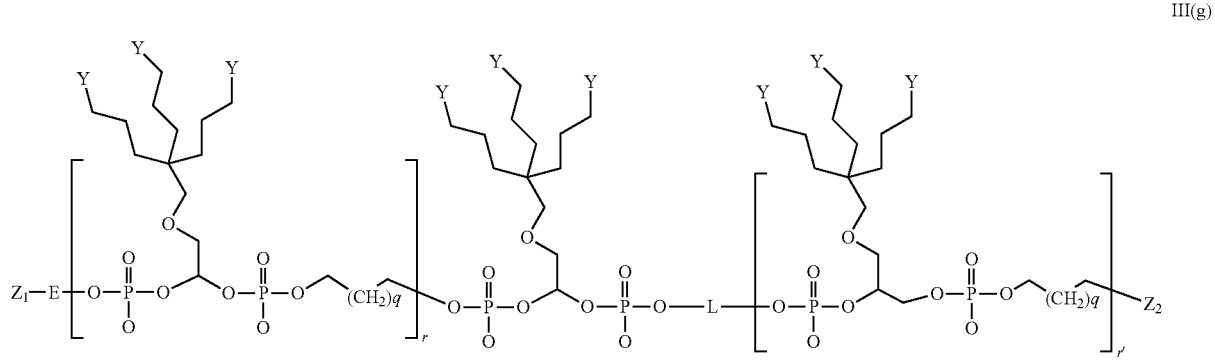

III(g)

wherein

Y is a delivering group, wherein Y is an amine, histidine, guanidine, polyguanidine, imidazole, polyimidazole or any combination thereof;

each of $Z_1$ and $Z_2$ is independently a reactive group capable of binding a biologically active moiety; or a hydrogen atom, provided that at least one of $Z_1$ and $Z_2$ is a reactive group wherein said reactive group is hydroxy, amine, halide, a phosphorous-containing group, phosphoramidite, —N=C=S, —NH—CO—NH$_2$, —NH—CS—NH$_2$ C-amide, N-amide, thiol or COOH;

E is a third linking group or absent;

r and r' are each independently an integer number of between 0 and 50; in another embodiment, between 1 and 10; in another embodiment, 2 and 3 respectively; and q is an integer number of between 0 and 20; In another embodiment, q is between 0 and 10. In another embodiment, q is 1. In another embodiment, q is 2. In another embodiment, q is 3. In another embodiment, q is 4. In another embodiment, q is 5;

and

L is a substituted or unsubstituted linear or branched alkyl of 2-50 carbon atoms or substituted or unsubstituted linear or branched alkyl phosphate of 2-50 carbon atoms. In another embodiment, the alkyl or alkylphosphate is of 2-8 carbon atoms. In another embodiment, L is alkylphosphate chain, represented by the structure of formula (B):

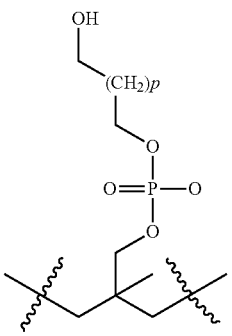

(B)

wherein p is an integer between 0 and 10. In another embodiment, p is 1. In another embodiment, p is 2. In another embodiment, p is 3. In another embodiment, p is 4. In another embodiment, L is a linear alkyl of 2-50 carbon atoms. In another embodiment, L is a linear alkyl of 2-8 carbon atoms. In another embodiment, L is a branched alkyl of 2-50 carbon atoms. In another embodiment, L is a branched alkyl of 2-8 carbon atoms. In another embodiment, L is a —(CH$_2$)$_s$—, wherein s is an integer of between 1 and 10. In another embodiment, s is 4. In another embodiment, s is 5. In another embodiment, s is 6. In another embodiment, s is 7. In another embodiment, L is hexyl.

In another embodiment, this invention provides a conjugate represented by the structure of Formula IV:

(IV)
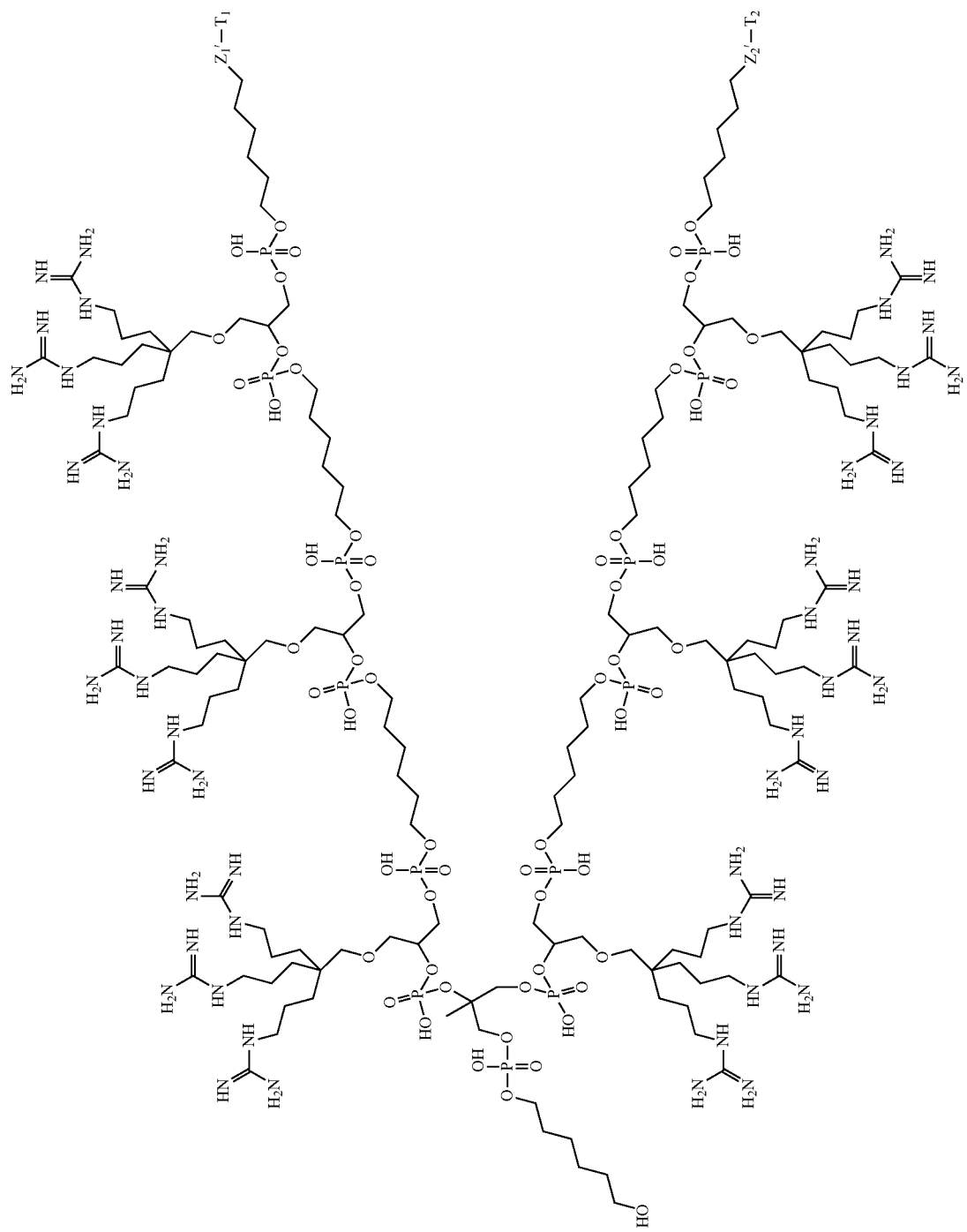

wherein each of $T_1$ and $T_2$ is independently a biologically active moiety or absent, wherein at least one of $T_1$ and $T_2$ is present; and each of $Z_1'$, $Z_2'$, is independently a derivative of $Z_1$ and $Z_2$, respectively, as a result of binding the biologically active group, wherein said $Z_1$ and $Z_2$ reactive group is hydroxyl, amine, halide, a phosphorous-containing group, phosphoramidite, —N=C=S, —NH—CO—NH$_2$, —NH—CS—NH$_2$, C-amide, N-amide, thiol or COOH.

It is understood that in the case $T_1$ or $T_2$ is absent, $Z_1'$ or $Z_2'$ respectively is replaced with $Z_1$ or $Z_2$ respectively.

In another embodiment, this invention provides a conjugate represented by the structure of Formula IV(a):

IV(a)
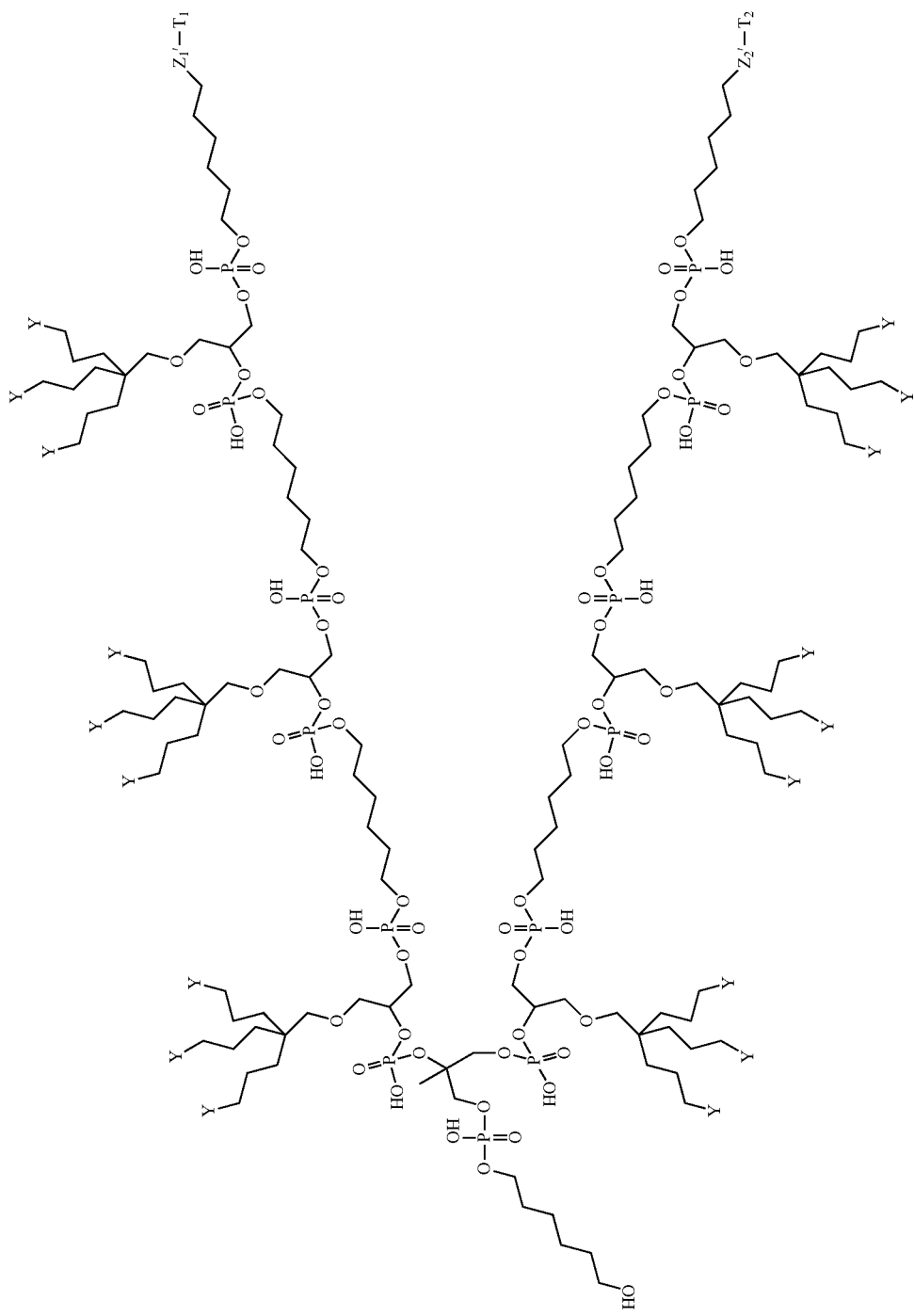

wherein

Y is a delivering group, wherein Y is an amine, histidine, guanidine, polyguanidine, imidazole, polyimidazole or any combination thereof;

each of $T_1$ and $T_2$ is independently a biologically active moiety or absent, wherein at least one of $T_1$ and $T_2$ is present; and each of $Z_1'$, $Z_2'$, is independently a derivative of $Z_1$ and $Z_2$, respectively, as a result of binding the biologically active group, wherein said $Z_1$ and $Z_2$ reactive group is hydroxyl, amine, halide, a phosphorous-containing group, phosphoramidite, —N=C=S, —NH—CO—NH$_2$, —NH—CS—NH$_2$, C-amide, N-amide, thiol or COOH.

It is understood that in the case $T_1$ or $T_2$ is absent, $Z_1'$ or $Z_2'$ respectively is replaced with $Z_1$ or $Z_2$ respectively.

In another embodiment, this invention provides a conjugate represented by the structure of Formula IV (b):

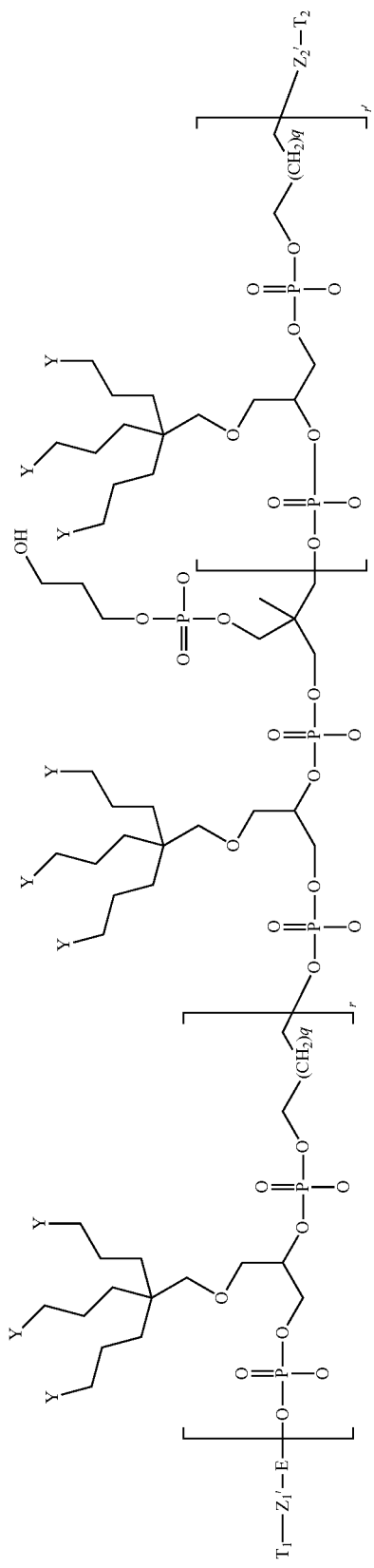
IV(b)

wherein

Y is a delivering group, wherein Y is an amine, histidine, guanidine, polyguanidine, imidazole, polyimidazole or any combination thereof;

each of $T_1$ and $T_2$ is independently a biologically active moiety or absent, wherein at least one of $T_1$ and $T_2$ is present; and each of $Z_1'$, $Z_2'$, is independently a derivative of $Z_1$ and $Z_2$, respectively, as a result of binding the biologically active group, wherein said $Z_1$ and $Z_2$ reactive group is hydroxyl, amine, halide, a phosphorous-containing group, phosphoramidite, —N=C=S, —NH—CO—NH$_2$, —NH—CS—NH$_2$, C-amide, N-amide, thiol or COOH.

E is a third linking group or absent;

r and r' are each independently an integer number of between 0 and 50; in another embodiment, between 1 and 10; in another embodiment, 2 and 3 respectively; and q is an integer number of between 0 and 20. In another embodiment, q is between 0 and 10. In another embodiment, q is 1. In another embodiment, q is 2. In another embodiment, q is 3. In another embodiment, q is 4. In another embodiment, q is 5.

In another embodiment, this invention provides a conjugate represented by the structure of Formula IV (c):

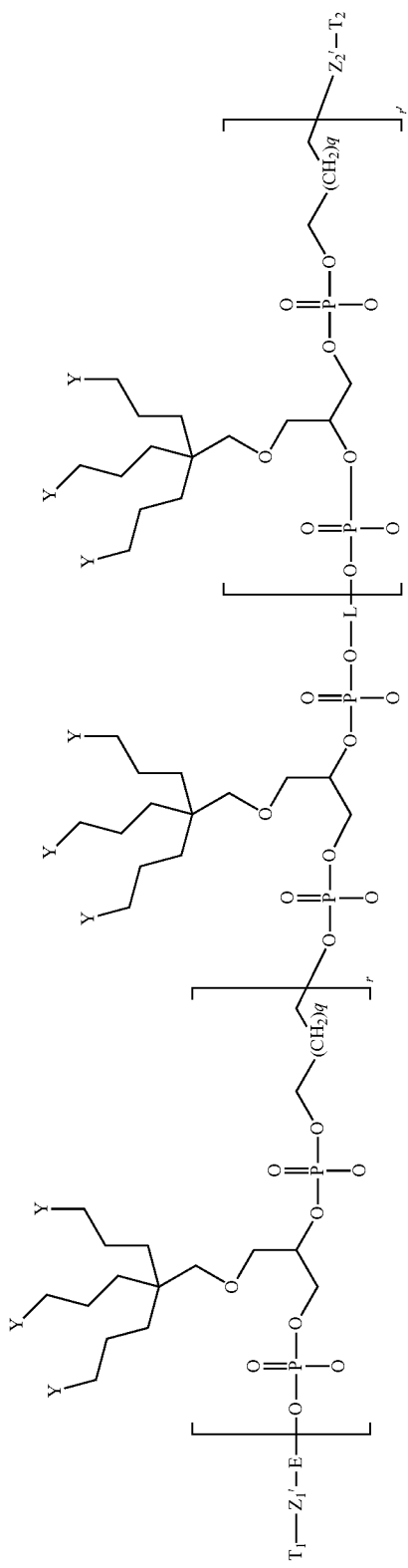

wherein

Y is a delivering group, wherein Y is an amine, histidine, guanidine, polyguanidine, imidazole, polyimidazole or any combination thereof;

each of $T_1$ and $T_2$ is independently a biologically active moiety or absent, wherein at least one of $T_1$ and $T_2$ is present; and each of $Z_1'$, $Z_2'$, is independently a derivative of $Z_1$ and $Z_2$, respectively, as a result of binding the biologically active group, wherein said $Z_1$ and $Z_2$ reactive group is hydroxyl, amine, halide, a phosphorous-containing group, phosphoramidite, —N=C=S, —NH—CO—NH$_2$, —NH—CS—NH$_2$, C-amide, N-amide, thiol or COOH.

E is a third linking group or absent;

r and r' are each independently an integer number of between 0 and 50; in another embodiment, between 1 and 10; in another embodiment, 2 and 3 respectively;

q is an integer number of between 0 and 20. In another embodiment, q is between 0 and 10. In another embodiment, q is 1. In another embodiment, q is 2. In another embodiment, q is 3. In another embodiment, q is 4. In another embodiment, q is 5; and L is a substituted or unsubstituted linear or branched alkyl of 2-50 carbon atoms or substituted or unsubstituted linear or branched alkyl phosphate of 2-50 carbon atoms. In another embodiment, the alkyl or alkylphosphate is of 2-8 carbon atoms. In another embodiment, L is alkylphosphate chain, represented by the structure of formula (B):

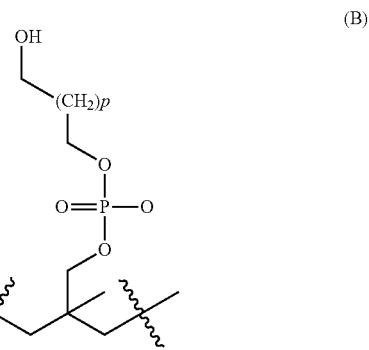

(B)

wherein p is an integer between 0 and 10. In another embodiment, p is 1. In another embodiment, p is 2. In another embodiment, p is 3. In another embodiment, p is 4. In another embodiment, L is a linear alkyl of 2-50 carbon atoms. In another embodiment, L is a linear alkyl of 2-8 carbon atoms. In another embodiment, L is a branched alkyl of 2-50 carbon atoms. In another embodiment, L is a branched alkyl of 2-8 carbon atoms. In another embodiment, L is a —(CH$_2$)$_s$—, wherein s is an integer of between 1 and 10. In another embodiment, s is 4. In another embodiment, s is 5. In another embodiment, s is 6. In another embodiment, s is 7. In another embodiment, L is hexyl.

In another embodiment, this invention provides a conjugate represented by the structure of Formula IV(d):

IV(d)
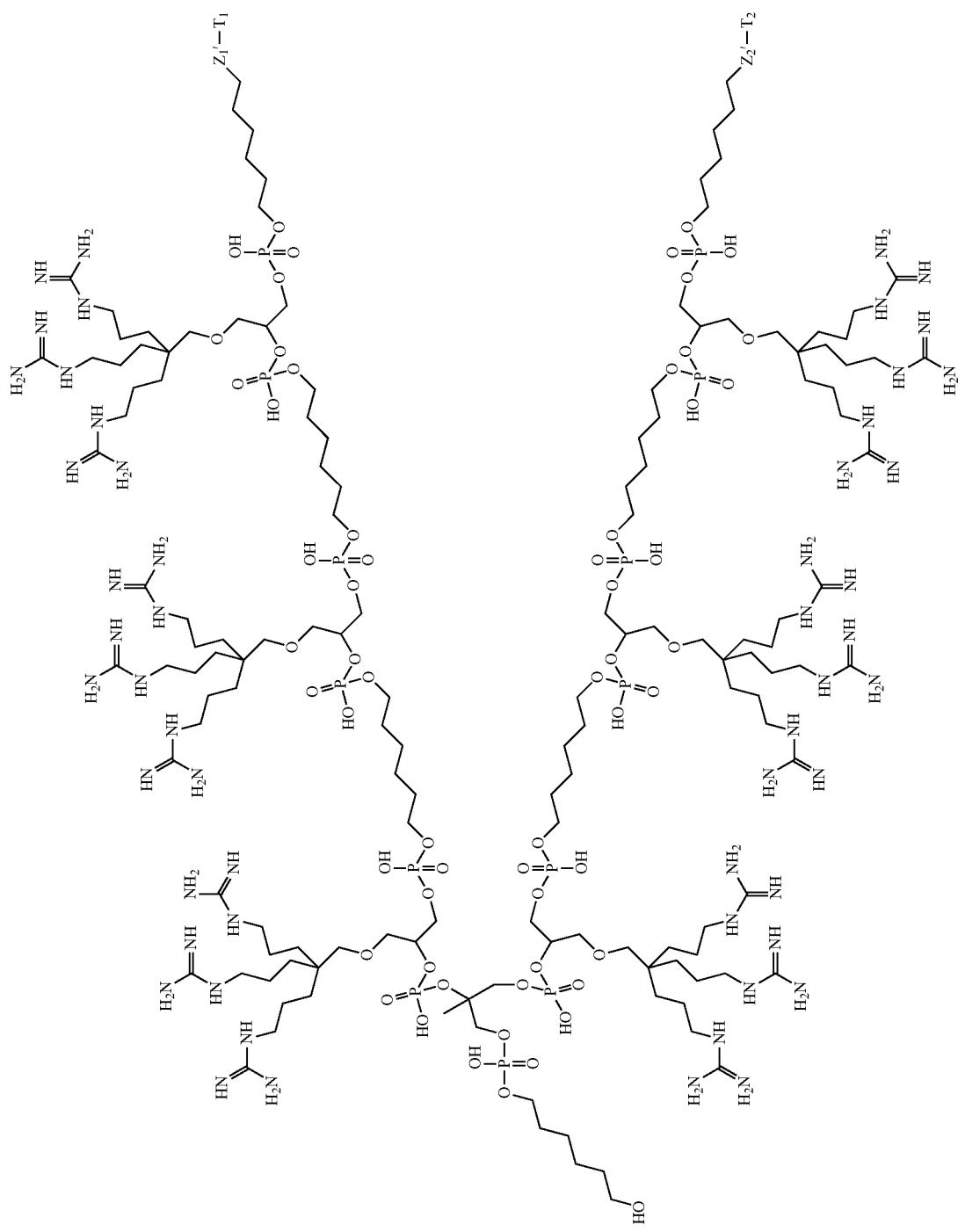

wherein each of $T_1$ and $T_2$ is independently a biologically active moiety or absent, wherein at least one of $T_1$ and $T_2$ is present; and each of $Z_1'$, $Z_2'$, is independently a derivative of $Z_1$ and $Z_2$, respectively, as a result of binding the biologically active group, wherein said $Z_1$ and $Z_2$ reactive group is hydroxyl, amine, halide, a phosphorous-containing group, phosphoramidite, —N=C=S, —NH—CO—NH$_2$, —NH—CS—NH$_2$, C-amide, N-amide, thiol or COOH.

It is understood that in the case $T_1$ or T2 is absent, $Z_1'$ or $Z_2'$ respectively is replaced with $Z_1$ or $Z_2$ respectively.

In another embodiment, this invention provides a conjugate represented by the structure of Formula IV(e):

IV(e)
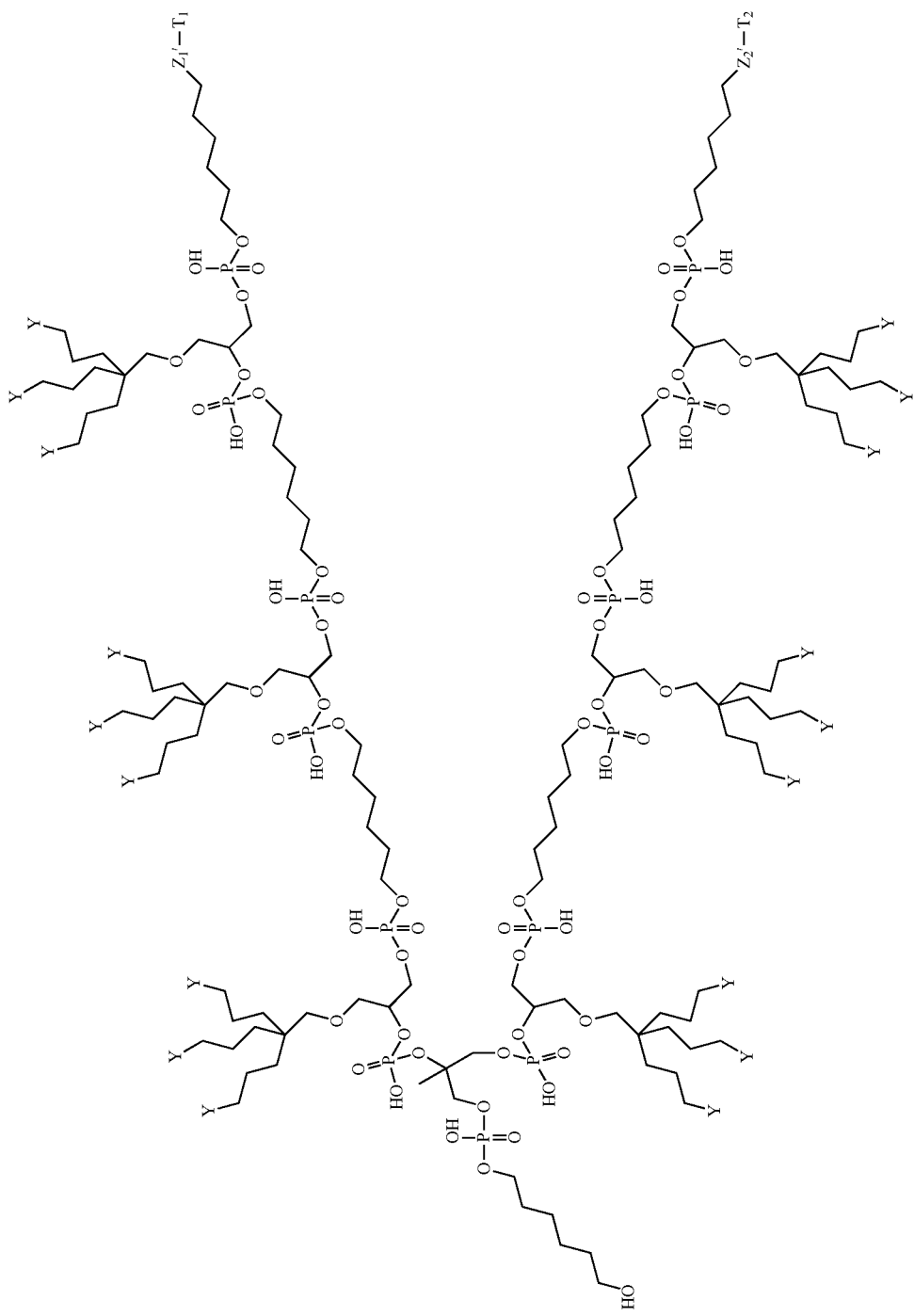

wherein

Y is a delivering group, wherein Y is an amine, histidine, guanidine, polyguanidine, imidazole, polyimidazole or any combination thereof;

each of $T_1$ and $T_2$ is independently a biologically active moiety or absent, wherein at least one of $T_1$ and $T_2$ is present; and each of $Z_1'$, $Z_2'$, is independently a derivative of $Z_1$ and $Z_2$, respectively, as a result of binding the biologically active group, wherein said $Z_1$ and $Z_2$ reactive group is hydroxyl, amine, halide, a phosphorous-containing group, phosphoramidite, —N=C=S, —NH—CO—NH$_2$, —NH—CS—NH$_2$, C-amide, N-amide, thiol or COOH.

It is understood that in the case $T_1$ or $T_2$ is absent, $Z_1'$ or $Z_2'$ respectively is replaced with $Z_1$ or $Z_2$ respectively.

In another embodiment, this invention provides a conjugate represented by the structure of Formula IV(f)

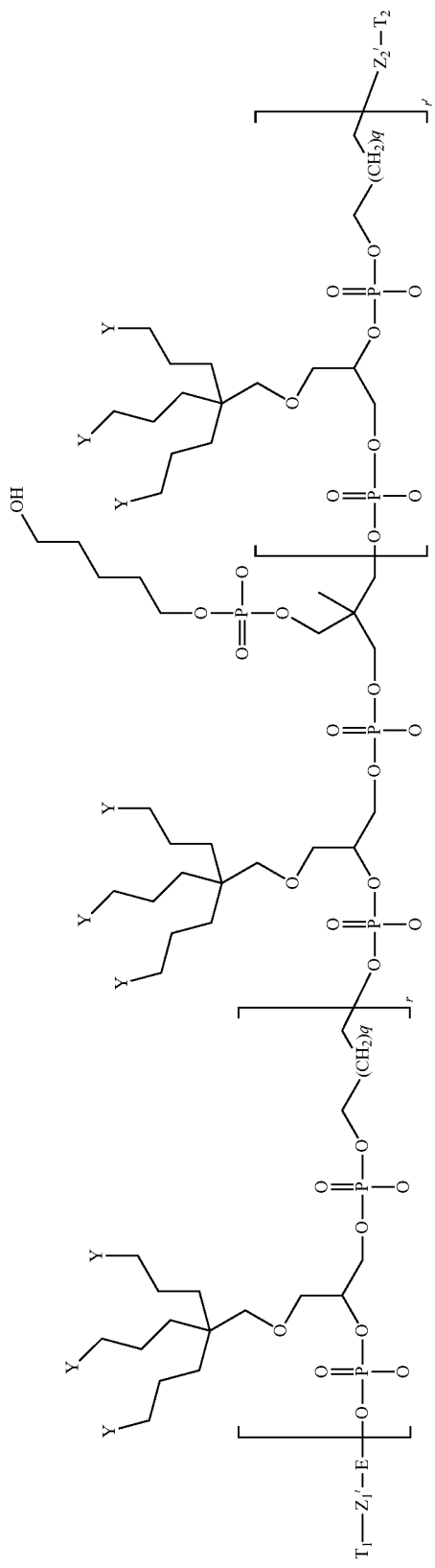

wherein

Y is a delivering group, wherein Y is an amine, histidine, guanidine, polyguanidine, imidazole, polyimidazole or any combination thereof;

each of $T_1$ and $T_2$ is independently a biologically active moiety or absent, wherein at least one of $T_1$ and T2 is present; and each of $Z_1'$, $Z_2'$, is independently a derivative of $Z_1$ and $Z_2$, respectively, as a result of binding the biologically active group, wherein said $Z_1$ and $Z_2$ reactive group is hydroxyl, amine, halide, a phosphorous-containing group, phosphoramidite, —N=C=S, —NH—CO—NH$_2$, —NH—CS—NH$_2$, C-amide, N-amide, thiol or COOH.

E is a third linking group or absent;

r and r' are each independently an integer number of between 0 and 50; in another embodiment, between 1 and 10; in another embodiment, 2 and 3 respectively; and q is an integer number of between 0 and 20. In another embodiment, q is between 0 and 10. In another embodiment, q is 1. In another embodiment, q is 2. In another embodiment, q is 3. In another embodiment, q is 4. In another embodiment, q is 5.

In one embodiment, this invention provides a conjugate represented by the structure of formula IV(g)

q is an integer number of between 0 and 20. In another embodiment, q is between 0 and 10. In another embodiment, q is 1. In another embodiment, q is 2. In another embodiment, q is 3. In another embodiment, q is 4. In another embodiment, q is 5; and L is a substituted or unsubstituted linear or branched alkyl of 2-50 carbon atoms or substituted or unsubstituted linear or branched alkyl phosphate of 2-50 carbon atoms. In another embodiment, the alkyl or alkylphosphate is of 2-8 carbon atoms. In another embodiment, L is alkylphosphate chain, represented by the structure of formula (B):

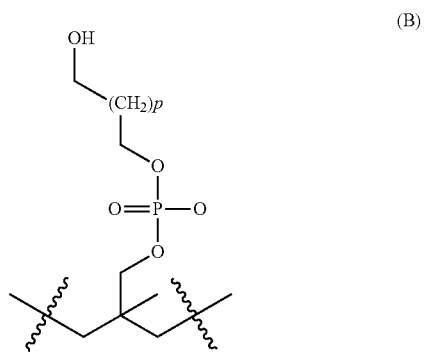

(B)

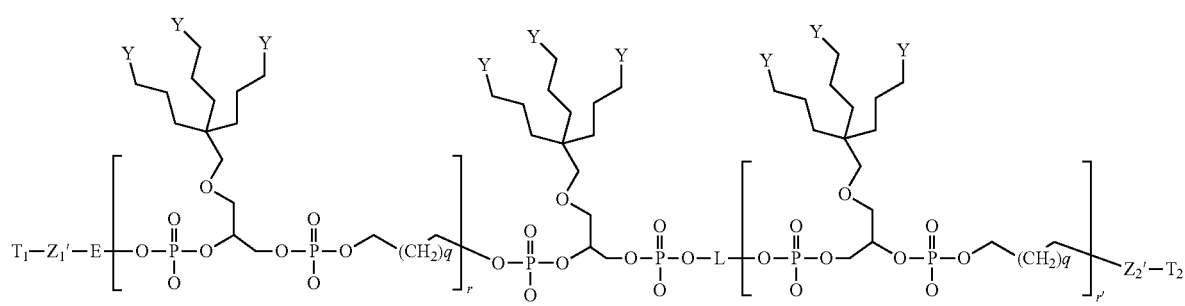

IV(g)

wherein

Y is a delivering group, wherein Y is an amine, histidine, guanidine, polyguanidine, imidazole, polyimidazole or any combination thereof;

each of $T_1$ and $T_2$ is independently a biologically active moiety or absent, wherein at least one of $T_1$ and $T_2$ is present; and each of $Z_1'$, $Z_2'$, is independently a derivative of $Z_3$ and $Z_2$, respectively, as a result of binding the biologically active group, wherein said $Z_1$ and $Z_2$ reactive group is hydroxyl, amine, halide, a phosphorous-containing group, phosphoramidite, —N=C=S, —NH—CO—NH$_2$, —NH—CS—NH$_2$, C-amide, N-amide, thiol or COOH.

E is a third linking group or absent;

r and r' are each independently an integer number of between 0 and 50; in another embodiment, between 1 and 10; in another embodiment, 2 and 3 respectively;

wherein p is an integer between 0 and 10. In another embodiment, p is 1. In another embodiment, p is 2. In another embodiment, p is 3. In another embodiment, p is 4. In another embodiment, L is a linear alkyl of 2-50 carbon atoms. In another embodiment, L is a linear alkyl of 2-8 carbon atoms. In another embodiment, L is a branched alkyl of 2-50 carbon atoms. In another embodiment, L is a branched alkyl of 2-8 carbon atoms. In another embodiment, L is a —(CH$_2$)$_s$—, wherein s is an integer of between 1 and 10. In another embodiment, s is 4. In another embodiment, s is 5. In another embodiment, s is 6. In another embodiment, s is 7. In another embodiment, L is hexyl.

In one embodiment, this invention provides a conjugate represented by the structure of formula V:

v
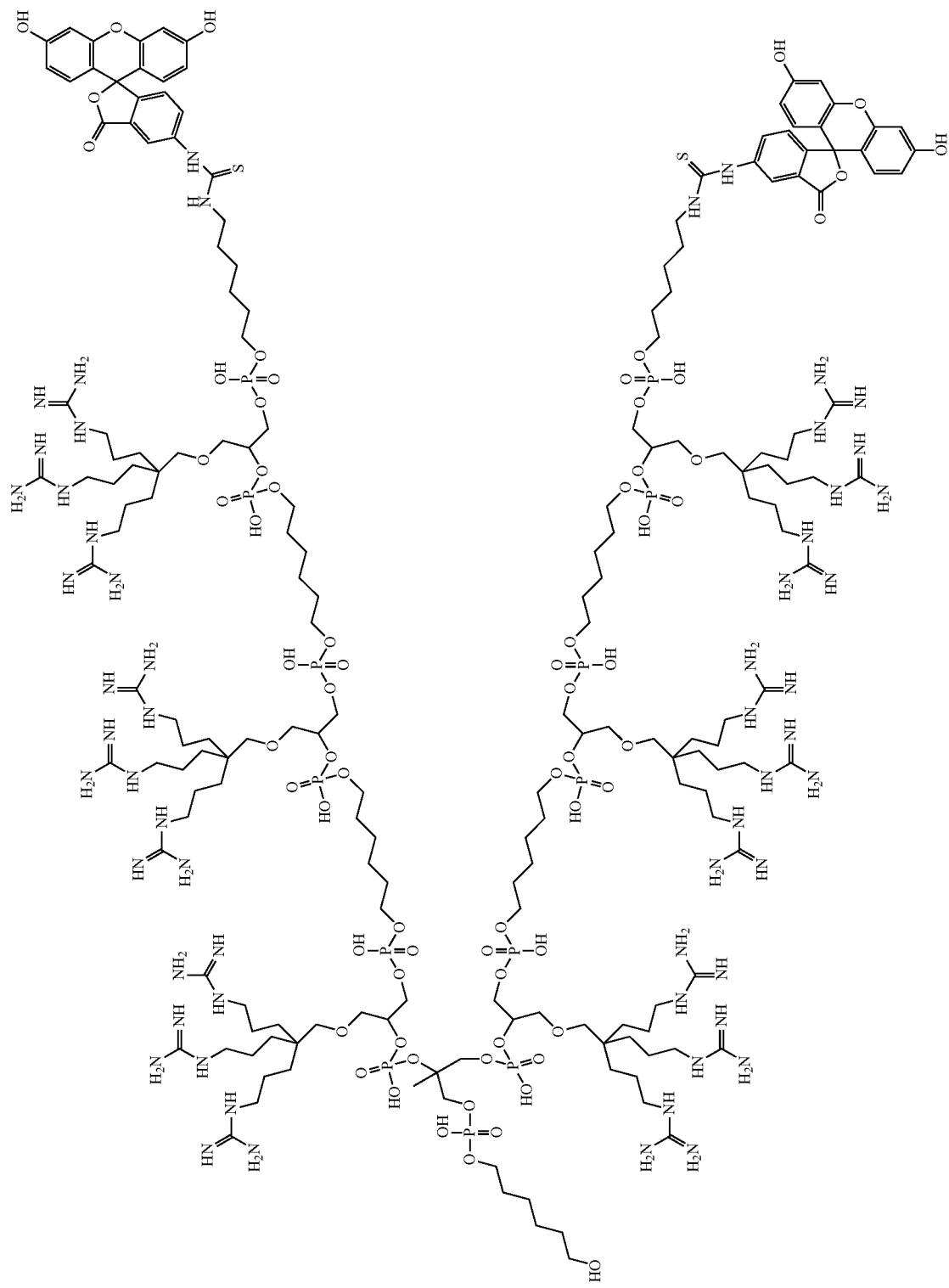

In one embodiment, this invention provides a conjugate represented by the structure of formula V(a):

V(a)
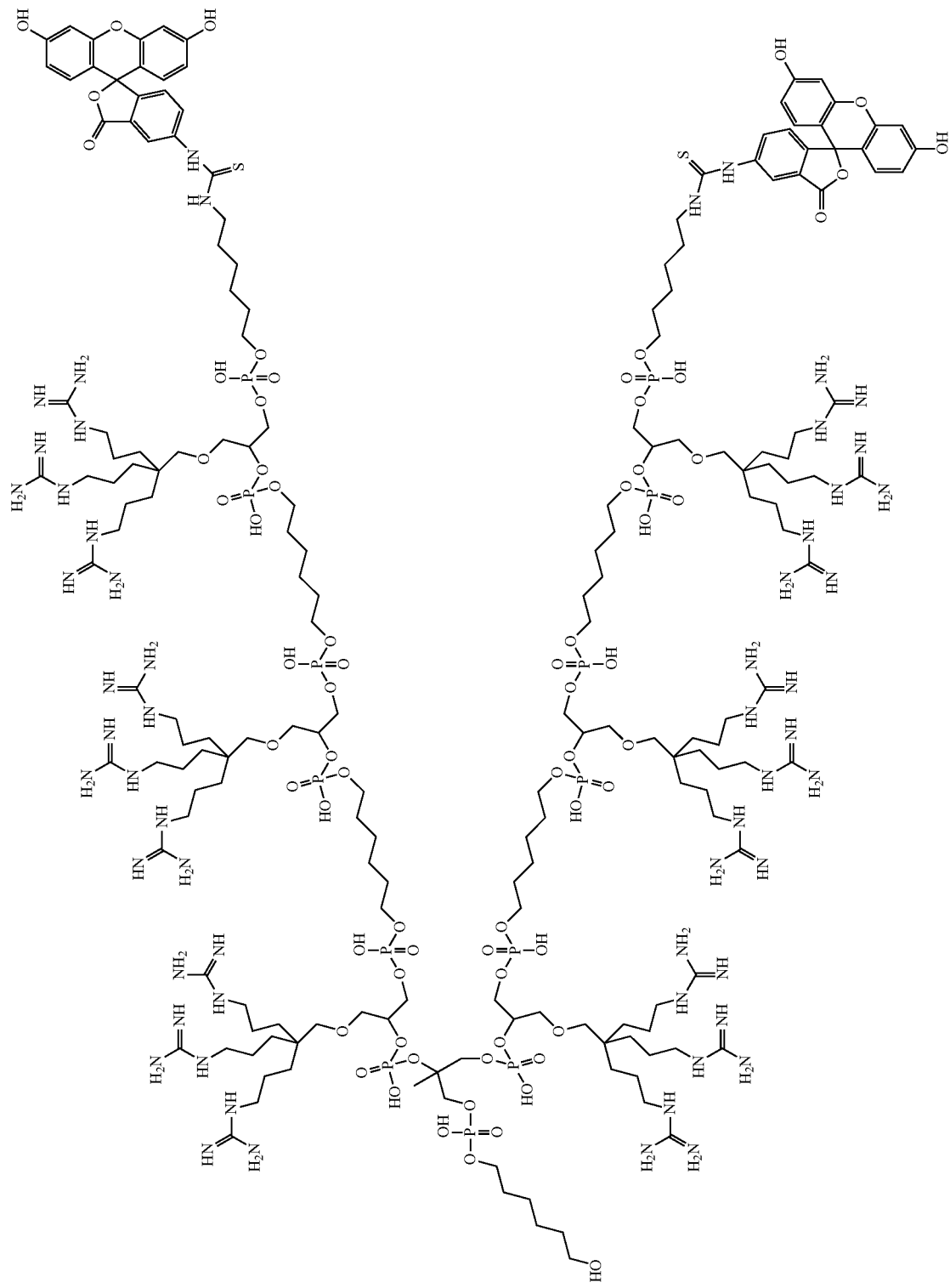

In one embodiment, this invention provides a conjugate represented by the structure of formula VI:
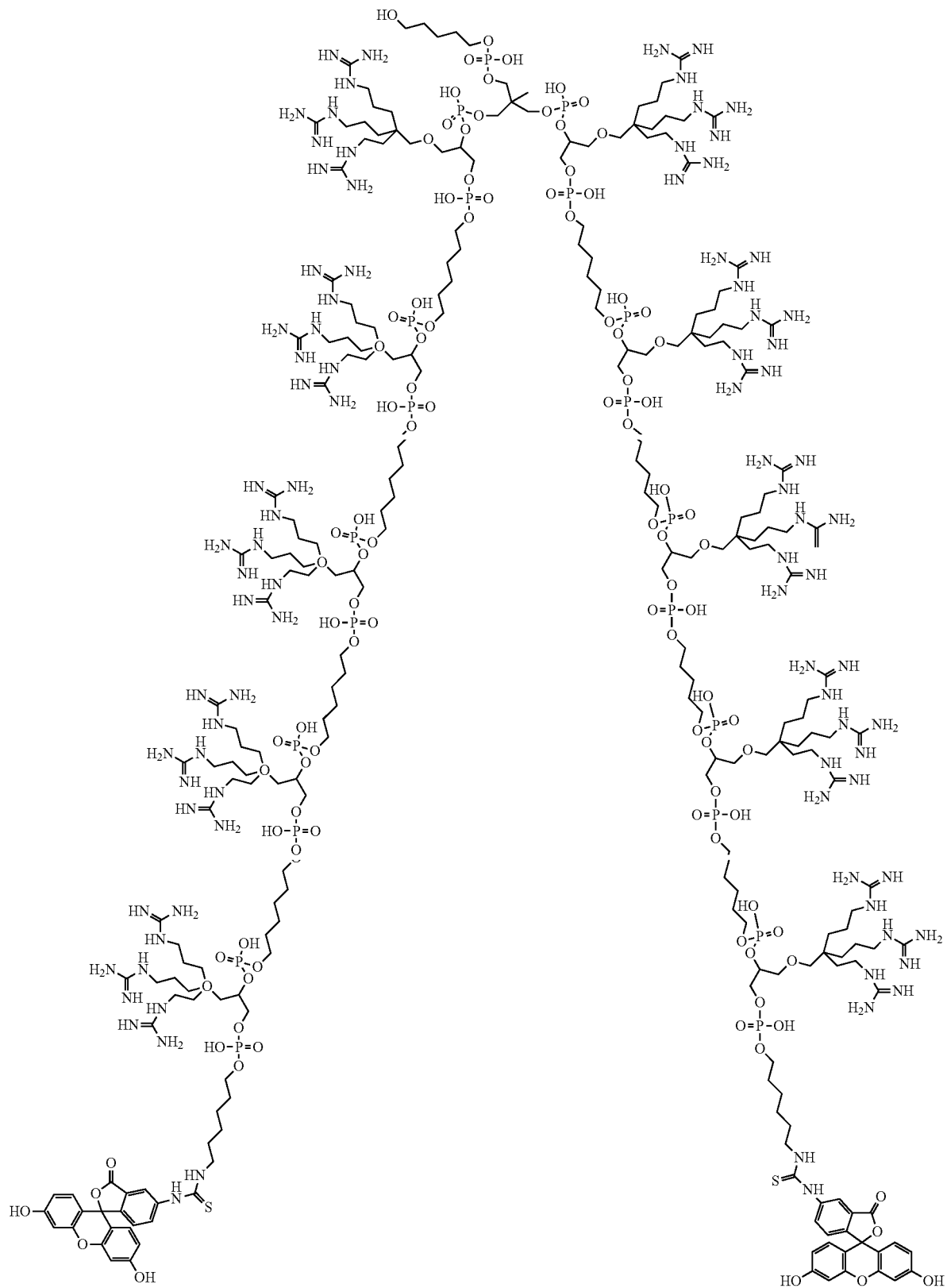
(VI)

In one embodiment, this invention provides a complex of a conjugate of this invention and an oligonucleotide. In one embodiment, this invention provides a complex of an oligomeric compound of this invention and an oligonucleotide. In another embodiment, the oligonucleotide moiety is Ribonucleic acid (RNA). In another embodiment, the oligonucleotide moiety is Deoxyribonucleic acid (DNA). In another embodiment, the oligonucleotide moiety is a combination of RNA and DNA.

In one embodiment, the oligomeric compound, conjugate and/or complex of this invention is used for delivering biologically active moieties such as various oligonucleotides, including plasmids, nucleic acid constructs, antisenses, a plasmid, a polynucleotide, an amino acid, a peptide, a polypeptide, a hormone, a steroid, an antigen, a radioisotope, a chemotherapeutic agent, a toxin, an anti-inflammatory agent, a growth factor and nucleic acids, to a target. In another embodiment, the target is a cell. In another embodiment, the target is a cancerous cell.

In one embodiment, this invention provides a method of delivering a biologically active moiety to a target, wherein the method comprises contacting a complex of this invention with a target, thereby delivering a biologically active moiety to a target. In another embodiment, the target is a cell. In another embodiment, the target is a cancerous cell.

In one embodiment, this invention provides a method of delivering a biologically active moiety to a target, wherein the method comprises contacting a conjugate of this invention with a target, thereby delivering a biologically active moiety to a target. In another embodiment, the target is a cell. In another embodiment, the target is a cancerous cell.

In one embodiment, this invention provides a method of delivering a DNA, RNA or combination thereof to a target, wherein the method comprises contacting a conjugate of this invention with a cell, thereby delivering said DNA, RNA or combination thereof to said target. In another embodiment, the target is a cell. In another embodiment, the target is a cancerous cell.

In one embodiment, this invention provides a method of delivering a DNA, RNA or combination thereof to a target, wherein the method comprises contacting a complex of this invention with a cell, thereby delivering said DNA, RNA or combination thereof to a target. In another embodiment, the target is a cell. In another embodiment, the target is a cancerous cell.

In one embodiment, this invention is directed to a method of treating cancer, comprising administering a complex of this invention to a subject, thereby treating cancer.

In one embodiment, this invention is directed to a method of treating cancer, comprising administering a conjugate of this invention to a subject, thereby treating cancer.

According to this invention, the term "complex" refers to interconnected structures, which are bound to each other by non-covalent bonds. In another embodiment the complex of this invention comprises an oligomeric compound or a conjugate of this invention, and at least one oligonucleotide moiety which are bound to each other by non-covalent bonds. In another embodiment the complex comprises an oligomeric compound or a conjugate, and at least one oligonucleotide moiety which is bound to the oligomeric compound or the conjugate electrostatically. In another embodiment the complex comprises an oligomeric compound or a conjugate, and at least one oligonucleotide moiety, which is bound to the oligomeric compound or the conjugate by hydrogen bonds. In another embodiment the complex comprises an oligomeric compound or a conjugate, and at least one oligonucleotide moiety, which is bound to the oligomeric compound or the conjugate by Van Der Waals (VDW) bonds. In another embodiment, the oligonucleotide moiety is Ribonucleic acid (RNA). In another embodiment, the oligonucleotide moiety is Deoxyribonucleic acid (DNA). In another embodiment, the oligonucleotide moiety is a combination of RNA and DNA. In another embodiment, the complex is formed by electrostatic interaction between guanidine groups of the oligomeric compound or the conjugate, and phosphate moieties of RNA and/or DNA.

The term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly. The term includes modified RNA or modified DNA. In another embodiment the modified RNA and/or DNA include protected bases.

The complexation of the oligomeric compounds and conjugates (delivery systems) according to the invention, with the oligonucleotide active agents described hereinbelow is highly beneficial since (i) such agents may be beneficially used to treat medical conditions by interfering with the condition cause rather than symptoms; and (ii) the use of such agents in in vivo applications is limited by their poor resistance to biological environment. Thus, by complexation of such agents to the delivery systems described herein, efficient and rapid delivery thereof into cells and cell nuclei is achieved, thus overcoming the limitations associated with rapid elimination thereof.

In one embodiment, the oligomeric compounds, conjugates and/or complex of this invention are referred herein as "delivery systems".

In some embodiments, the oligomeric structures of formula I, I(a), I(b) II, II(a), II(b) and/or II(c) comprises a $X_1$-Xn and/or Xq residue. In another embodiment, $X_1$-Xn and/or Xq is a cyclic hydrocarbon moiety such as, for example, a cycloalkyl, or an aryl. In another embodiment, $X_1$-Xn and/or Xq is a heterocyclic moiety, such as heteroalicyclic or heteroaryl. In another embodiment, $X_1$-Xn and/or Xq is a linear or branched alkyl.

In one embodiment, $X_1$-Xn and/or Xq of Formula I, I(a), I(b) II, II(a), II(b) and/or II(c) is a cycloalkyl. As used herein, the term "cycloalkyl" describes an all-carbon monocyclic or fused ring (i.e., rings which share an adjacent pair of carbon atoms) group where one or more of the rings does not have a completely conjugated pi-electron system. In another embodiment, the cycloalkyl is saturated cycloalkyl. In another embodiment, the cycloalkyl is an unsaturated ring, which does not have an aromatic character. In another embodiment, the cycloalkyl refers to a 3 to 12 membered ring. In another embodiment, the cycloalkyl refers to a 4-8 member ring. In another embodiment, the cycloalkyl refers to a 5 membered ring. In another embodiment, the cycloalkyl refers to a 6 member ring. Examples include cyclopentane, cyclohexane, 1-cyclohexene and the like. In another embodiment, the cycloalkyl may be substituted or unsubstituted ring, wherein said substituent is for example, but not limited to an halogen, alkyl, cyano, a phosphate, nitro an amine or any combination thereof.

In one embodiment, $X_1$-Xn and/or Xq of Formula I, I(a), I(b) II, II(a), II(b) and/or II(c) is a heteroalicyclic. The term "heteroalicyclic" refers to an aliphatic chain and heterocyclic ring. In another embodiment, a heteroalicyclic ring contain one or more rings which may be either saturated or unsaturated, but do not have aromatic character. The heteroalicyclic group includes, for example, tetrahydrofuryl, tetrahydrothienyl, chromanyl, or cyclic ether (e.g., a monosaccharide). In another embodiment, the heteroalicyclic refers to a 3-12 member ring. In another embodiment, the heteroalicyclic refers to a 4-8 member ring. In another embodiment, the heteroalicyclic refers to a 5 member ring. In another embodiment, the heteroalicyclic refers to a 6 member ring. In another embodiment, the heteroalicyclic may be substituted or unsubstituted ring, wherein said substituent is for example, but not limited to an halogen, alkyl, a phosphate, cyano, nitro, an amine or any combination thereof.

In one embodiment, $X_1$-Xn and/or Xq of Formula I, I(a), I(b) II, II(a), II(b) and/or II(c) is an aryl. The term "aryl" describes an all-carbon monocyclic or fused-ring polycyclic (i.e., rings which share adjacent pairs of carbon atoms) groups having a completely conjugated pi-electron system. Examples include phenyl, biphenyl, oligomeric phenyl groups, naphthalene, cummulenes, and the like. In another embodiment, the aryl refers to a 3-12 member ring. In another embodiment, the aryl refers to a 4-8 member ring. In another embodiment, the aryl refers to a 5 member ring. In another embodiment, the aryl refers to a 6 member ring. In another embodiment, the aryl may be substituted or unsubstituted ring, wherein said substituent is for example, but not limited to an halogen, alkyl, cyano, nitro, a phosphate, an amine or any combination thereof.

In one embodiment, $X_1$-Xn and/or Xq of Formula I, I(a), I(b) II, II(a), II(b) and/or II(c) is a heteroaryl. The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. In another embodiment, the heteroaryl refers to a 3-12 member ring. In another embodiment, the heteroaryl refers to a 4-8 member ring. In another embodiment, the heteroaryl refers to a 5 membered ring. In another embodiment, the heteroaryl refers to a 6 membered ring. In another embodiment, the heteroaryl may be substituted or unsubstituted ring, wherein said substituent is for example, but not limited to an halogen, alkyl, cyano, a phosphate, nitro, an amine or any combination thereof In one embodiment, $X_1$-Xn and/or Xq of Formula I, I(a), I(b) II, II(a), II(b) and/or II(c) is a monosaccharide. The term "monosaccharide", as used herein and is well known in the art, refers to a simple form of a sugar that consists of a single saccharide molecule which cannot be further decomposed by hydrolysis. In another embodiment the monosaccharides is glucose (dextrose), fructose, galactose, or ribose. In another embodiment, monosaccharides are classified according to the number of carbon atoms of the carbohydrate, i.e., triose, having 3 carbon atoms such as glyceraldehyde and dihydroxyacetone; tetrose, having 4 carbon atoms such as erythrose, threose and erythrulose; pentose, having 5 carbon atoms such as arabinose, lyxose, ribose, xylose, ribulose and xylulose; hexose, having 6 carbon atoms such as allose, altrose, galactose, glucose, gulose, idose, mannose, talose, fructose, psicose, sorbose and tagatose; heptose, having 7 carbon atoms such as mannoheptulose, sedoheptulose; octose, having 8 carbon atoms such as 2-keto-3-deoxy-manno-octonate; nonose, having 9 carbon atoms such as sialose; and decose, having 10 carbon atoms. In another embodiment, monosaccharides are the building blocks of oligosaccharides like sucrose (common sugar) and other polysaccharides (such as cellulose and starch).

In one embodiment $X_1$-Xn and/or Xq of Formula I, I(a), I(b) II, II(a), II(b) and/or II(c) is a substituted or unsubstituted alkyl. The term "alkyl" refers both to linear and to branched alkyl. In one embodiment, the alkyl is interrupted by a heteroatom. In another embodiment, the term "alkyl" refers to a saturated linear aliphatic hydrocarbon chain. In another embodiment, the term "alkyl" refers to a saturated branched aliphatic hydrocarbon chain. In another embodiment, In one embodiment, the alkyl group has 1-12 carbons. In another embodiment, the alkyl group has 2-50 carbons. In another embodiment, the alkyl group has 2-8 carbons. In another embodiment, the alkyl group has 1-6 carbons. In another embodiment, the alkyl group has 1-4 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or substituted, wherein said substitutions include but are not limited to: halogen, alkyl of 1 to 6 carbons, alkoxy of 1 to 6 carbons, ester of 1 to 6 carbons, carboxy, cyano, nitro, hydroxyl, thiol, amine, amide, reverse amide, sulfonamide, phosphate, aryl, phenyl or any combination thereof.

In one embodiment $X_1$-Xn and/or Xq of Formula I, I(a), I(b) II, II(a), II(b) and/or II(c) is a substituted or unsubstituted alkylether, wherein alkyl is defined as described above. In one embodiment the alkylether is branched. In another embodiment the alkylether is linear. In another embodiment the alkylether has 1-12 carbon atoms. In another embodiment the alkylether has 2-50 carbon atoms. In another embodiment the alkylether has 2-8 carbon atoms. In another embodiment the alkylether has 1-6 carbon atoms. In another embodiment the alkylether has 1-5 carbon atoms. In another embodiment the alkylether has 4 carbon atoms. In another embodiment the alkylether has 5 carbon atoms. Substitutions include but are not limited to: halogen, alkyl of 1 to 6 carbons, alkoxy of 1 to 6 carbons, ester of 1 to 6 carbons, carboxy, cyano, nitro, hydroxyl, thiol, amine, amide, reverse amide, sulfonamide, phosphate, aryl, phenyl or any combination thereof.

In another embodiment the alkylether is:

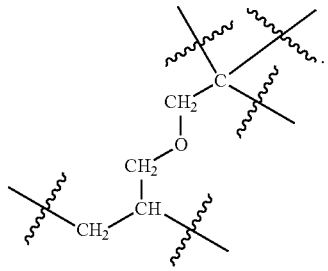 [SMILES: *CC(*)COCC(*)(*)*]

In another embodiment the alkylether is:

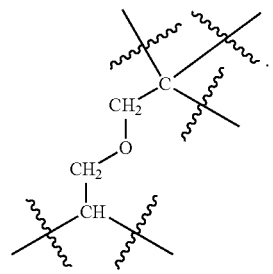 [SMILES: *C(*)COCC(*)(*)*]

In another embodiment, $X_1$-Xn and/or Xq of Formula I, I(a), I(b) II, II(a), II(b) and/or II(c) is:

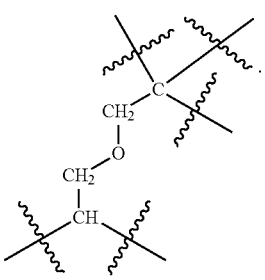 [SMILES: *C(*)COCC(*)(*)*]

In another embodiment, $X_1$-Xn and/or Xq of Formula I, I(a), I(b) II, II(a), II(b) and/or II(c) is:

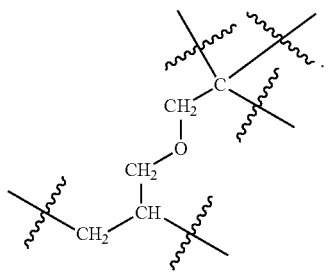 [SMILES: *CC(*)COCC(*)(*)*]

In one embodiment $X_1$-Xn and/or Xq of Formula I, I(a), I(b) II, II(a), II(b) and/or II(c) is a substituted or unsubstituted alkylphosphate, wherein alkyl is defined as described above. In one embodiment the alkylphosphate is branched. In another embodiment the alkylphosphate is linear. In another embodiment the alkylphosphate has 1-12 carbon atoms. In another embodiment the alkylphosphate has 1-50 carbon atoms. In another embodiment the alkylphosphate has 2-8 carbon atoms. In another embodiment the alkylphosphate has 1-6 carbon atoms. In another embodiment the alkylphosphate has 1-4 carbon atoms. In another embodiment the alkylphosphate has 4 carbon atoms. In another embodiment the alkylphosphate has 5 carbon atoms. Substitutions include but are not limited to: halogen, alkyl of 1 to 6 carbons, alkoxy of 1 to 6 carbons, ester of 1 to 6 carbons, carboxy, cyano, nitro, hydroxyl, thiol, amine, amide, reverse amide, sulfonamide, phosphate, aryl, phenyl or any combination thereof.

In one embodiment $X_1$-Xn and/or Xq of Formula I, I(a), I(b) II, II(a), II(b) and/or II(c) is a substituted or unsubstituted, linear or cyclic alkyl as defined above interrupted by one or more heteroatom selected from O, N, S and P.

In some embodiments, the oligomeric structures of formula I and/or II comprise an F bridge. In another embodiment, each F is independently selected from the group consisting of nitrogen, oxygen, phosphate and sulfur, or absent. In another embodiment, F is phosphate. In another embodiment F is oxygen. In another embodiment F is sulfur. In another embodiment F is nitrogen. In another embodiment F is absent. In another embodiment, all F bridges are either phosphate or absent.

In some embodiments, the oligomeric structures of formula I(a), I(b), II(a), II(b) and/or II(c) comprise a $F_1$-$F_n$, $F_1'$-$F_n'$ and for Fq bridges. In another embodiment, each of $F_1$-$F_n$, $F_1'$-$F_n'$ and for Fq is independently selected from the group consisting of nitrogen, oxygen, phosphate and sulfur, or absent. In another embodiment, $F_1$-$F_n$, $F_1'$-$F_n'$ and/or Fq is phosphate. In another embodiment $F_1$-$F_n$, $F_1'$-$F_n'$ and/or Fq is oxygen. In another embodiment $F_1$-$F_n$, $F_1'$-$F_n'$ and/or Fq is sulfur. In another embodiment, $F_1$-$F_n$, $F_1'$-$F_n'$ and/or Fq is nitrogen. In another embodiment, $F_1$-$F_n$, $F_1'$-$F_n'$ and/or Fq is absent. In another embodiment, each of $F_1$-$F_n$, $F_1'$-$F_n'$ and/or Fq is either phosphate or absent.

In some embodiments, the oligomeric structures of formula I, II, and/or II(b) comprise an m integer from 1 to 10. In another embodiment, m is an integer between 1 to 5. In another embodiment, m is 3. In another embodiment, m is 4 or 5 and $X_1$-Xn and/or Xq is a cyclic moiety comprises a 5- or 6-membered ring respectively. In another embodiment, m is lower than 4 or 5, and the remaining positions of $X_1$-Xn and/or Xq are either hydrogen or bear substituents such as alkyl as defined above.

In some embodiments, the oligomeric structures of formula I(b) and/or II(c) comprise a k integer from 0 to 100. In another embodiment, each k is independently an integer between 1 to 100. In another embodiment, each k is independently an integer between 1 to 50. In another embodiment, each k is independently an integer between 0 to 50. In another embodiment, each k is independently an integer between 1 to 10. In another embodiment, each k is independently 1 or 0. In another embodiment, each k is 1. In another embodiment, each k is independently between 1 and 5. In another embodiment, each k is independently between 1 and 8. In another embodiment, each k is independently between 1 and 20.

In some embodiments, the oligomeric structures of formula I(b) and/or II(c) comprise a t integer from 0 to 100. In another embodiment, each t is independently an integer between 1 to 100. In another embodiment, each t is independently an integer between 0 to 50. In another embodiment, each t is independently an integer between 0 to 10. In another embodiment, each t is independently an integer between 1 to 10. In another embodiment, each t is independently 1 or 0. In another embodiment, each of t is 1. In another embodiment, each of t is 0. In another embodiment, each t is independently between 0 and 5. In another embodiment, each t is independently between 0 and 8. In another embodiment, each t is independently between 1 and 20.

In some embodiments, the oligomeric structures of formula I, I(a), I(b), II, II(a), II(b) and/or II(c) comprise an n integer from 0 to 100. In another embodiment, n is an integer between 1 and 100. In another embodiment, n is an integer between 2 and 10. In another embodiment, n is an integer between 2 and 15. In another embodiment, n is an integer between 1 and 15. In another embodiment, n is an integer between 0 and 20. In another embodiment, n is an integer between 2 and 20. In another embodiment, n is an integer between 20 and 40. In another embodiment, n is an integer between 40 and 60. In another embodiment, n is an integer between 2 and 50. In another embodiment, n is an integer between 1 and 60. In another embodiment, n is 6. In another embodiment, n is 7. In another embodiment, n is 8. In another embodiment, n is 9. In another embodiment, n is 10.

In some embodiments, the oligomeric structures of Formula III(b), III(c), IV(b) and/or IV(c) comprise an r integer from 0 to 100. In another embodiment, r is an integer between 0 and 50. In another embodiment, r is an integer between 1 and 50. In another embodiment, r is an integer between 2 and 10. In another embodiment, r is an integer between 2 and 15. In another embodiment, r is an integer between 1 and 15. In another embodiment, r is an integer between 0 and 20. In another embodiment, r is an integer between 2 and 20. In another embodiment, r is an integer between 20 and 40. In another embodiment, r is an integer between 40 and 60. In another embodiment, r is an integer between 2 and 50. In another embodiment, r is an integer between 1 and 60. In another embodiment, r is 0. In another embodiment, r is 1. In another embodiment, r is 2. In another embodiment, r is 3. In another embodiment, r is 4. In another embodiment, r is 5. In another embodiment, r is 6.

In some embodiments, the oligomeric structures of Formula III(b), III(c), IV(b) and/or IV(c) comprise an r' integer from 0 to 100. In another embodiment, r' is an integer between 0 and 50. In another embodiment, r' is an integer between 1 and 50. In another embodiment, r' is an integer between 2 and 10. In another embodiment, r' is an integer between 2 and 15. In another embodiment, r' is an integer between 1 and 15. In another embodiment, r' is an integer between 0 and 20. In another embodiment, r' is an integer between 2 and 20. In another embodiment, r' is an integer between 20 and 40. In another embodiment, r' is an integer between 40 and 60. In another embodiment, r' is an integer between 2 and 50. In another embodiment, r' is an integer between 1 and 60. In another embodiment, r' is 0. In another embodiment, r' is 1. In another embodiment, r' is 2. In another embodiment, r' is 3. In another embodiment, r' is 4. In another embodiment, r' is 5. In another embodiment, r' is 6.

In some embodiments, the oligomeric structures of Formula III(b), III(c), IV(b) and/or IV(c) comprise a q integer from 0 to 10. In another embodiment, q is an integer between 1 and 10. In another embodiment, q is an integer between 2 and 10. In another embodiment, q is an integer between 2 and 4. In another embodiment, q is an integer between 1 and 6. In another embodiment, q is 0. In another embodiment, q is 1. In another embodiment, q is 2. In another embodiment, q is 3. In another embodiment, q is 4. In another embodiment, q is 5. In another embodiment, q is 6.

In one embodiment, the $X_1$-$X_n$, residues that form the oligomer backbone according to the present invention may be connected one to the other either directly or via a linking group. Such a linking group is referred to herein as the first linking group and is denoted $L_1$-$L_{n+1}$ and/or Lq of structures of Formula I, II and/or II(b); or $L_1$-$L_n$ of structures of Formula I(a), I(b), II(a) and/or II(c). In another embodiment, $L_1$-$L_n$, $L_1$-$L_{n+1}$ and/or Lq is a substituted or unsubstituted, saturated or unsaturated hydrocarbon chain. In another embodiment, $L_1$-$L_n$, $L_1$-$L_{n+1}$ and/or Lq is a linear alkyl of 2-50 carbon atoms. In another embodiment, $L_1$-$L_n$, $L_1$-$L_{n+1}$ and/or Lq is a linear alkyl of 2-8 carbon atoms. In another embodiment, $L_1$-$L_n$, $L_1$-$L_{n+1}$ and/or Lq is a methylene. In another embodiment, $L_1$-$L_n$, $L_1$-$L_{n+1}$ and/or Lq is —$(CH_2)_s$—, wherein s is between 1 and 50. In another embodiment, s is 6. In another embodiment, s is between 1 and 8. In another embodiment, $L_1$-$L_n$, $L_1$-$L_{n+1}$ and/or Lq is a substituted or unsubstituted branched alkyl of 2-50 carbon atoms. In another embodiment, $L_1$-$L_n$, $L_1$-$L_{n+1}$ and/or Lq is a substituted or unsubstituted branched alkyl of 2-8 carbon atoms. In another embodiment, $L_1$-$L_n$, $L_1$-$L_{n+1}$ and/or Lq is a substituted linear alkyl. In another embodiment, $L_1$-$L_n$, $L_1$-$L_{n+1}$ and/or Lq is a substituted branched alkyl, wherein substitutions are as defined for "alkyl" supra. In another embodiment, $L_1$-$L_n$, $L_1$-$L_{n+1}$ and/or Lq is a branched alkyl, substituted with an alkoxy group. In another embodiment, $L_1$-$L_n$, $L_1$-$L_{n+1}$ and/or Lq is an unsubstituted linear alkyl of 2-50 carbon atoms. In another embodiment, $L_1$-$L_n$, $L_1$-$L_{n+1}$ and/or Lq is an unsubstituted linear alkyl of 2-8 carbon atoms. In another embodiment, $L_1$-$L_n$, $L_1$-$L_{n+1}$ and/or Lq is a hexyl. In another embodiment, $L_1$-$L_n$, $L_1$-$L_{n+1}$ and/or Lq is a pentyl. In another embodiment, $L_1$-$L_n$, $L_1$-$L_{n+1}$ and/or Lq is independently a substituted or unsubstituted hydrocarbon chain interrupted by at least one double bond or triple bond, a heteroatom or any combination thereof, wherein, the heteroatom being selected from the group consisting of oxygen, nitrogen and sulfur.

In another embodiment, $L_1$-$L_n$, $L_1$-$L_{n+1}$ and/or Lq is substituted or unsubstituted linear alkylether. In another embodiment, $L_1$-$L_n$, $L_1$-$L_{n+1}$ and/or Lq is polyethyleneglycol (PEG). In another embodiment, $L_1$-$L_n$, $L_1$-$L_{n+1}$ and/or Lq is

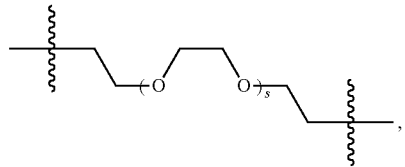

wherein s is between 1 and 50. In another embodiment, $L_1$-$L_n$, $L_1$-$L_{n+1}$ and/or Lq is

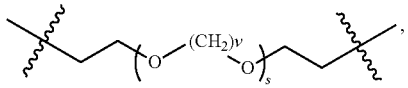

wherein v is between 1 and 10, and s is between 1 and 50. In another embodiment, $L_1$-$L_n$, $L_1$-$L_{n+1}$ and/or Lq is substituted or unsubstituted branched alkylether. Substitutions include but are not limited to: halogen, hydroxyl, thiol, alkyl of 1 to 6 carbons, alkoxy of 1 to 6 carbons, thioalkoxy of 1 to 6 carbons, ester of 1 to 6 carbons, carboxy, cyano, nitro, hydroxyl, thiol, amine, amide, reverse amide, sulfonamide, phosphate, aryl, phenyl or any combination thereof.

In another embodiment, $L_1$-$L_n$, $L_1$-$L_{n+1}$ and/or Lq is substituted or unsubstituted linear alkylphosphate of 2-50 carbon atoms. In another embodiment, $L_1$-$L_n$, $L_1$-$L_{n+1}$ and/or Lq is substituted or unsubstituted linear alkylphosphate of 2-8 carbon atoms. In another embodiment, $L_1$-$L_n$, $L_1$-$L_{n+1}$ and/or Lq is substituted or unsubstituted branched alkylphosphate of 2-50 carbon atoms. In another embodiment, $L_1$-$L_n$, $L_1$-$L_{n+1}$ and/or Lq is substituted or unsubstituted branched alkylphosphate of 2-8 carbon atoms. Substitutions include but are not limited to: halogen, hydroxyl, thiol, alkyl of 1 to 6 carbons, alkoxy of 1 to 6 carbons, thioalkoxy of 1 to 6 carbons, ester of 1 to 6 carbons, carboxy, cyano, nitro, hydroxyl, thiol, amine, amide, reverse amide, sulfonamide, phosphate, aryl, phenyl or any combination thereof. In another embodiment, $L_1$-$L_n$, $L_1$-$L_{n+1}$ and/or Lq is a branched alkylphosphate, substituted by hydroxyl moiety. In another embodiment, each of $L_1$-$L_n$, $L_1$-$L_{n+1}$ and/or Lq is either a hexyl or a branched alkylphosphate, substituted by hydroxyl moiety. In another embodiment, $L_1$-$L_n$, $L_1$-$L_{n+1}$ and/or Lq is represented by the structure of formula (B):

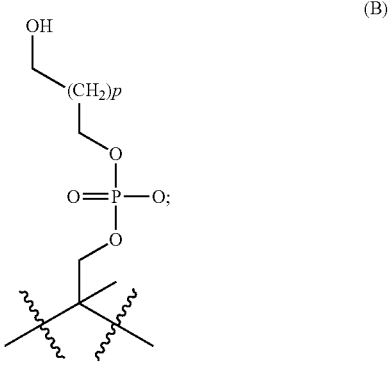

(B)

wherein p is an integer between 0 and 10; In another embodiment, p is 1. In another embodiment, p is 2. In another embodiment, p is 3. In another embodiment, p is 4.

In one embodiment, the term "hydrocarbon chain" of this invention refers to a substance that includes a plurality of carbon atoms having mostly hydrogen atoms attached thereto. In another embodiment, the hydrocarbon chain of $L_1$-$L_n$, $L_1$-$L_{n+1}$ and/or Lq can be aliphatic, alicyclic and/or aromatic and thus may be composed of, for example, alkyls, alkenyls, alkynyls, cycloalkyls, and aryls, as these terms are defined herein, or any combination thereof.

The term "alkenyl" refers to a substance that includes at least two carbon atoms and at least one double bond. In one embodiment, the alkenyl has 2-7 carbon atoms. In another embodiment, the alkenyl has 2-12 carbon atoms. In another embodiment, the alkenyl has 2-10 carbon atoms. In another embodiment, the alkenyl has 3-6 carbon atoms. In another embodiment, the alkenyl has 2-4 carbon atoms.

The term "alkynyl" refers to a substance that includes at least two carbon atoms and at least one triple bond. In one embodiment, the alkynyl has 2-7 carbon atoms. In another embodiment, the alkynyl has 2-12 carbon atoms. In another embodiment, the alkynyl has 2-10 carbon atoms. In another embodiment, the alkynyl has 3-6 carbon atoms. In another embodiment, the alkynyl has 2-4 carbon atoms.

In another embodiment, the hydrocarbon chain of $L_1$-$L_n$, $L_1$-$L_{n+1}$ and/or Lq comprises between 2 to 50 carbon atoms. In another embodiment, the hydrocarbon chain of $L_1$-$L_n$, $L_1$-$L_{n+1}$ and/or Lq comprises between 2 to 20 carbon atoms. In another embodiment, the hydrocarbon chain comprises between 2 to 10 carbon atoms. In another embodiment, the hydrocarbon chain comprises between 2 to 6 carbon atoms. In another embodiment, the hydrocarbon chain comprises between 4 to 6 carbon atoms. In another embodiment, the hydrocarbon chain comprises between 4 to 10 carbon atoms. In another embodiment, the hydrocarbon chain comprises 6 carbon atoms. In another embodiment, the hydrocarbon chain is a hexyl chain.

The incorporation of such linking moieties within the backbone of the oligomer described herein can provide the oligomer with certain characteristics such as a hydrophobic nature, a hydrophilic nature, an amphiphilic nature and the like. In addition, the incorporation of such linking moieties can further serve for spacing the delivering groups from one another or for determining the space there between, in cases where such a space is desired.

In one embodiment, the oligomer/conjugate/complex of this invention comprise a delivering group (Y). In another embodiment, Formula I, I(a), I(b), II, II(a), II(b) and/or II(c) comprises a delivery group which is termed $Y_1$-$Y_n$ and/or Yq in Formula I, I(a), I(b), II, II(a), II(b) and/or II(c); and Y in Formula III(a-c) and IV(a-c). The term "delivering group", refers to a chemical or biological group, which enables the transport of a substance that contains such a group to a desired bodily site. In another embodiment, the delivering group is independently a membrane-permeable group, recognition moieties, a ligand, an antibody, an antigen, a substrate, an inhibitor or any combination thereof. In another embodiment, the membrane-permeable group comprises at least one positively charged group.

In another embodiment, each of the structures of Formula I, II, and/or II(b) comprise at least one delivering group. In another embodiment, each of the structure of Formula I, II, and/or II(b) comprises 1 or 2 delivering groups. In another embodiment, each of the structure of Formula I, II, and/or II(b) comprises at least four delivering groups. In another embodiment, each of the structure of Formula I, II, and/or II(b) comprises at least three delivering groups. In another embodiment, each of the structure of Formula I, II, and/or II(b) comprises between 1 and 30 delivering groups. In another embodiment, each of the structure of Formula I, II, and/or II(b) comprises 18 delivering groups. In another embodiment, each of the structure of Formula I, II, and/or II(b) comprises 21 delivering groups. In another embodiment, each of the structure of Formula I, II, and/or II(b) comprises 24 delivering groups. In another embodiment, each of the structure of Formula I, II, and/or II(b) comprises 27 delivering groups. In another embodiment, each of the structure of Formula I, II, and/or II(b) comprises 30 delivering groups.

In another embodiment, each of the structure of Formula I(a), I(b) II(a), and/or II(c) comprises at least three delivering group. In another embodiment, each of the structure of Formula I(a), I(b) II(a), and/or II(c) comprises 3 or 6 delivering groups. In another embodiment, each of the structure of Formula I(a), I(b) II(a), and/or II(c) comprises between 3 and 30 delivering groups. In another embodiment, each of the structure of Formula I(a), I(b) II(a), and/or II(c) comprises 18 delivering group. In another embodiment, each of the structure of Formula I(a), I(b) II(a), and/or II(c) comprises 18 delivering group. In another embodiment, each of the structure of Formula I(a), I(b) II(a), and/or II(c) comprises 21 delivering group. In another embodiment, each of the structure of Formula I(a), I(b) II(a), and/or II(c) comprises 24 delivering group. In another embodiment, each of the structure of Formula I(a), I(b) II(a), and/or II(c) comprises 27 delivering group. In another embodiment, each of the structure of oligomeric Formula I(a), I(b) II(a), and/or II(c) comprises 30 delivering group.

In another embodiment, the oligomers/conjugates/complexes of this invention, provide between 1 to 8 delivering groups. In another embodiment, the oligomers/conjugates/complexes oligomers of this invention provide between 4 to 10 delivering groups. In another embodiment, the oligomers/conjugates/complexes of this invention, provide between 5 to 10 delivering groups. In another embodiment, the oligomers/conjugates/complexes of this invention provide between 4 to 20 delivering groups. In another embodiment, the oligomers/conjugates/complexes of this invention, provide between 3 to 18 delivering groups. In another embodiment, the oligomers/conjugates/complexes of this invention, provide between 3 to 30 delivering groups. In another embodiment, the oligomers/conjugates/complexes of this invention provide between 6 to 12 delivering groups. In another embodiment, the oligomers/conjugates/complexes of this invention provide between 6 to 18 delivering groups. In another embodiment, the oligomers/conjugates/complexes of this invention provide 18 delivering groups. In another embodiment, the delivering group of this invention is selected from an amine, histidine, guanidine, polyguanidine, imidazole, polyimidazole and any combination thereof.

In one embodiment, the oligomeric Formula I, I(a), I(b), II, II(a), II(b), II(c), III(a-c), IV(a-c) and/or structure (A) comprise a delivery group Y, $Y_1$-$Y_n$ and/or Yq wherein Y, $Y_1$-$Y_n$ and/or Yq. In another embodiment, the delivery group is a membrane-permeable group. The term "membrane-permeable groups" refers to a group that is capable of penetrating a bodily membrane, e.g., a cell membrane, a nucleus membrane and the like. Membrane-permeable groups therefore provide membrane-penetrative or membrane-permeability characteristics to compounds that incorporate same and enable the penetration of such compounds into cells, nuclei and the like. Such delivering groups therefore serve for delivering substances into cells and/or cellular compartments. In another embodiment, Y, $Y_1$-$Y_n$ and/or Yq is a membrane-permeable group comprising at least one positively charged group. In another embodiment, the positively charged group is selected from the group consisting of amine, histidine, guanidine, polyguanidine, imidazole, polyimidzole or combination thereof. In another embodiment, the positively charged group is guanidine. In another embodiment, Y, $Y_1$-$Y_n$ and/or Yq is guanidine.

In another embodiment, Y, $Y_1$-$Y_n$, and/or Yq is independently guanidine or a derivative of guanidine such as, but not limited to:

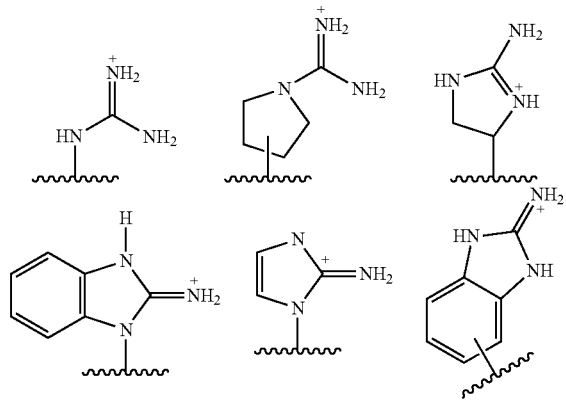

In another embodiment, Y, $Y_1$-$Y_n$ and/or Yq is independently histidine or a derivative of histidine such as, but not limited to or histidine derivatives such as:

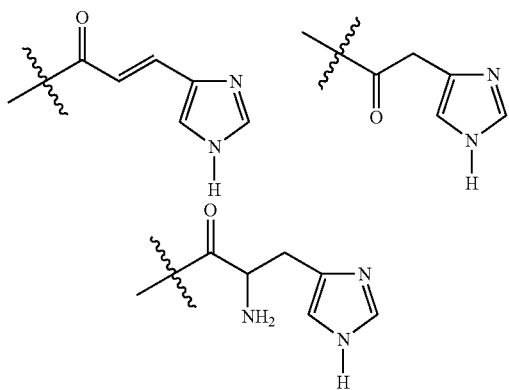

In one embodiment, the oligomeric Formula I, I(a), I(b), II, II(a), II(b), II(c), III(a-c), IV(a-c) and/or structure (A) comprises a delivery group Y, $Y_1$-$Y_n$ and/or Yq wherein Y, $Y_1$-$Y_n$ and/or Yq is a recognition moiety. The term "recognition moiety" describes a substance that interacts with a specific site by means of molecular recognition; a phenomenon also known as "host-guest chemistry", in which molecules are distinguished accurately from other molecules. Chemically, it indicates that certain molecules abnormally bond with other molecules (or the same species) with respect to other molecules found in the same environment. This phenomenon involves the three-dimensional positioning of various submolecular functionalities which can form interactions among molecules via such reciprocal actions as hydrogen bonds, hydrophobic interactions, ionic interaction, or other non-covalent bond interactions. Specific examples of molecular recognition include systems in which hydrophobic molecules are included in cyclodextrin as well as the relatively simple interaction between crown ether and alkali metals, ligand-receptor systems to complex systems such as protein-protein interaction.

Molecular recognition consists of static molecular recognition and dynamic molecular recognition. Static molecular recognition is likened to the interaction between a key and a keyhole; it is a 1:1 type complexation reaction between a host molecule and a guest molecule. To achieve advanced static molecular recognition, it is necessary to make recognition sites that are suitable for guest molecules. Dynamic molecular recognition is a molecular recognition reaction that dynamically changes the equilibrium to an n:m type host-guest complex by a recognition guest molecule. There are some equivalents by the combination of host molecules. Dynamic molecular recognition appearing in supramolecules is essential for designing highly functional chemical sensors and molecular devices. Thus, a recognition moiety is typically any substance that forms a part of a biological pair such as receptor-ligand, enzyme-substrate, antibody-antigen, biotin-avidin and the like.

Recognition moieties are used in the context of the present invention to selectively transport a biologically active moiety to a specific target, taking advantage of the high affinity of the recognition moiety to a biological moiety that is associated with or is present in the target.

In one embodiment, the structure of Formula I, I(a), I(b), II, II(a), II(b), II(c), III(a-c), IV(a-c) and structure (A) comprise a delivery group Y, $Y_1$-$Y_n$ and/or Yq wherein Y, $Y_1$-$Y_n$ and/or Yq which is a recognition moiety. In another embodiment, the recognition moiety is, for example, a ligand which in known to bind a receptor that is typically present in the desired target; a substrate or an inhibitor that can bind an enzyme that is typically present in the desired target; an antibody that an bind an antigen that is typically present in the desired target, an antigen of an antibody that is typically present in the desired target; a biotinylated moiety that can form a complex with strepavidin; or an avidin-containing moiety that can form a complex with mitochondrial biotin.

In one embodiment, the oligomer/conjugate/complexes described herein may include same or different delivering groups (Y, $Y_1$-$Y_n$, Yq) and thus can include several, same or different, membrane-permeability group, several, same or different, recognition moieties as described hereinabove and a combination of membrane-permeable groups and one or more recognition moieties.

In one embodiment, the oligomer/conjugate/complex of this invention may include one or more groups capable of being converted into delivering groups (Y, $Y_1$-$Y_n$, Yq). Such groups, which are also referred to herein as "pro-delivering groups" include, for example, functional groups that can be chemically converted to the delivering groups and functional groups to which the delivering moiety can be attached. Representative examples include amines, which, for example, by a simple reaction with 1h-Pyrazole-1-carboxamide, can be converted to guanidine, or which, by an addition reaction, can be used to attach various recognition moieties. Additional examples include reactive groups, as this term is defined herein, which are selected chemically compatible with functional groups in the recognition moiety and can thus be used to attached such moieties.

In one embodiment, the delivering and pro-delivering groups incorporated in the oligomer/conjugate described herein are optionally and preferably protected, namely, have protecting groups attached thereto. Protecting groups that are suitable for use in this context are detailed hereinbelow.

In one embodiment, the delivering group (Y, $Y_1$-$Y_n$, Yq) or the pro-delivering group can be attached to a building block residue in the oligomer/conjugate/complex either directly or via a linking group. A linking group linking the delivering group to the oligomer backbone is denoted as $A_1$-$A_n$ and/or Aq in the structures of Formula I, I(a), I(b), II, II(a), II(b) and/or II(c) above; and is also referred to herein as the second linking group. In another embodiment, the second linking group serves for chemically attaching the delivering moiety to the building block residue within the oligomer and may provide additional desired characteristics such a hydrophobic nature, a hydrophilic nature and an amphiphilic nature. The second linking group further enables to space the delivering group from the oligomer backbone. Such spacing is particularly advantageous in cases where the oligomer is an oligonucleotide since otherwise, the delivering group may affect the essential activity of the oligonucleotide in terms of hybridization (pairing) interactions, enzymatic reactions and the like. In another embodiment, the second linking groups include, without limitation, a substituted or unsubstituted, saturated or unsaturated hydrocarbon chain.

In another embodiment, $A_1$-$A_n$ and/or Aq in the structures of Formula I, I(a), I(b), II, II(a), II(b) and/or II(c) above is a linear alkyl. In another embodiment, $A_1$-$A_n$ and/or Aq is a branched alkyl. In another embodiment, $A_1$-$A_n$ and/or Aq is a substituted linear alkyl. In another embodiment, $A_1$-$A_n$ and/or Aq is a substituted branched alkyl, wherein substitutions are as defined for "alkyl" supra. In another embodiment, $A_1$-$A_n$ and/or Aq is a branched alkyl, substituted with an alkoxy group. In another embodiment, $A_1$-$A_n$ and/or Aq is an unsubstituted linear alkyl. In another embodiment, the alkyl has 2-50 carbon atoms. In another embodiment, the alkyl has 2-8 carbon atoms. In another embodiment, $A_1$-$A_n$ and/or Aq is a methylene. In another embodiment, $A_1$-$A_n$ and/or Aq is an ethylene ($CH_2$—$CH_2$). In another embodiment, $A_1$-$A_n$ and/or Aq is a propylene ($CH_2$—$CH_2$—$CH_2$). In another embodiment, $A_1$-$A_n$ and/or Aq is a butylene ($CH_2$—$CH_2$—$CH_2$—$CH_2$). In another embodiment, $A_1$-$A_n$ and/or Aq is a hexylene ($CH_2$—$CH_2$—$CH_2$—$CH_2$—$CH_2$—$CH_2$). In another embodiment, $A_1$-$A_n$ and/or Aq is a pentylene ($CH_2$—$CH_2$—$CH_2$—$CH_2$—$CH_2$). In another embodiment, $A_1$-$A_n$ and/or Aq are each independently ($CH_2$), wherein s is an integer between 1 and 10. In another embodiment, s is 3. In another embodiment, $A_1$-$A_n$ and/or Aq are each independently a methylene, ethylene, propylene, butylene, pentylene or hexylene.

In another embodiment, $A_1$-$A_n$ and/or Aq is independently a substituted or unsubstituted hydrocarbon chain interrupted by at least one double bond or triple bond, a heteroatom or any combination thereof, wherein, the heteroatom being selected from the group consisting of oxygen, nitrogen and sulfur. In another embodiment, $A_1$-$A_n$ and/or Aq is substituted or unsubstituted linear alkylether. In another embodiment, $A_1$-$A_n$ and/or Aq is substituted or unsubstituted branched alkylether. In another embodiment, the alkylether has 2-50 carbon atoms. In another embodiment, the alkylether has 2-8 carbon atoms. In another embodiment, $A_1$-$A_n$ and/or Aq is substituted or unsubstituted linear alkylphosphate. In another embodiment, $A_1$-$A_n$ and/or Aq is substituted or unsubstituted branched alkylphosphate. In another embodiment, the alkylphosphate has 2-50 carbon atoms. In another embodiment, the alkylphosphate has 2-8 carbon atoms. In another embodiment, the hydrocarbon chain of $A_1$-$A_n$ and/or Aq is an aliphatic, alicyclic and/or aromatic chain and thus may be composed of, for example, alkyls, alkenyls, alkynyls, cycloalkyls, and aryls, as these terms are defined herein, or any combination thereof.

In another embodiment, the hydrocarbon chain of $A_1$-$A_n$ and/or Aq comprises between 2 to 50 carbon atoms. In another embodiment, the hydrocarbon chain of $A_1$-$A_n$ and/or Aq comprises between 2 to 20 carbon atoms. In another embodiment, the hydrocarbon chain comprises between 2 to 10 carbon atoms. In another embodiment, the hydrocarbon chain comprises between 2 to 6 carbon atoms. In another embodiment, the hydrocarbon chain comprises between 4 to 6 carbon atoms. In another embodiment, the hydrocarbon chain comprises between 4 to 10 carbon atoms. In another embodiment, the hydrocarbon chain comprises between 2 to 8 carbon atoms. In another embodiment, the hydrocarbon chain comprises 2 carbon atoms. In another embodiment, the hydrocarbon chain comprises 3 carbon atoms.

In one embodiment, the bridging group $F_1$ in formula I(a) and I(b), or II(a), II(b) and II(c) may be connected to $Z_1$ or $Z_1'$ respectively either directly or via a linking group. Such a linking group is referred to herein as a third linking group and is denoted E of structures of Formula I(a), I(b), II(a), II(c), III(b-c) and/or IV(b-c). Likewise, the bridging group $F_{n+1}'$ in formula II(b) may be connected to $Z_2'$ either directly or via a linking group, which is denoted E'. In another embodiment, E and/or E' is a substituted or unsubstituted, saturated or unsaturated hydrocarbon chain of 2-50 carbon atoms. In another embodiment, E and/or E' is a linear alkyl of 2-50 carbon atoms. In another embodiment, E and/or E' is a linear alkyl of 2-8 carbon atoms. In another embodiment, E and/or E' is a branched alkyl of 2-50 carbon atoms. In another embodiment, E and/or E' is a branched alkyl of 2-8 carbon atoms. In another embodiment, E and/or E' is a substituted linear alkyl of 2-50 carbon atoms. In another embodiment, E and/or E' is a substituted linear alkyl of 2-8 carbon atoms. In another embodiment, E and/or E' is a substituted branched alkyl of 2-50 carbon atoms, wherein substitutions are as defined for "alkyl" supra. In another embodiment, E and/or E' is a substituted branched alkyl of 2-8 carbon atoms. In another embodiment, E and/or E' is a branched alkyl, substituted with an alkoxy group. In another embodiment, E and/or E' is an unsubstituted linear alkyl. In another embodiment, E and/or E' is a hexyl ($CH_2$—$CH_2$—$CH_2$—$CH_2$—$CH_2$—$CH_2$). In another embodiment, E and/or E' is a pentyl. In another embodiment, E and/or E is independently a substituted or unsubstituted hydrocarbon chain interrupted by at least one double bond or triple bond, a heteroatom or any combination thereof, wherein, the heteroatom being selected from the group consisting of oxygen, nitrogen and sulfur. In another embodiment, E and/or E' is substituted or unsubstituted linear alkylether of 2-50 carbon atoms. In another embodiment, E and/or E' is substituted or unsubstituted linear alkylether of 2-8 carbon atoms. In another embodiment, E and/or E' is substituted or unsubstituted branched alkylether of 2-50 carbon atoms. In another embodiment, E and/or E' is substituted or unsubstituted branched alkylether of 2-8 carbon atoms. In another embodiment, E and/or E' is substituted or unsubstituted linear alkylphosphate of 2-50 carbon atoms. In another embodiment, E and/or E' is substituted or unsubstituted linear alkylphosphate of 2-8 carbon atoms. In another embodiment, E and/or E' is substituted or unsubstituted branched alkylphosphate of 2-50 carbon atoms. In another embodiment, E and/or E' is substituted or unsubstituted branched alkylphosphate of 2-8 carbon atoms. In another embodiment, E and/or E' is absent.

In another embodiment, the hydrocarbon chain of E and/or E' comprises between 2 to 20 carbon atoms. In another embodiment, the hydrocarbon chain of E and/or E' comprises between 2 to 50 carbon atoms. In another embodiment, the hydrocarbon chain comprises between 2 to 10 carbon atoms. In another embodiment, the hydrocarbon chain comprises between 2 to 6 carbon atoms. In another embodiment, the hydrocarbon chain comprises between 4 to 6 carbon atoms. In another embodiment, the hydrocarbon chain comprises between 4 to 10 carbon atoms. In another embodiment, the hydrocarbon chain comprises between 2 to 8 carbon atoms.

In one embodiment, this invention is directed to a conjugate comprising an oligomer compound of this invention and a biologically active moiety, which are covalently attached to each other. In one embodiment, the conjugate of this invention (Formula II, II(a-c), IV, IV(a-c) and/or V), is a delivery system. In another embodiment, the delivery system of this invention delivers a biologically active moiety into a cell. In another embodiment, the oligomer of Formula I, I(a-b), III and/or III(a-c) terminates by at least one reactive group (denoted herein as $Z_1$-$Z_2$), as is further detailed hereinunder, which is capable of reacting with a desired biologically active moiety. The oligomer of this invention, therefore includes one or two reactive groups, depending on the desired number of biologically active moieties that would be attached thereto. Similarly, each of the reactive groups is selected depending on the chemical nature of the biologically active moiety, so as to be chemically compatible with functional groups present within the biological moiety.

In one embodiment, the oligomeric compound of this invention comprises a reactive group ($Z_1$-$Z_2$) capable of binding a biologically active moiety. According to still further features in the described preferred embodiments each of $Z_1$ and/or $Z_2$ is hydroxy, amine, halide, a phosphorous-containing group (such as a phosphoramidite), C-amide, N-amide, carboxy, thiol, COOH, thioamide, thiocarboxy, alkoxy, thioalkoxy, aryloxy, thioaryloxy, hydrazine, hydrazide, epoxide, —N=C=S, NH—CO—NH$_2$, NH—CS—NH$_2$ or any combination thereof. In another embodiment, at least one of the reactive groups is a protected reactive group. In another embodiment, $Z_1$ is a reactive group and $Z_2$ is hydrogen. In another embodiment, $Z_1$ is hydrogen and $Z_2$ is a reactive group. In another embodiment, both $Z_1$ and $Z_2$ are reactive groups.

In another embodiment, the oligomeric compound of Formula I, I(a-b), III and/or III(a-c) comprises a reactive group ($Z_1$-$Z_2$) capable of binding a biologically active moiety. Upon binding the biologically active moiety, by, for example, but not limited to, a coupling reaction or substituted reaction, the $Z_1$-$Z_2$ may be derivatized to yield the corresponding $Z_1$' and/or $Z_2$'. It is understood that if $Z_1$ and/or $Z_2$ is a halogen, then, upon reacting with the biologically active moiety, the halogen group may be removed from the oligomeric structure and T will be linked directly to F or L. It is also understood that if $Z_1$ and/or $Z_2$ are hydroxyl, then upon binding the biologically active moiety, the —OH group may be an —O— bridge ($Z_1$' or $Z_2$'); etc. . . .

The term "oligomer" as used herein, describes a chemical substance, or a residue of a chemical substance, which is made up of two or more basic units which are chemically linked one to another in a sequential manner, thus forming a chain of repeating residues of these units, which constitutes the oligomer.

As used herein, the phrase "building block" describes a basic unit, which serves for assembling an oligomer, as this term is defined herein. (denoted herein as "X")

As is well known in the art, the term "residue" refers herein to a major portion of a molecule, which is chemically linked to another molecule.

In one embodiment, the building blocks of this invention $X_1$-Xn and/or Xq constructing the oligomers provided herein are identical, similar (belonging to the same family of compounds) or different one from the other (belonging to a different family of compounds).

In one embodiment, the structures of Formula I, I(a), I(b) II, II(a), II(b) and/or II(c), comprises building block residues (denoted herein as "$X_1$-$X_n$ or Xq") constructing the oligomeric compound; have one or more, preferably two or more, more preferably three delivering groups linked thereto either directly or indirectly. The incorporation of the delivering groups can be performed by providing a corresponding unmodified oligomer and modifying the oligomer by attaching thereto a delivering group or a linking group to which a delivering group is attached. Alternatively, modified building blocks incorporating the delivering group can be first prepared and then assembled to form the oligomer. In any event, the building blocks are selected so as to allow the formation of such a delivering group-containing oligomer.

The term "delivering" or "delivery" as used in the context of the present invention refers to the act of enabling the transport of a substance to a specific location, and more specifically, to a desired bodily target, whereby the target can be, for example, an organ, a tissue, a cell, and a cellular compartment such as the nucleus, the mitochondria, the cytoplasm, etc. The reactive group(s) ($Z_1$-$Z_2$), as well as the delivering groups and the pro-delivering groups, in the oligomer described herein, can be protected by a protecting group. The protecting groups are selected chemical compatible with the oligomerization process and the binding process to the biologically active moiety that follows. The protecting group is therefore selected such that it provides a selective stability to the protected group during or subsequent to the various synthetic and/or enzymatic processes undertaken on route to the final oligomer and may be further selected by the conditions required for its removal. Such conditions should not affect other desirable moieties that are present within the oligomer. The term "protecting group" as used herein refers to a group that when attached to a reactive group in a molecule, selectively masks, reduces or prevents the reactivity of the reactive group. Examples of protecting groups can be found in Green et al., "Protective Groups in Organic Chemistry", (Wiley, 2.sup.nd ed. 1991) and Harrison et al., "Compendium of Synthetic Organic Methods", Vols. 1-8 (John Wiley and Sons, 1971.

In one embodiment, the X(A-Y)m of Formula I, I(a), I(b) II, II(a), II(b) and/or II(c) is represented by the structure of Formula XXIV:

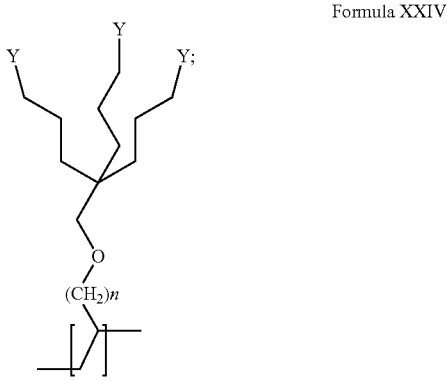

Formula XXIV wherein Y is as defined hereinabove; and n is an integer between 0 and 5.

In one embodiment, the precursor of the X(A-Y)m building block of oligomer of Formula I, I(a), I(b) II, II(a), II(b) and/or II(c) is represented by the structure of Compound XXIVa:

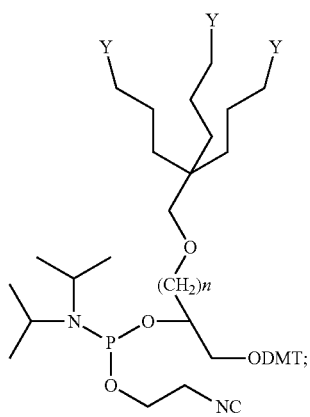

Compound XXIVa wherein Y is as defined hereinabove; and n is an integer between 0 and 5.

In one embodiment, the precursor of the X(A-Y)m building block of oligomer of Formula I, I(a), I(b) II, II(a), II(b) and/or II(c) is represented by the structure of Compound XXIVb:

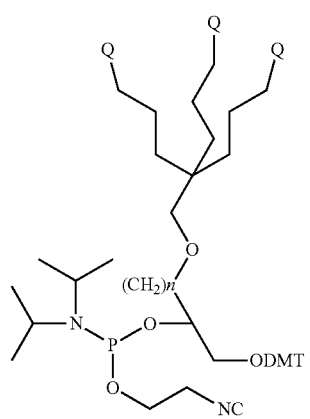

Compound XXIVb wherein Q is —NHC(O)CF$_3$ and DMT refers to dimethoxytrityl; and n is an integer between 1 and 5. By incorporating one or more delivering groups (denotes herein as $Q_1$-$Q_n$, Q moiety will be converted to Y by several chemical steps as it is described in the Examples.) In another embodiment Q is:

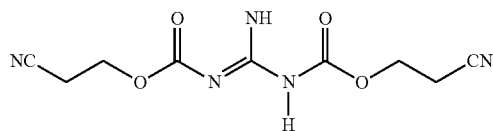 [SMILES: N#CCCOC(=O)/N=C(\N)NC(=O)OCCC#N]

The oligomeric compounds conjugates and complexes I, I(a-b), II, II(a-c), III, III(a-c), IV, IV(a-c) and/or V described herein can efficiently serve as a delivery system for delivering desired moieties to desired bodily targets, upon conjugating or complexing thereto such a desired moiety.

In one embodiment, the oligomeric conjugate of Formula II, II(a-c), IV and/or IV(a-c) comprises at least one biologically active moiety $T_1$-$T_4$. According to still further features in the described preferred embodiments the biologically active moiety is a therapeutically active agent, a drug, a labeling moiety, or any combination thereof. In another embodiment, the therapeutically active agent is an oligonucleotide, a nucleic acid construct, an antisense, a plasmid, a polynucleotide, an amino acid, a peptide, a polypeptide, a hormone, a steroid, an antibody, an antigen, a radioisotope, a chemotherapeutic agent, a toxin, an anti-inflammatory agent, a growth factor or any combination thereof. In another embodiment, the labeling moiety is a fluorescent moiety, a radiolabeled moiety, a phosphorescent moiety, a heavy metal cluster moiety or any combination thereof.

In one embodiment E of Formula I(a), I(b), II(a), II(c), III(b-c) and/or IV(b-c) binds to a reactive group (denoted herein as "$Z_1$ and/or $Z_2$") capable of binding a biologically active moiety being attached thereto, or derivative thereof (denoted herein as "$Z_1$' and/or $Z_2$'". In another embodiment, $T_1$, $T_2$, $T_3$ and/or $T_4$ binds to one of $L_1$-Ln, Lq or one of "F".

In one embodiment, the conjugate of Formula II, II(a), II(c), IV and/or IV(a-c) and the oligomer compound of Formula I, I(a), I(b), III and/or III(a-c) comprise the same backbone respectively, wherein the conjugate of Formula II, II(a), II(c), IV and/or IV(a-c) is formed upon conjugating the oligomeric compound of Formula I, I(a), I(b), III and/or III(a-c), via the $Z_1$ and/or $Z_2$ reactive groups (see, general Formula I, I(a), IN, III and/or III(a-c) above) with one or more biologically active moieties, as is detailed hereinbelow. Following such a conjugation, $T_1$ and $T_2$ biologically active moieties in general Formula II, II(a), II(c), IV and/or IV(a-c) above, are attached through reactive groups derivatives, $Z_1$' and/or $Z_2$', to the delivery system. It is to be understood that when either one of $T_1$-$T_2$ is absent in formula II, II(a), II(c), IV and/or IV(a-c), it is replaced with a hydrogen atom.

In one embodiment, the reactive group (e.g., $Z_1$) in the delivery system, oligomer compound of Formula I, I(a), I(b), III and/or III(a-c) is an epoxide, which is reacted with a drug having an amine functional group and a conjugate —CH(OH)—CH$_2$—NH-drug moiety is formed.

The nature of the reactive groups can be determined, based on the functional group of the biologically active moiety which is attached to the oligomer.

Biologically active moieties that can be beneficially delivered into various bodily targets by utilizing the delivery system described herein include, for example, therapeutically active agents, labeling agents (moieties) and combinations thereof, that is, labeled therapeutically active agents.

The term "biologically active moiety" as used herein describes a molecule, compound, complex, adduct and composite which has a biological function and/or exerts one or more pharmaceutical activities, either in vivo or in vitro, and is used to prevent, treat, diagnose or follow a medical condition of any sort at any stage and in any subject.

The term "therapeutically active agent" as used herein describes a molecule, compound, complex, adduct and composite, which exerts one or more pharmaceutical activities, and is used to prevent, ameliorate or treat a medical condition.

Representative examples of therapeutically active agents that can be beneficially incorporated in the delivery system described herein include, without limitation agonists, amino acids, antagonists, nucleic acid, protected nucleic acids, DNA, RNA, modified DNA, modified RNA, anti histamines, antibiotics, antigens, antidepressants, anti-hypertensive agents, anti-inflammatory agents, antioxidants, anti-proliferative agents, antisense, anti-viral agents, chemotherapeutic agents, co-factors, fatty acids, growth factors, haptens, hormones, inhibitors, ligands, oligonucleotides, labeled oligonucleotides, nucleic acid constructs peptides, polypeptides, polysaccharides, radioisotopes, steroids, toxins, vitamins and radioisotopes and any combination thereof. Non-limiting examples of chemotherapeutic agents include amino containing chemotherapeutic agents such as daunorubicin, doxorubicin, N-(5,5-diacetoxypentyl)doxorubicin, anthracycline, mitomycin C, mitomycin A, 9-amino camptothecin, aminopertin, antinomycin, $N^8$-acetyl spermidine, 1-(2-chloroethyl)-1,2-dimethanesulfonyl hydrazine, bleomycin, tallysomucin, and derivatives thereof; hydroxy containing chemotherapeutic agents such as etoposide, camptothecin, irinotecaan, topotecan, 9-amino camptothecin, paclitaxel, docetaxel, esperamycin, 1,8-dihydroxy-bicyclo[7.3.1]trideca-4-ene-2,6-diyne-13-one, anguidine, morpholino-doxorubicin, vincristine and vinblastine, and derivatives thereof, sulfhydril containing chemotherapeutic agents and carboxyl containing chemotherapeutic agents, as well as platinum-containing agents such as cisplatin.

Examples of radio-isotopes include cytotoxic radio-isotopes such as β radiation emitters, γ emitters and α-radiation emitting materials. Examples of β radiation emitters which are useful as cytotoxic agents, include isotopes such as scandium-46, scandium-47, scandium-48, copper-67, gallium-72, gallium-73, yttrium-90, ruthenium-97, palladium-100, rhodium-101, palladium-109, samarium-153, rhenium-186, rhenium-188, rhenium-189, gold-198, radium-212 and lead-212. The most useful γ emitters are iodine-131 and indium-m 114. Other radio-isotope useful with the invention include α-radiation emitting materials such as bismuth-212, bismuth-213, and At-211 as well as positron emitters such as gallium-68 and zirconium-89.

Examples of enzymatically active toxins and fragments thereof which can be used as cytotoxic agents include diphtheria A chain toxin, non-binding active fragments of diphtheria toxin, exotoxin A chain (from *Pseudomonas aeruginosa*), shiga toxin, verotoxin, ricin A chain, abrin A chain toxin, modeccin A chain toxin, α-sarcin toxin, *Abrus precatorius* toxin, amanitin, pokeweed antiviral protein, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

Non-limiting examples of antibiotics include octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids. Non-limiting examples of non-steroidal anti-inflammatory agents include oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone.

Non-limiting examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Non-limiting examples of anti-oxidants include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox$^R$), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of vitamins include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of hormones include androgenic compounds and progestin compounds such as methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, flurogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

Ligands, inhibitors, agonists, antagonists, co-factors and the like can be selected according to a specific indication.

According to a preferred embodiment of the present invention, the therapeutically active agent is a genetic material, namely, a nucleic acid agent, including oligonucleotides, polynucleotides (nucleic acids), antisense and antisense-producing oligonucleotides as these are defined herein, chromosomes and nucleic acid constructs such as plasmids. Such genetic substances are collectively referred to herein as nucleic acid agents or oligonucleotides.

The term "plasmid" refers to a circular, double-stranded unit of DNA that replicates within a cell independently of the chromosomal DNA. Plasmids are most often found in bacteria and are used in recombinant DNA research to transfer genes between cells, used as a vector for gene insertion or genetic engineering uses. Plasmids are often the site of genes that encode for resistance to antibiotics.

The term "chromosome" as used herein describes small bodies in the nucleus of a cell that carry the chemical "instructions" for reproduction of the cell and consist of double-stranded DNA wrapped in coils around a core of proteins. Each species of plant or animal has a characteristic number of chromosomes (46 in humans).

The term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly. The term includes modified RNA or modified DNA. In another embodiment the modified RNA and/or DNA include protected bases.

As used herein the term "an isolated polynucleotide" refers to a nucleic acid sequences which is isolated and provided in the form of an RNA sequence, a complementary polynucleotide sequence (cDNA), a genomic polynucleotide sequence and/or a composite polynucleotide sequences (e.g., a combination of the above).

As used herein the term "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the term "genomic polynucleotide sequence" refers to a sequence derived (isolated) from a chromosome and thus it represents a contiguous portion of a chromosome.

As used herein the term "composite polynucleotide sequence" refers to a sequence, which is at least partially complementary and at least partially genomic. A composite sequence can include some exonal sequences required to encode the polypeptide of the present invention, as well as some intronic sequences interposing there between. The intronic sequences can be of any source, including of other genes, and typically will include conserved splicing signal sequences. Such intronic sequences may further include cis acting expression regulatory elements.

Alternatively, oligonucleotides may include small interfering duplex oligonucleotides [i.e., small interfering RNA (siRNA)], which direct sequence specific degradation of mRNA through the previously described mechanism of RNA interference (RNAi) [Hutvagner and Zamore (2002) Curr. Opin. Genetics and Development 12:225-232].

As used herein, the phrase "duplex oligonucleotide" refers to an oligonucleotide structure or mimetics thereof, which is formed by either a single self-complementary nucleic acid strand or by at least two complementary nucleic acid strands. The "duplex oligonucleotide" of the present invention can be composed of double-stranded RNA (dsRNA), a DNA-RNA hybrid, single-stranded RNA (ssRNA), isolated RNA (i.e., partially purified RNA, essentially pure RNA), synthetic RNA and recombinantly produced RNA.

A small interfering duplex oligonucleotide can be an oligoribonucleotide composed mainly of ribonucleic acids.

Instructions for generation of duplex oligonucleotides capable of mediating RNA interference are provided in www.ambion.com.

Nucleic acid constructs are substances that enable the cellular expression of polynucleotides and typically include a polynucleotide or an oligonucleotide and at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). The nucleic acid construct can further include an enhancer, which can be adjacent or distant to the promoter sequence and can function in up regulating the transcription therefrom.

The nucleic acid construct can further include an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

The term "antisense" as used in the context of the present invention, is of or relating to a nucleotide sequence that is complementary to a sequence of messenger RNA. When antisense DNA or RNA is added to a cell, it binds to a specific messenger RNA molecule and inactivates it thus can be a useful tool for gene therapy.

Antisenses can also include antisense molecules, which are chimeric molecules. "Chimeric antisense molecules", are oligonucleotides, which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target polynucleotide. An additional region of the oligonucleotide may serve as a substrate for enzymes capable of cleaving RNA:DNA or RNA:RNA hybrids. An example for such include RNase H, which is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense molecules may be formed as composite structures of two or more oligonucleotides, modified oligonucleotides, as described above. Representative U.S. patents that teach the preparation of such hybrid structures include, but are not limited to, U.S. Pat. Nos. 5,013,830; 5,149,797, each of which is herein fully incorporated by reference.

The incorporation of the genetic therapeutically active agents described above in the delivery systems according to the present invention is highly beneficial since (i) as is discussed in detail hereinabove, such agents may be beneficially used to treat medical conditions by interfering with the condition cause rather than symptoms; and (ii) the use of such agents in in vivo applications is limited by their poor resistance to biological environment. Thus, by incorporating such agents in the delivery systems described herein, efficient and rapid delivery thereof into cells and cell nuclei is achieved, thus overcoming the limitations associated with rapid elimination thereof.

Other preferable therapeutically active agents that can be efficiently used as biologically active moieties delivered by the delivery system according to the present invention include amino acids peptides, and polypeptides (proteins).

As used herein, the term "labeling moiety" refers to a detectable moiety, a tag or a probe which can be used in the diagnosis and following of medical conditions both in vitro and in vivo, and includes, for example, chromophores, phosphorescent and fluorescent compounds, heavy metal clusters, radioactive labeling (radiolabeled) compounds, as well as any other known detectable moieties.

As used herein, the term "chromophore" refers to a chemical moiety that, when attached to another molecule, renders the latter colored and thus visible when various spectrophotometric measurements are applied.

The term "fluorescent compound" refers to a compound that emits light at a specific wavelength during exposure to radiation from an external source.

The term "phosphorescent compound" refers to a compound emitting light without appreciable heat or external excitation as by slow oxidation of phosphorous.

A heavy metal cluster can be for example a cluster of gold atoms used, for example, for labeling in electron microscopy techniques.

Radio-labeled compounds can be almost any compound into which a radioactive isotope is incorporated. A radioactive isotope is an element which is an $\alpha$-radiation emitters, a $\beta$-radiation emitters or a $\gamma$-radiation emitters.

An example of a therapeutically active agent which can also serve as a labeling moiety is a radio-labeled oligonucleotide into which, for example, an isotope of phosphorous is incorporated. Another example of a therapeutically active agent which can also serve as a labeling moiety is an oligonucleotide to which a chromophore, a fluorescent compound or a fluorescence compound is attached. An exemplary chromophore is Fluorescein.

Any of the biologically active moieties used in the context of the present invention can be incorporated into or onto a variety of carriers such as, but not limited to, liposomes, nanoparticles, microparticles and polymers, which are attached to the delivery moiety.

Liposomes are artificial microscopic vesicles consisting of an aqueous core enclosed in one or more phospholipid layers, used to convey vaccines, drugs, enzymes, or other substances to target cells or organs.

A nanoparticle or a microparticle is a microscopic particle whose size is measured in nanometers or micrometers which can be used in biomedical applications acting as drug carriers or imaging agents.

While, as is shown in general Formula I, I(a-b), II, II(a-c), III, III(a-c), IV and/or IV(a-c), the delivery system have up to two reactive groups to which the biologically active moiety is attached, the conjugates described herein comprise, in one embodiment, two biologically active moieties. In another embodiment, the conjugate of Formula II(a), II(c), IV or IV(a-c) comprise one biologically active moiety. In another embodiment, the conjugate of Formula II(a), II(c), IV or IV(a-c) comprise two biologically active moieties. In another embodiment, the conjugate of Formula II or II(b) comprise four biologically active moieties. In another embodiment, the conjugate of Formula II or II(b) comprise three biologically active moieties. The biologically active ($T_1$-$T_4$) moieties can be the same (identical), similar (of the same family of substances) or different. In one embodiment, $T_1$ is a drug. In another embodiment $T_1$ is a drug, $T_2$ is a fluorescent tag, and $COM_1$, $COM_2$, $T_3$ and $T_4$ are nothing. In another embodiment, $T_1$, $T_2$, $T_3$ or $T_4$ is a combination of a drug and a fluorescent tag. In another embodiment, both $T_1$ and $T_2$ of the conjugate of Formula II(a), II(c), IV or IV(a-c) is a fluorescent tag. In another embodiment, both $T_1$ and $T_2$ of the conjugate of Formula II(a), II(c), IV or IV(a-c) is a dye. In another embodiment, both $T_1$ and $T_2$ of the conjugate of Formula II(a), II(c), IV or IV(a-c) is Fluorecein.

Thus, for example, the biologically active moieties can include a therapeutically active agent and a labeling moiety, which would enable detection of the active agents in the body.

In a preferred embodiment of the present invention, the biologically active moieties conjugated to the oligomeric compounds are fluorescent tags and the biologically active substances complexed to the delivery moiety by electrostatic interactions are oligonucleotides. In another embodiment, the oligonucleotides are RNA, DNA or combination thereof.

In another preferred embodiment of the present invention, the biologically active moieties conjugated to the delivery moiety are oligonucleotides.

Such conjugates can be formed by designing a delivery moiety to which the 5' end and/or the 3' end of an oligonucleotide can be attached.

As is exemplified in the Examples section that follows, such delivery moieties have been designed and successfully used for providing such conjugates, by appropriately selecting the building blocks, the reactive groups and the protecting groups used for constructing such a conjugate by convenient solid phase syntheses and/or enzymatic syntheses.

In one embodiment, a conjugate of Formula II and/or II(a-c) is presented by the structure of Compound 23:

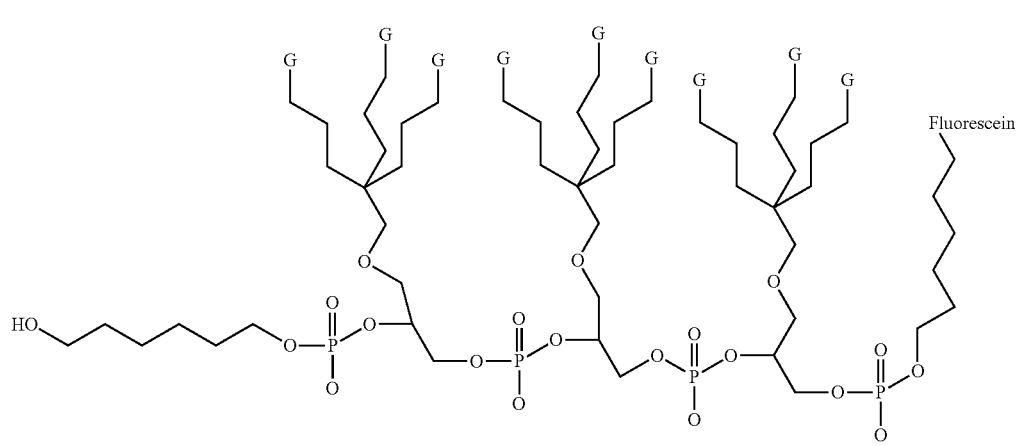

Compound 23

Wherein G is a guanidine group.

In one embodiment, a conjugate of Formula II or II(b) is presented by the structure of Compound 42:

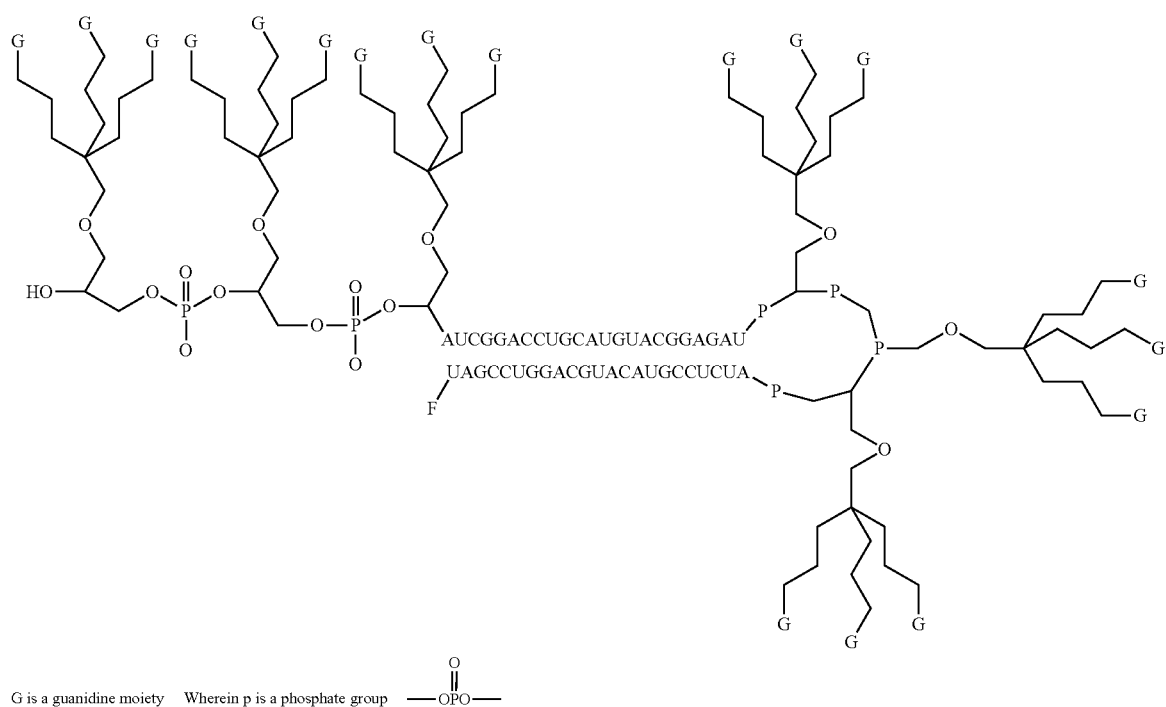

G is a guanidine moiety    Wherein p is a phosphate group    $-O-\overset{\overset{O}{\|}}{\underset{OH}{P}}-O-$ AUCGGACCUGCAUGUACGGAGAU (SEQ ID No: 3)

UAGCCUGGACGUACAUGCCUCUA (SEQ ID No: 4)

A conjugate according to this embodiment of the present invention can be beneficially utilized for delivering various oligonucleotides, including plasmids, nucleic acid constructs, antisenses and nucleic acids, as described hereinabove, into cells.

The conjugates described herein, by containing a biologically active moiety, can therefore be efficiently used for delivering various biologically active moieties into a desired bodily site. These conjugates are particularly useful for delivering various biologically active moieties to cells.

Methods of Delivering Biologically Active Moiety into the Cell

Hence, according to another aspect of the present invention there is provided a method of delivering a biologically active moiety to a target. In another embodiment the target is a cell. In another embodiment, the biologically active moiety is an oligonucleotide. The method is effected by contacting cells with an oligomer, a conjugate or a complex as described hereinabove, and preferably with complexes of conjugates and oligonucleotides and/or nucleic acid agents, as described hereinabove.

According to another embodiment, there is provided a method of delivering an oligonucleotide to a cell, said method comprises contacting a complex of an oligomer or a conjugate according to the invention and an oligonucleotide, with the cell, thereby delivering said oligonucleotide to said cell. In another embodiment, the oligonucleotide is RNA. In another embodiment, the oligonucleotide is DNA. In another embodiment, the oligonucleotide is a combination of RNA and DNA. In another embodiment, the cell is a cancerous cell.

According to another embodiment, there is provided a method of treating cancer, comprising contacting a complex of an oligomer or a conjugate according to the invention and an oligonucleotide, with a cancer cell, thereby treating cancer.

Contacting the cells with the conjugate and/or complex can be effected either in-vivo or ex-vivo. When performed ex-vivo, the cells can be contacted with the conjugate and/or complex by incubating the cells with a solution containing the conjugate and/or complex and a buffer, at a temperature that ranges from 4° C. to 37° C.

In a preferred embodiment, the cell can be an animal cell that is maintained in tissue culture such as cell lines that are immortalized or transformed. These include a number of cell lines that can be obtained from American Type Culture Collection (Bethesda) such as, but not limited to: 3T3 (mouse fibroblast) cells, Rat1 (rat fibroblast) cells, CHO (Chinese hamster ovary) cells, CV-1 (monkey kidney) cells, COS (monkey kidney) cells, 293 (human embryonic kidney) cells, HeLa (human cervical carcinoma) cells, HepG2 (human hepatocytes) cells, Sf9 (insect ovarian epithelial) cells and the like.

In another preferred embodiment, the cell can be a primary or secondary cell which means that the cell has been maintained in culture for a relatively short time after being obtained from an animal. These include, but are not limited to, primary liver cells and primary muscle cells and the like. The cells within the tissue are separated by mincing and digestion with enzymes such as trypsin or collagenases which destroy the extracellular matrix. Tissues consist of several different cell types and purification methods such as gradient centrifugation or antibody sorting can be used to obtain purified amounts of the preferred cell type. For example, primary myoblasts are separated from contaminating fibroblasts using Percoll (Sigma) gradient centrifugation.

In another preferred embodiment, the cell can be an animal cell that is within the tissue in situ or in vivo meaning that the cell has not been removed from the tissue or the animal. When performed in-vivo, contacting the cells with the conjugate can be effected by administering the compound to a subject in need thereof.

The oligomers/conjugates and/or complexes described herein can be administered or otherwise utilized according to the various aspects of the present inventions either per se or as a part of a pharmaceutical composition.

According to another aspect of the present invention there is provided a method of delivering a biologically active moiety to a cell, said method comprises attaching at least one biologically active moiety to an oligomer, said oligomer comprises at least two backbone residues to which are attached at least two delivering groups which enable the transport of the oligomer to a desired bodily site; at least one linking group linking between the backbone residues; and phosphate moieties connecting between the linking groups and the backbone residues; said method is effected by contacting cells with said oligomer.

According to another embodiment, there is provided a use of an oligomer/conjugate and/or a complex according to the present invention for delivering a biologically active moiety into a cell. In another embodiment, the biologically active moiety is electrostatically bound to the oligomer and/or conjugate, thereby forming a complex with said oligomer and/or conjugate. In another embodiment, the cell is a cancer cell.

According to another embodiment, there is provided a use of an oligomer/conjugate and/or a complex according to the present invention for preparation of a medicament for treating cancer.

According to another embodiment, there is provided a use of a conjugate according to the present invention for diagnosing a condition, comprising contacting a conjugate according to the present invention with a cell, thereby delivering the labeling moiety of the conjugate to the cell and diagnosing the condition.

Pharmaceutical Composition

Thus, according to another aspect of the present invention there is provided a pharmaceutical composition, which comprises the oligomer, conjugate or complex, as described herein, and a pharmaceutically acceptable carrier.

As used herein a "pharmaceutical composition" refers to a preparation of one or more of the oligomers, conjugates and/or complexes described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

In one embodiment, pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the oligomers, conjugates or complexes into preparations which, can be used pharmaceutically. Proper formulation is dependent upon the route of administration chosen.

For injection, the oligomers, conjugates or complexes described herein may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the oligomers, conjugates or complexes described herein can be formulated readily by combining the oligomers, conjugates or complexes with pharmaceutically acceptable carriers well known in the art. Such carriers enable the oligomers, conjugates or complexes of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active doses of the oligomers, conjugates or complexes.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the oligomers, conjugates or complexes may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

The oligomers, conjugates or complexes described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the oligomers, conjugates or complexes preparation in water-soluble form. Additionally, suspensions of the oligomers, conjugates or complexes may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the oligomers, conjugates or complexes to allow for the preparation of highly concentrated solutions.

Alternatively, the oligomers, conjugates or complexes may be in powder form for constitution with a suitable vehicle, e.g., sterile, pyrogen-free water, before use.

The oligomers, conjugates or complexes described herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of oligomers, conjugates or complexes effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any oligomers, conjugates or complexes used in the context of the invention, the therapeutically effective amount or dose can be estimated initially from activity assays in animals. For example, a dose can be formulated in animal models to achieve a circulating concentration range that includes the $IC_{50}$ as determined by activity assays. Such information can be used to more accurately determine useful doses in humans.

Toxicity and therapeutic efficacy of the oligomers, conjugates or complexes described herein can be determined by standard pharmaceutical procedures in experimental animals, e.g., by determining the $EC_{50}$, the $IC_{50}$ and the $LD_{50}$ (lethal dose causing death in 50% of the tested animals) for a subject conjugates. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the desired effects, termed the minimal effective concentration (MEC). The MEC will vary for each preparation, but can be estimated from in vitro data; e.g., the concentration necessary to achieve 50-90% vasorelaxation of contracted arteries. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising an oligomer, conjugate or complex as described herein formulated in a compatible pharmaceutical carrier may also be prepared, placed in an appropriate container, and labeled for treatment of an indicated condition or diagnosis, depending on the biological moiety used.

Thus, according to an embodiment of the present invention, depending on the selected components of the oligomers, conjugates or complexes, the pharmaceutical compositions of the present invention are packaged in a packaging material and identified in print, in or on the packaging material, for use in the treatment of a condition in which delivering of the biological moiety to a certain bodily target is beneficial. Such conditions include, for example, any medical conditions in which intracellular administration of the active moiety is therapeutically or diagnostically beneficial.

As mentioned hereinabove, the design of the oligomers, conjugates or complexes described herein was done while taking into consideration the conditions at which such oligomers, conjugates or complexes can be assembled, in view of the relative high reactivity and instability of at least some of the components thereof. Thus, special synthetic methods have been developed to that end, as follows.

Figure 2:
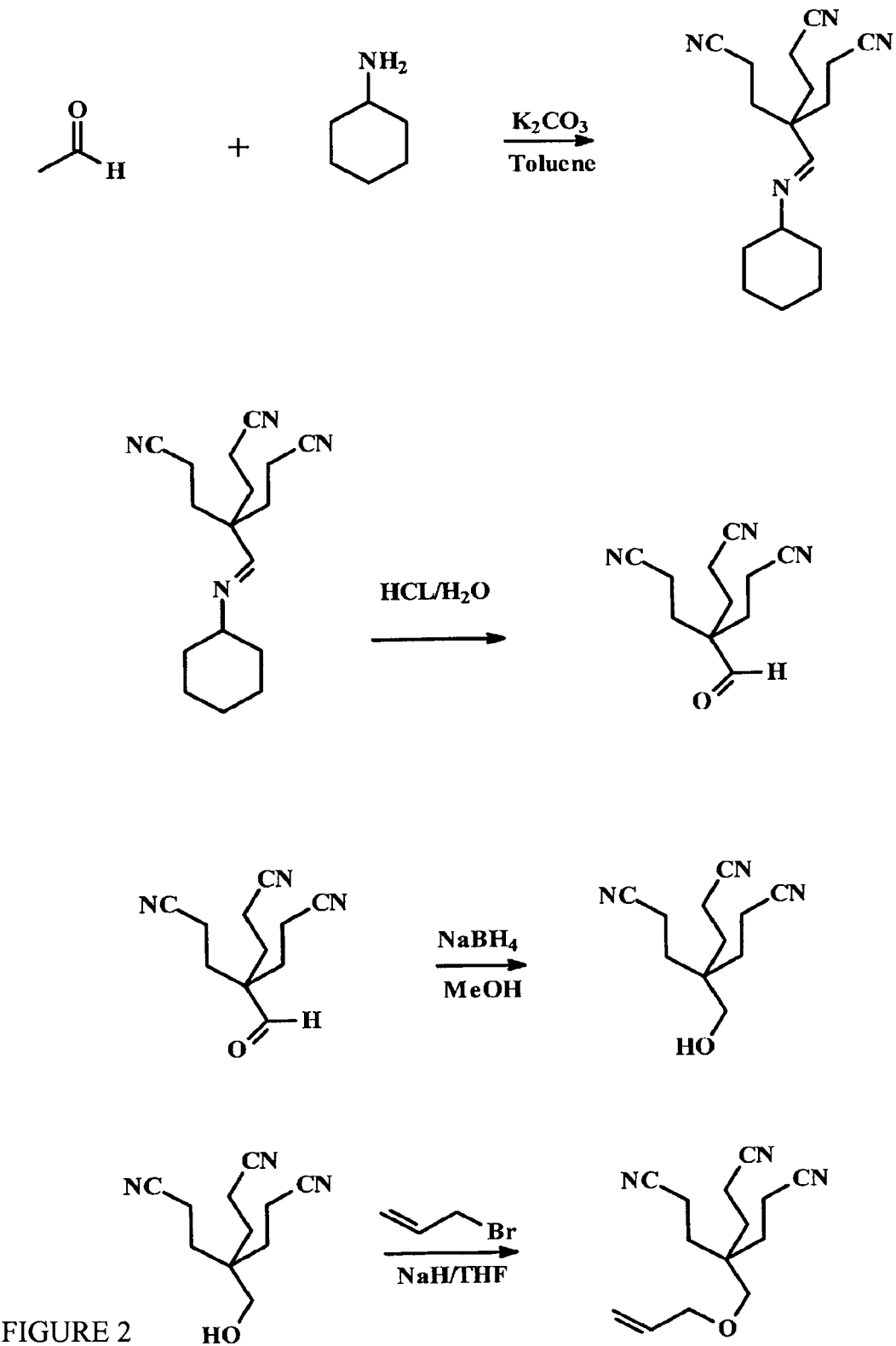
FIG. 2 depicts a synthetic scheme for the preparation of Compound 23.
Figure 2:
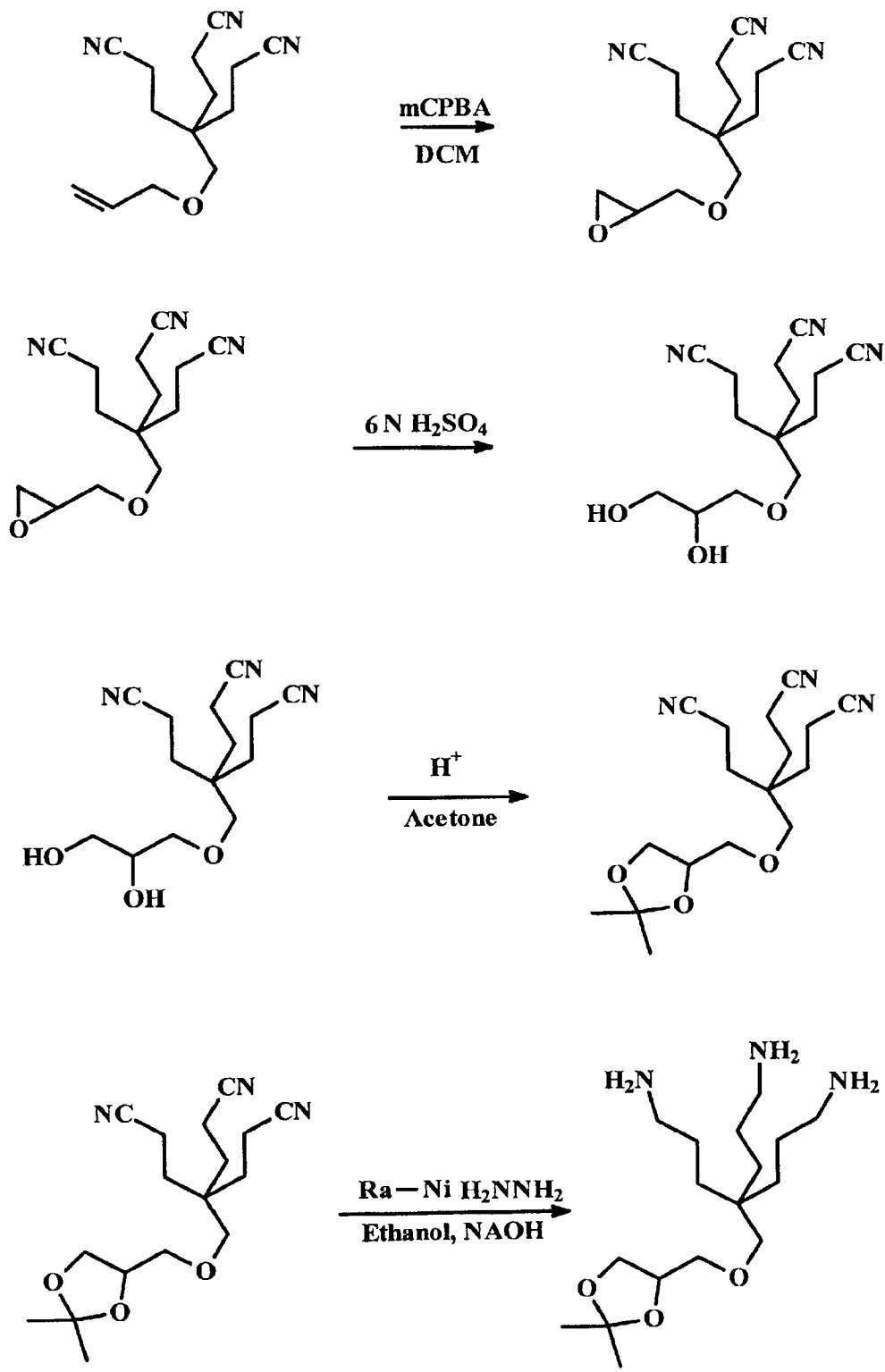
Figure 2:
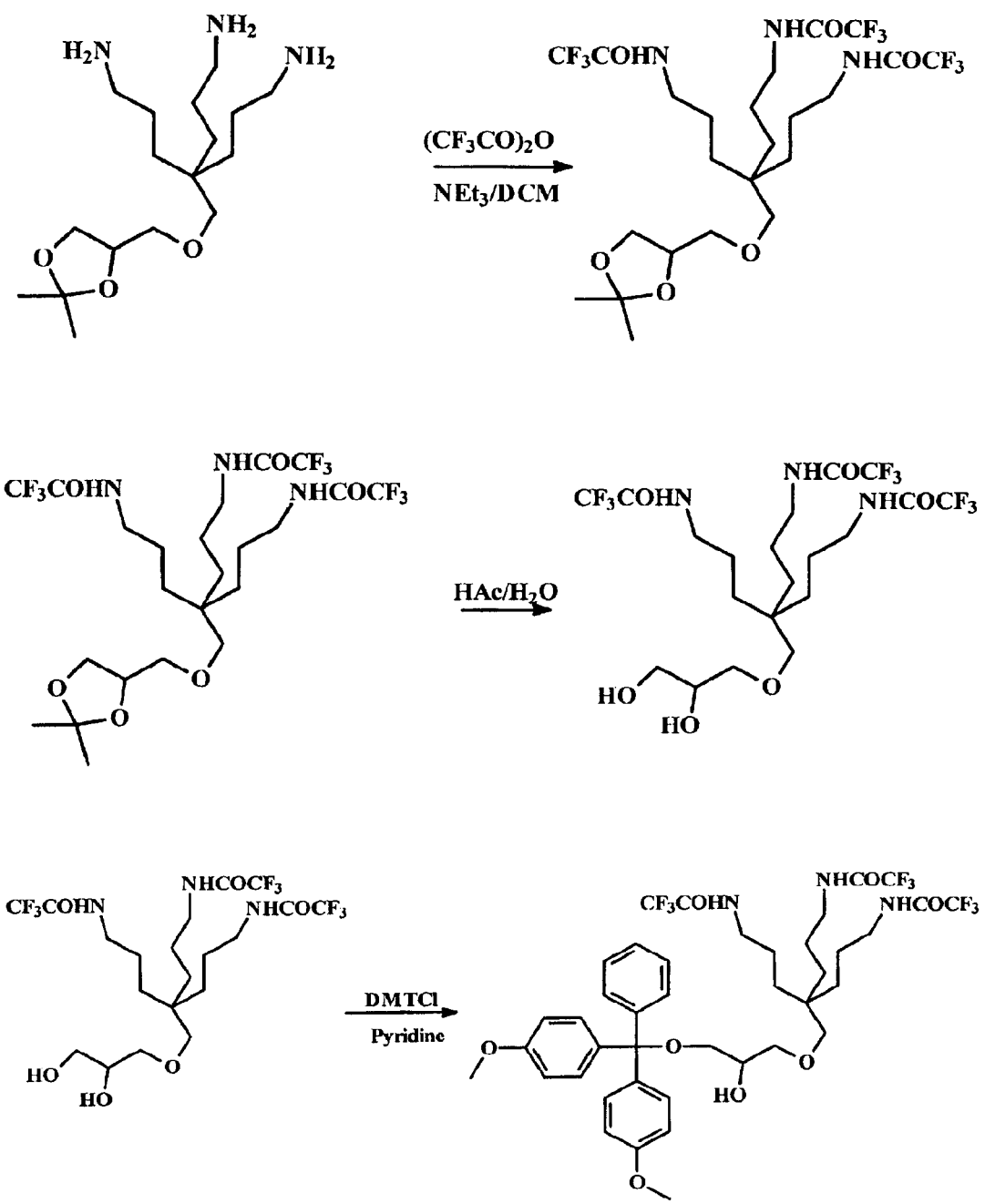
Figure 2:
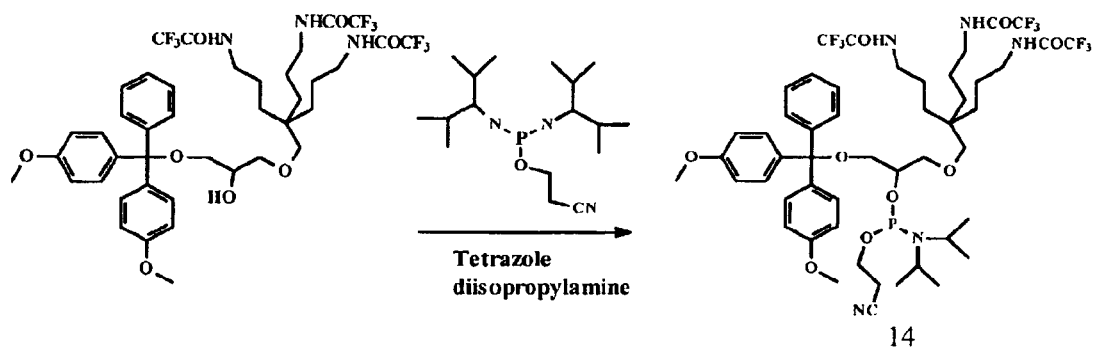
Figure 2:
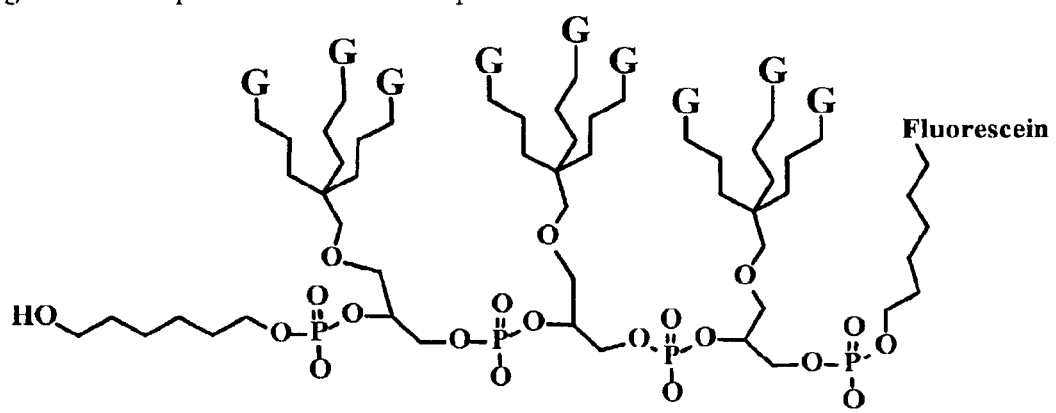
Figure 3:
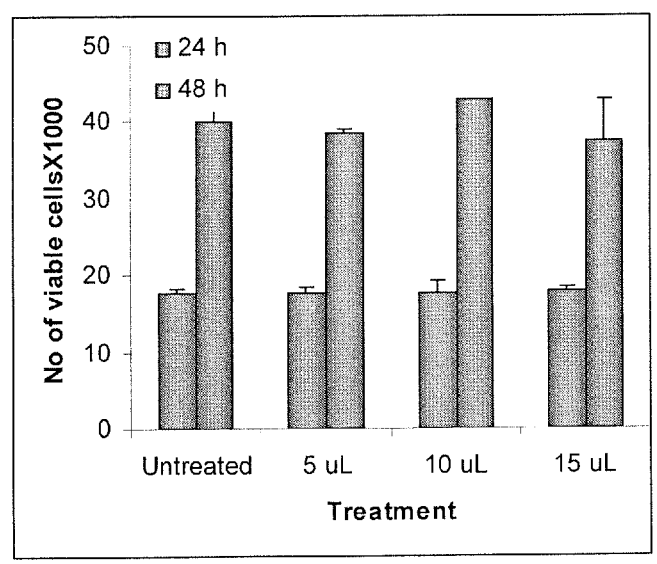
FIG. 3 depicts the growing cells which were treated with Compound 38 and comparison of viability of the cells in 24 h and 48 h.

According to further aspects of the present invention, there are provided processes of preparing the oligomers, conjugates, and the building blocks described herein. In one embodiment Compound 38, is prepared according to the synthetic scheme as presented in Example 7. In one embodiment, the conjugate, Compound 24, is prepared according to the synthetic scheme as presented in Example 5. In one embodiment, the conjugate, Compound 23, is prepared according to the synthetic scheme as presented in FIG. 2 and Example 4.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions; illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986 all of which are incorporated by reference as if fully set forth herein. Other general references are provided throughout this document. The procedures therein are believed to be well known in the art and are provided for the convenience of the reader. All the information contained therein is incorporated herein by reference.

Example 1

All starting material compounds and reagents were purchased from Aldrich.

Preparation of
N-(2-cyanoethoxycarbonyloxy)succinimide
(CEOC-O-Succinimide

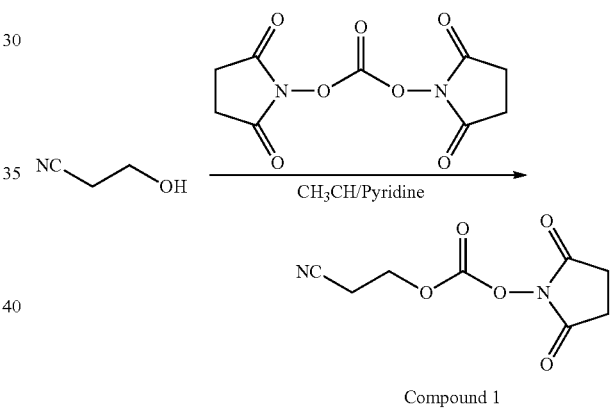

Compound 1

To a stirred solution of 2-cyanoethanol (7.23 grams, 102 mmol) in anhydrous $CH_3CN$ (300 ml), under argon atmosphere, N,N'-disuccinimidyl carbonate (34.0 grams, 133 mmol) was added, followed by the addition of pyridine (11.3 ml, 140 mmol). The resulting suspension was stirred and became a clear solution after about 1 hour. The solution was stirred for additional 6 hours and was then concentrated under reduced pressure. The residue was re-dissolved in dichloromethane (200 ml), and was washed with a saturated $NaHCO_3$ solution (3×50 ml) and a saturated NaCl solution (3×50 ml). The organic layer was then dried over anhydrous $Na_2SO_4$ and concentrated to afford the crude product as a white solid. Traces of pyridine were removed from the crude product by co-evaporation with dry acetonitrile. The obtained white solid was dried overnight under reduced pressure and was then triturated with ether (150 ml) to yield 20.23 grams (94% yield) of partially purified Compound 1 as a colorless amorphous powder. The partially purified product was stable at room temperature, when stored in desiccators for an extended period (1-2 years). Proton and carbon NMR spectra showed that the partially purified compound is homogeneous. Further purification of the product was performed by chromatography on silica gel using a 50:50 CH$_2$Cl$_2$:EtOAc mixture as eluent, to give pure Compound 1 a white crystalline compound (18.72 grams, 87% yield).

TLC: (50:50 CH$_2$Cl$_2$:EtOAc) R$_f$=0.21;
m.p.=105.5° C.;
$^1$H-NMR (CDCl$_3$): δ=2.85 (t, J=6.62 Hz, 2H), 2.86 (s, 4H), 4.45 (t, J=5.96 Hz).

Preparation of N,N'-bis-CEOC-2-methyl-2-thiopseudourea 2-Methyl-2-thiopseudourea (Compound 2)

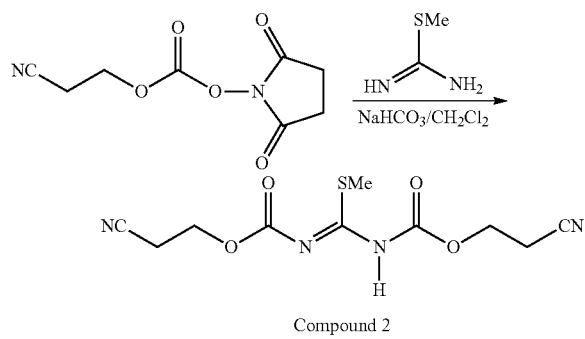

Compound 2

S-methylisothiourea hemisulfate (5.29 grams, 38.0 mmol) was suspended in CH$_2$Cl$_2$ (250 ml) and a saturated NaHCO$_3$ solution (250 ml). Cyanoethoxycarbonyloxysuccinimide (Compound 1, 20.2 grams, 95.3 mmol) was added and the resulting mixture was stirred for 2 hours. The organic phase was then separated, the aqueous phase was extracted with DCM (2×200 ml) and the combined organic phase was dried over Na$_2$SO$_4$), filtered and evaporated. The crude product was purified by flash chromatography using a 95:5 AcOEt/DCM as eluent, to afford Compound 2 (3.78 grams, 35% yield) as a white solid.

$^1$H-NMR (CDCl$_3$): δ=11.80 (br s, 1H), 4.39 (q, 4H), 2.80 (t, 4H), 2.45 (s, 3H).
Yield: 5.22 gr, 95%.

Example 2

Preparation of Compound 14 and Other Heterocyclic-Based Oligomeric Compounds

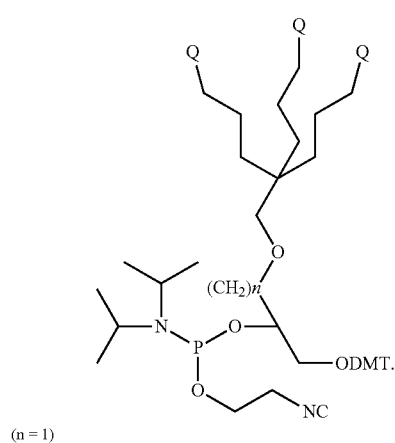

Compound 14

Preparation of Compound 3

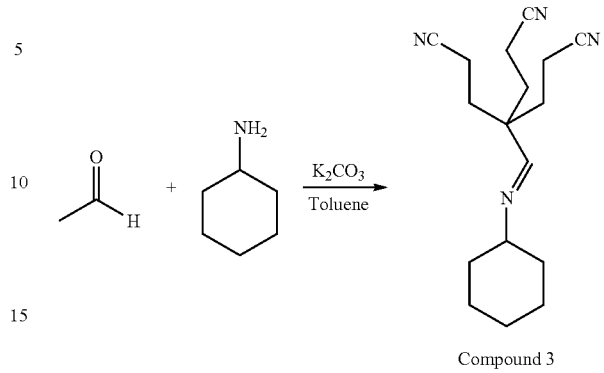

Compound 3

Acetaldehyde (16.9 mL) was slowly added to a solution of cyclohexylamine (34.3 gr., 0.3 mmol) in dry toluene (15 mL) at 0° C., over 20 min. Potassium carbonate (2.5 gr.) was added and the reaction mixture was stirred for 10 min. and then allowed to warm to room temperature. The organic layer was placed in an autoclave and acrylonitrile (68.5 mL) was added. The solution was stirred for 6 hours at 160° C. The black reaction mixture was cooled to room temperature and poured to ether (800 mL). The precipitate (see, Compound 3) was filtered and washed with ether to give 40 grams (yellow solid, 48%), which was used without further purification. Mp: 99° C.

Preparation of Compound 4

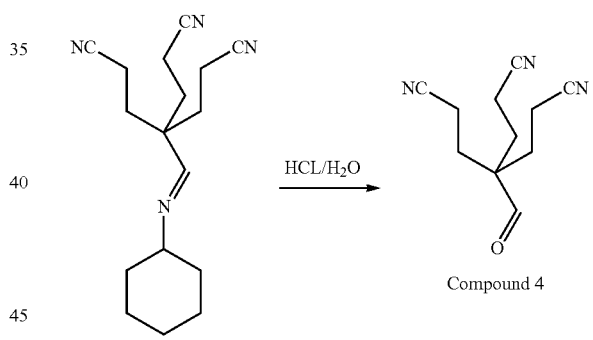

Compound 4

Compound 3 (10 gr. 35.2 mmol) was dissolved in a solution of concentrated HCl (5 mL) and water (130 mL). The resulting mixture was refluxed for 30 min, filtered hot and allowed to cool to 0° C. The yellow precipitate (see, Compound 4) was collected, washed with water, dried and purified by recrystallization from methanol, giving (white crystals, 6.6 gr, 92%).
Mp 108° C. Rf—0.49 in (Ethylacetate 2:1 Hexane)

Preparation of Compound 5

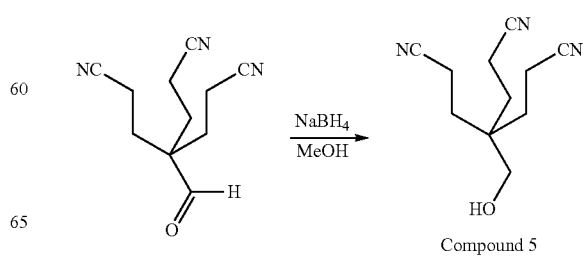

Compound 5

NaBH$_4$ (1.5 gr.) was added to a solution of Compound 4 (5 gr., 24.6 mmol) in dried methanol (250 mL) under Argon at 0° C. within 30 min. The solution was stirred for an additional 2 hours at room temperature. Water (50 mL) was added and the resulting mixture was cooled to 0° C. and then acidified with concentrated HCL to pH 1. Methanol was evaporated and the product was extracted with dichloromethane (3×75 mL), the combined extracts were dried with anhydrous sodium sulfate. The solvent was removed to yield the product (see, Compound 5) as a white crystalline material (4.6 gr., 92%).

Mp: 69° C. Rf—0.31 in (Ethylacetate 2:1 Hexane).

H$^1$ NMR—(CDCl$_3$): δ 1.68 (m, 6H), 2.45 (m, 6H), 3.30 (s, 2H), 4.83 (s, 1H).

Preparation of Compound 6

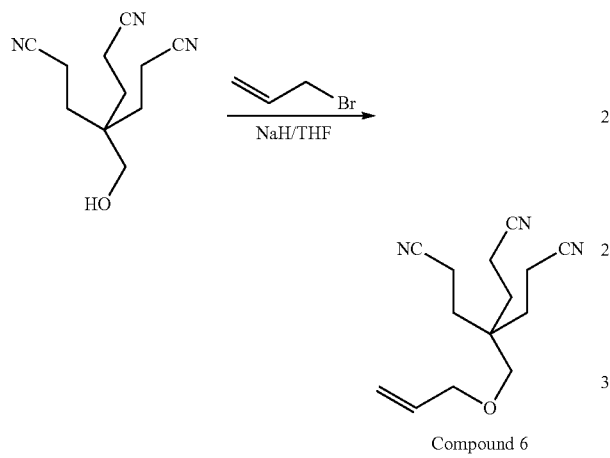

A solution of Compound 5 (10 gr., 48.8 mmol) in dry tetrahydrofuran (70 mL) was added dropwise to a slurry mixture of 60% NaH (2.34 gr., 58.5 mmol) in tetrahydrofuran (100 mL) at room temperature during 40 minutes. To the slurry reaction mixture, was added dropwise allylbromide (13 mL, 146 mmol). The reaction mixture was stirred at 50° C. during 3 hours and continuous stirring at room temperature during 16 hours.

The reaction mixture was thereafter evaporated to dryness under reduced pressure, the residue was extracted with ethyl acetate (250 ml), brine (200 ml), and the organic layer was dried over anhydrous sodium sulfate, and concentrated by rotary evaporator to a foam. The product (see, Compound 6) was purified by column chromatography on neutralized silica gel column, using a linear gradient of hexane 100% to (Ethylacetate 1:1 Hexane). Yielding (11 grams, 92%) of a yellowish oil.

Rf—0.38 in (Ethylacetate 1:1 Hexane)

H$^1$ NMR—(CDCl$_3$): δ 1.73 (m, 6H), 2.36 (m, 6H), 3.21 (2H), 3.94 (m, 2H), 5.24 (m, 2H), 5.83 (m, 1H).

Preparation of Compound 7

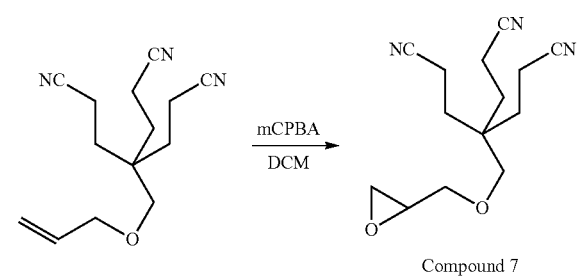 [SMILES: C=CCOCC(CCC#N)(CCC#N)CCC#N ; N#CCCC(CCC#N)(CCC#N)COCC1CO1]

To a cold (0° C.) solution of Compound 6 (5 gr., 20.4 mmol) in dichloromethane (100 mL), was added dropwise a solution of meta-chloroperbenzoic acid (77%, 5.49 gr., 24.48 mmol). The reaction mixture was stirred at room temperature for 16 hours. This solution was extracted with saturated bisulfate (20 mL) followed by washings with saturated sodium bicarbonate (100 mL), water and with brine The organic layer was dried over anhydrous sodium sulfate, and concentrated by rotary evaporator to an oil. The product (see, Compound 7) was purified by column chromatography on neutralized silica gel column, using (Ethylacetate 1:1 Hexane) as eluent, yielding (4.93 gr., 92%). Rf—0.16 in (Ethylacetate 1:1 Hexane).

Preparation of Compound 8

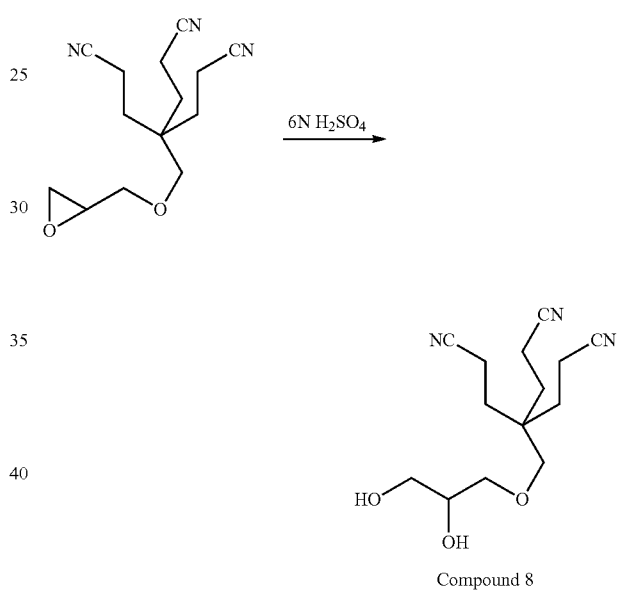

To a solution of Compound 7 (3.2 gr., 12.24 mmol) in dioxane (100 mL), water (50 mL) and acetonitrile was added a solution of 6N sulfuric acid (4 mL). The reaction mixture was stirred at room temperature during 5 hours, followed by neutralization with a saturated solution of sodium bicarbonate up to pH 7.8. The reaction mixture was thereafter evaporated to dryness under reduced pressure, the residue was extracted with ethyl acetate (250 ml), brine (200 ml), and the organic layer was dried over anhydrous sodium sulfate, and concentrated by rotary evaporator to a foam. The product (see, Compound 8) was purified by column chromatography on neutralized silica gel column, using a Ethylacetate as eluent. Yielding (3.31 grams, 96%) of an oil.

Rf—0.25 in (Ethylacetate).

H$^1$ NMR—(CDCl$_3$): δ 1.68 (m, 6H), 2.45 (m, 6H), 3.30 (s, 2H), 3.40 (m, 2H), 3.59 (m, 2H), 3.78 (m, 1H).

Preparation of Compound 9

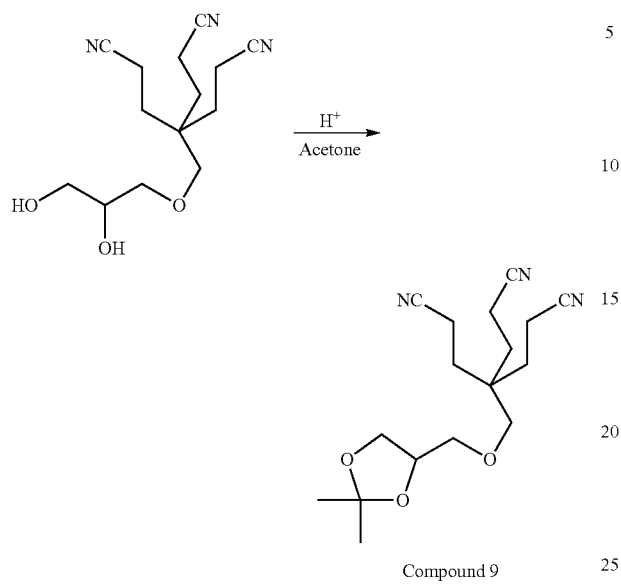

Compound 9

To a solution of Compound 8 (10.31 gr., 36.9 mmol) in dry acetone (100 mL) and dimethoxypropane (100 mL), was added para-toluenesulfonic acid (300 mgr.) and anhydrous sodium sulfate (10 grams). The reaction mixture was stirred at room temperature during 30 minutes. The reaction mixture was filtered and neutralized with a saturated solution of sodium bicarbonate up to pH 7.5. The reaction mixture was thereafter evaporated to dryness under reduced pressure, the residue was extracted with ethyl acetate (250 ml), brine (200 ml), and the organic layer was dried over anhydrous sodium sulfate, and concentrated by rotary evaporator to an oil. The product (see, Compound 9) was purified by column chromatography on neutralized silica gel column, using a Ethylacetate as eluent. Yielding (9.59 grams, 81.4%) of an oil.

Rf—0.72 in (Ethylacetate).

$H^1$ NMR—(CDCl$_3$): δ 1.28, 1.34 (2s, 6H), 1.65 (m, 6H), 2.47 (m, 6H), 3.35 (s, 2H), 3.40 (m, 2H), 3.9 (m, 2H), 4.20 (m, 1H).

Preparation of Compound 10

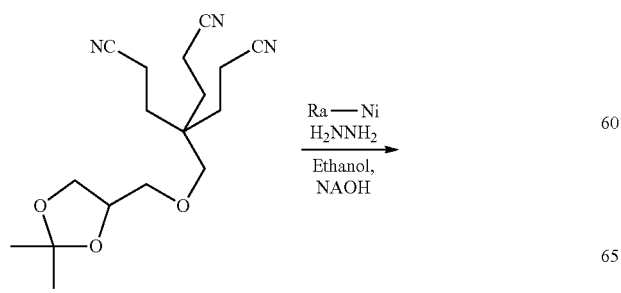

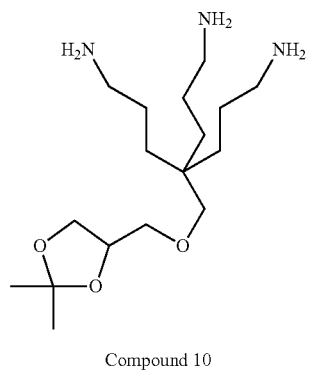

Compound 10

A solution of Compound 9 (3.19 gr., 10 mmol) in ethanol (95%, 100 mL), was cooled to 0° C. To the reaction mixture was added NaOH (1.51 gr., 37.75 mmol), hydrazine hydrate (5 mL) and Ra—Ni slurry in water in portions. The reaction mixture was stirred at room temperature for 2 hours, followed by reflux during 2 hours. The hot solution was filtered on Celite and washed with ethanol (50 mL). The reaction mixture was thereafter evaporated to dryness under reduced pressure, and the residue was coevaporated with toluene several times until NaOH precipitated. The yellowish slurry solution was refluxed with dichloromethane during 1 hour and filtered. The supernatant was evaporated to dryness and the product (see, Compound 10) was used for the next step without further purification.

Preparation of Compound 11

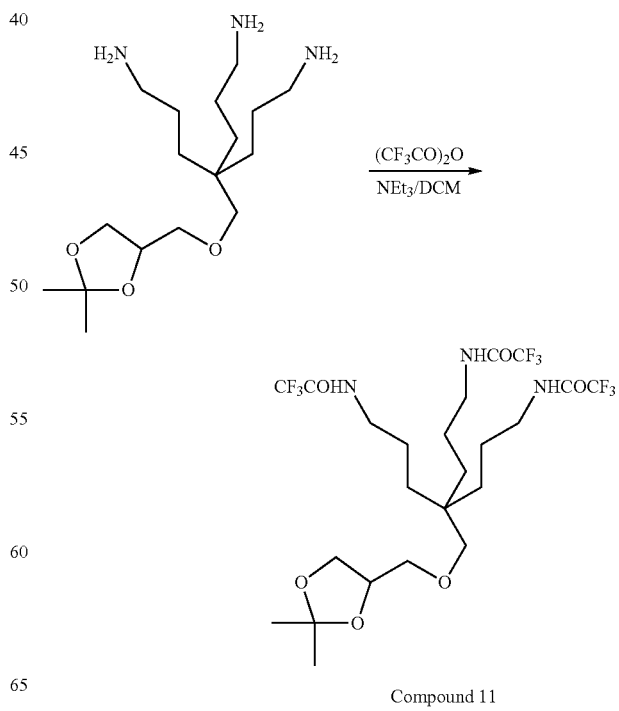

Compound 11

To a solution of Compound 10 from the previous step in dichloromethane (50 mL), was added triethylamine (10 mL). The solution was cooled to 0° C., and a solution of trifluoroacetic anhydride (5 mL) in dichloromethane (50 mL) was added dropwise. The reaction mixture was stirred at room temperature during 30 minutes. The reaction mixture was thereafter evaporated to dryness under reduced pressure, the residue was extracted with ethyl acetate (250 ml), brine (200 ml), and the organic layer was dried over anhydrous sodium sulfate, and concentrated by rotary evaporator to an oil. The product (see, Compound 11) was purified by column chromatography on neutralized silica gel column, using (Ethylacetate 1:1 Hexane) as eluent. Yielding (4.3 grams, 89.7%) of an oil.

Rf—0.29 in (Ethylacetate 1:1 Hexane)

$H^1$ (CDCl$_3$): δ 1.28, 1.34 (2s, 6H), 1.65 (m, 6H), 3.21 (m, 2H), 3.30 (s, 6H), 3.41 (m, 2H), 3.9 (m, 2H), 4.25 (m, 1H).

Preparation of Compound 12

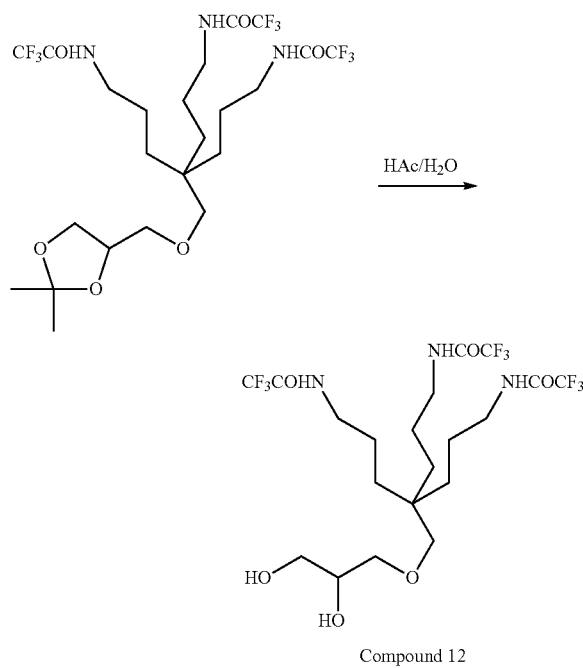

Compound 12

Compound 11 (6.19 gr., 10 mmol) was dissolved in a solution of (80 acetic acid:20 water, 100 mL), and stirred during 18 hours at room temperature. The reaction mixture was thereafter evaporated to dryness under reduced pressure, the residue was extracted with ethyl acetate (250 ml), brine (200 ml), and the organic layer was dried over anhydrous sodium sulfate, and concentrated by rotary evaporator to oil. The product (see, Compound 12) was used for the next step without further purification. Rf—0.16 in (Ethylacetate 7:3 Hexane)

Preparation of Compound 13

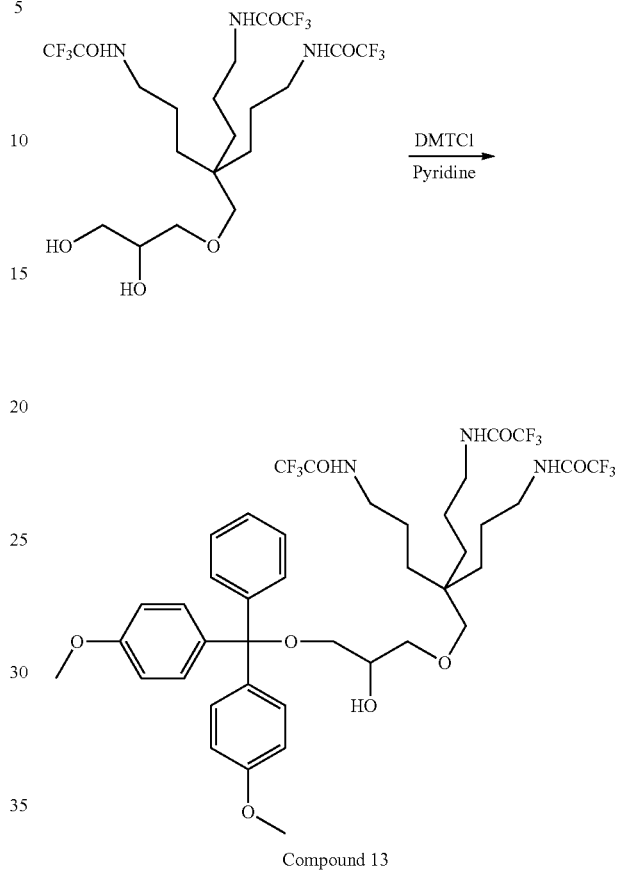

Compound 13

Compound 12 (13.2 gr., 22.78 mmol) was coevaporated twice with dry pyridine (50 mL) in reduced pressure, thereafter the residue was dissolved in dry pyridine (100 mL) and cooled to 0° C. To this solution was added dropwise a solution of 4,4'-dimethoxytrityl chloride (8.47 gr., 25.06 mmol) in dry pyridine (100 ml) under Argon. After the addition, the reaction mixture was allowed to warm to room temperature, and stirred during 5 hours. The reaction mixture was thereafter evaporated to dryness under reduced pressure, the residue was extracted with ethyl acetate (250 ml), brine (200 ml), and the organic layer was dried over anhydrous sodium sulfate, and concentrated by rotary evaporator to a foam. The product (see, Compound 13) was purified by column chromatography on neutralized silica gel column, using a linear gradient of 100% hexane containing 0.2% triethylamine to a mixture of (Ethylacetate 7:3 Hexane) as eluent, yielding (12.66 gr., grams 77%). Rf—0.67 in (Ethylacetate 7:3 Hexane).

$H^1$ NMR—(CDCl$_3$): δ 1.21 (m, 6H), 1.44 (m, 6H), 3.15 (m, 4H), 3.25 (s, 6H), 3.41 (m, 2H), 3.78 (s, 6H), 6.81-7.4 (aromatics, 131-1).

Preparation of Compound 14

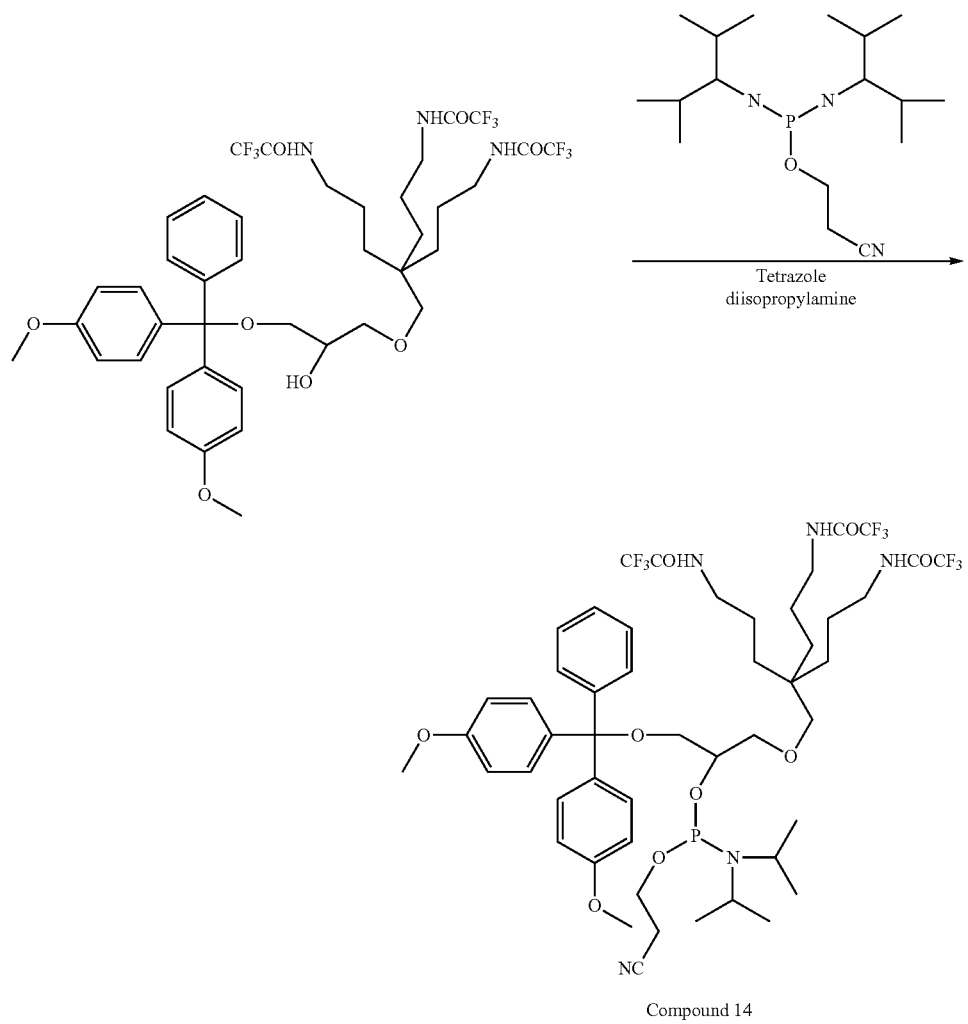

Compound 14

A mixture of Compound 13 (8.81 gr., 10 mmol), and tetrazole diisopropylamine salt (2.53 gr., 15 mmol) was dried in high vacuum during 2 hours. Thereafter, the flask was filled with Argon and dry acetonitrile was added. To the reaction mixture was injected dropwise under Argon, a solution of N,N,N',N'-tetraisopropylphosphorodiamidite (4.52 gr., 15 mmol) in dry acetonitrile (20 mL). The reaction mixture was stirred under Argon during 16 hours at room temperature. The reaction mixture was thereafter evaporated to dryness under reduced pressure, the residue was extracted with ethyl acetate (250 ml), brine (200 ml), and the organic layer was dried over anhydrous sodium sulfate, and concentrated by rotary evaporator to a foam. The product (see, Compound 14) was purified by column chromatography on neutralized silica gel column, using a linear gradient of 100% hexane containing 0.2% triethylamine to a mixture of (Ethylacetate 1:1 Hexane) as eluent, yielding (9.83 gr., 90.8%). Rf—0.59 in (Ethylacetate 1:1 Hexane).

$H^1$ NMR—(CDCl$_3$): δ 1.12-1.18 (m, 18H), 1.39 (m, 6H), 2.4-2.5 (m, 2H), 3.09 (m, 4H), 3.15-3.25 (8H), 3.5-3.7 (m, 4H), 3.8 (s, 6H), 4.12 (m, 1H), 6.81-7.4 (aromatics, 13H).

Example 3

Preparation of a Typical Linker Precursor (Compound 16)

Compound 16

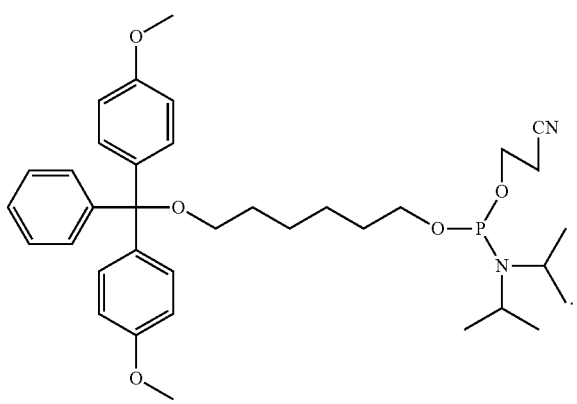

A. Preparation of the Alcohol Precursor (Compound 15)

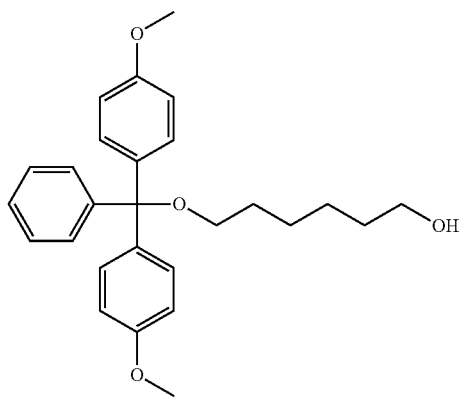

Compound 15

To a cooled (0° C.) solution of 1,6-Hexanediol (37 gr, 312.5 mmol) in Pyridine (200 mL), was added dropwise a solution of Dimethoxytrityl chloride (10.57 gr, 31.25 mmol) in Pyridine (100 mL). After stirring for 2 hours, methanol (20 mL) was added to quench the rest of Dimethoxytrityl chloride. The solvent was evaporated to dryness, and the rest was extracted with Ethylacetate (250 mL)/(2×250 mL) brine. The organic layer was separated and dried over anhydrous sodium sulfate. The solvent was evaporated, and the crude product was purified by column chromatography on silica gel using a gradient of 100% hexane up to 62 Hexane:33 ethylacetate:1 Pyridine. TLC:hexane 1:1 ethylacetate Rf 0.57. Yield: 10 grams (76%).

B. Preparation of the Phosphorus Amidite Linker Precursor (Compound 16)

To the alcohol Compound 15 (4.34 gr, 10.32 mmol) was added tetrazole (0.25 gr.) and was dried in a vacuum pump oil for 2 hours, the mixture was dissolved in dry acetonitrile (50 mL). To this solution was added 2-Cyanoethyl tetrakis(1-methylethyl)phosphorodiamidoate (4.9 mL, 15.43 mmol) dropwise at room temperature. After stirring for 18 hours under Argon, triethyl amine (2 mL) was added, and the solvent was evaporated. The resulting product was extracted with ethylacetate (200 mL) combine with 5% sodiumbicarbonate (100 mL) and finally with brine (2×150 mL). The organic phase was dried over anhydrous sodium sulfate and was evaporated to dryness, and the crude product was purified by column chromatography on silica gel using a gradient of 100% hexane up to 60 Hexane:39 ethylacetate:1 Pyridine. TLC:hexane 2:1 ethylacetate, Rf=0.63. Yield: 10.45 grams (68%) as an oil.

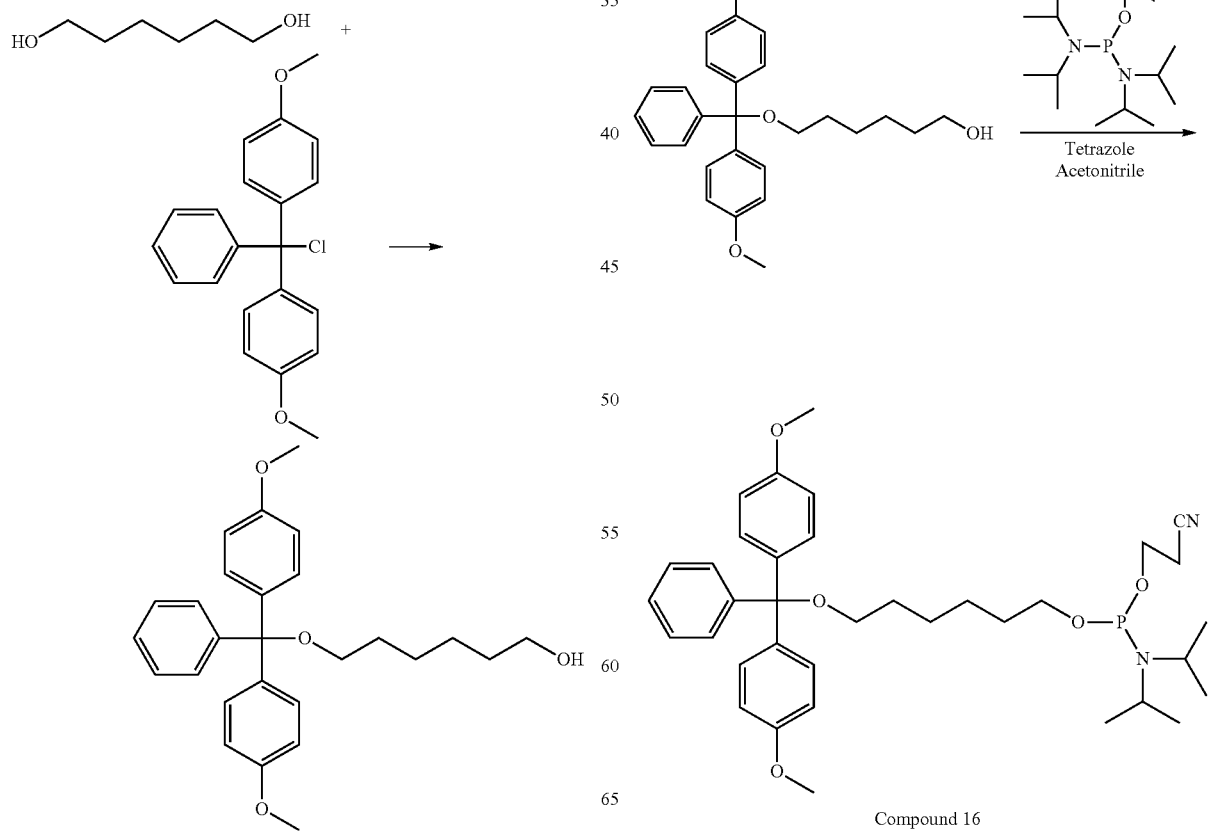

Compound 16

Example 4

Preparation of Compound 23

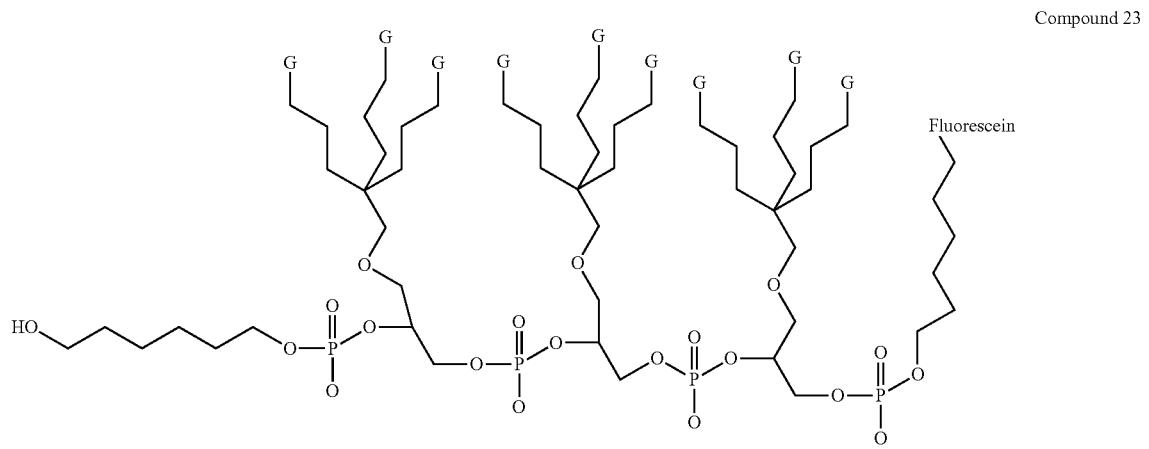

Wherein G is a guanidine group.

Compound 23 was prepared according to the following steps:

1. Derivatization of CPG (Controlled Pore Glass)

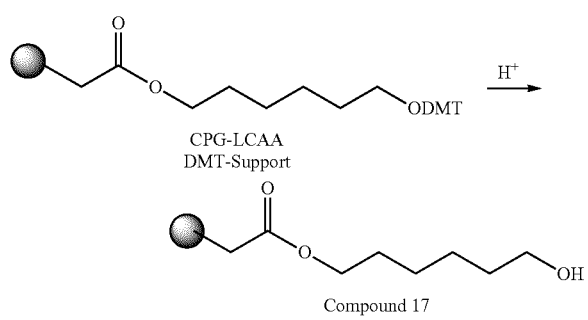

The synthesis of Compound 23 was carried out using a controlled pore glass (CPG) support of 1000 A° pore size, loaded at 35 micromoles per gram with 3'-succinylhexanol.

Compound 23 was prepared according to general procedure as described by Gait at "oligonucleotide synthesis" IRL Press (1984), page 47. The synthesis of the oligomeric polymer is started by deprotection of the Dimethoxytrityl group (DMT), by adding a solution of 2% trichloroacetic acid in dichloromethane, to 100 mgr. of the DMT-Support. The reaction mixture was stand at room temperature for 30 sec, followed by washings with methanol 2×10 mL, and with dichloromethane 2×10 mL.

2. Attachment of Compound 17 to Compound 14 to Obtain Compound 19

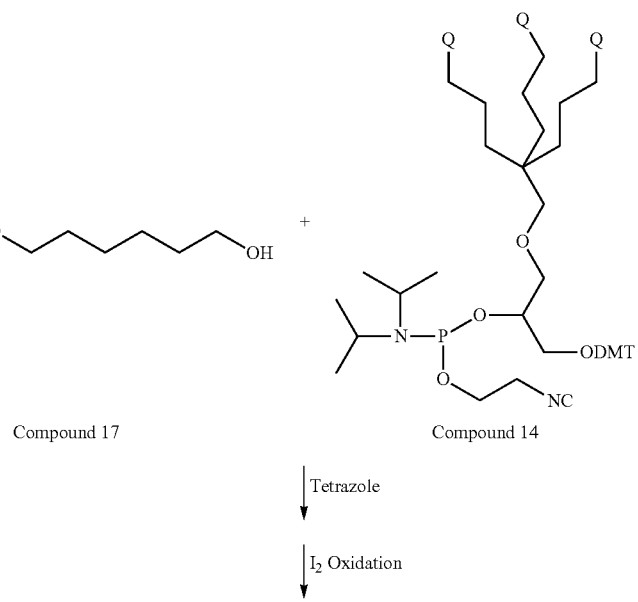

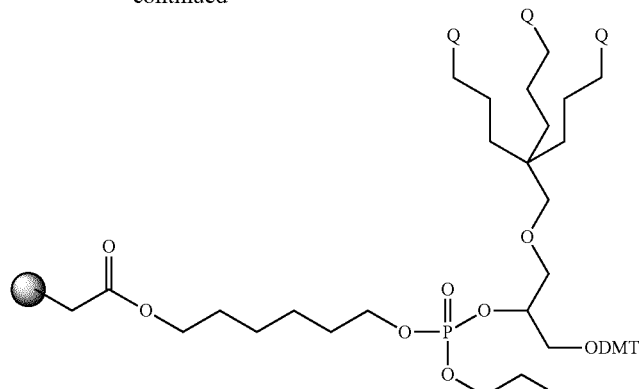

Compound 19

Q is HNĊCF₃ (O double bond)

Wherein Q = NHĊCF₃ (O double bond)

The synthesis of Compound 19 was carried out using a controlled pore glass (CPG) support of 1000 A° pore size, loaded at 35 micromoles per gram with 3'-succinyl hexanol (Compound 17). Followed by condensation of Compound 14, on an Applied Biosystems 381A DNA Synthesizer using standard deoxynucleoside phosphoramidites, as described by Beaucage et al., 1981, *Tetrahedron Letters* 22, 5843-5846.

3. Preparation of Compound 20

The above protocol was used to condense twice more Compound 14 to obtain Compound 20.

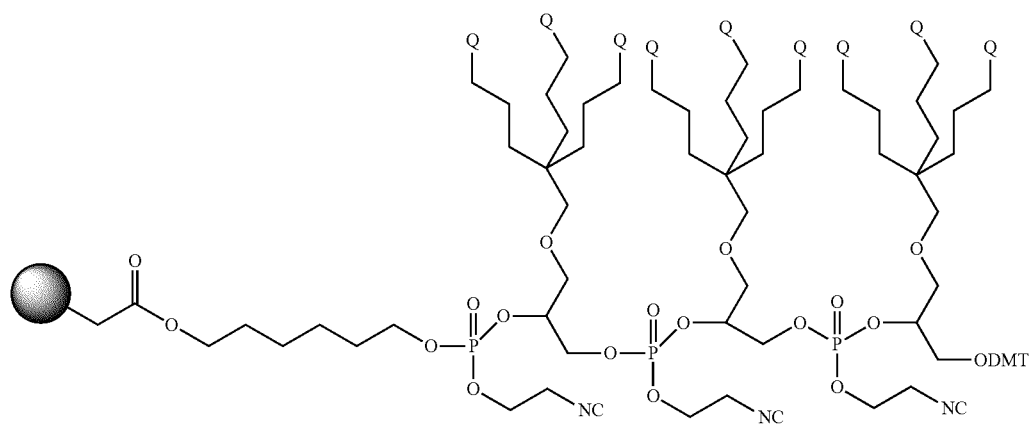

Compound 20

Where Q is NHCOCF₃,

Compound 19 was deprotected with a solution of 2% trichloroacetic acid in dichloromethane, following condensation, oxidation to obtain the following oligomeric Compound 20. The oligomeric polymer was prepared at the 0.35 mmol scale on an Applied Biosystems 381A DNA Synthesizer using standard deoxynucleoside phosphoramidites, as described by Beaucage et al., 1981, *Tetrahedron Letters* 22, 5843-5846.

Compound 14 was condensed three times using Beaucage protocol to obtain Complund 20.

4. Attachment of Fluorescein to Compound 20 to Obtain Compound 21

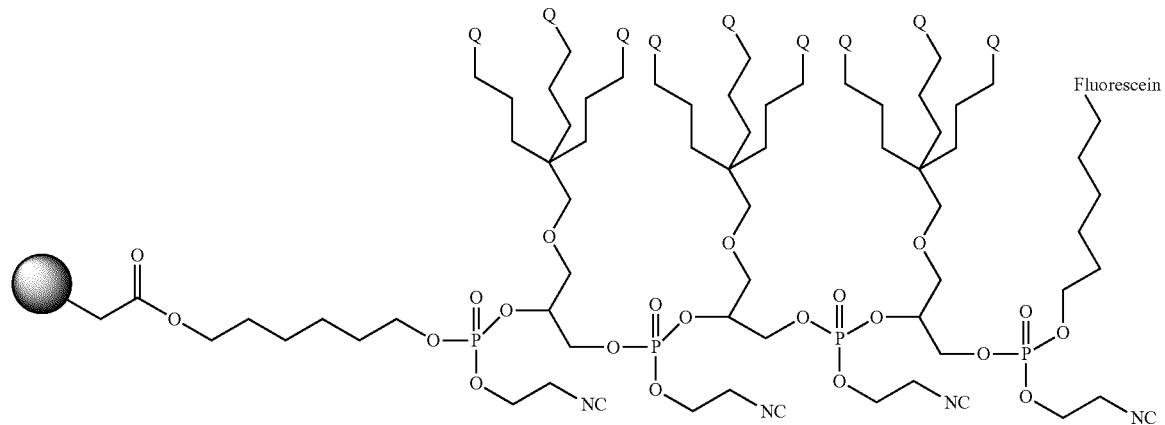

Compound 21

25

Where Q is NHCOCF$_3$

Compound 20 was deprotected with a solution of 2% trichloroacetic acid in dichloromethane, following condensation with Fluorescein-(di-t-butylate)-hexamethylene-phosphoramidite (FAM-HPA, Glen Research) was added to the 5'-hydroxyl group of the unprotected Compound 20 essentially as described by Beaucage et al., 1981, *Tetrahedron Letters* 22, 5843-5846.

5. Preparation of Compound 22

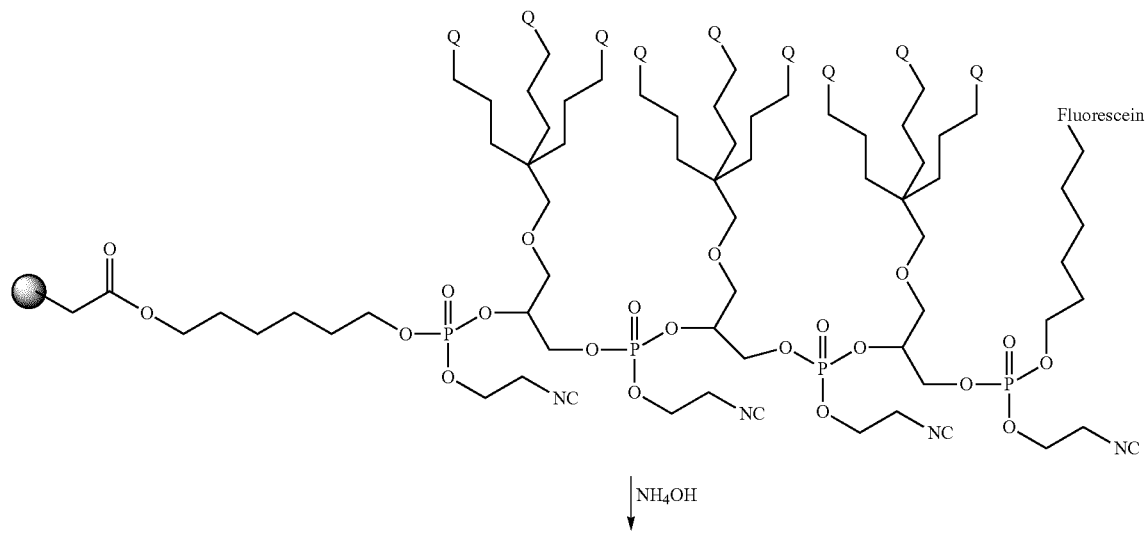

$\downarrow$ NH$_4$OH

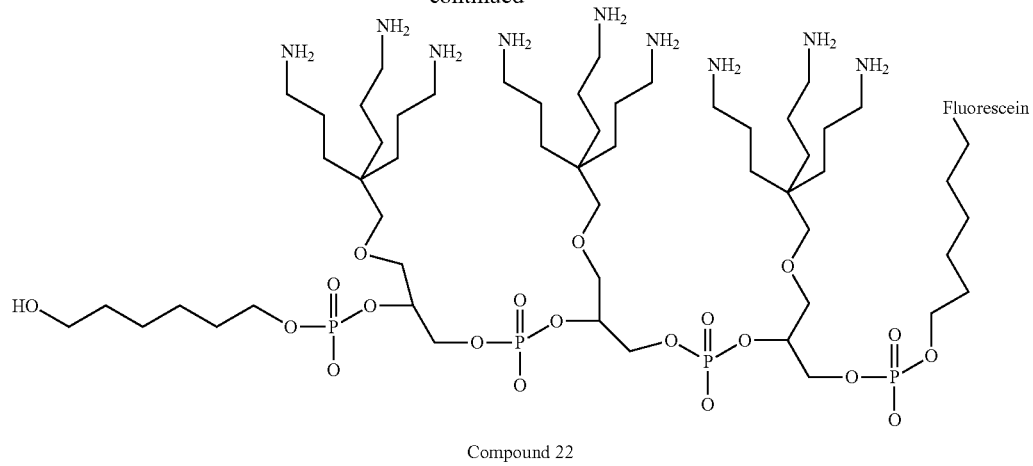
Compound 22
Compound 21 was mixed with concentrated ammonium hydroxide in sealed tube, and heated to 60° C. for 18 hours. After cooling to room temperature, the aqueous solution was decantanted and was evaporated to dryness to obtain Compound 22 as a pellet.
6. Preparation of Compound 23
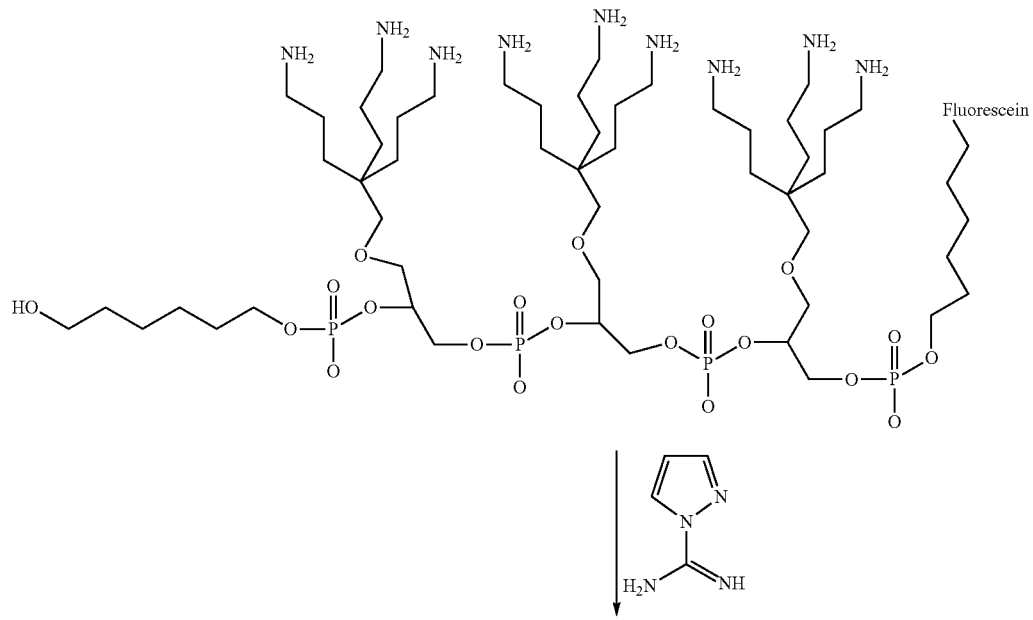

-continued

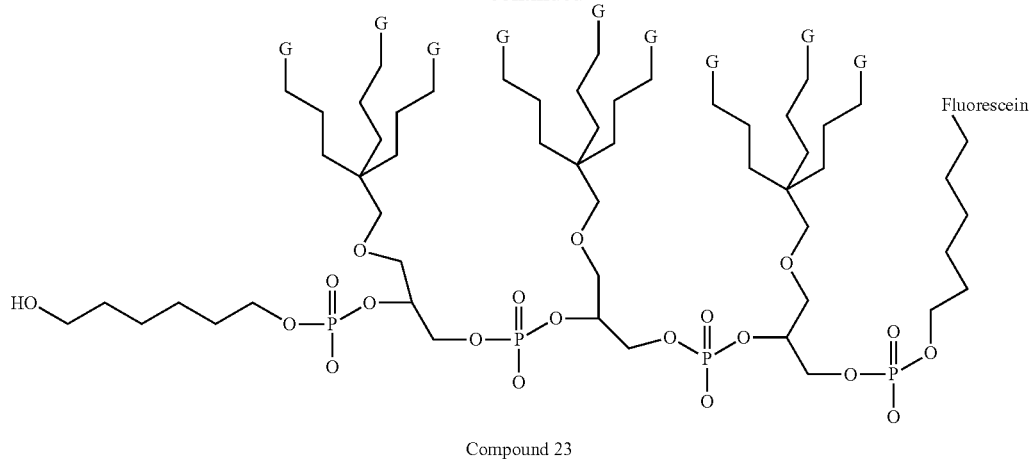

Compound 23

Wherein G is a guanidine group.

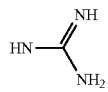

The resulting pellet (Compound 22), was treated with a solution of 1H-Pyrazole-1-carboxamidine hydrochloride (Aldrich) (50 equivalents) in 5% sodium carbonate (5 ml). The solution was heated to 50° C. for 24 hours. The reaction mixture was cooled to room temperature. The crude product (see, Compound 23) was dissolved in deionized doubly distilled water (1 ml) and was purified by HPLC. Compound 23 is ready for delivery into cells.

Example 5

Preparation of Compound of Formula V (Compound 24)

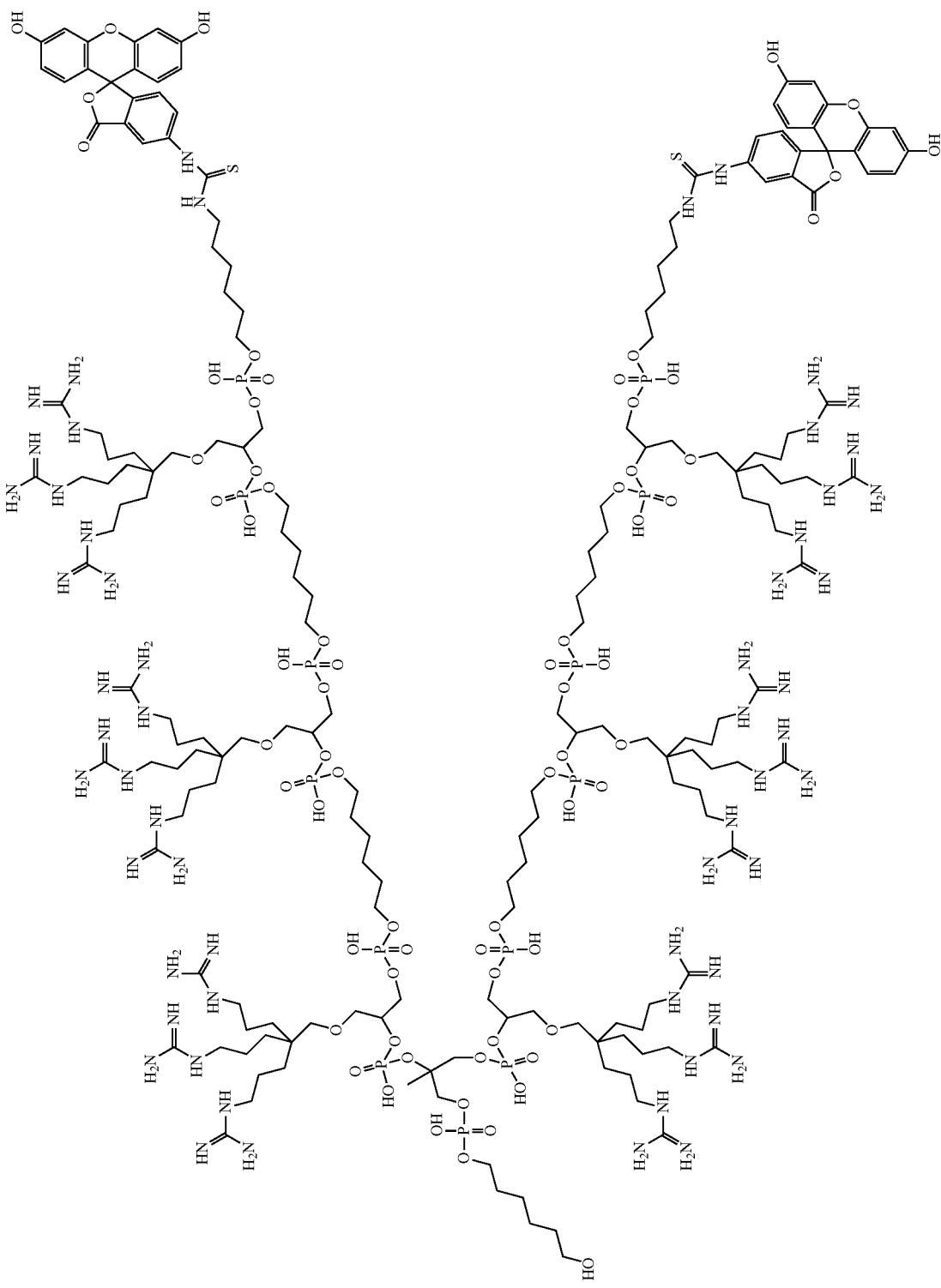
V (Compound 24)

1. Preparation of the Splitting precursor (Compound 25)

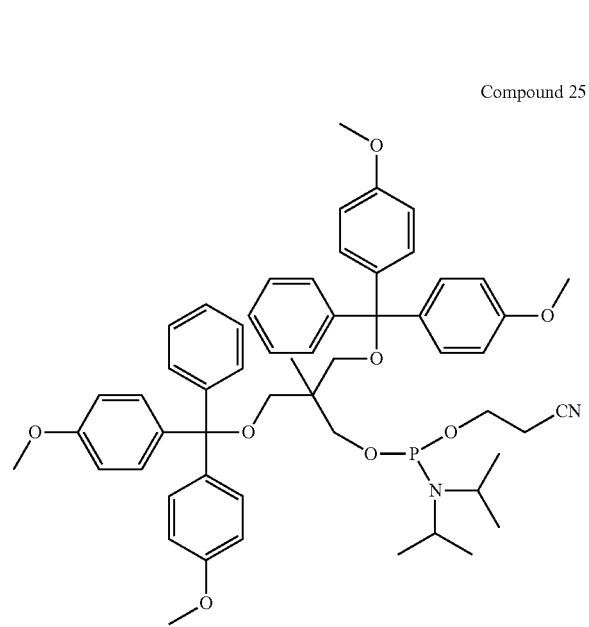

Compound 25 a. Preparation of Compound 26

To a cooled solution of 1,1,1-(trishydroxymethyl)-ethane (Aldrich) (3.3 gr, 27.47 mmol) in dry pyridine (50 mL), was added dropwise under Argon, a solution of dimethoxytrityl chloride (18.6 gr, 54.94 mmol)) in dry pyridine (100 mL). The reaction mixture was stirred at room temperature for 18 hours. The reaction mixture was treated with methanol (20 mL). The reaction mixture was thereafter evaporated to dryness under reduced pressure, the residue was extracted with ethyl acetate (250 ml), brine (200 ml), and the organic layer was dried over anhydrous sodium sulfate, and concentrated by rotary evaporator to an oil. The product (Compound 26) was purified by column chromatography on neutralized silica gel column, using a Ethylacetate 1:2 Hexane as eluent. Yielding (8.44 grams, 42%) of Compound 26 as an oil. TLC: Rf—0.41 in (Ethylacetate 1:2 Hexane).

Compound 26 b. Preparation of Compound 25 from Compound 26

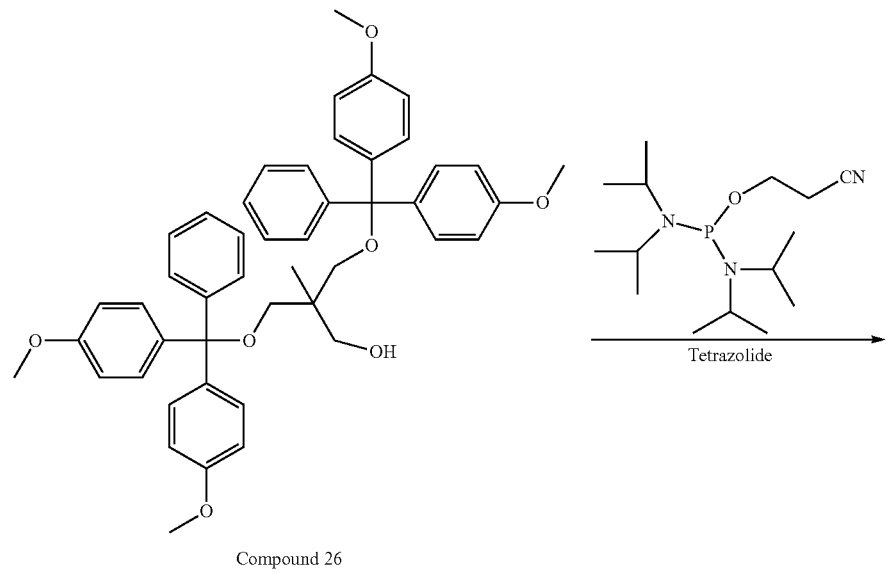

Compound 26

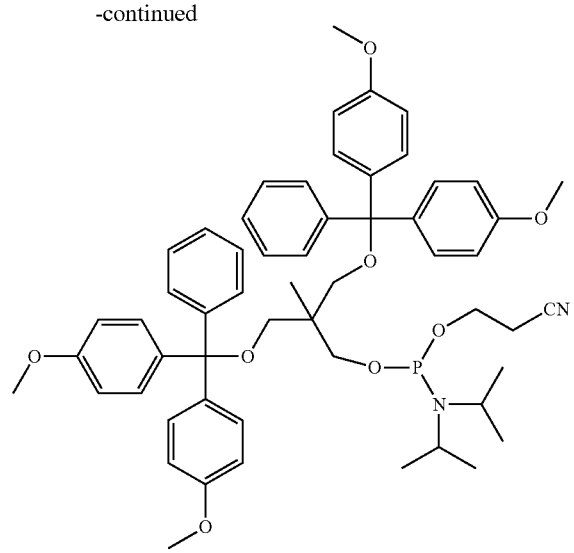

Compound 25

A mixture of Compound 26 (8.44 gr., 11.58 mmol), and tetrazole diisopropylamine salt (2.97 gr., 17.37 mmol) was dried in high vacuum during 2 hours. Thereafter, the flask was filled with Argon and dry acetonitrile (70 mL) was added. To the reaction mixture was injected dropwise under Argon, a solution of N,N,N',N'-tetraisopropylphosphorodiamidite (5.5 mL., 17.37 mmol) in dry acetonitrile (20 mL). The reaction mixture was stirred under Argon during 16 hours at room temperature, and triethylamine (2 mL) was added. The reaction mixture was thereafter evaporated to dryness under reduced pressure, the residue was extracted with ethyl acetate (250 ml), brine (200 ml), and the organic layer was dried over anhydrous sodium sulfate, and concentrated by rotary evaporator to a foam. The product (Compound 25) was purified by column chromatography on neutralized silica gel column, using a linear gradient of 100% hexane containing 0.2% triethylamine to a mixture of (Ethylacetate 1:2 Hexane) as eluent, yielding (9.85 gr., 90.14%) of Compound 25 as a white solid. TLC: Rf—0.57 in (Ethylacetate 1:2 Hexane).

2. Assembling of Compound of Formula V (Compound 24)

a. Condensation of Compound 25 with Compound 17 to Obtain Compound 27

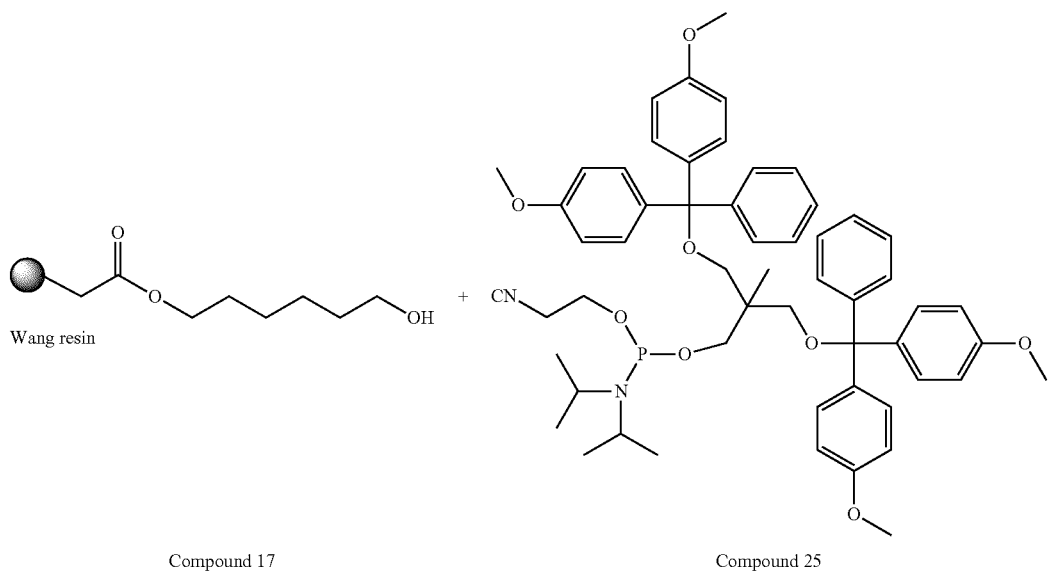

Compound 17         Compound 25

-continued

Tetrazole
Capping

↓

I₂ Oxidation

↓

2% Dichloro
acetic acid in DCM

↓

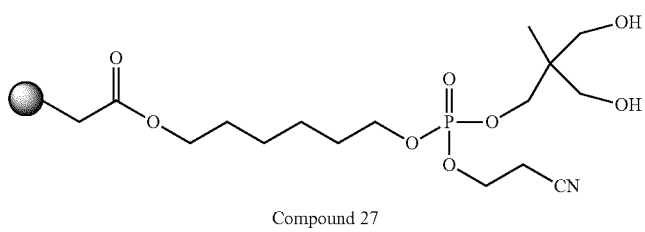

Compound 27

The synthesis of Compound 24 (Compound of Formula V) was carried out using a Polystyrene beads (100 mgr) (Wang resin) 1 mmol per gram with 3'-succinylhexanol. The beads were placed in a sinter glass under Argon and small stirrer. To the beads was added a solution of Compound 25 (1 gr. 1.08 mmol) in dry acetonitrile (3 mL), followed by addition of a solution of tetrazole 0.45 M in dry acetonitrile (3 mL). The solution was stirred at room temperature for 1 hour. The resulted beads were filtered and washed with methanol (10 mL) followed by Dichloromethane (DCM, 10 mL).

The beads were then covered with a solution of 5% of Dimethylamino pyridine in DCM (3 mL) and with a solution of (acetic anhydride 1:tetrhydrofurane 8.5:2,6-lutidine 0.5) (3 mL). The reaction mixture was stirred for 30 seconds followed by suction and washings with methanol (10 mL) followed by Dichloromethane (DCM, 10 mL).

The oxidation step was carried by adding a solution of Iodine Solution (0.02M in THF/pyridine/H₂O 70:20:10), (3 mL) with stirring for 30 seconds. Followed by suction and washings with methanol (3×10 mL) followed by Dichloromethane (DCM, 3×10 mL).

The deprotection step of the Dimethoxytrityl groups was carried out by adding a solution of 2% dichloroacetic acid in dichloromethane, (2 mL). After suction and washings with methanol (10 mL) followed by Dichloromethane (DCM, 10 mL) the deprotection step was repeated as much as needed, until absents of pink color.

b. Condensation of Compound 27 with Compound 14 to Obtain Compound 28

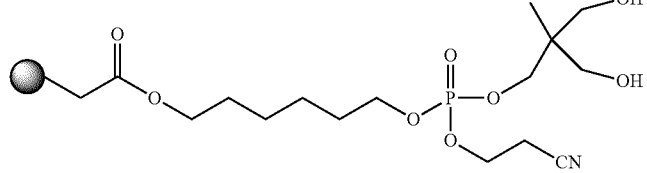

Compound 27

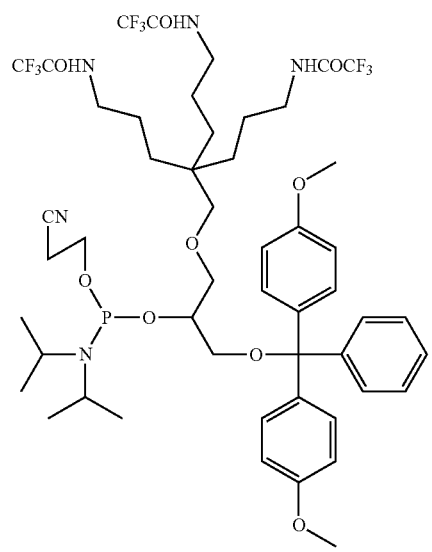

Compound 14

-continued

Tetrazole
Capping ↓

$I_2$ Oxidation ↓

2% Dichloro
acetic acid in DCM ↓

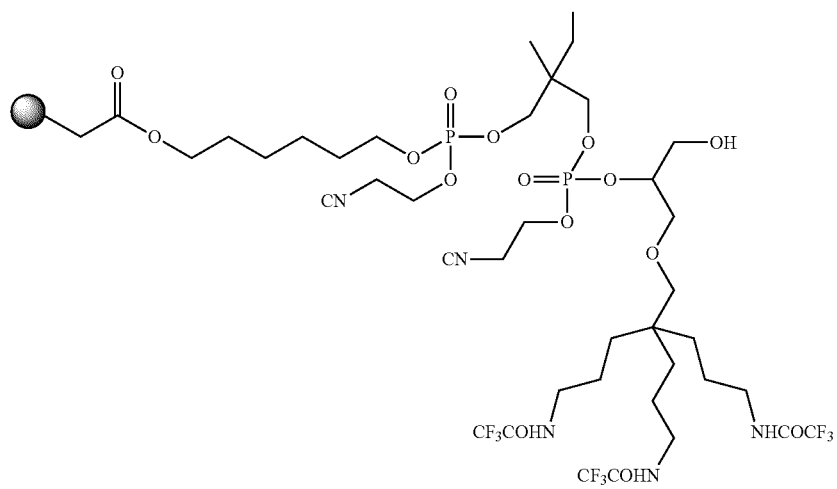

Compound 28

To the resulted beads from the previous step (Compound 27), was added a solution of Compound 14 (1.16 gr. 1.08 mmol) in dry acetonitrile (3 mL), followed by addition of a solution of tetrazole 0.45 M in dry acetonitrile (3 mL). The solution was stirred at room temperature for 1 hour. The resulted beads were filtered and washed with methanol (10 mL) followed by Dichloromethane (DCM, 10 mL).

The beads were then covered with a solution of 5% of Dimethylamino pyridine in DCM (3 mL) and with a solution of (acetic anhydride 1:tetrhydrofurane 8.5:2,6-lutidine 0.5) (3 mL). The reaction mixture was stirred for 30 seconds followed by suction and washings with methanol (10 mL) followed by Dichloromethane (DCM, 10 mL).

The oxidation step was carried by adding a solution of Iodine Solution (0.02M in THF/pyridine/$H_2O$ 70:20:10), (3 mL) with stirring for 30 seconds. Followed by suction and washings with methanol (3×10 mL) followed by Dichloromethane (DCM, 3×10 mL).

The deprotection step of the Dimethoxytrityl groups was carried out by adding a solution of 2% dichloroacetic acid in dichloromethane, (2 mL). After suction and washings with methanol (10 mL) followed by Dichloromethane (DCM, 10 mL) the deprotection step was repeated as much as needed, until absents of pink color.

c. Condensation of Linker Precursor Compound 16 with Compound 28 to Obtain compound 29
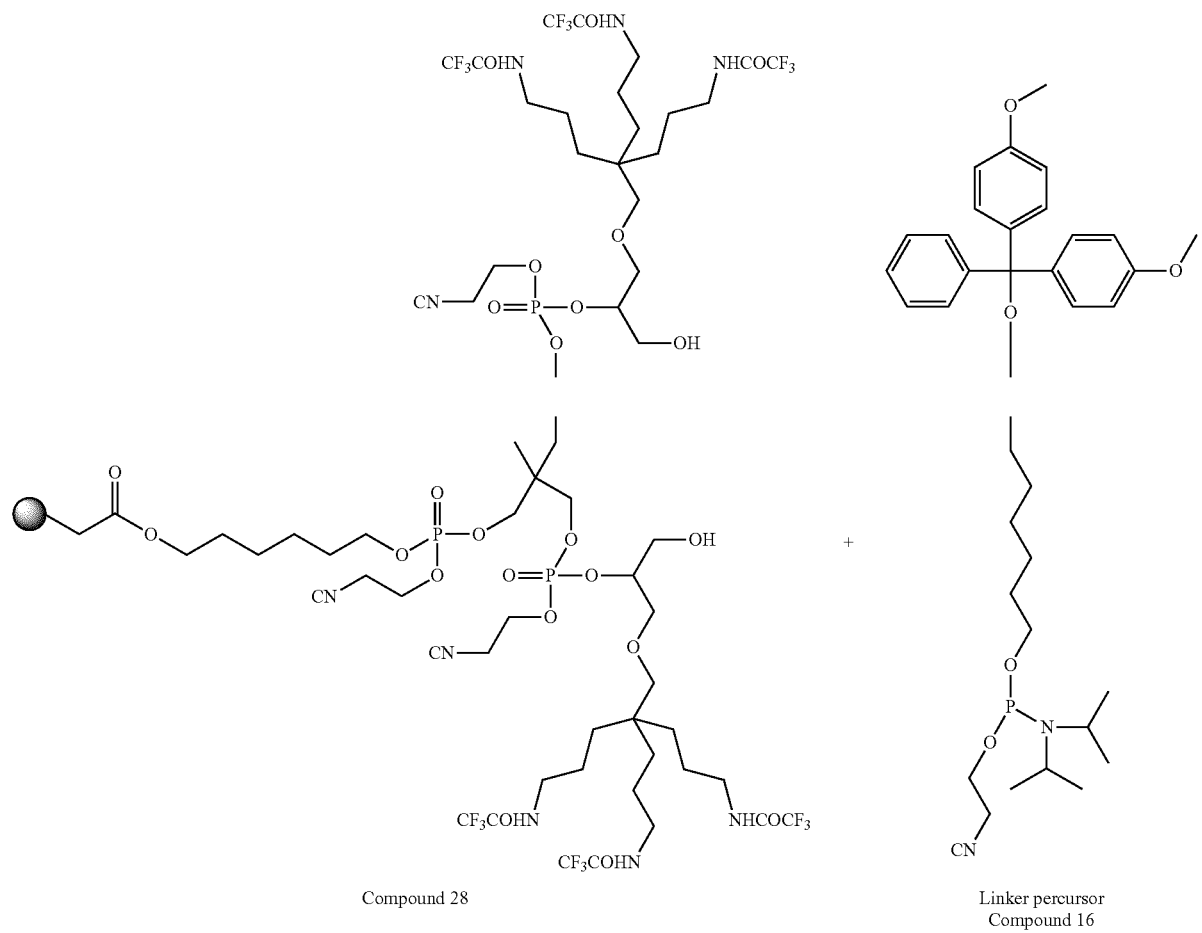
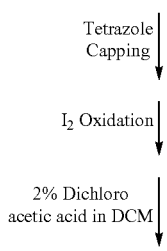
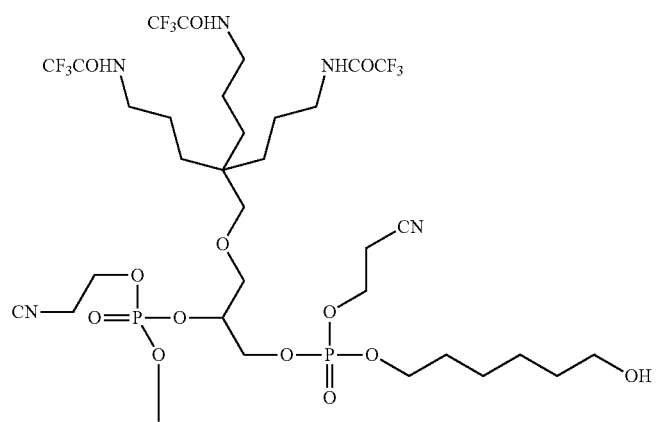

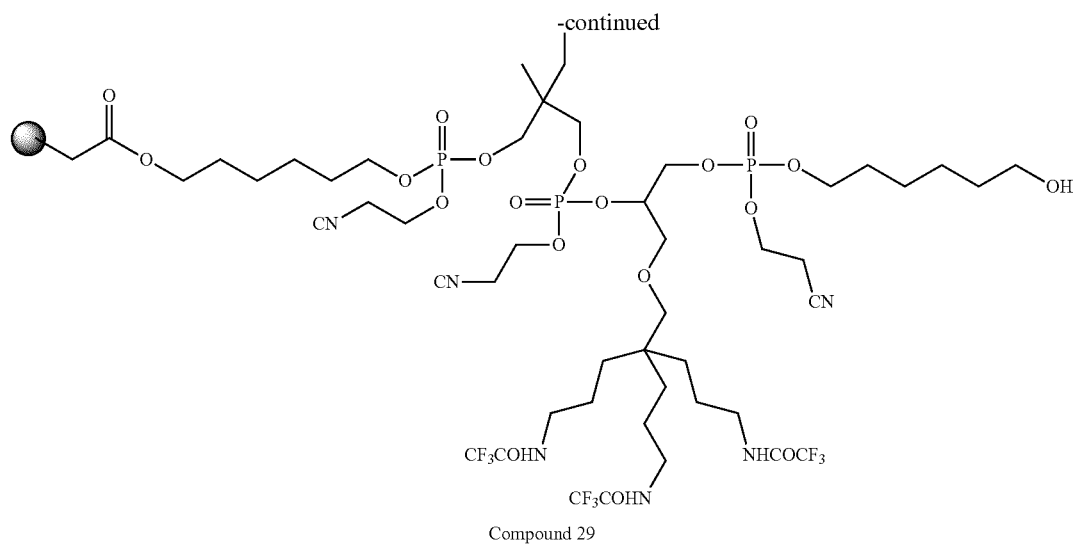

Compound 29

To the resulted beads from the previous step, was added a solution of Linker precursor Compound 16 (1 gr. 1.08 mmol) in dry acetonitrile (3 mL), followed by addition of a solution of tetrazole 0.45 M in dry acetonitrile (3 mL).

The cycle was repeated as it is described in the previous step (b), to obtain Compound 29.

In order to receive Compound 24 (Compound of Formula V), the above steps b and c were repeated, to get Compound 30

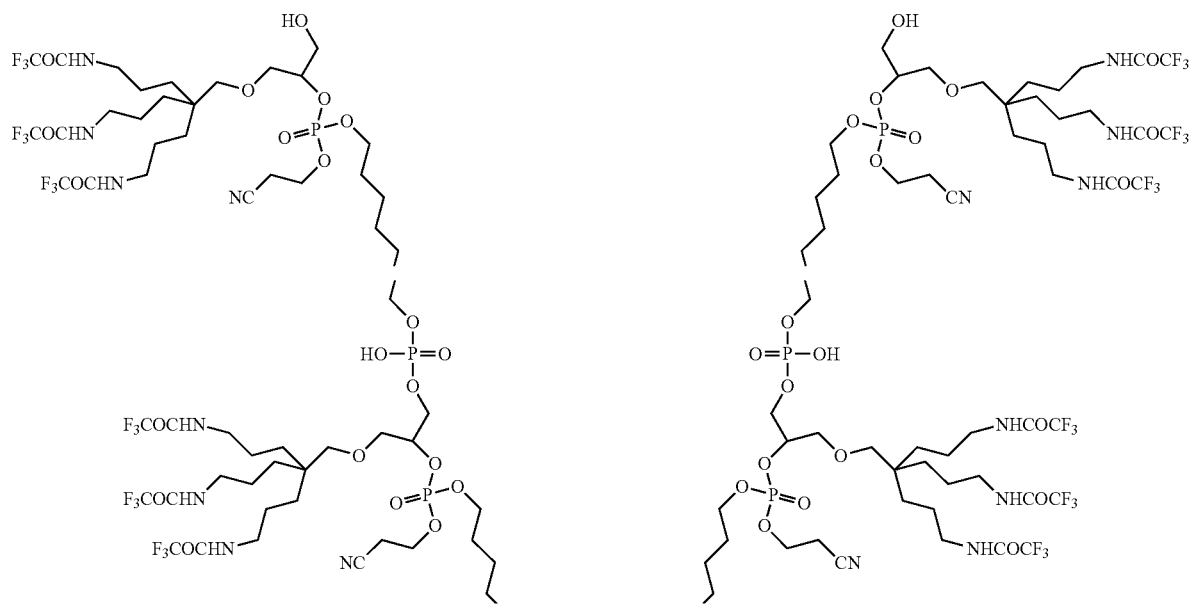

Compound 30

-continued
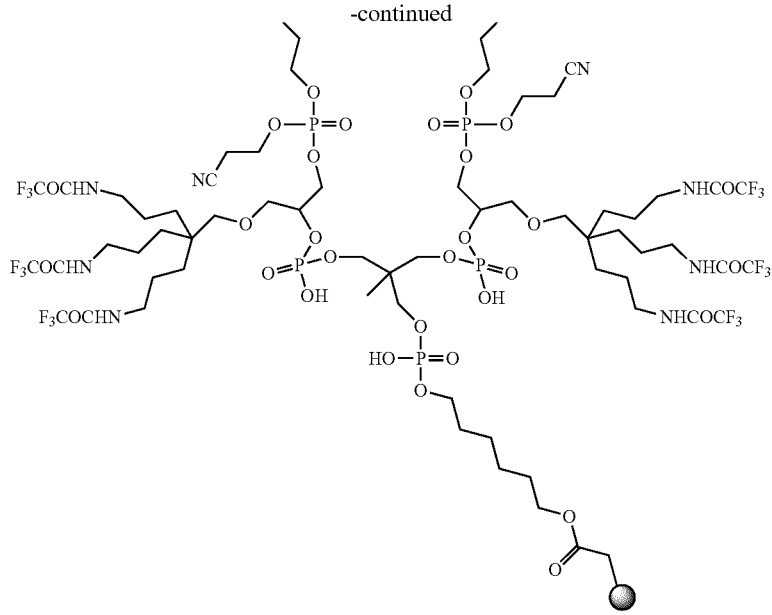
d. Condensation of Compound 30 with 6-FAM to Obtain Compound 31
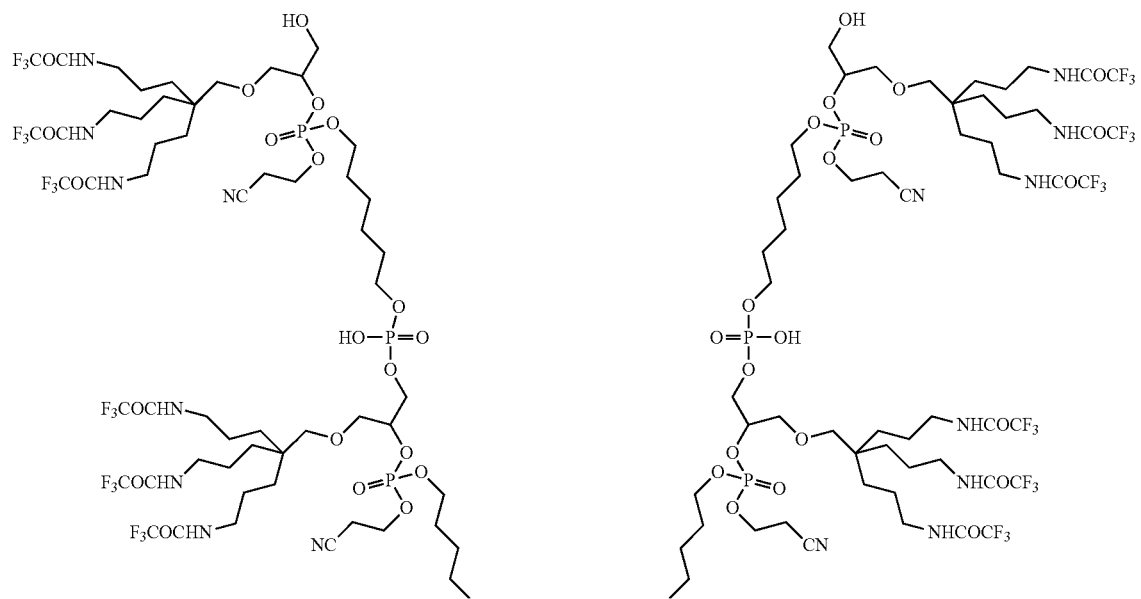

-continued
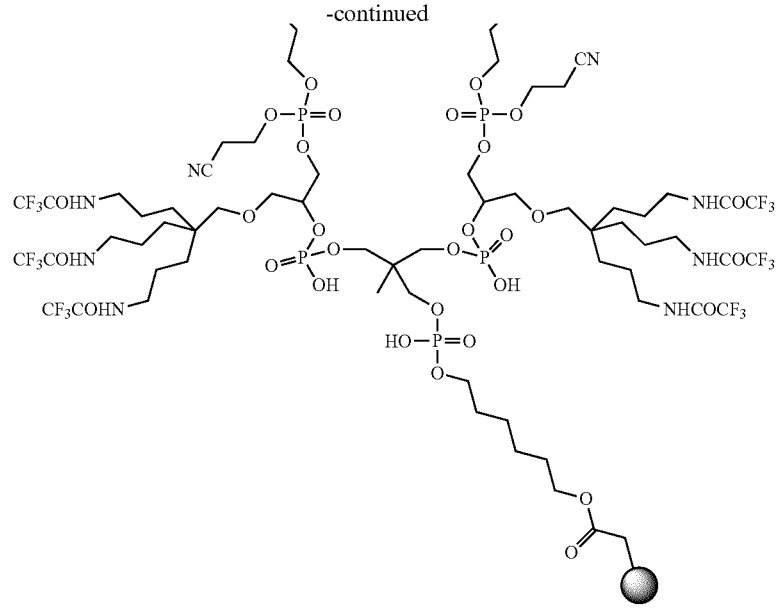
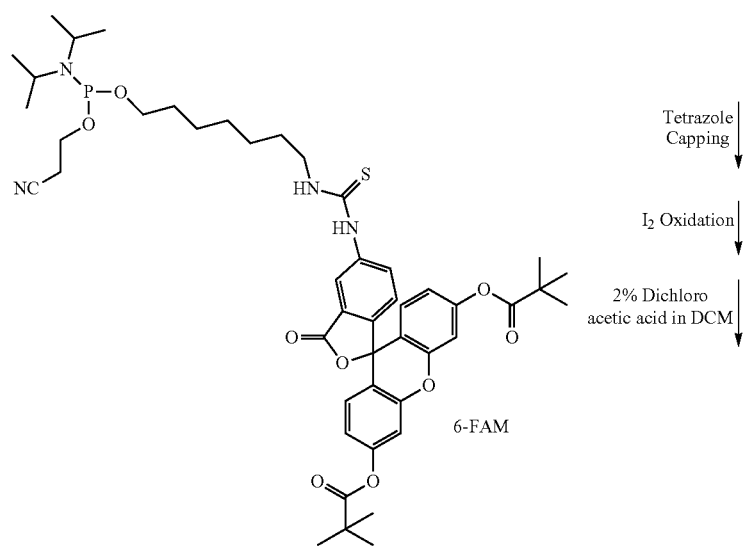
6-FAM
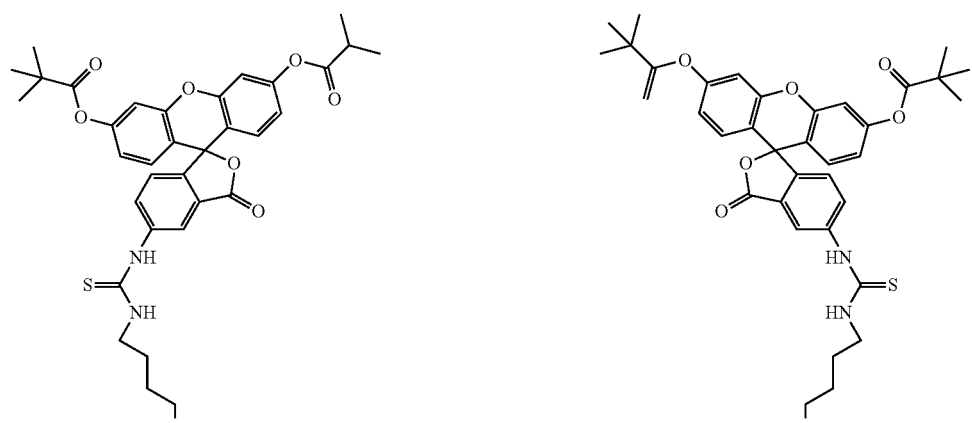

165

-continued

166

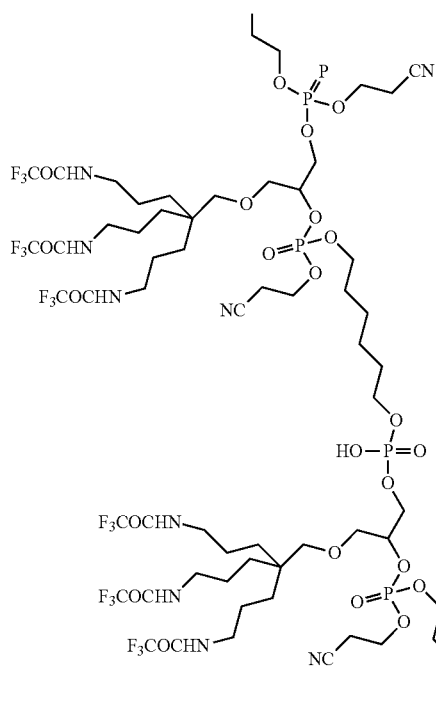
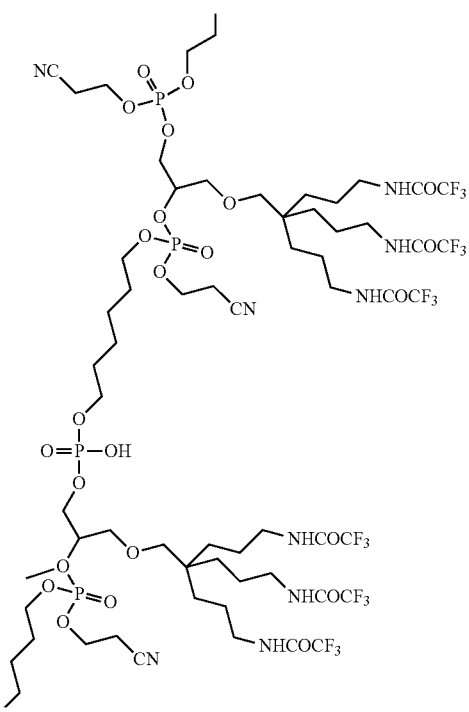
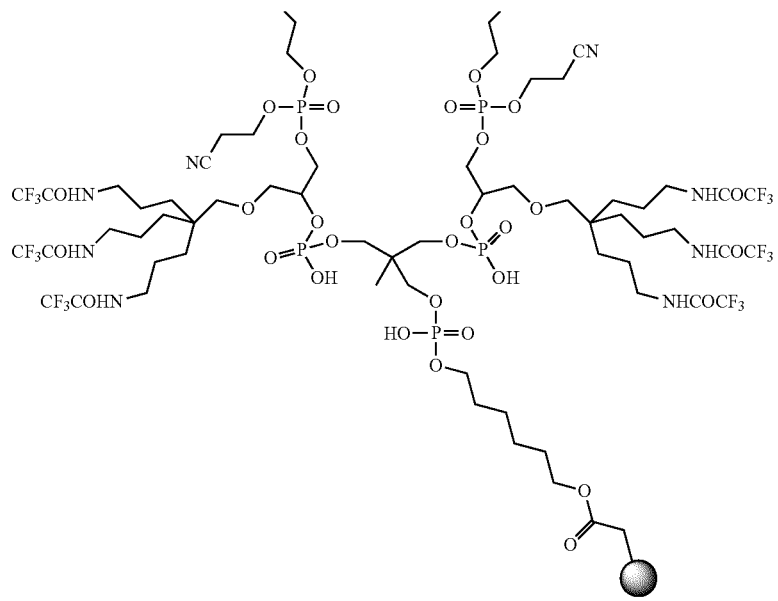

The beads resulted from step c, (Compound 30), were allowed to react with 6-FAM (Glen research) according to the cycle as is described in step 1 to obtain Compound 31.

e. Deprotection and Guanidization to Obtain Compound 24 (Compound of Formula V)

Compound 31 was mixed with concentrated ammonium hydroxide (6 mL) in sealed tube in the dark, and heated to 60° C. for 18 hours. After cooling to 0° C., the aqueous solution was centrifuge, filtered and the supernatant was evaporated to dryness to obtain as a pellet as following:

167  168
Compound 32
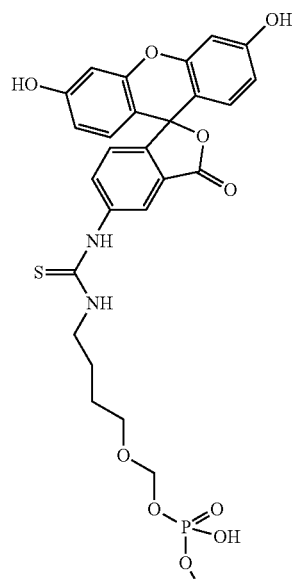
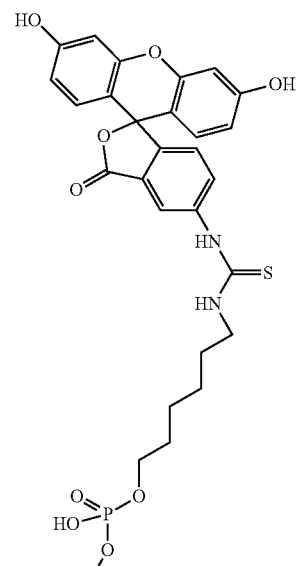
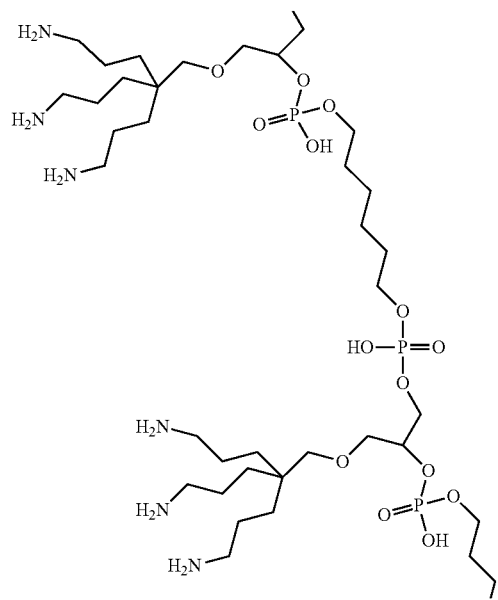
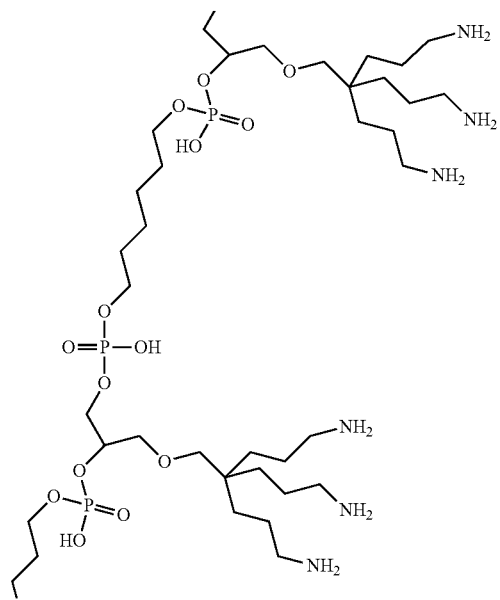

-continued

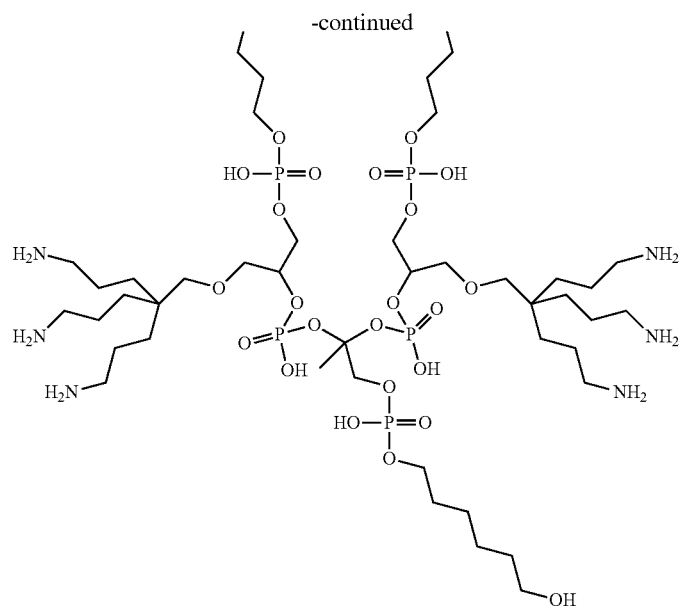

25

The resulting pellet (Compound 32), was treated with a solution of 1H-Pyrazole-1-carboxamidine hydrochloride (Aldrich) (5 equivalents per one amino group) in 5% sodium carbonate (5 ml). The solution was heated to 50° C. for 24 hours. The reaction mixture was cooled to room temperature. The crude product was dissolved in deionized doubly distilled DEPC treated water (1 ml) and was purified on Sephadex G-25 to obtain a fluorescent Compound 24 (Compound of Formula V), ready for delivery into cells.

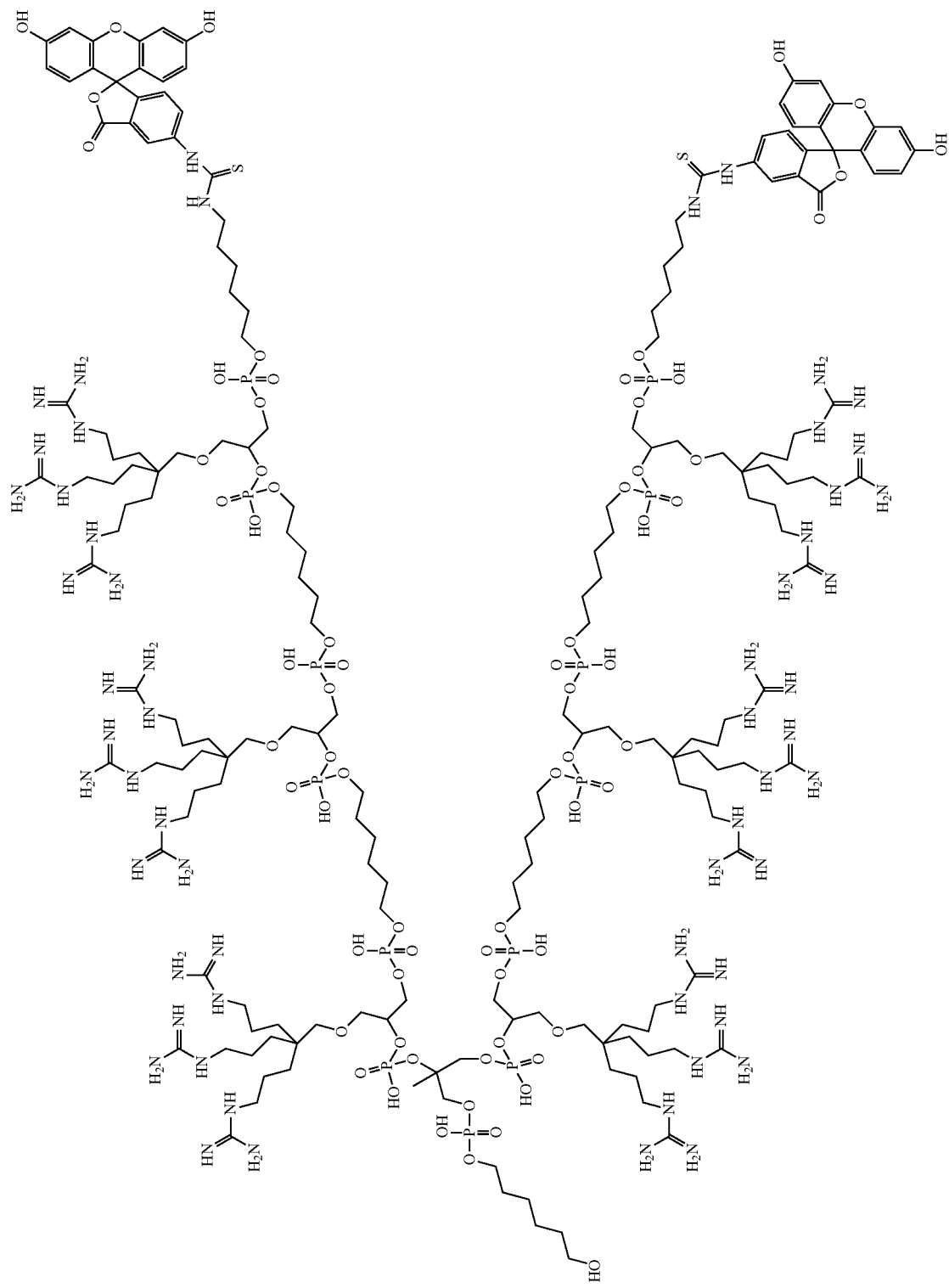

Example 6

In this example, we will describe the synthesis of Y shape Conjugate (Compound 33).

175 176
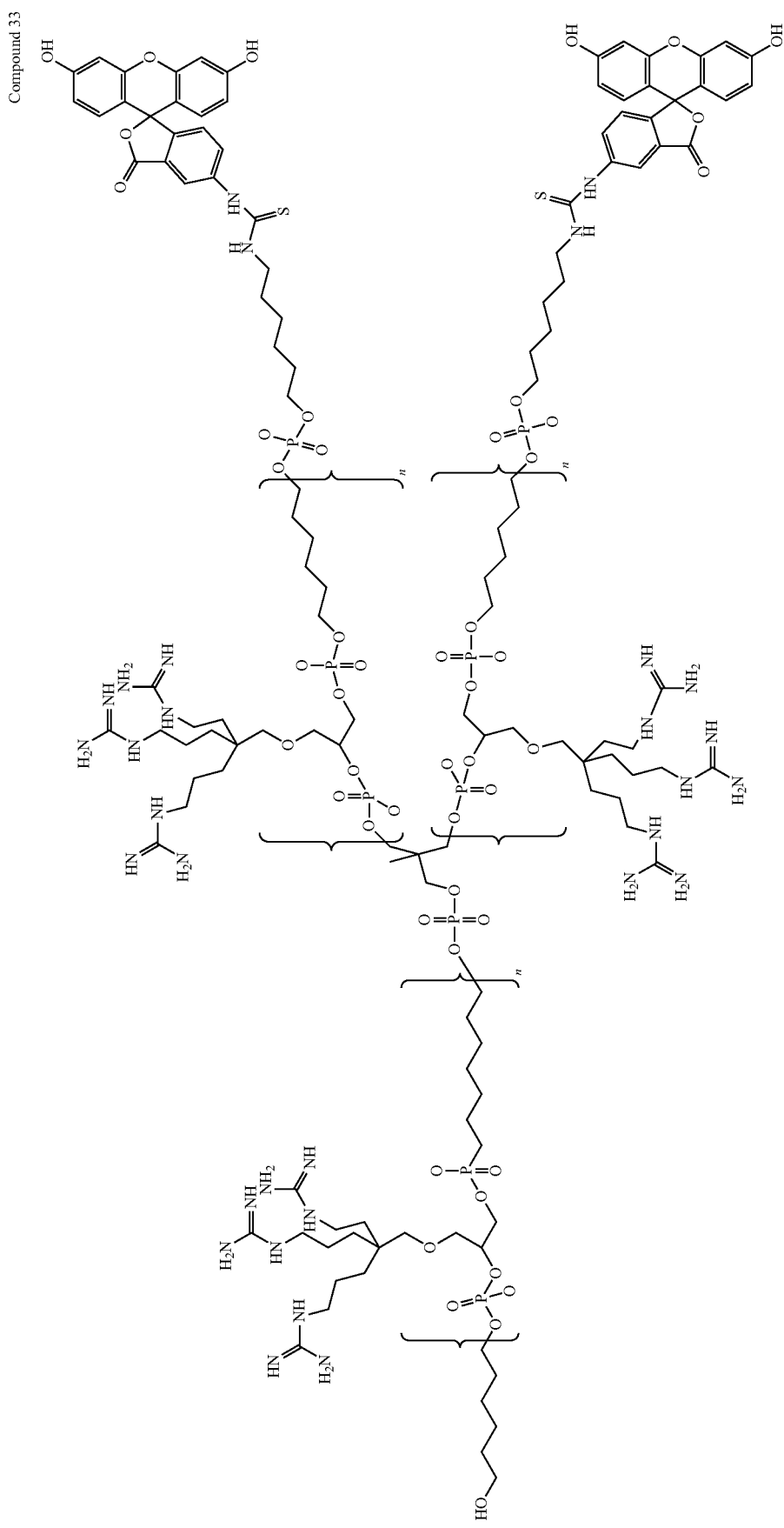

1. consecutive condensations of Compound 14 and Linker precursor Compound 16, to obtain an oligomeric compound as following:

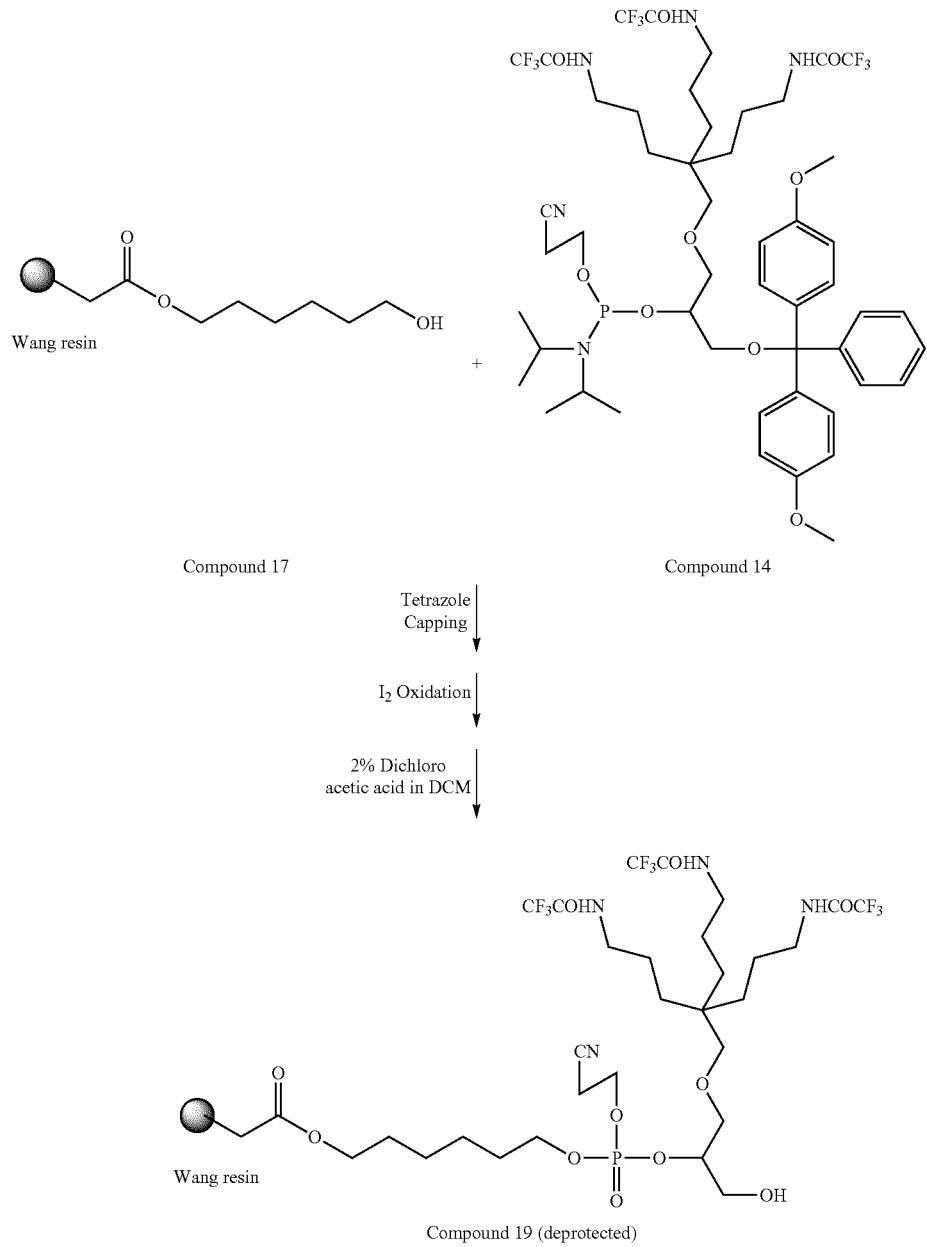

Compound 17

Compound 14

Tetrazole Capping

I₂ Oxidation

2% Dichloro acetic acid in DCM

Compound 19 (deprotected)

The synthesis of Compound 33 was carried out using a Polystyrene beads (100 mgr) (Wang resin) 1 mmol per gram with 3'-succinylhexanol. The beads were placed in a sinter glass under Argon and small stirrer. To the beads was added a solution of Compound 14 (1.16 gr. 1.08 mmol) in dry acetonitrile (3 mL), followed by addition of a solution of tetrazole 0.45 M in dry acetonitrile (3 mL). The solution was stirred at room temperature for 1 hour. The resulted beads were filtered and washed with methanol (10 mL) followed by Dichloromethane (DCM, 10 mL).

The beads were then covered with a solution of 5% of Dimethylamino pyridine in DCM (3 mL) and with a solution of (acetic anhydride 1:tetrhydrofurane 8.5:2,6-lutidine 0.5) (3 mL). The reaction mixture was stirred for 30 seconds followed by suction and washings with methanol (10 mL) followed by Dichloromethane (DCM, 10 mL).

The oxidation step was carried by adding a solution of Iodine Solution (0.02M in THF/pyridine/H₂O 70:20:10), (3 mL) with stirring for 30 seconds. Followed by suction and washings with methanol (3×10 mL) followed by Dichloromethane (DCM, 3×10 mL).

The deprotection step of the Dimethoxytrityl group was carried out by adding a solution of 2% dichloroacetic acid in dichloromethane, (2 mL). After suction and washings with methanol (10 mL) followed by Dichloromethane (DCM, 10 mL) the deprotection step was repeated as much as needed, until absents of pink color.

2. Condensation of Compound 19 (deprotected) with Linker Precursor Compound 16 to obtain Compound 34

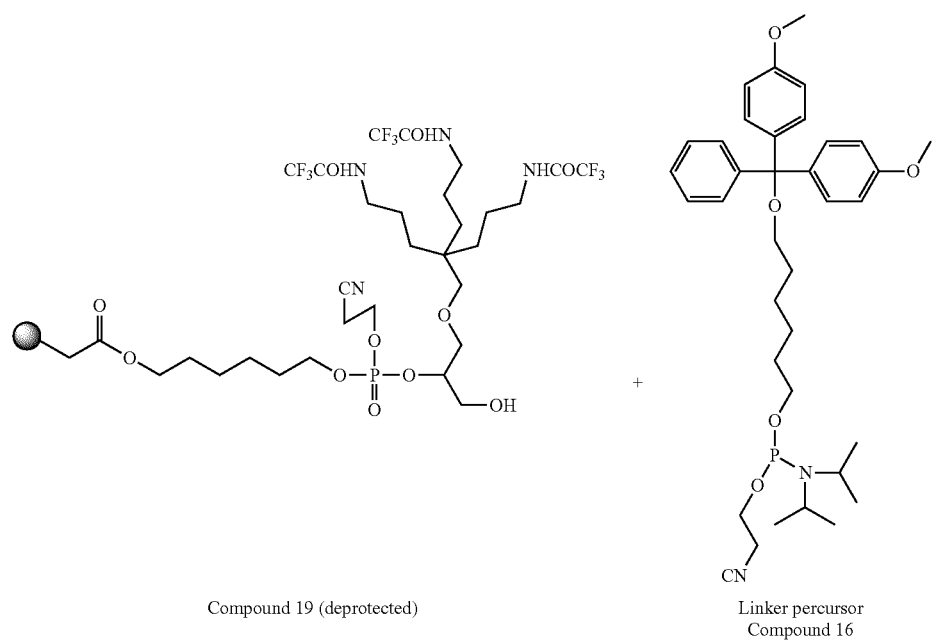

Compound 19 (deprotected)          Linker percursor Compound 16

Tetrazole Capping

I₂ Oxidation

2% Dichloro acetic acid in DCM

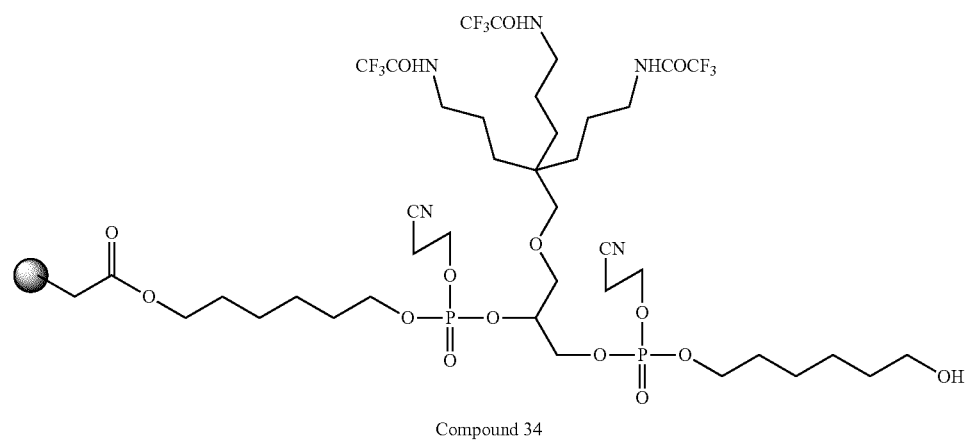

Compound 34

To the resulted beads from the previous step, was added a solution of Linker precursor Compound 16 (1 gr. 1.08 mmol) in dry acetonitrile (3 mL), followed by addition of a solution of tetrazole 0.45 M in dry acetonitrile (3 mL).

The cycle was repeated as it is described in the previous step 1, to obtain Compound 34.

In order to obtain an oligomeric compound (Compound 35), steps 1 and 2 are repeated as desired, to obtain the molecular weight as desired.

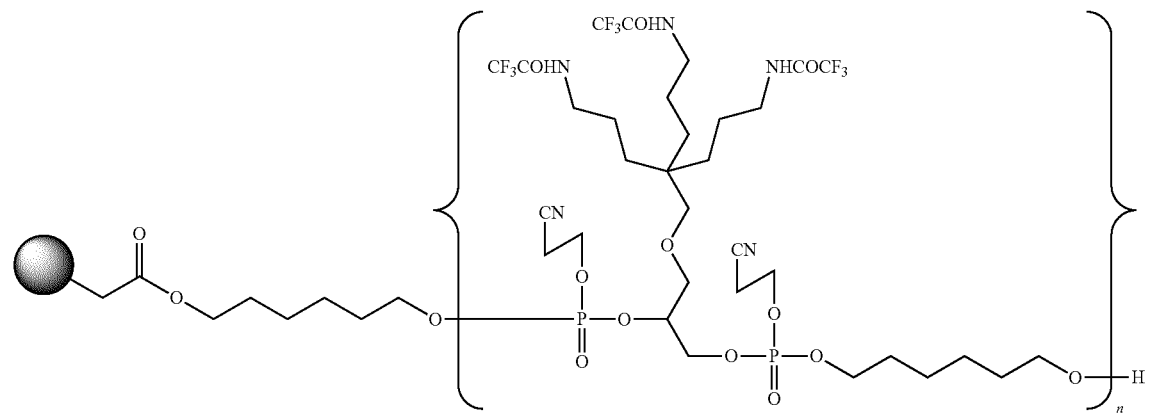
Compound 35
After the last condensation, the hydroxyl group can be condensed with the splitting molecule (Compound 25), followed by condensations steps 1 and 2 as above in this example to obtain the Y Shape compound precursor (Compound 36) as following:

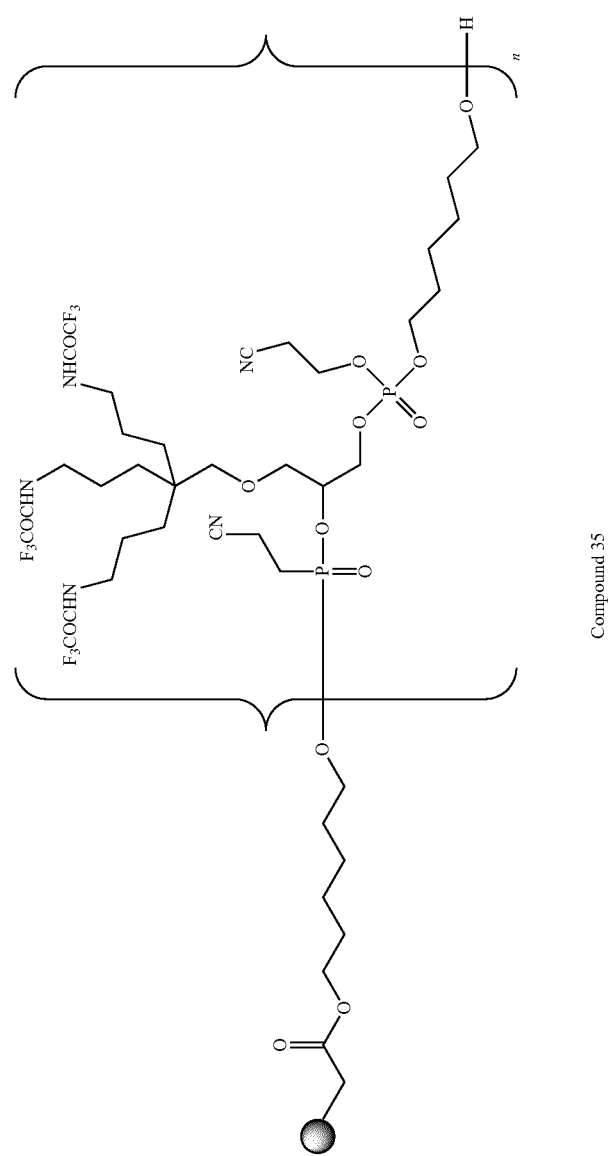
Compound 35

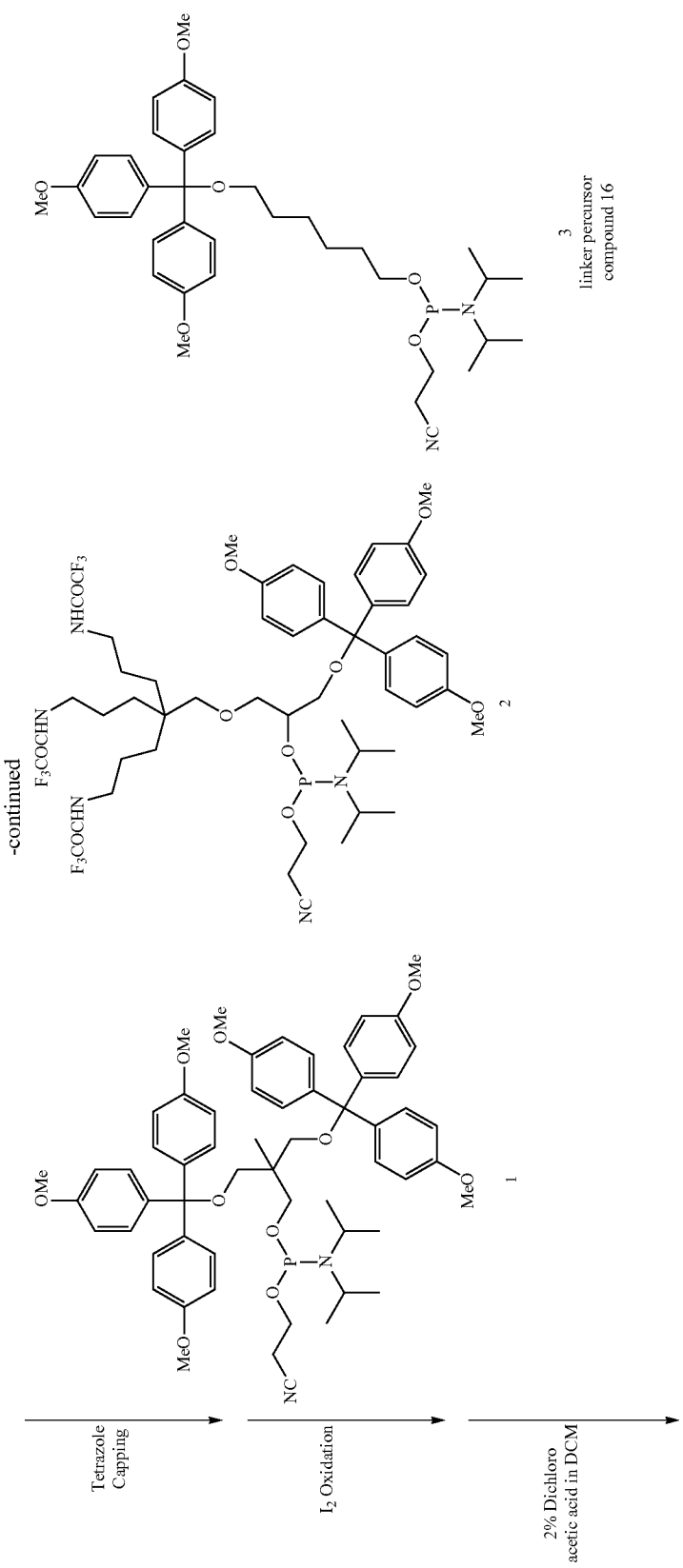

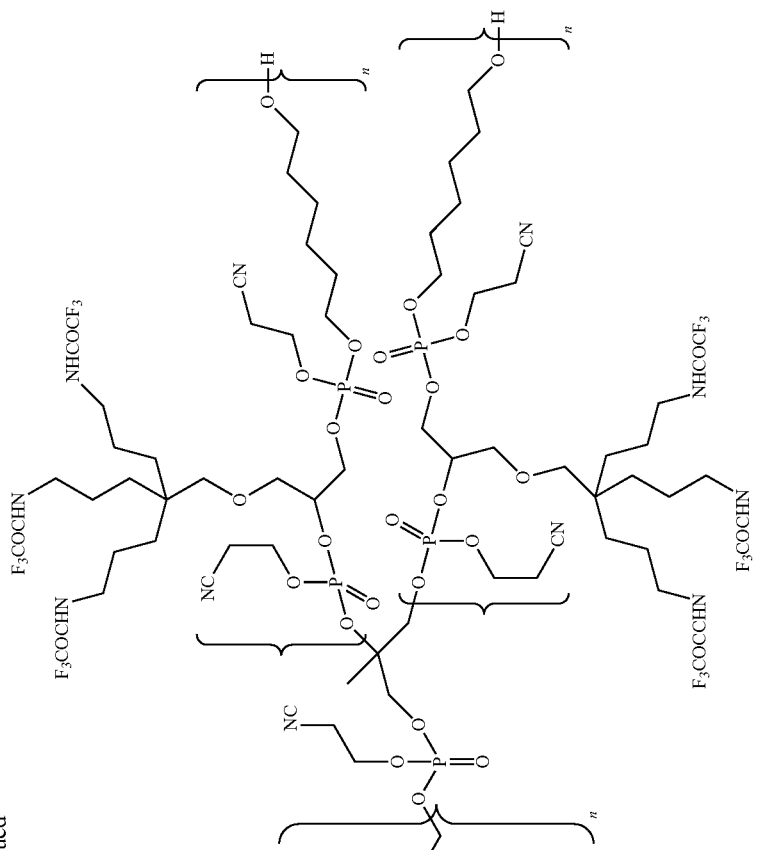
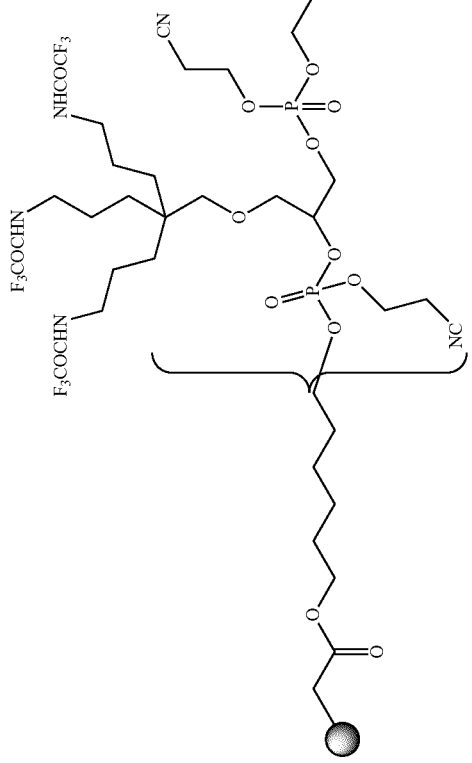
Compound 36

The next step is labeling with 6-FAM as it is described in Example 5, to obtain compound 37.

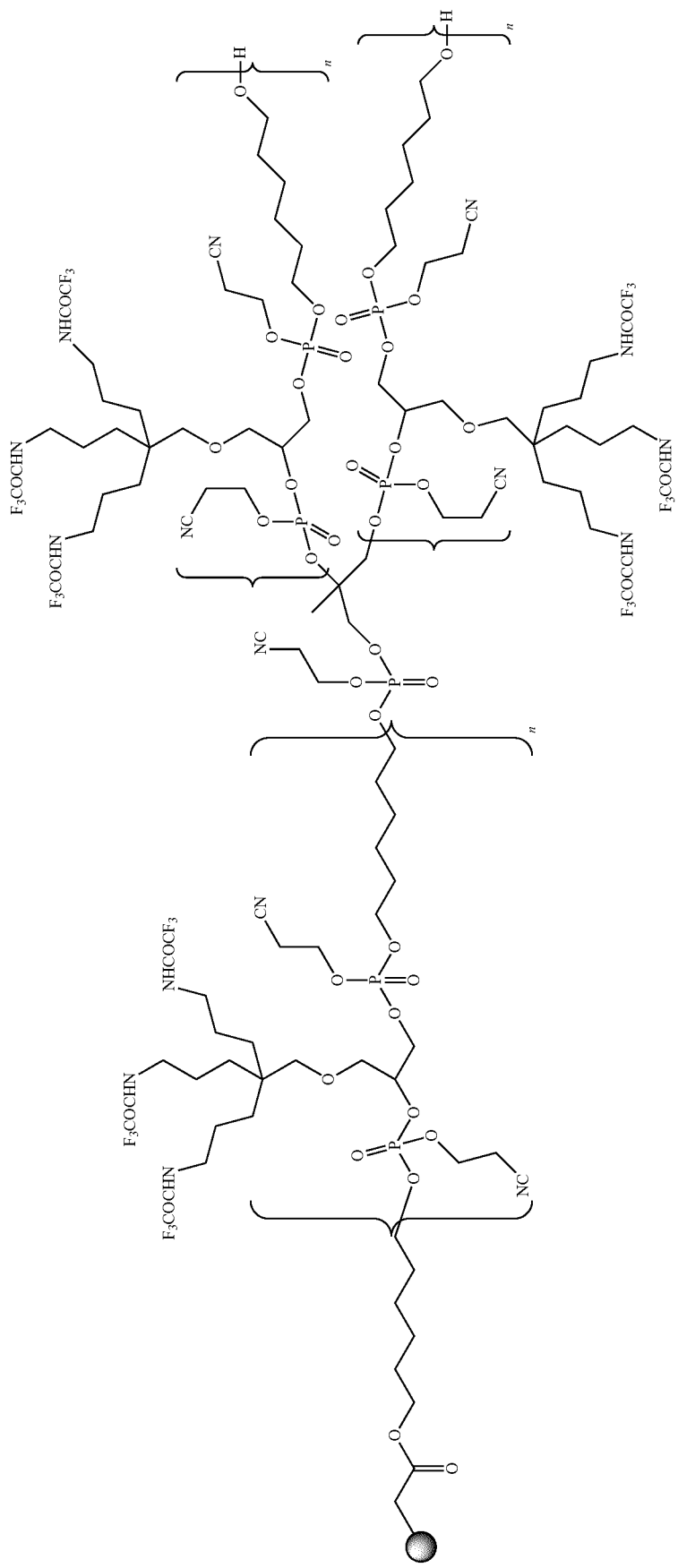

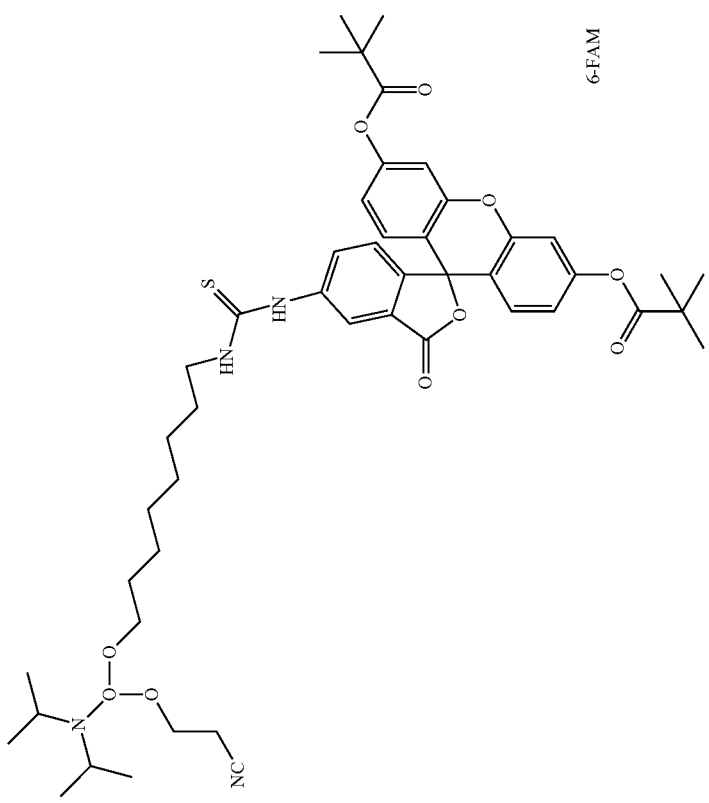

-continued
Compound 37
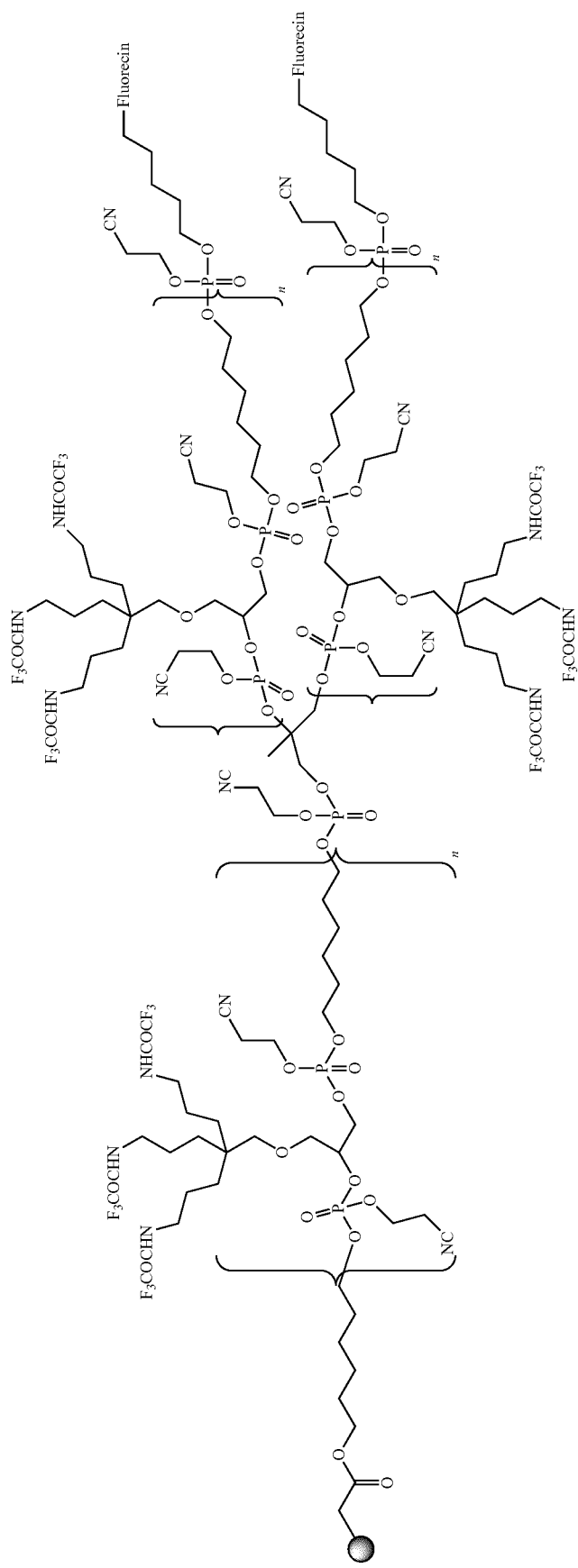

The next step is deprotection, following guanidization as it is described in Example 5 to obtain the Y Shape conjugate—Compound 33.

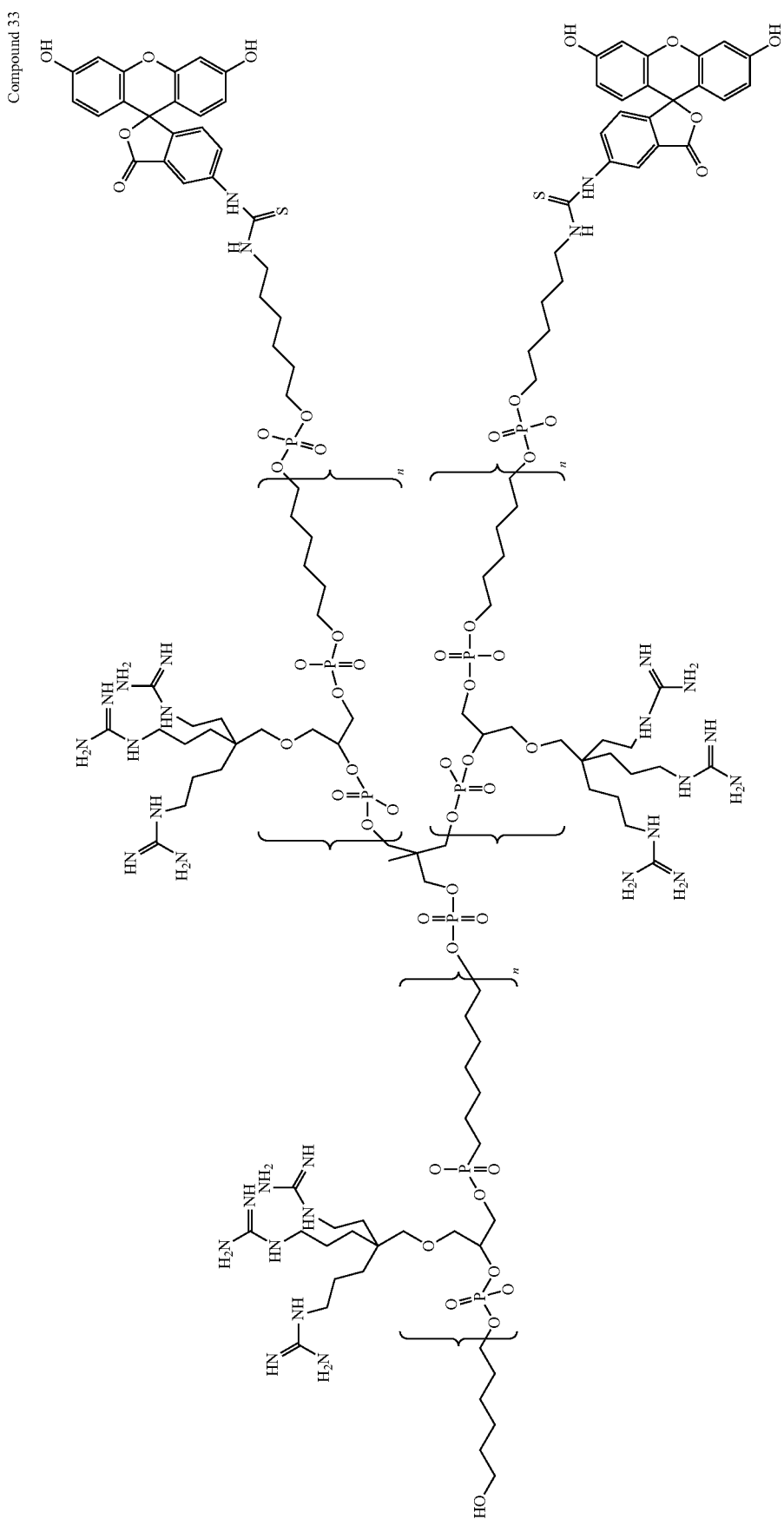

Example 7

Preparation of a Conjugate of Oligomeric Polymer Delivery Moiety Having Deoxyoligonucleotide Fragments Attached Thereto This example illustrates the online synthesis of DNA segment following the synthesis of the polymer by sequentially condensation of Compound 14 following condensation of continuing synthesis of another DNA segment, All of this synthesis is done on the same polymeric support.

It is understood that this example is not limited to the synthesis of a particularly DNA sequence, but any of DNA sequences could be synthesize by this methodology following number of condensations of Compound 14.

Attachment of Nucleic Acids, To an Oligomeric Heteroalicyclic Moiety

A. Preparation of an oligodeoxynucleotide of sequence 3'-AATTCGACTGAC-OH-5', and its complementary Sequence to an oligomeric heteroalicyclic moiety.

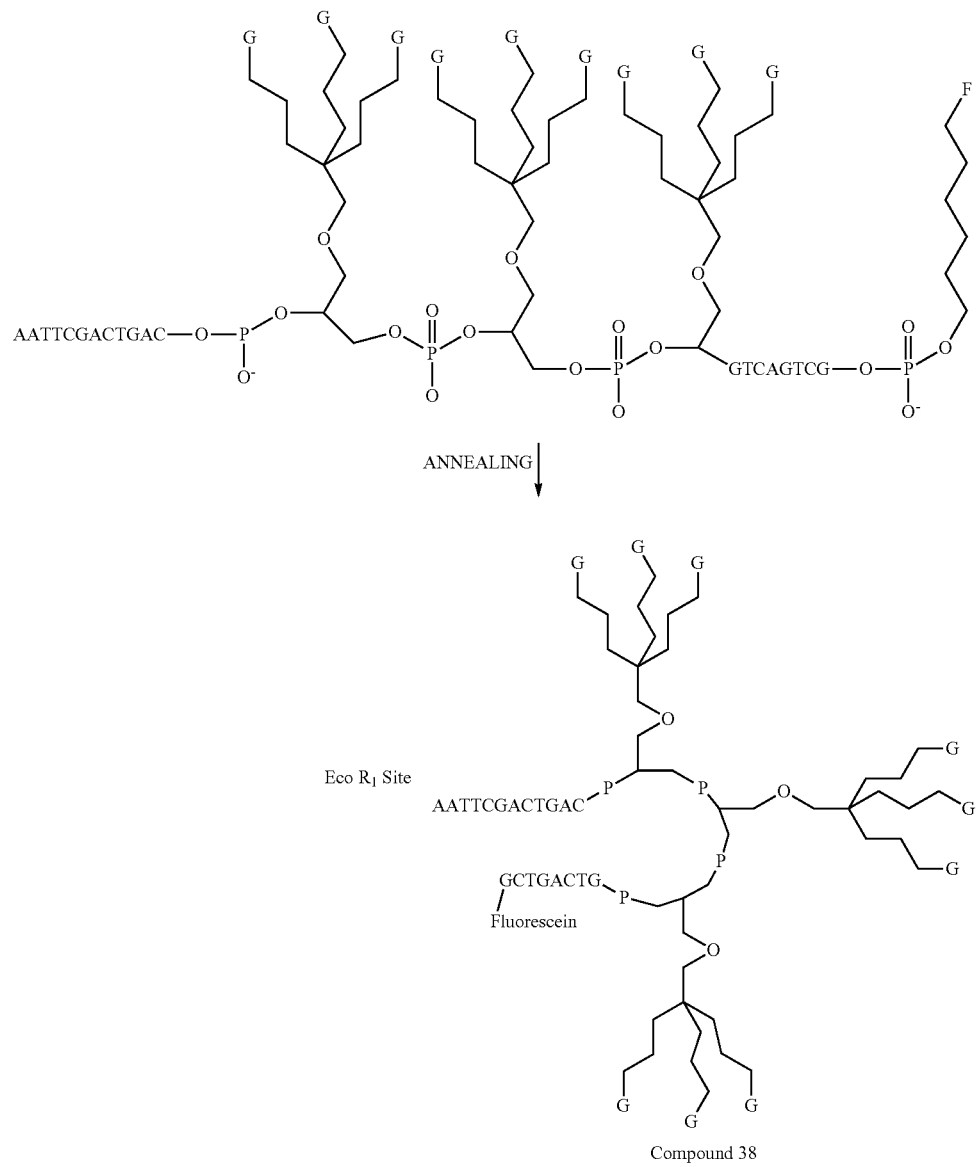

Compound 38

G is a guanido group

Wherein p is a phosphate group 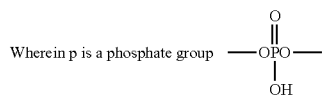

```
AATTCGACTGAC  (SEQ ID No: 8)
GTCAGTCG      (SEQ ID No: 9)
```

The synthesis of Compound 38 was carried out using a controlled pore glass (CPG) support of 1000 A° pore size, loaded at 35 micromoles per gram with 3'-succinylhexanol (Compound 17). The 12-mer oligodeoxynucleotide of sequence 3'-AATTCGACTGAC-OH-5' (a restriction site sequence for EcoR1 restriction enzyme) is prepared at the 0.35 mmol scale on an Applied Biosystems 381A DNA Synthesizer using standard deoxynucleoside phosphoramidites, followed by sequentially condensation of Compound 14, and condensation of complementary sequence 3'-GTCAGTCG-5', followed by condensation of FAM-HPA as is described above. Using the protocol as described by Beaucage et al., 1981, *Tetrahedron Letters* 22, 5843-5846. Compound 39 was detached from the CPG resin, by treating the polymeric support with concentrated ammonium hydroxie, followed by purification of the fluoresceinated product, using Sephadex G-25. Compound 38 is ready for cellular uptake. This example illustrates the online synthesis of RNA segment following the synthesis of the polymer by sequentially condensation of Compound 14 following condensation of continuing synthesis of another RNA segment, All of this synthesis is done on the same polymeric support It is understood that this example is not limited to the synthesis of a particularly RNA sequence, but any of RNA sequences could be synthesize by this methodology following number of condensations of Compound 14.

RNA Synthesis, Deprotection and Purification Protocol oligodeoxynucleotide of sequence 3'-AUCGGACCUGCAU-GUACGGAGAU and its complementary sequence 5'-(F)-UAGCCUGGACGUACAUGCCUCUA and attachment to an oligomeric heteroalicyclic moiety.

The synthesis of Compound 40 was carried out using a controlled pore glass (CPG) support of 1000 A° pore size, loaded at 35 mmol per gram with 3'-succinylhexanol. The support was placed in a column which fits to 394 ABI machine and allowed to react with Compound 14 as described above, followed by RNA synthesis, and again condensation with Compound 14 as desired followed by RNA synthesis and last condensation with fluorescein. The RNA molecules were synthesized using the standard steps cycle written by the manufacturer (Glen Research) with modifications to a few wait steps as described below. The monomers were RNA phosphoramidites (Glen research) with standard protecting groups ($N^6$-benzoyl-5'-O-dimethoxytrityladenosine-2'-(tri-isopropylsilylo xymethyl)TOM-3'-O—N,N'-diisopropyl-2-cyanoethylphosphoramidite, 5'-O-dimethoxytrityluridine-2'-TOM-3'-O—N,N'-diisopropyl-2-cyanoethylphosphoramidite, $N^2$-isobutyryl-5'-O-dimethoxytritylguanosine-2'-TOM-3'-O—N,N'-diisopropyl-2-cyanoethylphosphoramidite, and $N^4$-benzoyl-5'-O-dimethoxytritylcytidine-2'-TOM-3'-O—N,N'-diisopropyl-2-cyanoethylphosphoramidite from (Glen research) used at a concentration of 0.15M in acetonitrile ($CH_3CN$) and a coupling time of 7.5 min. The activator was thiotetrazole (0.25M), For the PO-oxidation Iodine/Water/Pyridine was used. All reagents for synthesis were also from Glen Research.

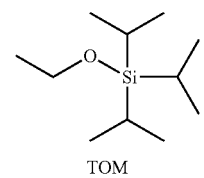

TOM

Compound 40

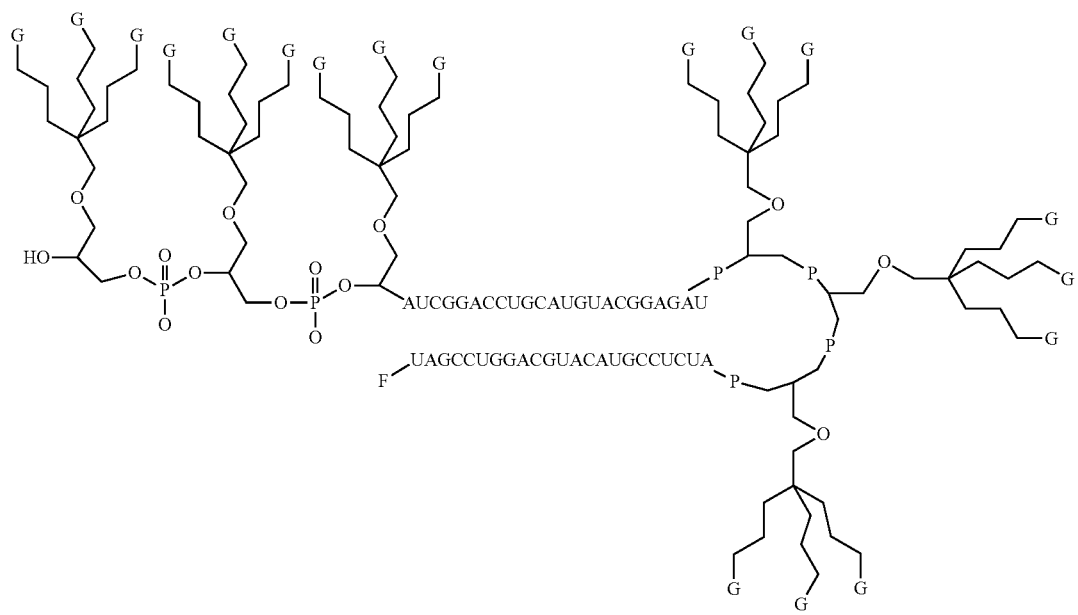

G is a guanido moiety

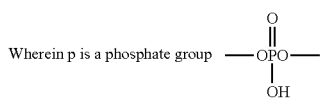

F is fluorescein

Deprotection-I (Compound Cleavage, Base and Phosphate Deprotection)

After completion of synthesis, the controlled pore glass (CPG) was transferred to a screw cap vial (Fisher, catalog number 03-340-5N) or a screw cap RNase free microfuge tube. The oligonucleotide was cleaved from the CPG with simultaneous deprotection of base and phosphate groups with 1.0 mL of a mixture of ethanolic ammonia [ammonia:ethanol (3:1)] for 6 hours to overnight at 55° C. The vial was cooled briefly on ice and then the ethanolic ammonia mixture was transferred to a new microfuge tube. The CPG was washed with 3.times.0.25 mL portions of 50% acetonitrile and lyophilized. The crude product was dissolved in a solution of 1H-Pyrazole-1-carboxamidine hydrochloride (Aldrich) (50 equivalents) in 5% sodium carbonate (5 ml). The heterogenic solution was heated to 50° C. for 24 hours. The approximate 1.75 mL of solution is best divided equally into two microfuge tubes, capped tightly and then cooled at −80° C. for 15 min, before drying in a speed vac/lyophilizer for about 90 min.

Deprotection-II (Removal of 2' TOM Group)

The white residue obtained was resuspended in 200 μL of triethylamine trihydrofluoride (TEA.3HF, Aldrich) and heated at 65° C. for 1.5 h to remove the tertbutyldimethylsilyl (TBDMS) groups at the 2' position. The reaction was then quenched with 400 μL of isopropoxytrimethylsilane (iPrOMe$_3$Si Aldrich) and further incubated on the heating block leaving the caps open for 15 min; (This causes the volatile isopropxytrimethylsilylfluoride adduct to vaporize). The residual quenching reagent was removed by drying in a speed vac. The Compound was then precipitated in anhydrous methanol (MeOH, 800 .mu·L). The liquid was removed very carefully after spinning in a centrifuge for 5 minutes on the highest speed available. Residual methanol was removed by drying briefly in a speed vac after freezing at −80° C. The crude RNA was obtained as a white fluffy material in the microfuge tube.

Quantifying Crude Compound 40 or Raw Analysis

Samples were dissolved in 50% aqueous acetonitrile (0.5 mL) and quantified as follows: Blanking was first performed with 50% aqueous acetonitrile alone (1 mL). 5 μL of sample and 995 μL of 50% acetonitrile, were mixed well in a microfuge tube, transferred to cuvette and absorbance reading obtained at 260 nm. The crude material was dried down and stored at −20° C.

Purification of Salted-Compound 40

The crude Compounds were analyzed and purified by HPLC (Mono Q Pharmacia Biotech 5/50). The buffer system is A=100 mM Tris HCl 10% HPLC grade acetonitrile pH=8, B=100 mM Tris-HCl pH 8, 10% HPLC grade acetonitrile 1 M NaCl, flow 1.0 mL/min, wavelength 260 nm. For the unmodified RNA 21mer a gradient of 0-0.6M NaCl is usually adequate. One can purify a small amount of material (.about.5 OD) and analyze by CGE or MS. Once the identity of this material is confirmed the crude Compound can then be purified using a larger amount of material. i.e 40 OD's per run, flow rate of 1 ml/min and a less sensitive wavelength of 280 nm to avoid saturation of the detector. Fractions containing the full length oligonucleotides are then pooled together, evaporated and finally desalted as described below.

Desalting of Purified Compound 40

The purified dry Compound 40 was then desalted using either C-18 Sepak cartridges (Waters) or Sephadex G-25M (Amersham Biosciences). The cartridge was conditioned with 10 mL each of acetonitrile, followed 50% acetonitrile, 100 mM buffer (this can be triethylammonium acetate, sodium acetate or ammonium acetate). Finally the purified oligomer dissolved thoroughly in 10 mL RNAse free water was applied to the cartridge with very slow dropwise elution. The cartridge was washed with water (10 mL) to remove salts. And finally the salt free Compound 40 was eluted with 50% acetonitrile or 50% methanol directly into a screw cap vial. The fluoreseinated product was pooled and lyophilized for delivery into living cells.

Additional examples describing the activation of RNAi mechanism into cells are described in the following scheme, which is expressly included as part of the disclosure of this application.

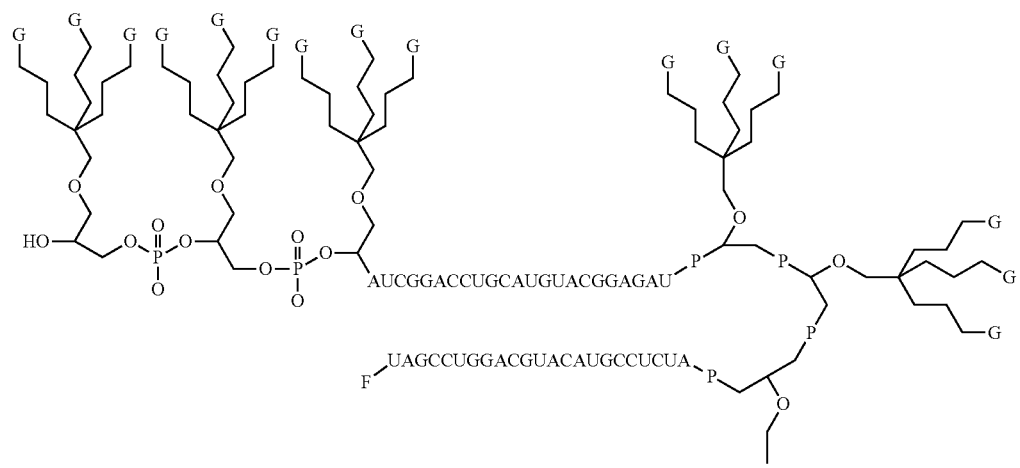

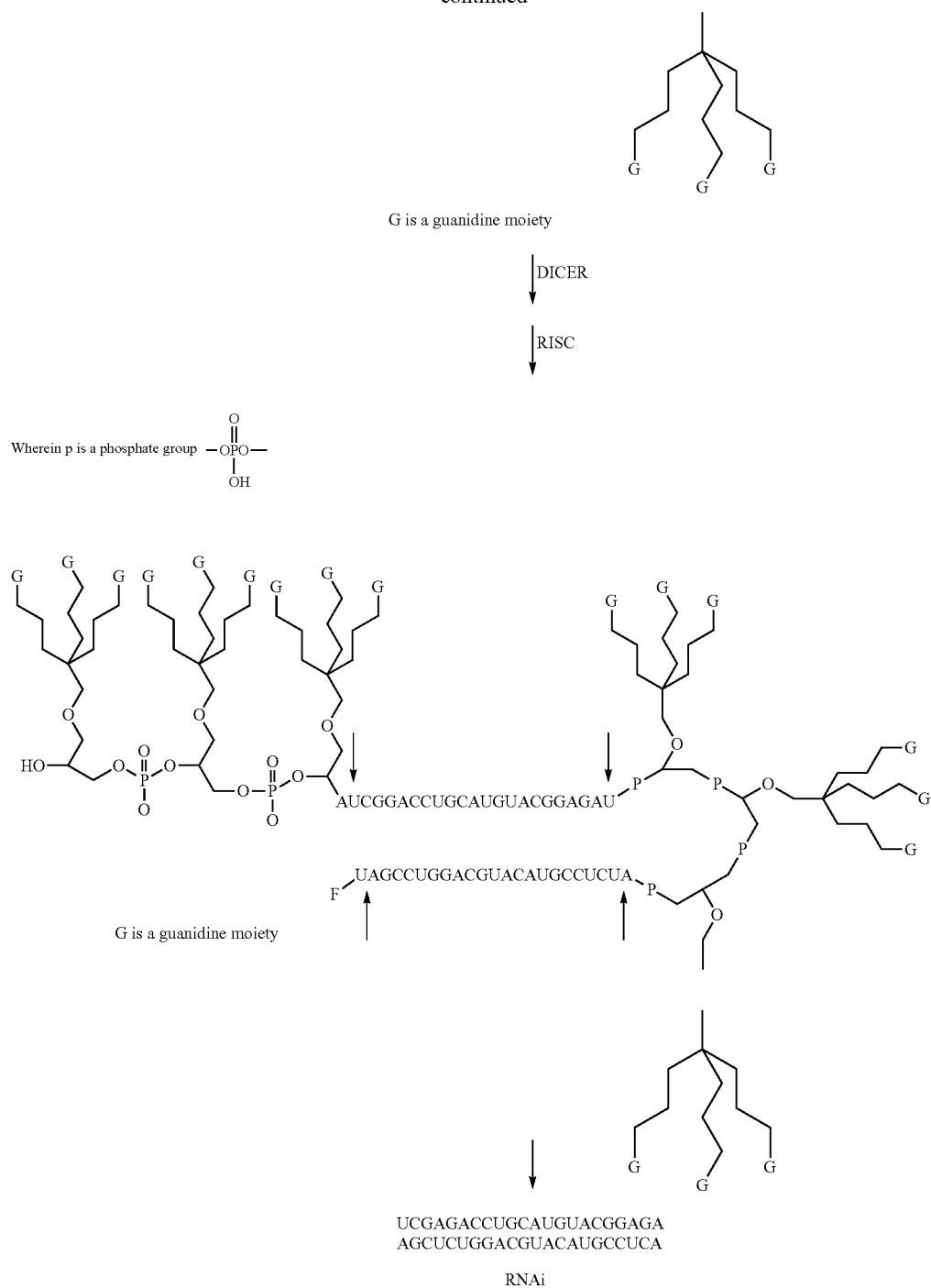
AUCGGACCUGCAUGUACGGAGAU (SEQ ID No: 3)
UAGCCUGGACGUACAUGCCUCUA (SEQ ID No: 4)
UCGGACCUGCAUGUACGGAGA (SEQ ID No: 6)
AGCCUGGACGUACAUGCCUCU (SEQ ID No: 7)

Example 8

A Conjugate of Protected Derivatized Nucleic Acids, Modified DNA or RNA to an Oligomeric Heteroalicyclic Moiety This example illustrates the online synthesis of RNA segment following the synthesis of the polymer by sequentially condensation of Compound 14 following condensation of continuing synthesis of another RNA segment. All of this synthesis is done on the same polymeric support. It is understood that this example is not limited to the synthesis of a particularly DNA/RNA sequence, but any of DNA/RNA sequences could be synthesize by this methodology following number of condensations of Compound 14.

In this example, the protected derivatized nucleic acids can be introduced in the protocol synthesis as it is described in Example 7, as presented in the following scheme:

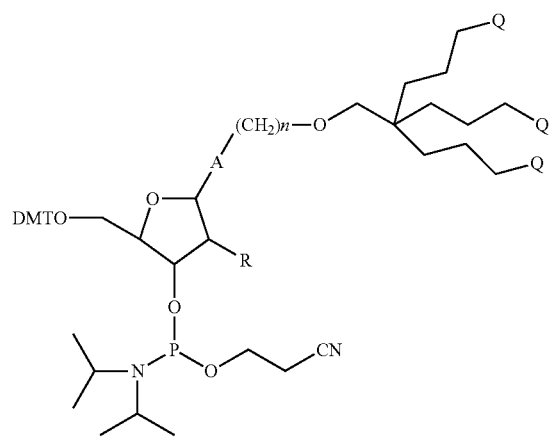

A is Adenine

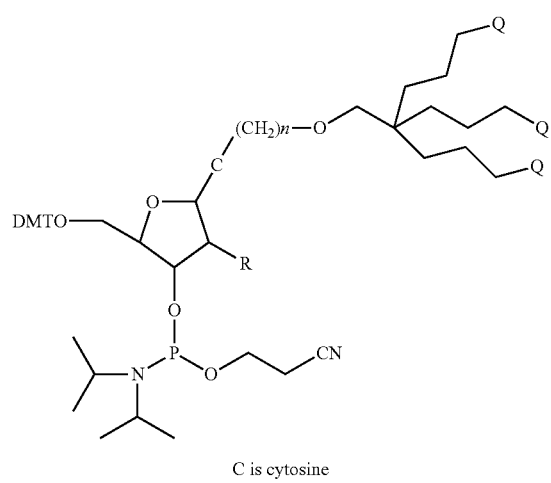

C is cytosine

Wherein Q is: $HN\overset{O}{\overset{\|}{C}}CF_3$

-continued

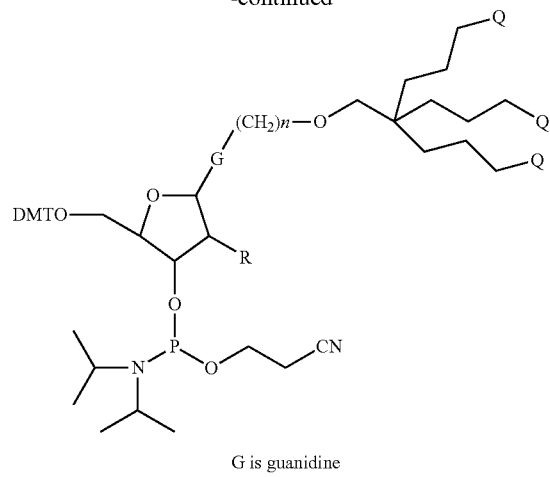

G is guanidine

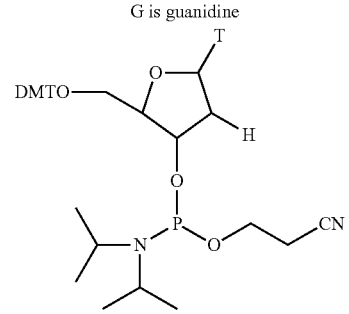

T is thymine

Wherein Q is: $HN\overset{O}{\overset{\|}{C}}CF_3$

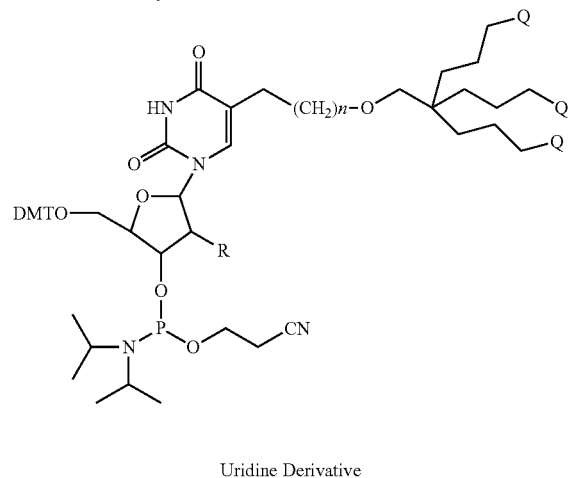

Uridine Derivative wherein R is H in case of DNA and OX in case of RNA;
X is a protecting group, which is used in RNA synthesis, like TOM

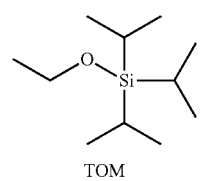

TOM

After application of the protocol as described in Example 7, the following Scheme is illustrating the use of these protected nucleic acids.

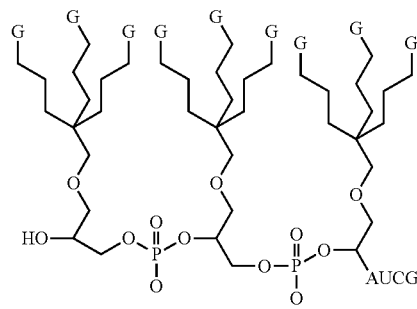
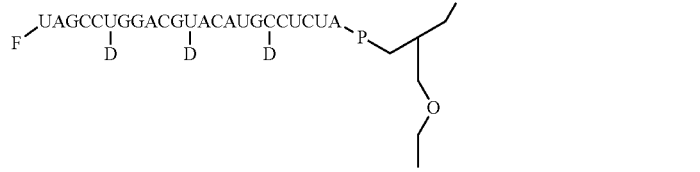
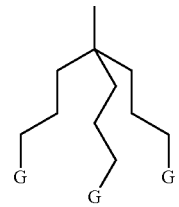

G is a guanidine moiety

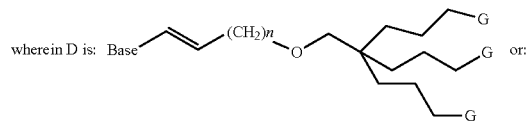

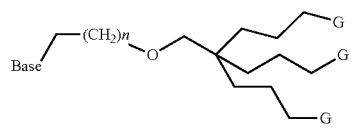

Leading to the formation of RNA protected sequence, which could be recognized by Dicer and Risc enzymes, and still allowing protection against nucleases and enhancing the delivery efficiency into living cells as following the protein Dicer initiates RNAi by processing dsRNA into small RNAs (smRNA) of ~19-22 nucleotides in length. The short segments then enter an effector complex, RISC, which seeks out and degrades homologous mRNA substrates RNA-induced silencing complex, or RISC, is a multi-protein siRNA complex which cleaves (incoming viral) dsRNA and binds short antisense RNA strands which are then able to bind complementary strands. When it finds the complementary strand, it activates RNAse activity and cleaves the RNA. This process is important both in gene regulation by micro-RNAs and in defense against viral infections, which often use double-stranded RNA as an infectious vector.

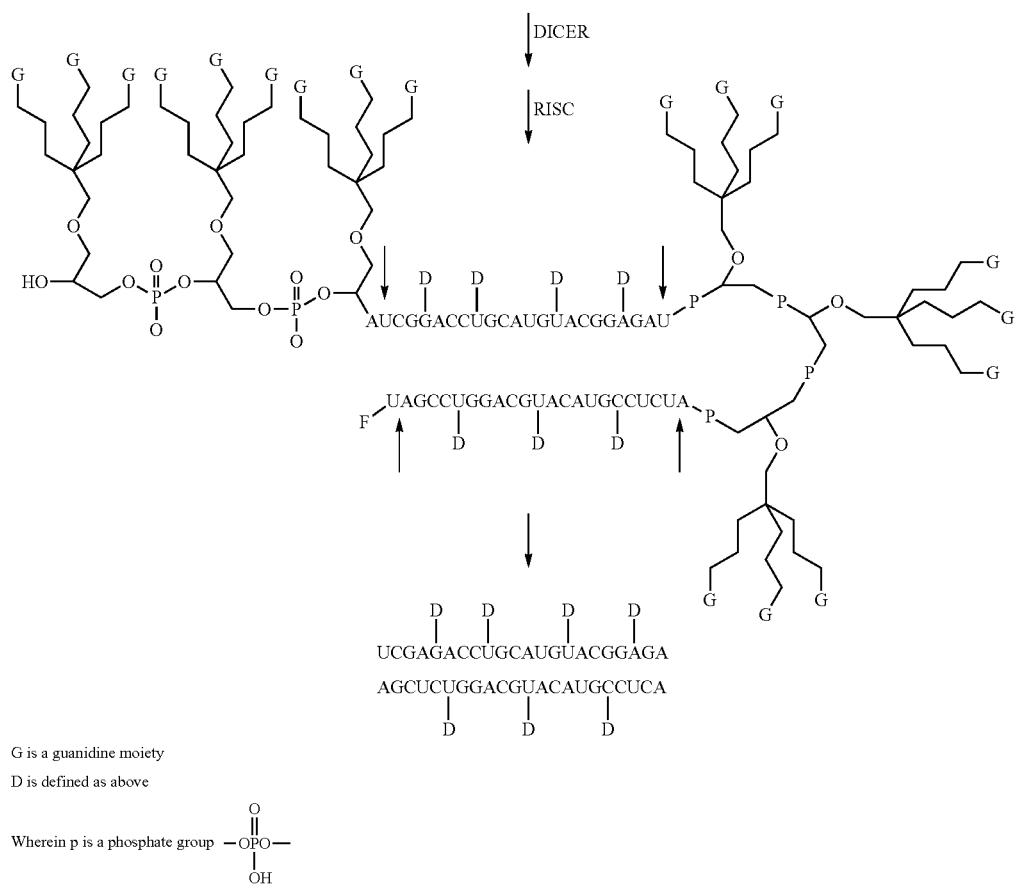

G is a guanidine moiety

D is defined as above

Wherein p is a phosphate group $-\overset{\overset{O}{\|}}{\underset{\underset{OH}{|}}{O-P-O-}}$ This protected RNA can serve as an activating moiety for RNAi mechanism.

Example 9

Cellular Uptake Assay for Compound 38 and Compound 40

The tested Compounds were dissolved separately in PBS buffer (pH 7.2) and their concentration were determined by absorption of fluorescein at 490 nm ($\epsilon$=67,000). The accuracy of this method for determining transporter concentration was established by weighing selected samples and dissolving them in known amount of PBS buffer. The concentrations were determined by UV spectroscopy correlated with the manually weighed standards.

Jurkat cells (human T cell lines) and murine B cells (CH27) were grown in 10% FCS and DMEM and were used for the cellular uptake experiments. Varying amounts of the tested Compounds were added to approximately 3×10$^6$ cells in 2% FCS/PBS (combined total of 200 µl) and the cells were placed into microtiter 96-well plates and incubated for varying amounts of times at 23° C. or 4° C. The microtiter plates were thereafter centrifuged and the cells were isolated, washed with cold PBS (3×250 µl), incubated with 0.05% trypsin/0.53 mM EDTA at 37° C. for 5 minutes, washed with cold PBS, and resuspended in PBS containing 0.1% propidium iodide. The cells were analyzed by using fluorescent flow cytometry (FACScan; Becton Dickinson).

Example 10

The Effect of Polymer DNA Adduct (Compound 38) on the Viability of the Human Glioblastoma Cell Line U251

In this example we demonstrate the delivery of Compound 38 into cells and determining the toxicity in vitro.

Tested Compound:

A sample of FITC labeled polymer DNA adduct (Compound 38), 750 nmoles/200 uL=3.75 uM.

For tissue culture work the sample was sterilized as follows: 1.2 mL of 0.01 M MgCl$_2$ and 0.3M Na acetate in ethanol were added to the sample, stored overnight at −20° C. The solution was centrifuged at 16,000 g 20 min at 4° C.

Cell Line:

The human glioblastoma U-251 cell line was obtained from ATCC and grown in RPMI-1640 (GIBCO-Invitrogene cell culture, USA). The mediums were supplemented with penicillin (250 µg/mL), streptomycin (125 µg/mL) and 10% fetal calf serum (FCS). The cells were transferred into fresh medium twice weekly and grown at 37° C. in a humidified 5% CO$_2$ incubator.

In Vitro Testing:

Exponentially growing cells 25,000/well were plated in 24 well plate over night. 5, 10 and 15 uL of polymer DNA adduct (Compound 38) were added to duplicate wells. After 3 and 24 h the stained cells were examined using a fluorescent microscope (IX70) (Olympus Tokyo, Japan) using excitation filter of 330-385 nm and barrier filter at 420 nm and under light phase (as presented in FIG. 1 side by side). Photographs were captured with an Olympus DP50 digital camera system, acquired by ViewfinderLite and edited by StudioLite softwares (Pixera Corporation, Los Gatos, Calif.). The cell in the different doses and exposure time were trypsinized and viable cells were counted with trypan blue. After 48 h the procedure was repeated.

Example 11

Cyclin D1 Knockdown in Liver and Lung of PANC-1-Implaned Mice Xenografts Using Compound 24 (Compound of Formula V) Complexed to Cyclin D1-siRNA Materials and Methods:
Human PANC-1 xenograft tumor model: model establishment and quantification of knockdown in vivo.

The protocol was adapted from Peer D and Margalit R., Neoplasia, 2004, 6(4): 343-353. Briefly, Nude CD1-Nu mice (6 weeks old) were housed in barrier facilities on a 12-hour light/dark cycle. Food and water were supplied ad libitum. On day 0, $2.5 \times 10^6$ of PANC-1 cells in 0.1 ml of HBS were implanted subcutaneously just above the right femoral joint. When tumors reached 125 mm$^3$ (day 14 from tumor inoculation), mice were intravenously injected with one of the following formulations:

Group 1 (n=10 mice/group) were Mock-treated with saline only to determine the basal expression level of cyclin D1 in the exerted tumors and other organs.

Group 2 (n=10 mice/group) were treated with luciferase-siRNA (sequence is provided below) complexed to Compound 24 (Segev polymer Mw 5.350 KDa). Complexation was done 20 min at room temp. in 1:100 w/w ratio–total siRNA injected per mice was 6 mg/Kg body (600 mg/Kg body polymer).

Group 3 (n=10 mice/group) were treated with Cyclin D1-siRNA (sequence is provided below) complexed to Compound 24 (Segev polymer Mw 5.350 KDa). Complexation was done 20 min at room temp. in 1:100 w/w ratio–total siRNA injected per mice was 6 mg/Kg body. (in 600 mg/Kg body polymer).

Tumors, lungs and liver were exerting from the mice after 24 h and mRNA level was quantify.

siRNA sequences against the CCND1 gene NM_053056 (sense strand: GUAGGACUCUCAUUCGGGAUU) and the luciferase gene as a control sequence (siLuc, sense strand: CUUACGCUGAGUACUUCGA) were designed and screened by Alnylam Pharmaceuticals (Cambridge Mass., USA). Total RNA was isolated using EZ-RNA kit (biological industries, Israel) and cDNA was generated with high capacity cDNA kit (Life Technologies, Carlsbad, Calif., USA) according to the manufacturers' protocols. qRT-PCR was performed with Fast SYBR® Green Master Mix and the ABI StepOnePlus™ instrument (Life Technologies). CCND1 (F:GAGGAGCCCCAACAACTTC C, R:GTCCGGGTCA-CACTTGATCAC) expression was normalized to the house keeping genes HTRP1 and GAPDH as previously described [Peer et al. Science 2008, 319, 627-630]. Analysis was done with the StepOne™ software V 2.1 (Life Technologies) using the multiple endogenous controls option. When using multiple endogenous controls, the software treats all endogenous controls as a single population, and calculates the experiment-appropriate mean to establish a single value against which the target of interest is normalized.

Results:
Selective and specific knockdown of Segev polymer-siRNA in human PNAC-1 xenograft model.

Upon model establishment, single i.v. injection was applied to PANC-1 tumor bearing nude mice of the following formulations: Cyclin D1-siRNA-Compound 24, Luciferase-siRNA-Compound 24, or were mock-treated with saline. 24 h post injections organs were taken out and analyzed using QPCR.

Figure 4:
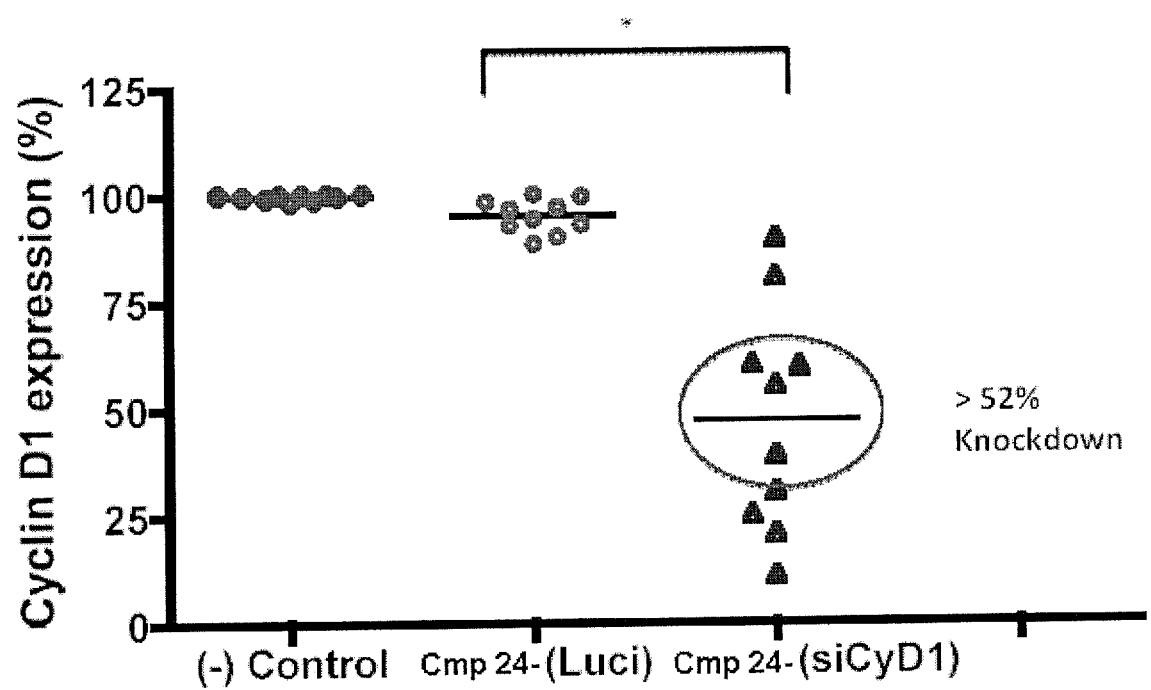
FIG. 4 depicts Individual data of Cyclin D1 knockdown in Tumors of PANC-1-implaned mice xenografts (in the tumor) using a complex of Compound 24 and Cyclin D1 siRNA-analyzed by QPCR and normalized to HTRP1 and GAPDH. Individual data—each mouse is a dot; P<0.01; Differences between treatment groups were evaluated by one-way ANOVA with significance determined by Bonferroni adjusted t-tests. Data suggest knockdown of more than 50% upon single i.v. injection which is specific to the tumor.

FIG. 4 shows individual data (n=10 mice/group) of Cyclin D1 knockdown in the isolated human tumors of PANC-1-implaned mice xenografts tissue. Data suggest that specific knockdown of >50% was achieved upon a single i.v. injection.

Figure 5:
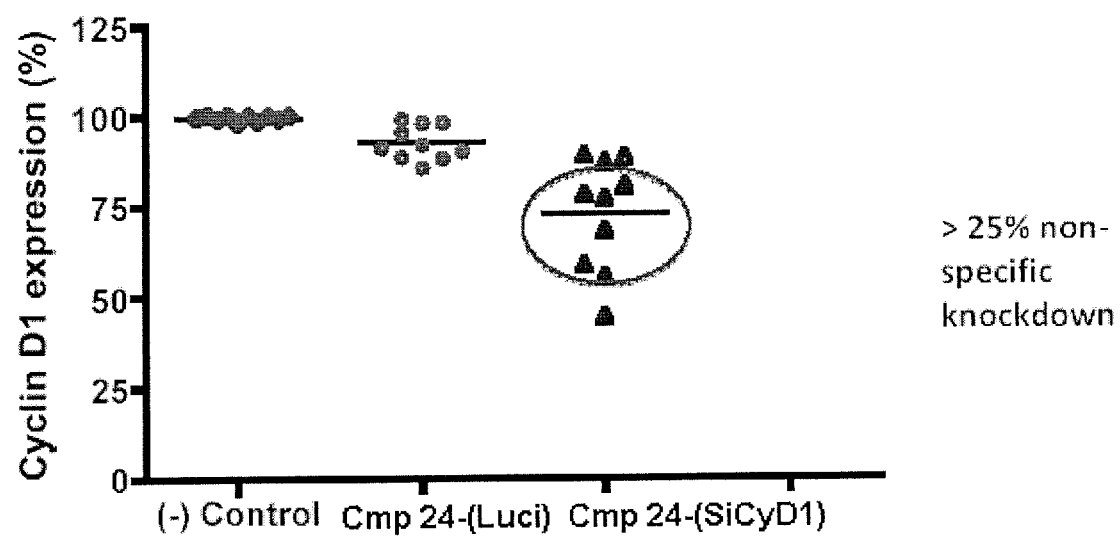
FIG. 5 depicts Cyclin D1 knockdown in Liver of PANC-1-implaned mice xenografts using a complex of compound 24 and Cyclin D1 siRNA-analyzed by QPCR and normalized to HTRP1 and GAPDH—Individual data—each mouse is a dot; P<0.01; Differences between treatment groups were evaluated by one-way ANOVA with significance determined by Bonferroni adjusted t-tests. Data suggest non-specific knockdown/infiltrating tumor cells to the liver with 25% knockdown.
Figure 6:
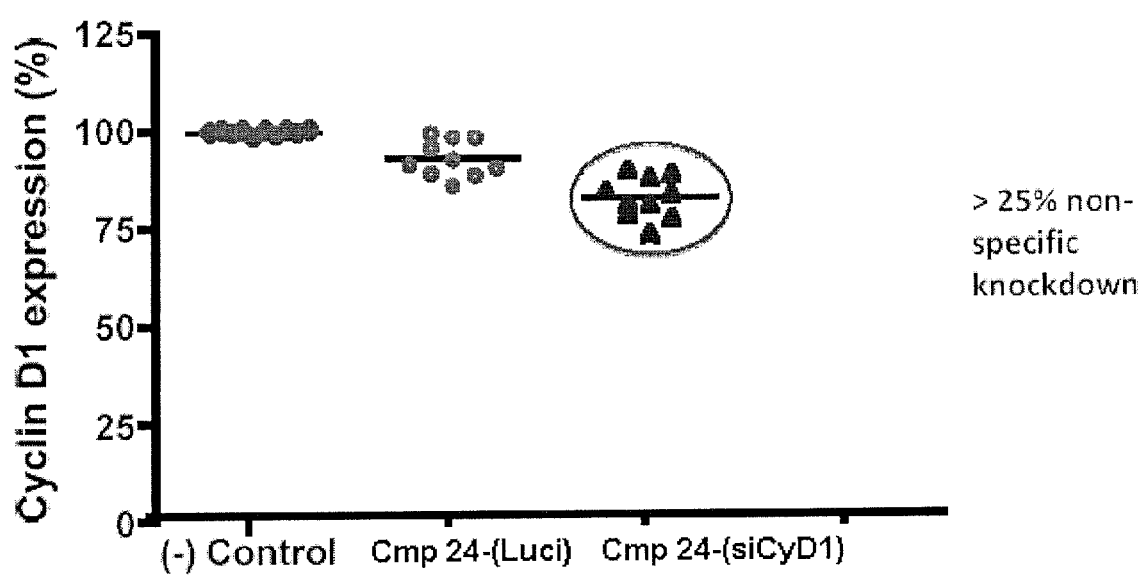
FIG. 6 depicts Cyclin D1 knockdown in Lungs of PANC-1-implaned mice xenografts using a complex of compound 24 and Cyclin D1 siRNA-analyzed by QPCR and normalized to HTRP1 and GAPDH. No statistical differences were found. Same experiment was repeated with smaller groups (n=3/group). This time with increase of the polymer size (from 5.350 to 7. KDa). No significant differences were observed.

The knockdown of this gene was tested in other organs such as Liver (FIG. 5) and lungs (FIG. 6). It is important to note that the Cyclin D1-siRNA sequence that was used is cross-reactive with human and mouse. Minimal knockdown (25%) was observed in the liver (FIG. 5) and no knockdown was observed in the lungs (FIG. 4). Taken together these results provide evidence for selective and specific knockdown in the tumor tissue which is highly vascularized and the mechanism fits well to the Enhanced Permeability and Retention (EPR) effect (Peer D et al. *Nat Nanotechnol.* 2007; 2:751-760).

Same experiment was repeated with smaller groups (n=3/group). This time with increase of the polymer size (from 5.350 to 7. KDa; i.e. complex of Compound of Formula VI (Compound 41)). No significant differences were observed.

Example 12

Toxicity Studies of Compound 24 Complexed to Cyclin D1-siRNA General Toxicity

General toxicity was assessed in C57BL/6 (n=20/group) mice injected with by the following formulations: a single dose of with Cyclin D1-siRNA (sequence is provided below) complexed to Compound 24 (Segev polymer Mw 5350). Complexation was done 20 min at room temp. in 1:100 w/w ratio–total siRNA injected per mice was 6 mg/Kg body. (in 600 mg/Kg body polymer) or mock-treated with saline.—no changes in body weight were observed.

Figure 7:
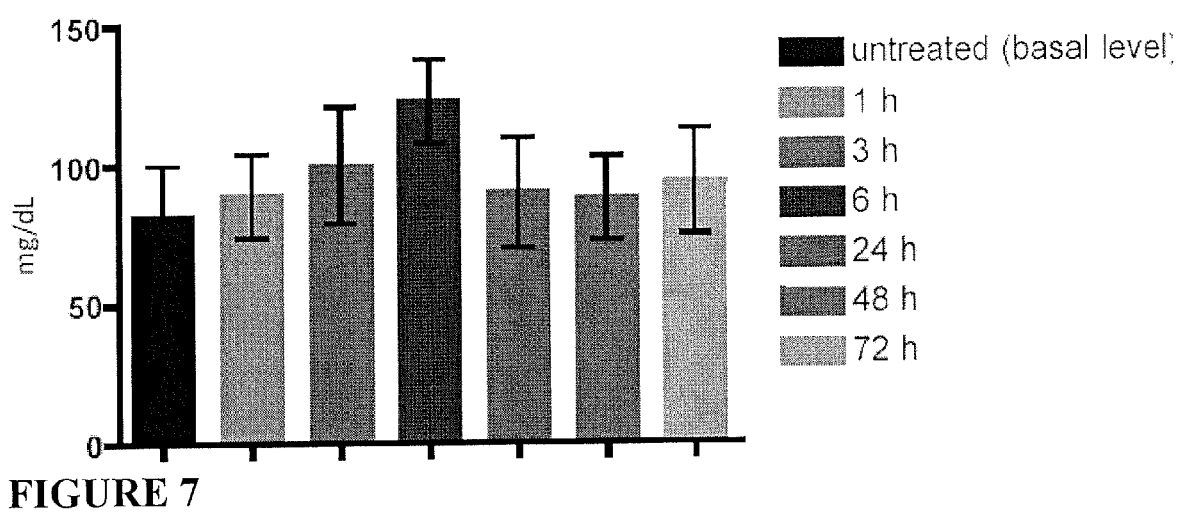
FIG. 7 depicts liver toxicity of a complex of compound 24 and Cyclin D1 siRNA: as measured by Triglycerides levels upon a single i.v. injection—4 mice/group. No significant differences were found.
Figure 8:
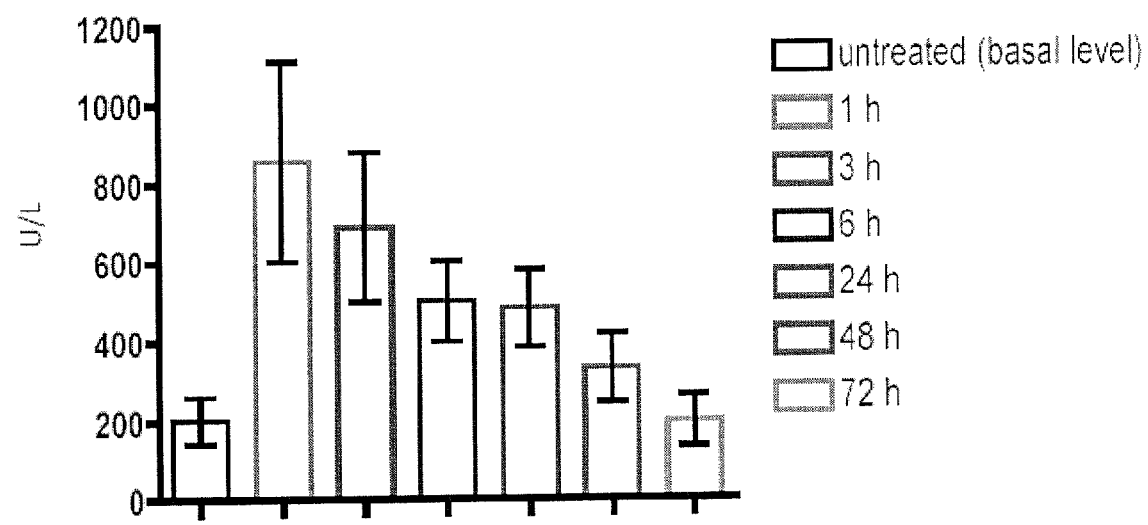
FIG. 8 depicts liver toxicity of a complex of compound 24 and Cyclin D1 siRNA: as measured by Liver enzyme release—ALT—4-mice/group. slight elevation is observed in the first 24 h which decrease to normal level within 72 h post single i.v. injection.
Figure 9:
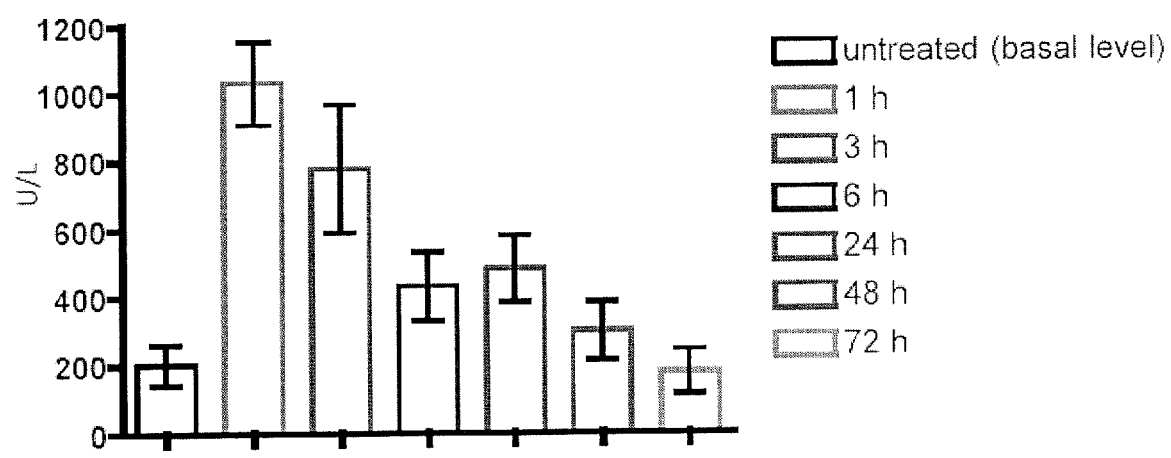
FIG. 9 depicts liver toxicity of a complex of compound 24 and Cyclin D1 siRNA: as measured by liver enzyme release—AST—4 mice per group. Slight elevation is observed in the first 24 h which decrease to normal levels within 72 h post single i.v. injection.

Assessing Liver Toxicity:
Healthy C57BL/6 mice (n=4/group/time point) were given a single bolus intravenous (i.v.) injections of saline or Cyclin D1-siRNA complexed to Compound 24 (Segev polymer Mw 5.350 KDa). 1, 3, 6, 24, 48 and 72 h post initial injection, blood was drawn and the serum was obtained by centrifugation of the whole blood at 850 g for 15 min. Liver enzyme levels of Alanine Aminotransferase (ALT), Aspartate Aminotransferase (AST) and Triglycerides were determined by COBAS MIRA auto analyzer (Roche). FIGS. 7-9 show the results obtained.

Results:
Compound 24-siRNA complex do not induce any general toxicity nor liver toxicity.

General toxicity was tested by measuring body weight changes upon single i.v. injection of a high dose siRNA (6 mg/Kg body) combined with a high Compound 24 concentration (125 mg/Kg). No changes in body weight were observed in 20 C57BL/6 mice. (data not shown) for a period of 14 days post injection suggesting that the complex is not causing any global toxicity.

Next, triglycerides levels were tested upon i.v. injection of the higher dose tested (6 mg/Kg siRNA complexed with Compound 24 at 125 mg/Kg body).

FIG. 7 shows the levels of triglycerides at different time points post i.v. injection (1, 3, 6, 24, 48, and 72 h) at groups of 4 mice per group. As clearly seen, there are no significant changes in the Triglycerides levels indicating that upon single i.v. injection no long term liver toxicity is observed.

Liver enzyme release in the serum of treated mice was also measured.

FIG. 8 shows the ALT levels (Liver enzyme release) and FIG. 9 shows the AST levels. At 1 hr post i.v. administration, a slight elevation in the release of these liver enzyme occurred, which within 72 h decreased to normal level, indicating the ability to go back to steady state condition.

Example 13

Immunotoxicity-Testing of siRNA-Compound 24 Complex in Isolated Human Peripheral Blood Cells (Lymphocytes and Monocytes Probing immuno-toxicity in isolated Human peripheral blood cells (lymphocytes and monocytes) with siRNA-Compound 24 complex.

PBMCs were isolated from donor blood and incubated with siRNA-Compound 24 (Segev polymer) complex at different concentrations (effective dose, ED×10, ED×50) and time. Cytokine levels were evaluated using multiplex ELISA kit.

Results:
siRNA-Compound 24 complex did not induce pro-inflammatory cytokines when incubated with human peripheral blood mononuclear cells (lymphocytes and monocytes).

One of the most challenging tasks when developing an RNAi delivery strategy is to make sure it does not stimulate the immune system. Accordingly, the induction of the pro-inflammatory cytokines TNF-α and IL-6 was tested, when exposing the Compound-siRNA complexes at different concentrations ranging from 10-1000 nM siRNA to human PBMCs at different time points (4, 10 and 24 h post incubation).

Figure 10:
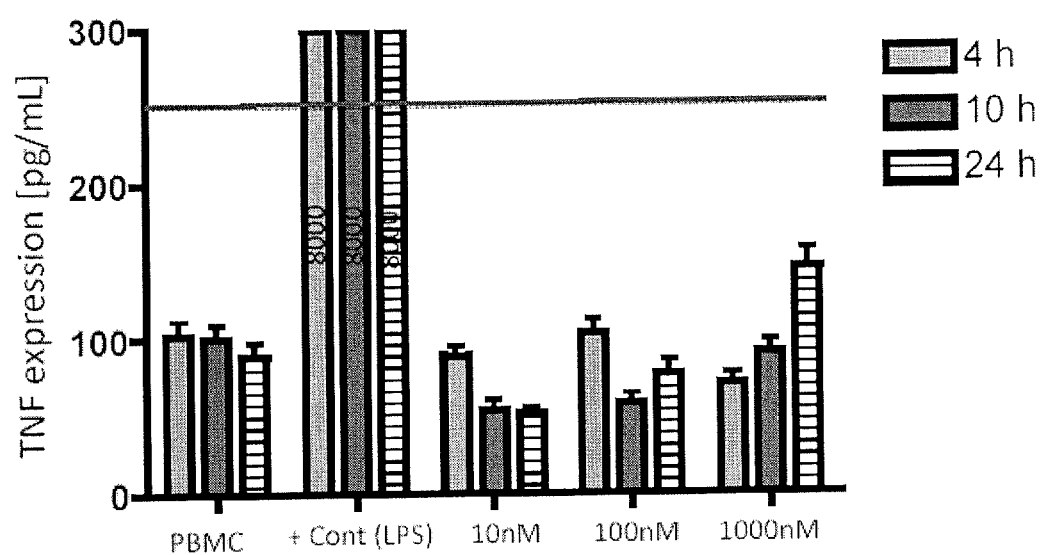
FIG. 10 depicts cytokin TNF a expression using a complex of compound 24 and Cyclin D1 siRNA. Three different time points were taken for measurements of TNF-α levels, 4, 10 and 24 h in three different siRNAs doses 10,100 and 1000 nM. no statistical differences are observed between the different doses and time points tested of TNF a induction. +control (LPS)>6000 pg/mL, Red line—above this line consider toxic.
Figure 11:
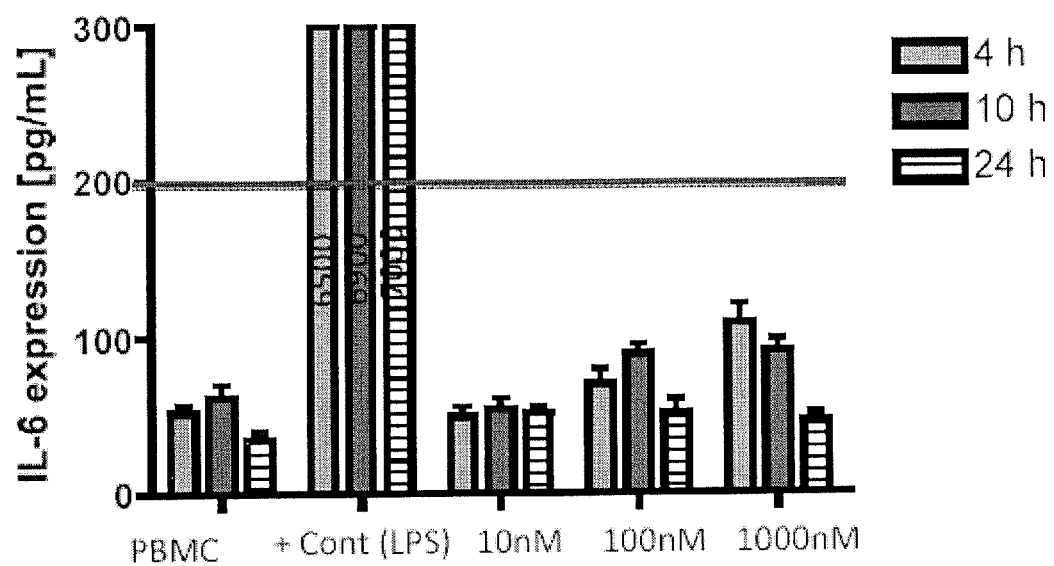
FIG. 11 depicts cytokin IL-6 expression using a complex of compound 24 and Cyclin D1 siRNA. Three different time points were taken for measurements of IL-6 levels, 4, 10 and 24 h in three different siRNAs doses 10,100 and 1000 nM. no statistical differences are observed between the different doses and time points tested of IL-6 induction. +control (LPS)>6000 pg/mL, Red line—above this line consider toxic.

FIGS. 10 and 11 show two representatives of major pro-inflammatory cytokines TNF-α and IL-6. No significant changes in expression of either one of these cytokines was observed, suggesting that even at a very high dose of 1000 nM siRNAs, the complexes do not induce a pro-inflammatory cytokines.

No sign of toxicity was found in the tumors upon injection of the siRNA-polymer complexes into C57BL/6 mice-bearing B16F10 melanoma tumors.

Figure 12:
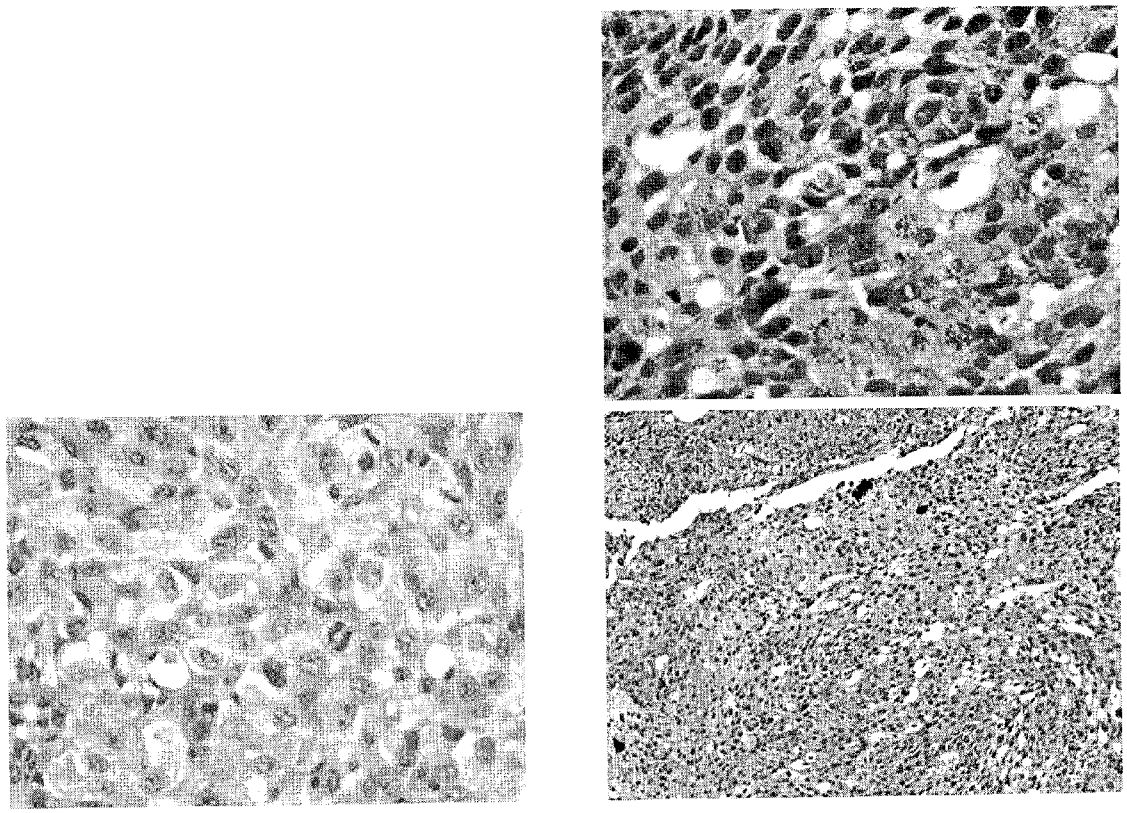
FIG. 12 depicts tumor histology—no changes in morphology of the tumor due to Compound 24-siRNA complex. No pathological sign of toxicity upon injection of Compound 24-siRNA complex into C57BL/6 mice (representative image). H & staining was preformed.

The siRNA-Compound 24 complex was injected at the highest dose (6 mg/Kg siRNA and 125 mg/Kg body polymer) into C57BL/6 mice-bearing B16F10 mouse melanoma. 24 h post injection of a single dose, mice were sacrificed and the tumors were exerted. Histology by H & E staining did not confirm any toxicity or damage to the tumors as indicated in FIG. 12.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:
1. A conjugate of a phosphate based oligomeric compound with at least one biologically active substance, comprising a repeating unit represented by the structure of formula (A):

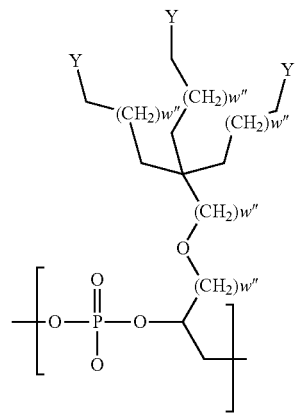

wherein
Y is a delivery group; wherein said delivery group is amine, histidine, guanidine, polyguanidine, imidazole, polyimidzole or any combination thereof; and
w, w' and w" are each independently an integer between 1 and 10;
wherein said biologically active substance is covalently attached to the terminus of said phosphate based oligomeric compound.

2. A complex of the conjugate according to claim 1 and an oligonucleotide, wherein said oligonucleotide, is electrostatically bound to said conjugate.

3. The complex according to claim 2, wherein said oligonucleotide is DNA, RNA or combination thereof.

4. A method of delivering a DNA, RNA or combination thereof to a cell, said method comprises contacting a complex of claim 3 with said cell, thereby delivering said DNA, RNA or combination thereof to said cell.

5. The method of claim 4, wherein said cell is cancerous.

6. A method of treating cancer, comprising administering a complex of claim 2 to a subject, thereby treating cancer.

7. A method of delivering a biologically active moiety to a cell, said method comprises contacting a conjugate of claim 1 with said cell, thereby delivering said biologically active moiety to said cell.

8. A method of diagnosing a condition, comprising contacting a conjugate of claim 1 with a cell, wherein said biologically active substance covalently attached to said conjugate is a labeling moiety, thereby delivering the labeling moiety of said conjugate to said cell and diagnosing said condition.

9. A pharmaceutical composition comprising the conjugate of claim 1 and a pharmaceutically acceptable carrier.

10. A pharmaceutical composition comprising the complex of claim 2 and a pharmaceutically acceptable carrier.

11. The conjugate of claim 1, further comprising linker units, which link between repeating units of said conjugate, wherein said linker comprises a substituted or unsubstituted linear alkyl chain of 2-50 carbon atoms, substituted or unsubstituted linear or branched alkylphosphate chain of 2-50 carbon atoms, substituted or unsubstituted linear alkylether chain of 2-50 carbon atoms or any combination thereof.

12. A complex of the conjugate according to claim 11 and an oligonucleotide, wherein said oligonucleotide, is electrostatically bound to said conjugate.

13. A pharmaceutical composition comprising the complex of claim 2 and a pharmaceutically acceptable carrier.

14. The complex according to claim 12, wherein said oligonucleotide is DNA, RNA or combination thereof.

* * * * *